United States Patent
Liu et al.

(10) Patent No.: US 10,227,581 B2
(45) Date of Patent: *Mar. 12, 2019

(54) ENGINEERED TRANSCRIPTION ACTIVATOR-LIKE EFFECTOR (TALE) DOMAINS AND USES THEREOF

(71) Applicant: President and Fellows of Harvard College, Cambridge, MA (US)

(72) Inventors: David R. Liu, Lexington, MA (US); John Paul Guilinger, Ridgway, CO (US); Vikram Pattanayak, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 361 days.

This patent is subject to a terminal disclaimer.

(21) Appl. No.: 14/913,458

(22) PCT Filed: Aug. 22, 2014

(86) PCT No.: PCT/US2014/052231
§ 371 (c)(1),
(2) Date: Feb. 22, 2016

(87) PCT Pub. No.: WO2015/027134
PCT Pub. Date: Feb. 26, 2015

(65) Prior Publication Data
US 2016/0201040 A1  Jul. 14, 2016

Related U.S. Application Data

(63) Continuation of application No. 14/320,519, filed on Jun. 30, 2014, now Pat. No. 9,359,599.

(60) Provisional application No. 61/868,846, filed on Aug. 22, 2013.

(51) Int. Cl.
C12N 15/01 (2006.01)
C12Q 1/68 (2018.01)
C12N 9/22 (2006.01)

(52) U.S. Cl.
CPC .............. *C12N 15/01* (2013.01); *C12N 9/22* (2013.01); *C12Q 1/68* (2013.01); *C07K 2319/00* (2013.01); *C07K 2319/80* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 5,780,053 A | 7/1998 | Ashley et al. | |
| 6,057,153 A | 5/2000 | George et al. | |
| 6,453,242 B1 | 9/2002 | Eisenberg et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,163,824 B2 | 1/2007 | Cox, III et al. | |
| 7,479,573 B2 | 1/2009 | Chu et al. | |
| 7,794,931 B2 | 9/2010 | Breaker et al. | |
| 8,569,256 B2 | 10/2013 | Heyes et al. | |
| 8,680,069 B2 | 3/2014 | De Fougerolles et al. | |
| 8,691,750 B2 | 4/2014 | Constien et al. | |
| 8,709,466 B2 | 4/2014 | Coady et al. | |
| 8,728,526 B2 | 5/2014 | Heller | |
| 8,748,667 B2 | 6/2014 | Budzik et al. | |
| 8,758,810 B2 | 6/2014 | Okada et al. | |
| 8,759,103 B2 | 6/2014 | Kim et al. | |
| 8,759,104 B2 | 6/2014 | Unciti-Broceta et al. | |
| 8,771,728 B2 | 7/2014 | Huang et al. | |
| 8,790,664 B2 | 7/2014 | Pitard et al. | |
| 8,846,578 B2 | 9/2014 | McCray et al. | |
| 8,993,233 B2 | 3/2015 | Zhang et al. | |
| 8,999,641 B2 | 4/2015 | Zhang et al. | |
| 9,068,179 B1 | 6/2015 | Liu et al. | |
| 9,163,284 B2 | 10/2015 | Liu et al. | |

(Continued)

FOREIGN PATENT DOCUMENTS

| | | |
|---|---|---|
| AU | 2012244264 A1 | 11/2012 |
| AU | 2015252023 A1 | 11/2015 |

(Continued)

OTHER PUBLICATIONS

U.S. Appl. No. 14/234,031, filed Mar. 24, 2014, Liu et al.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

Engineered transcriptional activator-like effectors (TALEs) are versatile tools for genome manipulation with applications in research and clinical contexts. One current drawback of TALEs is their tendency to bind and cleave off-target sequence, which hampers their clinical application and renders applications requiring high-fidelity binding unfeasible. This disclosure provides engineered TALE domains and TALEs comprising such engineered domains, e.g., TALE nucleases (TALENs), TALE transcriptional activators, TALE transcriptional repressors, and TALE epigenetic modification enzymes, with improved specificity and methods for generating and using such TALEs.

16 Claims, 34 Drawing Sheets

Specification includes a Sequence Listing.

(56) References Cited

U.S. PATENT DOCUMENTS

| | | |
|---|---|---|
| 9,228,207 B2 | 1/2016 | Liu et al. |
| 9,234,213 B2 | 1/2016 | Wu |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 2005/0222030 A1 | 10/2005 | Allison et al. |
| 2006/0088864 A1 | 4/2006 | Smolke et al. |
| 2007/0264692 A1 | 11/2007 | Liu et al. |
| 2008/0182254 A1 | 7/2008 | Hall et al. |
| 2009/0130718 A1 | 5/2009 | Short |
| 2009/0234109 A1 | 9/2009 | Han et al. |
| 2010/0076057 A1 | 3/2010 | Sontheimer et al. |
| 2010/0316643 A1 | 12/2010 | Eckert et al. |
| 2011/0059160 A1 | 3/2011 | Essner et al. |
| 2011/0104787 A1 | 5/2011 | Church et al. |
| 2011/0189776 A1 | 8/2011 | Terns et al. |
| 2012/0129759 A1 | 5/2012 | Liu et al. |
| 2012/0141523 A1 | 6/2012 | Castado et al. |
| 2012/0270273 A1 | 10/2012 | Zhang et al. |
| 2013/0117869 A1 | 5/2013 | Duchateau et al. |
| 2013/0130248 A1 | 5/2013 | Haurwitz et al. |
| 2013/0165389 A1 | 6/2013 | Schellenberger et al. |
| 2013/0344117 A1 | 12/2013 | Mirosevich et al. |
| 2014/0005269 A1 | 1/2014 | Ngwuluka et al. |
| 2014/0018404 A1 | 1/2014 | Chen et al. |
| 2014/0044793 A1 | 2/2014 | Goll et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0252358 A1 | 9/2015 | Maeder et al. |
| 2016/0017393 A1 | 1/2016 | Jacobson et al. |
| 2016/0017396 A1 | 1/2016 | Cann et al. |
| 2016/0032353 A1 | 2/2016 | Braman et al. |
| 2016/0046952 A1 | 2/2016 | Hittinger et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |

FOREIGN PATENT DOCUMENTS

| | | |
|---|---|---|
| AU | 2015101792 | 1/2016 |
| CA | 2 852 593 A1 | 11/2015 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 104004778 A | 8/2014 |
| CN | 104109687 A | 10/2014 |
| CN | 104178461 A | 12/2014 |
| CN | 104342457 | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |

(56) References Cited

FOREIGN PATENT DOCUMENTS

| | | |
|---|---|---|
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567734 A | 5/2016 |
| CN | 105567735 A | 5/2016 |
| CN | 105567738 A | 5/2016 |
| EP | 2 604 255 A1 | 6/2013 |
| EP | 2 966 170 A1 | 1/2016 |
| EP | 3 009 511 A2 | 4/2016 |
| GB | 2 528 177 A | 1/2016 |
| GB | 2 531 454 A1 | 4/2016 |
| KR | 101584933 B1 | 1/2016 |
| WO | WO 2006/002547 A1 | 1/2006 |
| WO | WO 2006/042112 A2 | 4/2006 |
| WO | WO 2010/054108 A2 | 5/2010 |
| WO | WO 2010/054154 A2 | 5/2010 |
| WO | WO 2010/068289 A2 | 6/2010 |
| WO | WO 2010/102257 A2 | 9/2010 |
| WO | WO 2010/129019 A2 | 11/2010 |
| WO | WO 2010/144150 A2 | 12/2010 |
| WO | WO 2011/017293 A2 | 2/2011 |
| WO | WO 2011/053868 A1 | 5/2011 |
| WO | WO 2011/053982 A2 | 5/2011 |
| WO | WO 2011/075627 A1 | 6/2011 |
| WO | WO 2011/109031 A1 | 9/2011 |
| WO | WO 2012/054726 A1 | 4/2012 |
| WO | WO 2012/065043 A2 | 5/2012 |
| WO | WO 2012/138927 A2 | 10/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO 2013/013105 A2 | 1/2013 |
| WO | WO 2013/066438 A2 | 5/2013 |
| WO | WO 2013/098244 A1 | 7/2013 |
| WO | WO 2013/130824 A1 | 9/2013 |
| WO | WO 2013/141680 A1 | 9/2013 |
| WO | WO 2013/142578 A2 | 9/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176915 A1 | 11/2013 |
| WO | WO 2013/176916 A1 | 11/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/036219 A2 | 3/2014 |
| WO | WO 2014/039523 A1 | 3/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/071235 A1 | 5/2014 |
| WO | WO 2014/081729 A1 | 5/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A1 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/153470 A2 | 9/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |

(56) References Cited

FOREIGN PATENT DOCUMENTS

| | | |
|---|---|---|
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/010114 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066637 A1 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075195 A1 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A2 | 6/2015 |
| WO | WO 2015/086798 A1 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A1 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117041 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/131101 A1 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | 2015/153889 A2 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164748 A1 | 10/2015 |
| WO | WO 2015/166272 A2 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |

(56) References Cited

FOREIGN PATENT DOCUMENTS

| | | |
|---|---|---|
| WO | WO 2015/171894 A1 | 11/2015 |
| WO | WO 2015/175642 A2 | 11/2015 |
| WO | WO 2015/179540 A1 | 11/2015 |
| WO | WO 2015/183885 A1 | 12/2015 |
| WO | WO 2015/184259 A1 | 12/2015 |
| WO | WO 2015/188056 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/004010 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/012544 A2 | 1/2016 |
| WO | WO 2016/014409 A1 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A1 | 2/2016 |
| WO | WO 2016/028887 A1 | 2/2016 |
| WO | WO 2016/033088 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044416 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A2 | 4/2016 |
| WO | WO 2016/057951 A2 | 4/2016 |
| WO | WO 2016/057961 A2 | 4/2016 |
| WO | WO 2016/061073 A1 | 4/2016 |
| WO | WO 2016/061374 A1 | 4/2016 |
| WO | WO 2016/061523 A1 | 4/2016 |
| WO | WO 2016/069591 A2 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/073433 A1 | 5/2016 |
| WO | WO 2016/073559 A1 | 5/2016 |
| WO | WO 2016/073990 A2 | 5/2016 |

OTHER PUBLICATIONS

U.S. Appl. No. 14/320,271, filed Jun. 30, 2014, Liu et al.
U.S. Appl. No. 14/320,519, filed Jun. 30, 2014, Liu et al.
U.S. Appl. No. 14/320,370, Jun. 30, 2014, Liu et al.
U.S. Appl. No. 14/320,413, filed Jun. 30, 2014, Liu et al.
U.S. Appl. No. 14/874,123, filed Oct. 2, 2015, Liu et al.
U.S. Appl. No. 14/911,117, filed Feb. 9, 2016, Liu et al.
U.S. Appl. No. 14/462,163, filed Aug. 18, 2014, Liu et al.
U.S. Appl. No. 14/462,189, filed Aug. 18, 2014, Liu et al.
U.S. Appl. No. 14/916,679, filed Mar. 4, 2016, Liu et al.
U.S. Appl. No. 14/320,498, filed Jun. 30, 2014, Liu et al.
U.S. Appl. No. 14/320,467, filed Jun. 30, 2014, Liu et al.
U.S. Appl. No. 14/916,681, filed Mar. 4, 2016, Liu et al.
U.S. Appl. No. 14/326,329, filed Jul. 8, 2014, Liu et al.
U.S. Appl. No. 14/326,340, filed Jul. 8, 2014, Liu et al.
U.S. Appl. No. 14/326,361, filed Jul. 8, 2014, Liu et al.
U.S. Appl. No. 14/916,683, filed Mar. 4, 2016, Liu et al.
U.S. Appl. No. 14/325,815, filed Jul. 8, 2014, Liu et al.
U.S. Appl. No. 14/326,109, filed Jul. 8, 2014, Liu et al.
U.S. Appl. No. 14/326,140, filed Jul. 8, 2014, Liu et al.
U.S. Appl. No. 14/326,269, filed Jul. 8, 2014, Liu et al.
U.S. Appl. No. 14/326,290, filed Jul. 8, 2014, Liu et al.
U.S. Appl. No. 14/326,318, filed Jul. 8, 2014, Liu et al.
U.S. Appl. No. 14/326,303, filed Jul. 8, 2014, Liu et al.
U.S. Appl. No. 14/529,010, filed Oct. 30, 2014, Liu et al.
PCT/US2013/032589, Jul. 26, 2013, International Search Report.
EP 123845790.0, Mar. 18, 2015, Partial Supplementary European Search Report.
EP 123845790.0, Oct. 12, 2015, Supplementary European Search Report.
PCT/US2012/047778, May 30, 2013, International Search Report and Written Opinion.
PCT/US2012/047778, Feb. 6, 2014, International Preliminary Report on Patentability.
PCT/US2014/052231, Dec. 4, 2014, International Search Report and Written Opinion.
PCT/US2014/052231, Jan. 30, 2015, International Search Report and Written Opinion (Corrected Version).
PCT/US2014/052231, Mar. 3, 2016, International Preliminary Report on Patentability.
PCT/US2014/050283, Nov. 6, 2014, International Search Report and Written Opinion.
PCT/US2014/050283, Feb. 18, 2016, International Preliminary Report on Patentability.
PCT/US2014/054247, Mar. 27, 2015, International Search Report and Written Opinion.
PCT/US2014/054247, Mar. 17, 2016, International Preliminary Report on Patentability.
PCT/US2014/054291, Dec. 18, 2014, Invitation to Pay Additional Fees.
PCT/US2014/054291, Mar. 27, 2015, International Search Report and Written Opinion.
PCT/US2014/054291, Mar. 17, 2016, International Preliminary Report on Patentability.
Partial Supplementary European Search Report for Application No. EP 12845790.0, dated Mar. 18, 2015.
Supplementary European Search Report for Application No. EP 12845790.0, dated Oct. 12, 2015.
International Search Report and Written Opinion for PCT/US2012/047778, dated May 30, 2013.
International Preliminary Report on Patentability for PCT/US2012/047778, dated Feb. 6, 2014.
International Search Report and Written Opinion for PCT/US2014/052231, dated Dec. 4, 2014.

(56) References Cited

OTHER PUBLICATIONS

International Search Report and Written Opinion for PCT/US2014/052231, dated Jan. 30, 2015. (Corrected Version).
International Preliminary Report on Patentability for PCT/US2014/052231, dated Mar. 3, 2016.
International Search Report and Written Opinion for PCT/US2014/050283, dated Nov. 6, 2014.
International Preliminary Report on patentability for PCT/US2014/050283, dated Feb. 18, 2016.
International Search Report and Written Opinion for PCT/US2014/054247, dated Mar. 27, 2015.
International Preliminary Report on Patentability for PCT/US2014/054247, dated Mar. 17, 2016.
Invitation to Pay Additional Fees for PCT/US2014/054291, dated Dec. 18, 2014.
International Search Report and Written Opinion for PCT/US2014/054291, dated Mar. 27, 2015.
International Preliminary Report on Patentability for PCT/US2014/054291, dated Mar. 17, 2016.
International Search Report and Written Opinion for PCT/US2014/054252, dated Mar. 5, 2015.
International Preliminary Report on Patentability or PCT/US2014/054252, dated Mar. 17, 2016.
International Search Report and Written Opinion for PCT/US2014/070038, dated Apr. 14, 2015.
International Search Report and Written Opinion for PCT/US2015/042770, dated Feb. 23, 2016.
International Search Report and Written Opinion for PCT/US2015/058479, dated Feb. 11, 2016.
International Search Report for PCT/US2013/032589, dated Jul. 26, 2013.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
NCBI Reference Sequence: NM_002427.3. Wu et al., May 3, 2014. 5 pages.
Uniprot Submission; UniProt, Accession No. P01011. Last modified Jun. 11, 2014, version 2. 15 pages.
Uniprot Submission; UniProt, Accession No. P01011. Last modified Sep. 18, 2013, version 2. 15 pages.
Uniprot Submission; UniProt, Accession No. P04264. Last modified Jun. 11, 2014, version 6. 15 pages.
Uniprot Submission; UniProt, Accession No. P04275. Last modified Jul. 9, 2014, version 107. 29 pages.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Alexandrov et al., Signatures of mutational processes in human cancer. Nature. Aug. 22, 2013;500(7463):415-21. doi: 10.1038/nature12477. Epub Aug. 14, 2013.
Barrangou, RNA-mediated programmable DNA cleavage. Nat Biotechnol. Sep. 2012;30(9):836-8. doi: 10.1038/nbt.2357.
Bedell et al., In vivo genome editing using a high-efficiency TALEN system. Nature. Nov. 1, 2012;491(7422):114-8. Doi: 10.1038/nature11537. Epub Sep. 23, 2012.
Boch et al., Breaking the code of DNA binding specificity of TAL-type III effectors. Science. Dec. 11, 2009;326(5959):1509-12. Doi: 10.1126/science.1178811.
Boch, TALEs of genome targeting. Nat Biotechnol. Feb. 2011;29(2):135-6. Doi: 10.1038/nbt.1767.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Charpentier et al., Biotechnology: Rewriting a genome. Nature. Mar. 7, 2013;495(7439):50-1. doi: 10.1038/495050a.
Chichili et al., Linkers in the structural biology of protein-protein interactions. Protein Science. 2013;22:153-67.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chung-Il et al., Artificial control of gene expression in mammalian cells by modulating RNA interference through aptamer-small molecule interaction. RNA. May 2006;12(5):710-6. Epub Apr. 10, 2006.
Cong et al., Comprehensive interrogation of natural TALE DNA-binding modules and transcriptional repressor domains. Nat Commun. Jul. 24, 2012;3:968. doi: 10.1038/ncomms1962.

(56) References Cited

OTHER PUBLICATIONS

Cradick et al., ZFN-site searches genomes for zinc finger nuclease target sites and off-target sites. BMC Bioinformatics. May 13, 2011;12:152. doi: 10.1186/1471-2105-12-152.

Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.

De Souza, Primer: genome editing with engineered nucleases. Nat Methods. Jan. 2012;9(1):27.

Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Esvelt et al., A system for the continuous directed evolution of biomolecules. Nature. Apr. 28, 2011;472(7344):499-503. doi: 10.1038/nature09929. Epub Apr. 10, 2011.

Esvelt et al., Genome-scale engineering for systems and synthetic biology. Mol Syst Biol. 2013;9:641. doi: 10.1038/msb.2012.66.

Fuchs et al., Polyarginine as a multifunctional fusion tag. Protein Sci. Jun. 2005;14(6):1538-44.

Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.

Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.

Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.

Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.

Guo et al., Protein tolerance to random amino acid change. Proc Natl Acad Sci U S A. Jun. 22, 2004;101(25):9205-10. Epub Jun. 14, 2004.

Hale et al., RNA-guided RNA cleavage by a CRISPR RNA-Cas protein complex. Cell. Nov. 25, 2009;139(5):945-56. doi: 10.1016/j.cell.2009.07.040.

Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.

Hill et al., Functional analysis of conserved histidines in ADP-glucose pyrophosphorylase from *Escherichia coli*.Biochem Biophys Res Commun. Mar. 17, 1998;244(2):573-7.

Hockemeyer et al., Genetic engineering of human pluripotent cells using TALE nucleases. Nat Biotechnol. Jul. 7, 2011;29(8):731-4. doi: 10.1038/nbt.1927.

Houdebine, The methods to generate transgenic animals and to control transgene expression. J Biotechnol. Sep. 25, 2002;98(2-3):145-60.

Huang et al., Heritable gene targeting in zebrafish using customized TALENs. Nat Biotechnol. Aug. 5, 2011;29(8):699-700. doi: 10.1038/nbt.1939.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Joung et al.,TALENs: a widely applicable technology for targeted genome editing. Nat Rev Mol Cell Biol. Jan. 14, 2013;14(1):49-55. doi: 10.1038/nrm3486. Epub Nov. 21, 2012.

Kaiser et al., Gene therapy. Putting the fingers on gene repair. Science. Dec. 23, 2005;310(5756):1894-6.

Kappel et al., Regulating gene expression in transgenic animals. Curr Opin Biotechnol. Oct. 1992;3(5):548-53.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., TALENs and ZFNs are associated with different mutationsignatures. Nat Methods. Mar. 2013;10(3):185. doi: 10.1038/nmeth.2364. Epub Feb. 10, 2013.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Lazar et al., Transforming growth factor alpha: mutation of aspartic acid 47 and leucine 48 results in different biological activities. Mol Cell Biol. Mar. 1988;8(3):1247-52.

Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Current approaches for engineering proteins with diverse biological properties. Adv Exp Med Biol. 2007;620:18-33.

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Fast Colorimetric Sensing of Adenosine and Cocaine Based on a General Sensor Design Involving Aptamers and Nanoparticles. Angew Chem. 2006;118(1):96-100.

Lundberg et al., Delivery of short interfering RNA using endosomolytic cell-penetrating peptides. FASEB J. Sep. 2007;21(11):2664-71. Epub Apr. 26, 2007.

Maeder et al., Robust, synergistic regulation of human gene expression using TALE activators. Nat Methods. Mar. 2013;10(3):243-5. doi: 10.1038/nmeth.2366. Epub Feb. 10, 2013.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Mak et al., The crystal structure of TAL effector PthXo1 bound to its DNA target. Science. Feb. 10, 2012;335(6069):716-9. doi: 10.1126/science.1216211. Epub Jan. 5, 2012.

Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.

Miller et al., A TALE nuclease architecture for efficient genome editing. Nat Biotechnol. Feb. 2011;29(2):143-8. doi:10.1038/nbt.1755. Epub Dec. 22, 2010.

Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.

Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

Moscou et al., A simple cipher governs DNA recognition by TAL effectors. Science. Dec. 11, 2009;326(5959):1501. doi: 10.1126/science.1178817.

Mullins et al., Transgenesis in nonmurine species. Hypertension. Oct. 1993;22(4):630-3.

(56) References Cited

OTHER PUBLICATIONS

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.

O'Connell et al., Programmable RNA recognition and cleavage by CRISPR/Cas9. Nature. Dec. 11, 2014;516(7530):263-6. doi: 10.1038/nature13769. Epub Sep. 28, 2014.

Osborn et al., TALEN-based gene correction for epidermolysis bullosa. Mol Ther. Jun. 2013;21(6):1151-9. doi: 10.1038/mt.2013.56. Epub Apr. 2, 2013.

Pan et al., Biological and biomedical applications of engineered nucleases. Mol Biotechnol. Sep. 2013;55(1):54-62. doi: 10.1007/s12033-012-9613-9.

Pennisi et al., The CRISPR craze. Science. Aug. 23, 2013;341(6148):833-6. doi: 10.1126/science.341.6148.833.

Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Petek et al., Frequent endonuclease cleavage at off-target locations in vivo. Mol Ther. May 2010;18(5):983-6. Doi: 10.1038/mt.2010.35. Epub Mar. 9, 2010.

Phillips, The challenge of gene therapy and DNA delivery. J Pharm Pharmacol. Sep. 2001;53(9):1169-74.

Porteus, Design and testing of zinc finger nucleases for use in mammalian cells. Methods Mol Biol. 2008;435:47-61. doi: 10.1007/978-1-59745-232-8_4.

Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi et al., Repurposing CRISPR as an RNA-guided platform for sequence-specific control of gene expression. Cell. Feb. 28, 2013;152(5):1173-83. doi: 10.1016/j.cell.2013.02.022.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.

Reyon et al., Flash assembly of TALENs for high-throughput genome editing. Nat Biotechnol. May 2012;30(5):460-5. doi: 10.1038/nbt.2170.

Samal et al., Cationic polymers and their therapeutic potential. Chem Soc Rev. Nov. 7, 2012;41(21):7147-94. doi: 10.1039/c2cs35094g. Epub Aug. 10, 2012.

Sander et al., Targeted gene disruption in somatic zebrafish cells using engineered TALENs. Nat Biotechnol. Aug. 5, 2011;29(8):697-8. doi: 10.1038/nbt.1934.

Sang, Prospects for transgenesis in the chick. Mech Dev. Sep. 2004;121(9):1179-86.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schriefer et al., Low pressure DNA shearing: a method for random DNA sequence analysis. Nucleic Acids Res. Dec. 25, 1990;18(24):7455-6.

Schwarze et al., In vivo protein transduction: delivery of a biologically active protein into the mouse. Science. Sep. 3, 1999;285(5433):1569-72.

Sells et al., Delivery of protein into cells using polycationic liposomes. Biotechniques. Jul. 1995;19(1):72-6, 78.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Sheridan, Gene therapy finds its niche. Nat Biotechnol. Feb. 2011;29(2):121-8. doi: 10.1038/nbt.1769.

Siebert et al., An improved PCR method for walking in uncloned genomic DNA. Nucleic Acids Res. Mar. 25, 1995;23(6):1087-8.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Tesson et al., Knockout rats generated by embryo microinjection of TALENs. Nat Biotechnol. Aug. 5, 2011;29(8):695-6. doi: 10.1038/nbt.1940.

Thorpe et al., Functional correction of episomal mutations with short DNA fragments and RNA-DNA oligonucleotides. J Gene Med. Mar.-Apr. 2002;4(2):195-204.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Wacey et al., Disentangling the perturbational effects of amino acid substitutions in the DNA-binding domain of p53. Hum Genet. Jan. 1999;104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wang et al., Efficient delivery of genome-editing proteins using bioreducible lipid nanoparticles. Proc Natl Acad Sci U S A. Feb. 29, 2016. pii: 201520244. [Epub ahead of print].

Weber et al., Assembly of designer TAL effectors by Golden Gate cloning. PLoS One. 2011;6(5):e19722. doi:10.1371/journal.pone.0019722. Epub May 19, 2011.

Wiedenheft et al., RNA-guided genetic silencing systems in bacteria and archaea. Nature. Feb. 15, 2012;482(7385):331-8. doi: 10.1038/nature10886. Review.

Winkler et al., Thiamine derivatives bind messenger RNAs directly to regulate bacterial gene expression. Nature. Oct. 31, 2002;419(6910):952-6. Epub Oct. 16, 2002.

Wood et al., Targeted genome editing across species using ZFNs and TALENs. Science. Jul. 15, 2011;333(6040):307. doi: 10.1126/science.1207773. Epub Jun. 23, 2011.

Zelphati et al., Intracellular delivery of proteins with a new lipid-mediated delivery system. J Biol Chem. Sep. 14, 2001;276(37):35103-10. Epub Jul. 10, 2001.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.

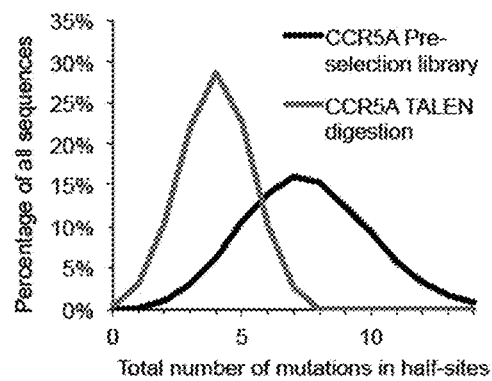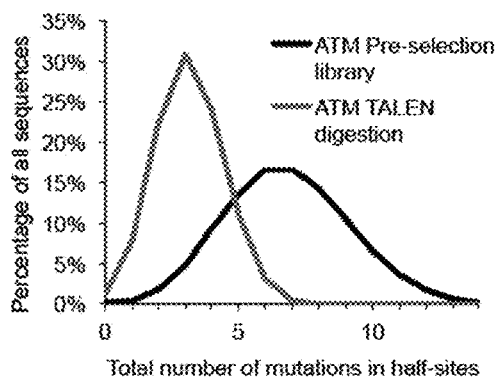
FIG. 2A  FIG. 2B
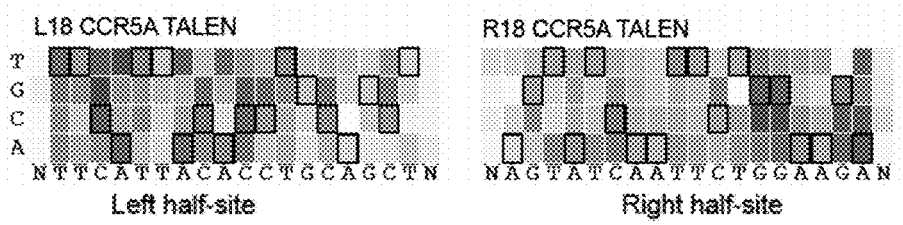
FIG. 2C
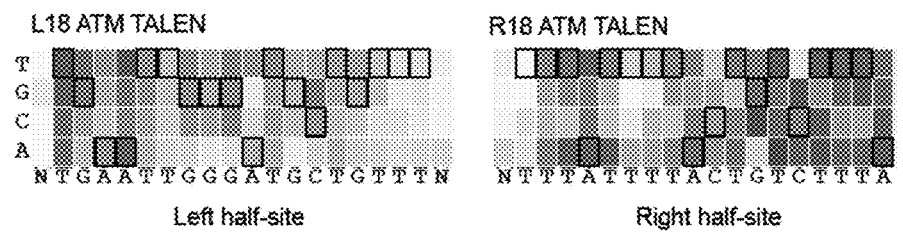
FIG. 2D

| DNA | Enrichment | Left half-site | Right half-site |
|---|---|---|---|
| OnB | 1.0 | TCATTACACCTGC | CATACAGTCAGTA |
| B1 | 0.47 | TCATTACACCTGt | CATACAGTCAGTA |
| B2 | 0.46 | TCATaACACCTGC | CATACAGTCAGTA |
| B3 | 0.13 | TCATTACACCcGC | CATACAGTCAGTA |
| B4 | 1.1 | TCATTACACCTGC | CATACAGTaAGTA |
| B5 | 0.84 | TCATTACACCTGC | gATACAGTCAGTA |
| B6 | 0.21 | TCATTACACCTGC | CATtCAGTCAGTA |
| B7 | 0.03 | TCATTACACCTGC | CATACAGTCgGTA |
| B8 | 0.25 | TCATaACACCTGt | CATACAGTCAGTA |
| B9 | 0.25 | TCATTAtACCTaC | CATACAGTCAGTA |
| B10 | 0.00 | TCATTgCACCcGC | CATACAGTCAGTA |
| B11 | 0.55 | TCATTACACCTGC | gATACAGTaAGTA |
| B12 | 0.04 | TCATTACACCTGC | CAcACAtTCAGTA |
| B13 | 0.03 | TCATTACACCTGC | CATACtaTCAGTA |
| B14 | 0.30 | TCATTACACCTGt | CATACAGTaAGTA |
| B15 | 0.18 | TCATaACACCTGC | gATACAGTCAGTA |
| B16 | 0.04 | TCATTACACCTGt | CATtCAGTCAGTA |

FIG. 2E

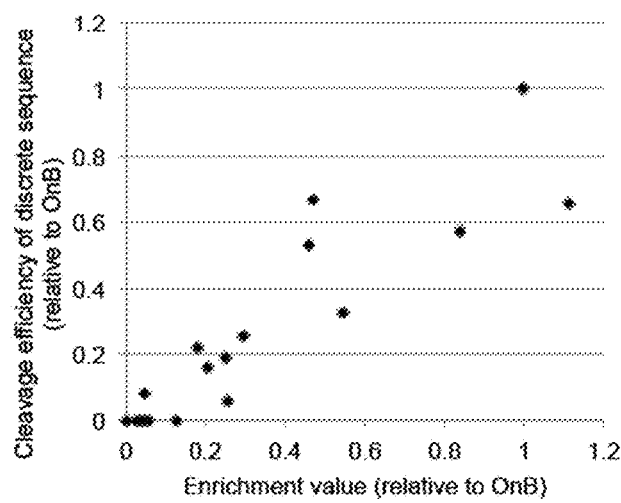

FIG. 2F

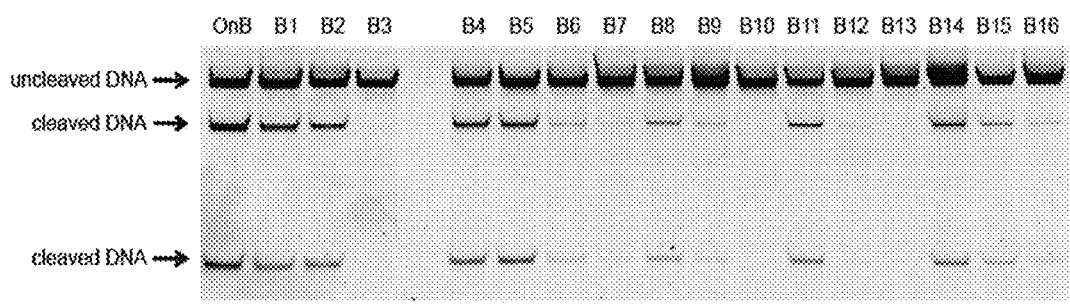

FIG. 2G

| Site | No TALEN | CCR5A EL/KK FokI | CCR5A ELD/KKR FokI | CCR5A Homo FokI |
|---|---|---|---|---|
| OnCCR5A | <0.006% | 9.84% | 27.6% | 46.8% |
| OffC-2 | <0.006% | <0.006% | 0.006% | <0.006% |
| OffC-5 | <0.006% | 0.45% | 1.96% | 2.78% |
| OffC-15 | <0.020% | <0.014% | 0.230% | 0.043% |
| OffC-16 | <0.006% | <0.006% | 0.031% | <0.006% |
| OffC-28 | <0.009% | 0.014% | 0.163% | 0.056% |
| OffC-36 | <0.006% | <0.006% | 0.152% | 0.028% |

FIG. 3A

| Site | No TALEN | ATM EL/KK FokI | ATM ELD/KKR FokI | ATM Homo FokI |
|---|---|---|---|---|
| OnATM | 0.006% | 6.78% | 16.2% | 18.2% |
| OffA-1 | <0.006% | <0.006% | 0.03% | 0.08% |
| OffA-11 | <0.006% | <0.006% | 0.04% | 0.39% |
| OffA-13 | <0.006% | 0.01% | 0.02% | <0.006% |
| OffA-16 | <0.006% | <0.006% | <0.006% | 0.06% |
| OffA-17 | <0.05% | <0.14% | <0.17% | 0.94% |
| OffA-23 | 0.02% | <0.006% | 0.29% | 0.23% |
| OffA-35 | <0.006% | <0.006% | <0.006% | 0.07% |

FIG. 3B

OnCCR5A
TTCATTACACCTGCAGCTCTCATTTTCCATACAGTCAGTATCAATTCTGGAAGA (7267)
TTCATTACACCTGCAGCTCTCAT-------ACAGTCAGTATCAATTCTGGAAGA (76)
TTCATTACACCTGCAG------------------TCAGTATCAATTCTGGAAGA (63)
TTCATTACACCTG-----------------------------------GAAGA (61)

OffC-2
TACATCACATATGCAAATTGACTCAAAATGGATCATAGACCTAAATGTGTATCATTTCTGGGAGA (163332)
TACATCACATATGCAAATTGACTCAAAATGGATCA---ACCTAAATGTGTATCATTTCTGGGAGA (6)
TACATCACATATGCAAATTGACTCAAAATG------GACCTAAATGTGTATCATTTCTGGGAGA (4)

OffC-5
TCCAATACCTCTGCCACACCCAGGCATTGGCCAGGAGCAACTCTGGGAGA (17045)
TCCAATACCTCTGCCACAC-------------CCAGGAGCAACTCTGGGAGA (28)
TCCAATACCTCTG-----------GCATTGGCCAGGAGCAACTCTGGGAGA (12)
TCCAATAC-----------------------------CTCTGGGAGA (10)

OffC-15
TCCATGACACAAAAGACTTCCCTGATTTCTTCTAAGGCATCACTGGTATCTATCCTGGAATA (6967)
TCCATGACACAAAAGACTTCCCTGATTTCTTCTAAGG-----CTGGTATCTATCCTGGAATA (6)

OffC-16
TTCCTTCCACCAGTGTCCACAGTCTTCACACTGATCACCAAATCCCAGCATCAATCCTGGAAGA (38536)
TTCCTTCCACCAGTGTCCACAGTC-----------CACCAAATCCCAGCATCAATCCTGGAAGA (4)

OffC-28
TTTATTACACTTCCAGATCTTTTATTTTAAGTTACCAGATATCCTTTCTGGAAGA (7379)
TTTATTACACTT----------------------CCAGATATCCTTTCTGGAAGA (3)
TTTATTACACTTCCAGATCTTTT---------------ATATCCTTTCTGGAAGA (2)
TTTATTACACTTCCAGATCTTT-----------------TATCCTTTCTGGAAGA (2)

OffC-36
CTCCTAATACCTGCAAATTATAAGGACACTATTTGACTTGATATTATTTCTGGAGGA (12461)
CTCCTAATACCTGCAAATTATAAGGACACT----GACTTGATATTATTTCTGGAGGA (11)

FIG. 3C

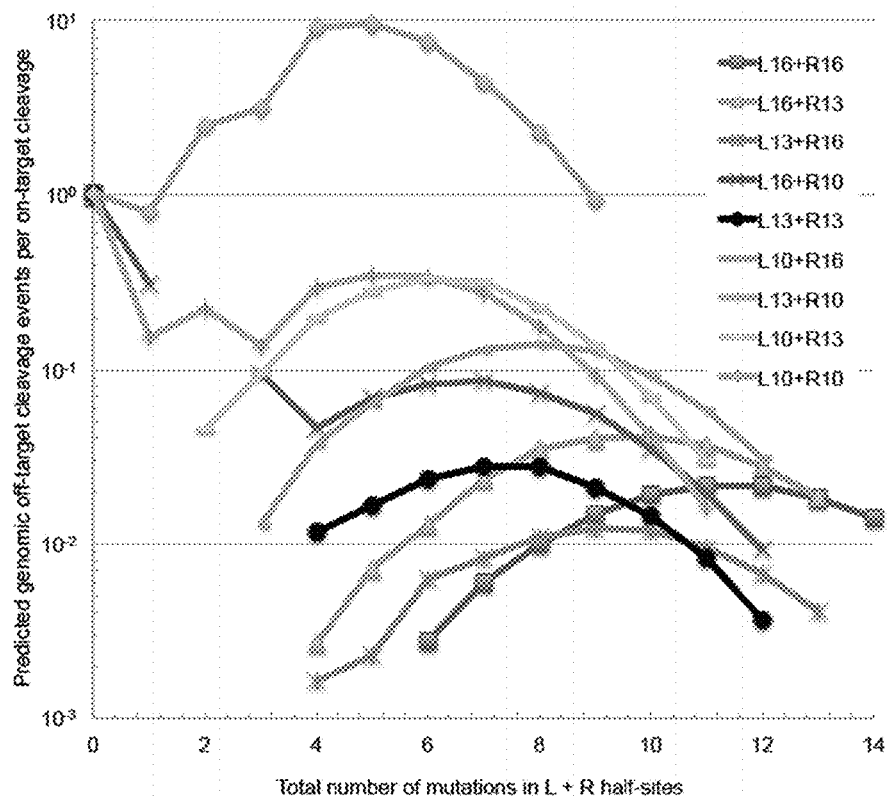
FIG. 4C
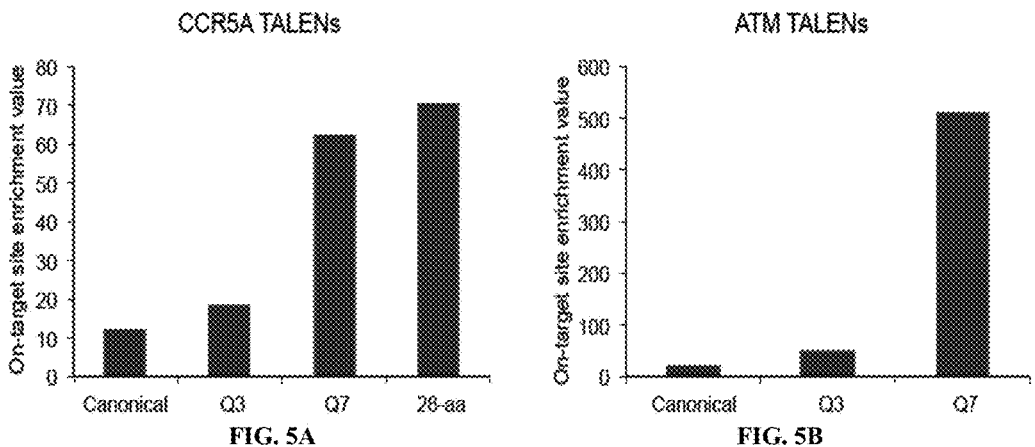
FIG. 5A
FIG. 5B

| DNA | Left half-site | Right half-site |
|---|---|---|
| OnC | TTCATTACACCTGCAGCT | AGTATCAATTCTGGAAGA |
| C1 | TTCATTACAtCTGCAcCT | AGTATCAATTCTGGAAGA |
| C2 | TCAaTACACCTGtAGCT | AGTATCAATTCTGGAAGA |
| C3 | TTCATTACACCcGCAGCa | AGTATCAATTCTGGAAGA |
| C4 | TTaATTgCACCTGCAGCT | AGTATCAATTCTGGAAGA |
| C5 | TTCATTACACCTGCAGCT | AGTATgAATTCTGtAAGA |
| C6 | TTCATTACACCTGCAGCT | AGTATCAAcTCTGGAgGA |
| C7 | TTCATTACACCTGCAGCT | AtTATCAATTCaGGAAGA |
| C8 | TTCATTACACCTGCAGCT | AGTAaCAATgCTGGAAGA |

FIG. 5C

| DNA | Left half-site | Right half-site |
|---|---|---|
| OnA | TGAATTGGGATGCTGTTT | TTTATTTACTGTCTTTA |
| A1 | TGAATTGGGtTGCTGTTT | TTTATTTACTGTCTTTA |
| A2 | TGAATTGcGATGCTGTTT | TTTATTTACTGTCTTTA |
| A3 | TGAATTGGGATGCTGTTT | TTTATTcACTGTCTTTA |
| A4 | TGAATTGGGATGCTGTTT | TTTATTTACTaTCTTTA |
| A5 | TGAATTGcGATGCTGTTT | TTTATTTACTaTCTTTA |
| A6 | TGAgTTGGGATGCTGTTT | TTTATgTTACTGTCTTTA |
| A7 | TGAATTGGGtTGCTGTTT | TTTATTTgACTGTCTTTA |
| A8 | TGAATTGGGATGCTGaTT | TTTATTTACTGTCcTTA |

FIG. 5D

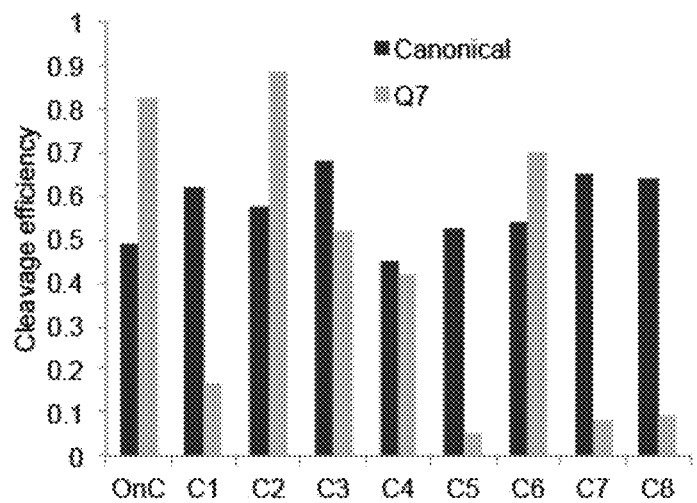

FIG. 5E

CCR5 target sites

TALEN monomer
```
CCR5A L18    5'-TTCATTACACCTGCAGCT
CCR5B L16    5'-TCTTCATTACACCTGC
CCR5B L13    5'-TCATTACACCTGC
CCR5B L10       5'-TTACACCTGC
```

```
TCTTCATTACACCTGCAGCTCTCATTTTCCATACAGTCAGTATCAATTCTGGAAGA
AGAAGTAATGTGGACGTCGAGAGTAAAAGGTATGTCAGTCATAGTTAAGACCTTCT
```

```
CCR5A R18                              TCATAGTTAAGACCTTCT-5'
CCR5B R16                              GTATGTCAGTCATAGT-5'
CCR5B R13                              GTATGTCAGTCAT-5'
CCR5B R10                              GTATGTCAGT-5'
```

FIG. 7A

ATM target site

TALEN monomer
```
ATM L18   5'-TGAATTGGGATGCTGTTT
```

```
TGAATTGGGATGCTGTTTTTAGGTATTCTATTCAAATTTATTTTACTGTCTTTA
ACTTAACCCTACGACAAAAATCCATAAGATAAGTTTAAATAAAATGACAGAAAT
```

```
ATM R18                                AAATAAAATGACAGAAAT-5'
```

FIG. 7B

ENGINEERED TRANSCRIPTION ACTIVATOR-LIKE EFFECTOR (TALE) DOMAINS AND USES THEREOF

RELATED APPLICATION

This application is a national stage filing under 35 U.S.C. § 371 of international PCT application, PCT/US2014/052231, filed Aug. 22, 2014, which claims priority under 35 U.S.C. § 365(c) to U.S. application, U.S. Ser. No. 14/320,519, filed Jun. 30, 2014, which claims priority under 35 U.S.C. § 119(e) to U.S. provisional patent application, U.S. Ser. No. 61/868,846, filed Aug. 22, 2013, and international PCT application, PCT/US2014/052231 also claims priority under 35 U.S.C. § 119(e) to U.S. provisional patent application, U.S. Ser. No. 61/868,846, filed Aug. 22, 2013, each of which is incorporated herein by reference.

GOVERNMENT SUPPORT

This invention was made with U.S. Government support under grant HR0011-11-2-0003 and N66001-12-C-4207, awarded by the Defense Advanced Research Projects Agency; grant T32GM007753, awarded by the National Institute of General Medical Sciences; and grant DPI GM105378 awarded by the National Institutes of Health. The U.S. Government has certain rights in this invention.

BACKGROUND OF THE INVENTION

Transcription activator-like effector nucleases (TALENs) are fusions of the FokI restriction endonuclease cleavage domain with a DNA-binding transcription activator-like effector (TALE) repeat array. TALENs can be engineered to specifically bind and cleave a desired target DNA sequence, which is useful for the manipulation of nucleic acid molecules, genes, and genomes in vitro and in vivo. Engineered TALENs are useful in the context of many applications, including, but not limited to, basic research and therapeutic applications. For example, engineered TALENs can be employed to manipulate genomes in the context of the generation of gene knockouts or knock-ins via induction of DNA breaks at a target genomic site for targeted gene knockout through non-homologous end joining (NHEJ) or targeted genomic sequence replacement through homology-directed repair (HDR) using an exogenous DNA template, respectively. TALENs are thus useful in the generation of genetically engineered cells, tissues, and organisms.

TALENs can be designed to cleave any desired target DNA sequence, including naturally occurring and synthetic sequences. However, the ability of TALENs to distinguish target sequences from closely related off-target sequences has not been studied in depth. Understanding this ability and the parameters affecting it is of importance for the design of TALENs having the desired level of specificity and also for choosing unique target sequences to be cleaved, e.g., in order to minimize the chance of undesired off-target cleavage.

SUMMARY OF THE INVENTION

TALENs are versatile tools for the manipulation of genes and genomes in vitro and in vivo, as they can be designed to bind and cleave virtually any target sequence within a nucleic acid molecule. For example, TALENs can be used for the targeted deletion of a DNA sequence within a cellular genome via induction of DNA breaks that are then repaired by the cellular DNA repair machinery through non-homologous end joining (NHEJ). TALENs can also be used for targeted sequence replacement in the presence of a nucleic acid comprising a sequence to be inserted into a genomic sequence via homology-directed repair (HDR). As TALENs can be employed to manipulate the genomes of living cells, the resulting genetically modified cells can be used to generate transgenic cell or tissue cultures and organisms.

In scenarios where a TALEN is employed for the targeted cleavage of a DNA sequence in the context of a complex sample, e.g., in the context of a genome, it is often desirable for the TALEN to bind and cleave the specific target sequence only, with no or only minimal off-target cleavage activity (see, e.g., PCT Application Publication WO2013/066438 A2, the entire contents of which are incorporated herein by reference). In some embodiments, an ideal TALEN would specifically bind only its intended target sequence and have no off-target activity, thus allowing the targeted cleavage of a single sequence, e.g., a single allele of a gene of interest, in the context of a whole genome.

Some aspects of this disclosure are based on the recognition that the tendency of TALENs to cleave off-target sequences and the parameters affecting the propensity of off-target TALEN activity are poorly understood. The work presented here provides a better understanding of the structural parameters that result in TALEN off-target activity. Methods and systems for the generation of engineered TALENs having no or minimal off-target activity are provided herein, as are engineered TALENs having increased on-target cleavage efficiency and minimal off-target activity. It will be understood by those of skill in the art that the strategies, methods, and reagents provided herein for decreasing non-specific or off-target DNA binding by TALENs are applicable to other DNA-binding proteins as well. In particular, the strategies for modifying the amino acid sequence of DNA-binding proteins for reducing unspecific binding to DNA by substituting cationic amino acid residues with amino acid residues that are not cationic, are uncharged, or are anionic at physiological pH, can be used to decrease the specificity of, for example, other TALE effector proteins, engineered zinc finger proteins (including zinc finger nucleases), and Cas9 proteins.

Some aspects of this disclosure provide engineered isolated Transcription Activator-Like Effector (TALE) domains. In some embodiments, the isolated TALE domain is an N-terminal TALE domain and the net charge of the isolated N-terminal domain is less than the net charge of the canonical N-terminal domain (SEQ ID NO: 1) at physiological pH. In some embodiments, the isolated TALE domain is a C-terminal TALE domain and the net charge of the C-terminal domain is less than the net charge of the canonical C-terminal domain (SEQ ID NO: 22) at physiological pH. In some embodiments, the isolated TALE domain is an N-terminal TALE domain and the binding energy of the N-terminal domain to a target nucleic acid molecule is smaller than the binding energy of the canonical N-terminal domain (SEQ ID NO: 1). In some embodiments, the isolated TALE domain is a C-terminal TALE domain and the binding energy of the C-terminal domain to a target nucleic acid molecule is smaller than the binding energy of the canonical C-terminal domain (SEQ ID NO: 22). In some embodiments, the net charge of the C-terminal domain is less than or equal to +6, less than or equal to +5, less than or equal to +4, less than or equal to +3, less than or equal to +2, less than or equal to +1, less than or equal to 0, less than or equal to −1, less than or equal to −2, less than or equal to −3, less than or equal to −4, or less than or equal to −5. In some embodiments, the C-terminal domain comprises an amino acid sequence that differs from the canonical C-terminal domain sequence in that at least one cationic amino acid residue of the canonical C-terminal domain sequence is replaced with an amino acid residue that exhibits no charge or a negative charge at physiological pH. In some embodiments, the N-terminal domain comprises an amino acid sequence that differs from the canonical N-terminal domain sequence in that at least one cationic amino acid residue of the canonical N-terminal domain sequence is replaced with an amino acid residue that exhibits no charge or a negative charge at physiological pH. In some embodiments, at least 1, at least 2, at least 3, at least 4, at least 5, at least 6, at least 7, at least 8, at least 9, at least 10, at least 11, at least 12, at least 13, at least 14, or at least 15 cationic amino acid(s) in the isolated TALE domain is/are replaced with an amino acid residue that exhibits no charge or a negative charge at physiological pH. In some embodiments, the at least one cationic amino acid residue is arginine (R) or lysine (K). In some embodiments, the amino acid residue that exhibits no charge or a negative charge at physiological pH is glutamine (Q) or glycine (G). In some embodiments, at least one lysine or arginine residue is replaced with a glutamine residue. In some embodiments, the C-terminal domain comprises one or more of the following amino acid replacements: K777Q, K778Q, K788Q, R789Q, R792Q, R793Q, R801Q. In some embodiments, the C-terminal domain comprises a Q3 variant sequence (K788Q, R792Q, K801Q). In some embodiments, the C-terminal domain comprises a Q7 variant sequence (K777Q, K778Q, K788Q, R789Q, R792Q, R793Q, R801Q). In some embodiments, the N-terminal domain is a truncated version of the canonical N-terminal domain. In some embodiments, wherein the C-terminal domain is a truncated version of the canonical C-terminal domain. In some embodiments, the truncated domain comprises less than 90%, less than 80%, less than 70%, less than 60%, less than 50%, less than 40%, less than 30%, or less than 25% of the residues of the canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues. In some embodiments, the isolated TALE domain is comprised in a TALE molecule comprising the structure [N-terminal domain]-[TALE repeat array]-[C-terminal domain]-[effector domain]; or [effector domain]-[N-terminal domain]-[TALE repeat array]-[C-terminal domain]. In some embodiments, the effector domain comprises a nuclease domain, a transcriptional activator or repressor domain, a recombinase domain, or an epigenetic modification enzyme domain. In some embodiments, the TALE molecule binds a target sequence within a gene known to be associated with a disease or disorder.

Some aspects of this disclosure provide Transcription Activator-Like Effector Nucleases (TALENs) having a modified net charge and/or a modified binding energy for binding their target nucleic acid sequence as compared to canonical TALENs. Typically, the inventive TALENs include (a) a nuclease cleavage domain; (b) a C-terminal domain conjugated to the nuclease cleavage domain; (c) a TALE repeat array conjugated to the C-terminal domain; and (d) an N-terminal domain conjugated to the TALE repeat array. In some embodiments, (i) the net charge on the N-terminal domain at physiological pH is less than the net charge on the canonical N-terminal domain (SEQ ID NO: 1) at physiological pH; and/or (ii) the net charge of the C-terminal domain at physiological pH is less than the net charge of the canonical C-terminal domain (SEQ ID NO: 22) at physiological pH. In some embodiments, (i) the binding energy of the N-terminal domain to a target nucleic acid molecule is less than the binding energy of the canonical N-terminal domain (SEQ ID NO: 1); and/or (ii) the binding energy of the C-terminal domain to a target nucleic acid molecule is less than the binding energy of the canonical C-terminal domain (SEQ ID NO: 22). In some embodiments, the net charge on the C-terminal domain at physiological pH is less than or equal to +6, less than or equal to +5, less than or equal to +4, less than or equal to +3, less than or equal to +2, less than or equal to +1, less than or equal to 0, less than or equal to −1, less than or equal to −2, less than or equal to −3, less than or equal to −4, or less than or equal to −5. In some embodiments, the N-terminal domain comprises an amino acid sequence that differs from the canonical N-terminal domain sequence in that at least one cationic amino acid residue of the canonical N-terminal domain sequence is replaced with an amino acid residue that does not have a cationic charge, has no charge, or has an anionic charge. In some embodiments, the C-terminal domain comprises an amino acid sequence that differs from the canonical C-terminal domain sequence in that at least one cationic amino acid residue of the canonical C-terminal domain sequence is replaced with an amino acid residue that does not have a cationic charge, has no charge, or has an anionic charge. In some embodiments, at least 1, at least 2, at least 3, at least 4, at least 5, at least 6, at least 7, at least 8, at least 9, at least 10, at least 11, at least 12, at least 13, at least 14, or at least 15 cationic amino acid(s) is/are replaced with an amino acid residue that does not have a cationic charge, has no charge, or has an anionic charge in the N-terminal domain and/or in the C-terminal domain. In some embodiments, the at least one cationic amino acid residue is arginine (R) or lysine (K). In some embodiments, the amino acid residue that replaces the cationic amino acid is glutamine (Q) or glycine (G). Positively charged residues in the C-terminal domain that can be replaced according to aspects of this disclosure include, but are not limited to, arginine (R) residues and lysine (K) residues, e.g., R747, R770, K777, K778, K788, R789, R792, R793, R797, and R801 in the C-terminal domain (see. e.g., SEQ ID NO: 22, the numbering refers to the position of the respective residue in the full-length TALEN protein, the equivalent positions for the C-terminal domain as provide in SEQ ID NO: 22 are R8, R30, K37, K38, K48, R49, R52, R53, R57, R61). Positively charged residues in the N-terminal domain that can be replaced according to aspects of this disclosure include, but are not limited to, arginine (R) residues and lysine (K) residues, e.g., K57, K78, R84, R97, K110, K113, and R114 (see, e.g., SEQ ID NO: 1). In some embodiments, at least one lysine or arginine residue is replaced with a glutamine residue. In some embodiments, the C-terminal domain comprises one or more of the following amino acid replacements: K777Q, K778Q, K788Q, R789Q, R792Q, R793Q, R801Q. In some embodiments, the C-terminal domain comprises a Q3 variant sequence (K788Q, R792Q, R801Q). In some embodiments, the C-terminal domain comprises a Q7 variant sequence (K777Q, K778Q, K788Q, R789Q, R792Q, R793Q, R801Q). In some embodiments, the N-terminal domain is a truncated version of the canonical N-terminal domain. In some embodiments, the C-terminal domain is a truncated version of the canonical C-terminal domain. In some embodiments, the truncated domain comprises less than 90%, less than 80%, less than 70%, less than 60%, less than 50%, less than 40%, less than 30%, or less than 25% of the residues of the canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues. In some embodiments, the nuclease cleavage domain is a FokI nuclease domain. In some embodiments, the FokI nuclease domain comprises a sequence as provided in SEQ ID NOs: 26-30. In some embodiments, the TALEN is a monomer. In some embodiments, the TALEN monomer dimerizes with another TALEN monomer to form a TALEN dimer. In some embodiments, the dimer is a heterodimer. In some embodiments, the TALEN binds a target sequence within a gene known to be associated with a disease or disorder. In some embodiments, the TALEN cleaves the target sequence upon dimerization. In some embodiments, the disease being treated or prevented is HIV infection or AIDS, or a proliferative disease. In some embodiments, the TALEN binds a CCR5 (C—C chemokine receptor type 5) target sequence in the treatment or prevention of HIV infection or AIDS. In some embodiments, the TALEN binds an ATM (ataxia telangiectasia mutated) target sequence. In some embodiments, the TALEN binds a VEGFA (Vascular endothelial growth factor A) target sequence.

Some aspects of this disclosure provide compositions comprising a TALEN described herein, e.g., a TALEN monomer. In some embodiments, the composition comprises the inventive TALEN monomer and a different inventive TALEN monomer that form a heterodimer, wherein the dimer exhibits nuclease activity. In some embodiments, the composition is a pharmaceutical composition.

Some aspects of this disclosure provide a composition comprising a TALEN provided herein. In some embodiments, the composition is formulated to be suitable for contacting with a cell or tissue in vitro. In some embodiments, the pharmaceutical composition comprises an effective amount of the TALEN for cleaving a target sequence, e.g., in a cell or in a tissue in vitro or ex vivo. In some embodiments, the TALEN binds a target sequence within a gene of interest, e.g., a target sequence within a gene known to be associated with a disease or disorder, and the composition comprises an effective amount of the TALEN for alleviating a sign and/or symptom associated with the disease or disorder. Some aspects of this disclosure provide a pharmaceutical composition comprising a TALEN provided herein and a pharmaceutically acceptable excipient. In some embodiments, the pharmaceutical composition is formulated for administration to a subject. In some embodiments, the pharmaceutical composition comprises an effective amount of the TALEN for cleaving a target sequence in a cell in the subject. In some embodiments, the TALEN binds a target sequence within a gene known to be associated with a disease or disorder, and the composition comprises an effective amount of the TALEN for alleviating a sign and/or symptom associated with the disease or disorder.

Some aspects of this disclosure provide methods of cleaving a target sequence in a nucleic acid molecule using a TALEN provided herein. In some embodiments, the method comprises contacting a nucleic acid molecule comprising the target sequence with an inventive TALEN binding the target sequence under conditions suitable for the TALEN to bind and cleave the target sequence. In some embodiments, the TALEN is provided as a monomer. In some embodiments, the inventive TALEN monomer is provided in a composition comprising a different TALEN monomer that can dimerize with the inventive TALEN monomer to form a heterodimer having nuclease activity. In some embodiments, the inventive TALEN is provided in a pharmaceutical composition. In some embodiments, the target sequence is in the genome of a cell. In some embodiments, the target sequence is in a subject. In some embodiments, the method comprises administering a composition, e.g., a pharmaceutical composition, comprising the TALEN to the subject in an amount sufficient for the TALEN to bind and cleave the target site.

Some aspects of this disclosure provide methods of preparing engineered TALENs. In some embodiments, the method comprises replacing at least one amino acid in the canonical N-terminal TALEN domain and/or the canonical C-terminal TALEN domain with an amino acid having no charge or a negative charge as compared to the amino acid being replaced at physiological pH; and/or truncating the N-terminal TALEN domain and/or the C-terminal TALEN domain to remove a positively charged fragment; thus generating an engineered TALEN having an N-terminal domain and/or a C-terminal domain of decreased net charge at physiological pH. In some embodiments, the at least one amino acid being replaced comprises a cationic amino acid or an amino acid having a positive charge at physiological pH. Positively charged residues in the C-terminal domain that can be replaced according to aspects of this disclosure include, but are not limited to, arginine (R) residues and lysine (K) residues, e.g., R747, R770, K777, K778, K788, R789, R792, R793, R797, and R801 in the C-terminal domain. Positively charged residues in the N-terminal domain that can be replaced according to aspects of this disclosure include, but are not limited to, arginine (R) residues and lysine (K) residues, e.g., K57, K78, R84, R97, K110, K113, and R114. In some embodiments, the amino acid replacing the at least one amino acid is a cationic amino acid or a neutral amino acid. In some embodiments, the truncated N-terminal TALEN domain and/or the truncated C-terminal TALEN domain comprises less than 90%, less than 80%, less than 70%, less than 60%, less than 50%, less than 40%, less than 30%, or less than 25% of the residues of the respective canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 amino acid residues. In some embodiments, the method comprises replacing at least 2, at least 3, at least 4, at least 5, at least 6, at least 7, at least 8, at least 9, at least 10, at least 11, at least 12, at least 13, at least 14, or at least 15 amino acids in the canonical N-terminal TALEN domain and/or in the canonical C-terminal TALEN domain with an amino acid having no charge or a negative charge at physiological pH. In some embodiments, the amino acid being replaced is arginine (R) or lysine (K). In some embodiments, the amino acid residue having no charge or a negative charge at physiological pH is glutamine (Q) or glycine (G). In some embodiments, the method comprises replacing at least one lysine or arginine residue with a glutamine residue.

Some aspects of this disclosure provide kits comprising an engineered TALEN as provided herein, or a composition (e.g., a pharmaceutical composition) comprising such a TALEN. In some embodiments, the kit comprises an excipient and instructions for contacting the TALEN with the excipient to generate a composition suitable for contacting a nucleic acid with the TALEN. In some embodiments, the excipient is a pharmaceutically acceptable excipient.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIGS. 2A-G. In vitro selection results. The fraction of sequences surviving selection (green) and before selection (black) are shown for CCR5A TALENs (A) and ATM TALENs (B) as a function of the number of mutations in both half-sites. (C) Specificity scores for the L18+R18 CCR5A TALEN at all positions in the target half-sites plus a single flanking position. The colors range from a maximum specificity score of 1.0 to white (no specificity, score of 0) to a maximum negative score of −1.0. Boxed bases represent the intended target base. (D) Same as (C) for the L18+R18 ATM TALEN. (E) Enrichment values from the selection of L13+R13 CCR5B TALEN for 16 mutant DNA sequences (mutations in red) relative to on-target DNA (OnB). (F) Correspondence between discrete in vitro TALEN cleavage efficiency (cleaved DNA as a fraction of total DNA) for the sequences listed in (E) normalized to on-target cleavage (=1) versus their enrichment values in the selection normalized to the on-target enrichment value (=1). (G) Discrete assays of on-target and off-target sequences used in (F) as analyzed by PAGE. Sequences in FIG. 2C correspond, from left to right and top to bottom, to SEQ ID NOs: 51-54. Left half-site sequences in FIG. 2E correspond to SEQ ID NOs: 55-71 and right half-site sequences correspond to SEQ ID NOs: 72-88.

FIGS. 3A-C. Cellular modification induced by TALENs at on-target and predicted off-target genomic sites. (A) For cells treated with either no TALEN or CCR5A TALENs containing heterodimeric EL/KK, heterodimeric ELD/KKR, or the homodimeric (Homo) FokI variants, cellular modification rates are shown as the percentage of observed insertions or deletions (indels) consistent with TALEN cleavage relative to the total number of sequences for on-target (On) and predicted off-target sites (Off). (B) Same as (A) for ATM TALENs. (C) Examples of modified sequences at the on-target site and off-target sites for cells treated with CCR5A TALENs containing the ELD/KKR FokI domains (SEQ ID NOs: 89-109 from top to bottom). For each example shown, the unmodified genomic site is the first sequence, followed by the top three sequences containing deletions. The numbers in parentheses indicate sequencing counts and the half-sites are underlined and bolded.

FIGS. 4A-C. Predicted off-target genomic cleavage as a function of TALEN length considering both TALEN specificity and off-target site abundance in the human genome. (A) The enrichment value of on-target (zero mutation) and off-target sequences containing one to six mutations are shown for CCR5B TALENs of varying TALE repeat array lengths. The TALENs targeted DNA sites of 32 bp (L16+R16), 29 bp (L16+R13 or L13+R16), 26 bp (L16+R10 or L13+R13 or L10+R16), 23 bp (L13+R10 or L10+R13) or 20 bp (L10+R10) in length. (B) Number of sites in the human genome related to each of the nine CCR5B on-target sequences (L10, L13, or L16 combined with R10, R13, or R16), allowing for a spacer length from 12 to 25 bps between the two half-sites. (C) For all nine CCR5B TALENs, overall genomic off-target cleavage frequency was predicted by multiplying the number of sites in the human genome containing a certain number of mutations by the enrichment value of off-target sequences containing that same number of mutations shown in (A). Because enrichment values level off at high mutation numbers likely due to the limit of sensitivity of the selection, it was necessary to extrapolate high-mutation enrichment values by fitting enrichment value as function of mutation number (Table 9). The overall predicted genomic cleavage was calculated only for mutation numbers with sites observed to occur more than once in the human genome.

FIGS. 5A-F. In vitro specificity and discrete cleavage efficiencies of TALENs containing canonical or engineered C-terminal domains. (A and B) On-target enrichment values for selections of (A) CCR5A TALENs or (B) ATM TALENs containing canonical, Q3, Q7, or 28-aa C-terminal domains. (C) CCR5A on-target sequence (OnC) and double-mutant sequences with mutations in red. (D) ATM on-target sequence (OnA) and single-mutant sequences with mutations in red. (E) Discrete in vitro cleavage efficiency of DNA sequences listed in (C) with CCR5A TALENs containing either canonical or engineered Q7 C-terminal domains. (F) Same as (E) for ATM TALENs. Left half-site sequences in FIG. 5C correspond to SEQ ID NOs: 110-118 and right half-site sequences correspond to SEQ ID NOs: 119-127. Left half-site sequences in FIG. 5D correspond to SEQ ID NOs: 128-136 and right half-site sequences correspond to SEQ ID NOs: 137-145.

FIGS. 7A-B. Target DNA sequences in human CCR5 and ATM genes. The target DNA sequences for the TALENs used in this study are shown in black (A-B). The N-terminal TALEN end recognizing the 5' T for each half-site target is noted (5') and TALENs are named according to number of base pairs targeted. TALENs targeting the CCR5 L18 and R18 shown are referred to as CCR5A TALENs while TALENs targeting the L10, L13, L16, R10, R13 or R16 half-sites shown are referred to as CCR5B TALENs (A).

Negative specificity scores, down to complete antispecificity of −1.0, represents enrichment against that base pair. Specified positions were plotted as stacked bars above the X-axis (multiple specified base pairs at the same position were plotted over each other with the shortest bar in front, and not end-to-end) while anti-specified base pairs were plotted as narrow, grouped bars. The titles to the right notes the targeted left (L) and right (R) target half-sites for the CCR5B TALEN used in the selection. Selections correspond to conditions listed in Table 2. Sequences correspond to SEQ ID NO: 160 (left column) and SEQ ID NO: 163 (right column).

Figure 14A:
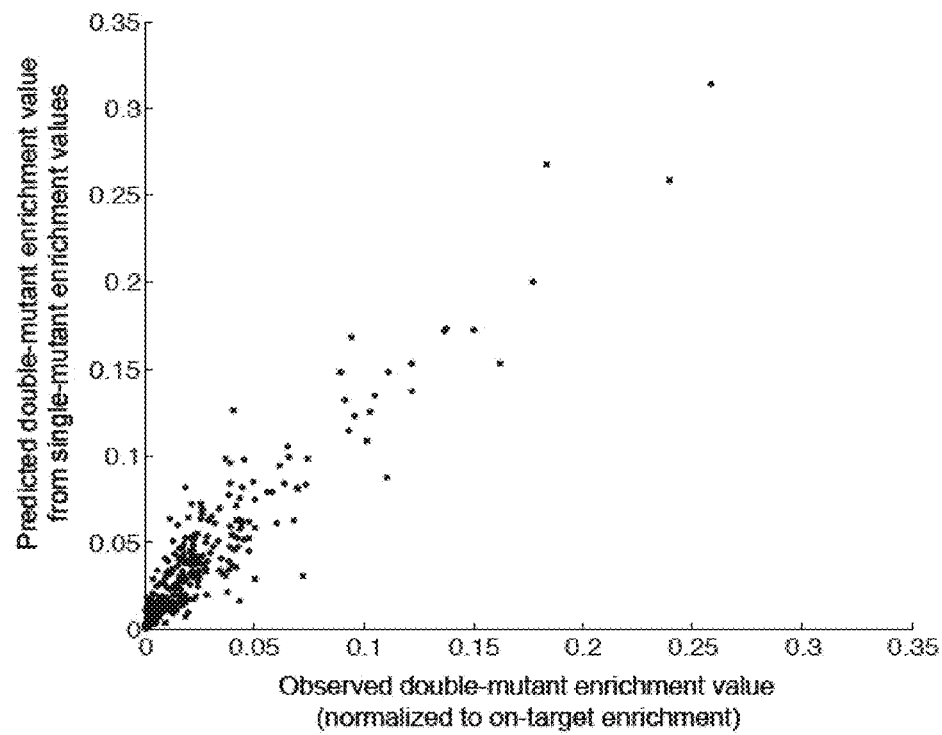
Figure 14B:
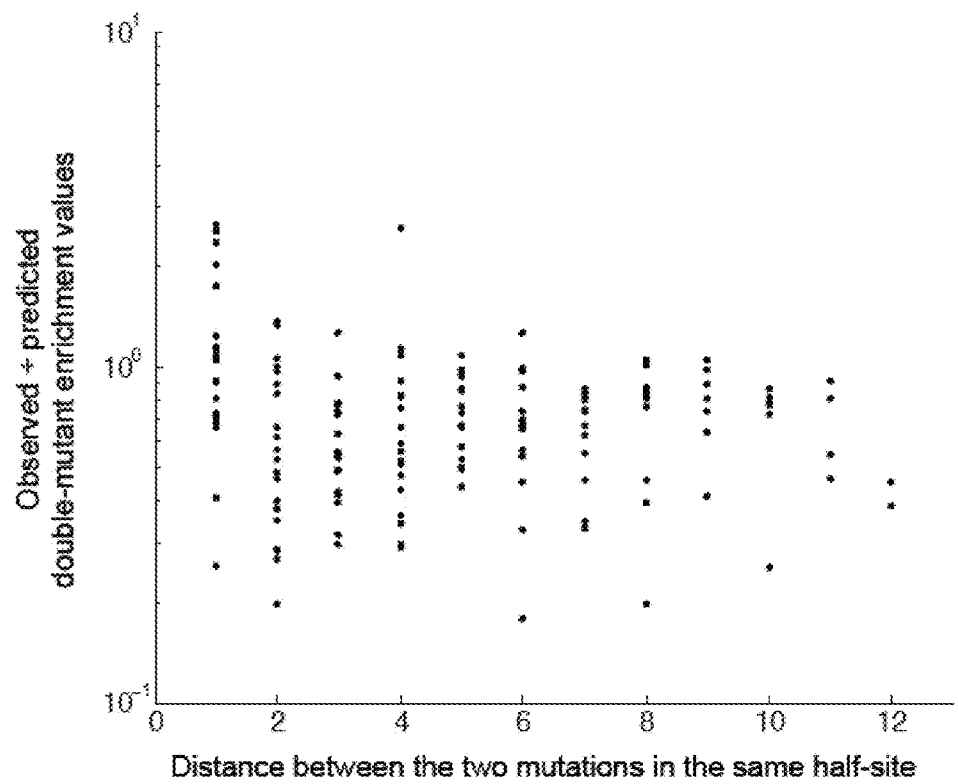
Figure 15A:
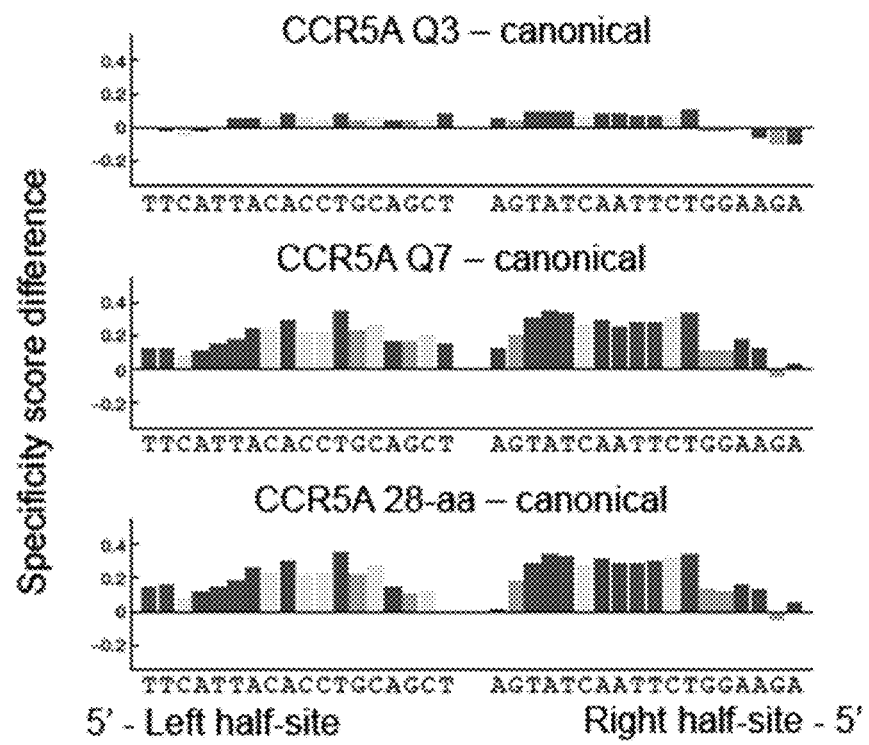
Figure 15B:
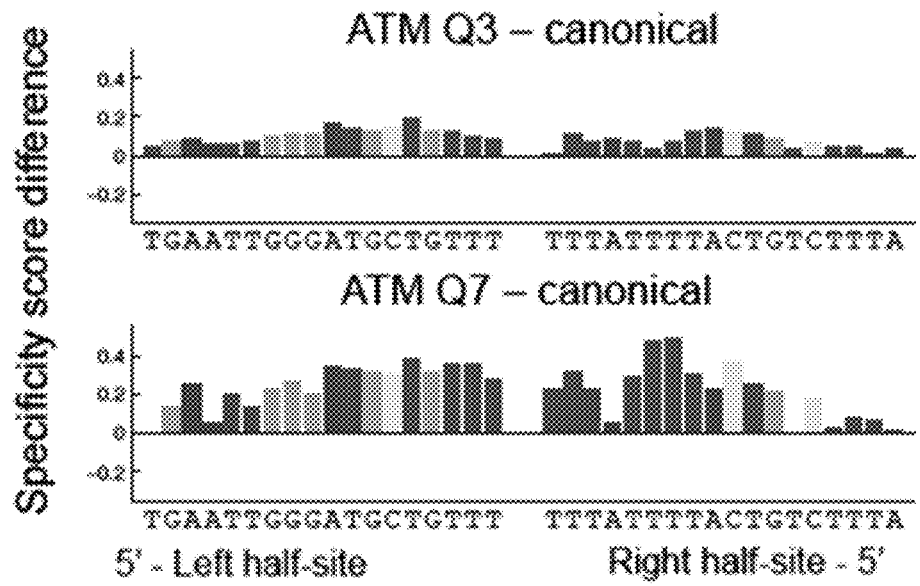
Figure 15C:
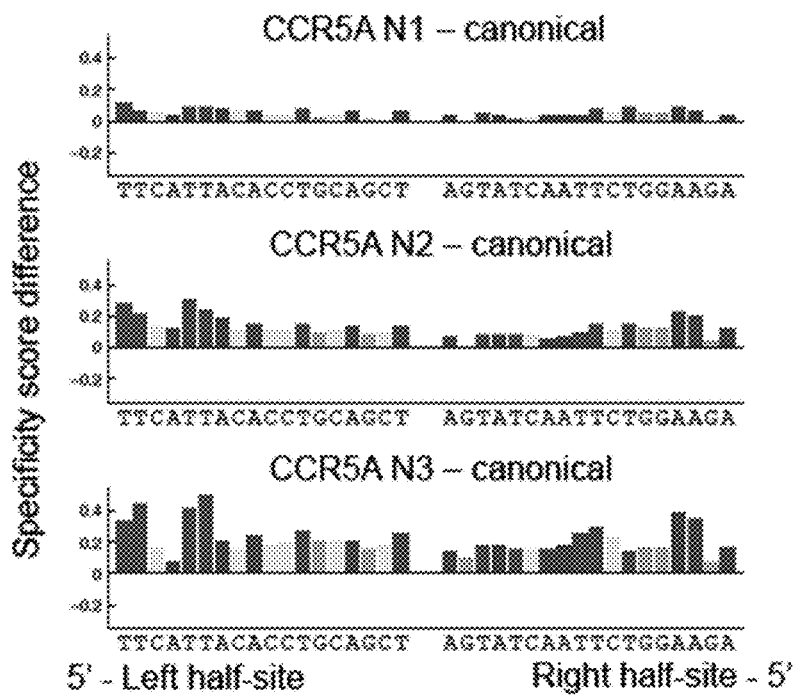
Figure 15D:
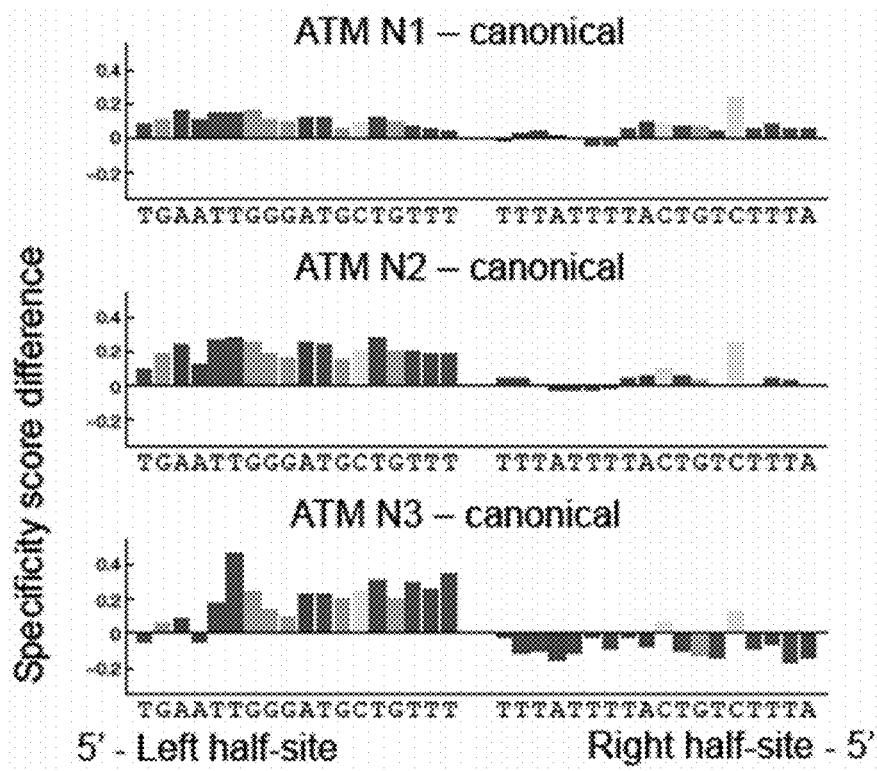
Figure 15E:
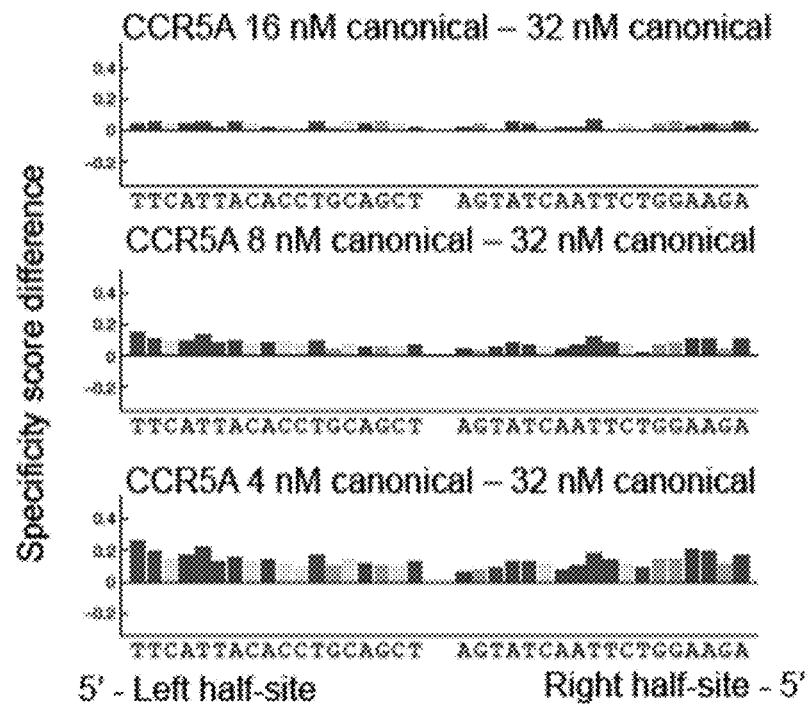
Figure 15F:
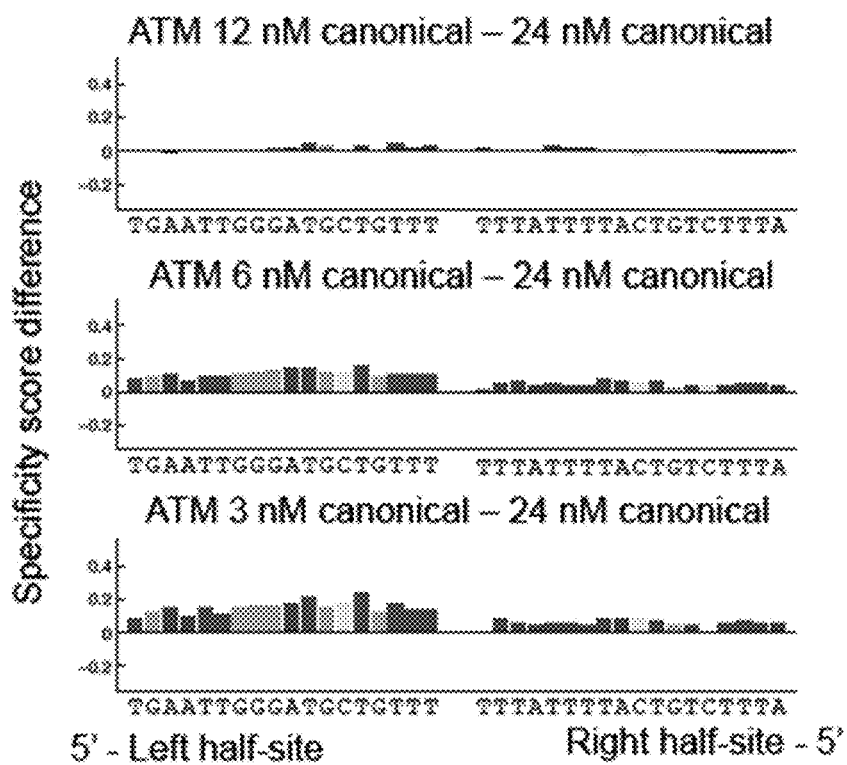

FIGS. 14A-B. Observed versus predicted double-mutant sequence enrichment values. (A) For the L13+R13 CCR5A TALEN selection, the observed double-mutant enrichment values of individual sequences (post-selection sequence abundance÷pre-selection sequence abundance) were normalized to the on-target enrichment value (=1.0 by definition) and plotted against the corresponding predicted double-mutant enrichment values calculated by multiplying the enrichment value of the component single-mutants normalized to the on-target enrichment. The predicted double mutant enrichment values therefore assume independent contributions from each single mutation to the double-mutant's enrichment value. (B) The observed double-mutant sequence enrichment divided by the predicted double-mutant sequence enrichment plotted as a function of the distance (in base pairs) between the two mutations. Only sequences with two mutations in the same half-site were considered.

FIG. 15. Effects of engineered TALEN domains and TALEN concentration on specificity. (A) The specificity score of the targeted base pair at each position of the CCR5A site was calculated for CCR5A TALENs containing the canonical, Q3, Q7, or 28-aa C-terminal domains. The specificity scores of the Q3, Q7, or 28-aa C-terminal domain TALENs subtracted by the specificity scores of the TALEN with the canonical C-terminal domain are shown. (B) Same as (A) but for CCR5A TALENs containing engineered N-terminal domains N1, N2, or N3. (C) Same as (A) but comparing specificity scores differences of the canonical CCR5A TALEN assayed at 16 nM, 8 nM, or 4 nM subtracted by the specificity scores of canonical CCR5A TALENs assayed at 32 nM. (D-F) Same as (A-C) but for ATM TALENs. Selections correspond to conditions listed in Table 2. ttcattacacctgcagct corresponds to SEQ ID NO: 44, agtatcaattctggaaga corresponds to SEQ ID NO: 46, tgaattgggatgctgttt corresponds to SEQ ID NO: 128 and tttattttactgtcttta corresponds to SEQ ID NO:137.

Figure 16A:
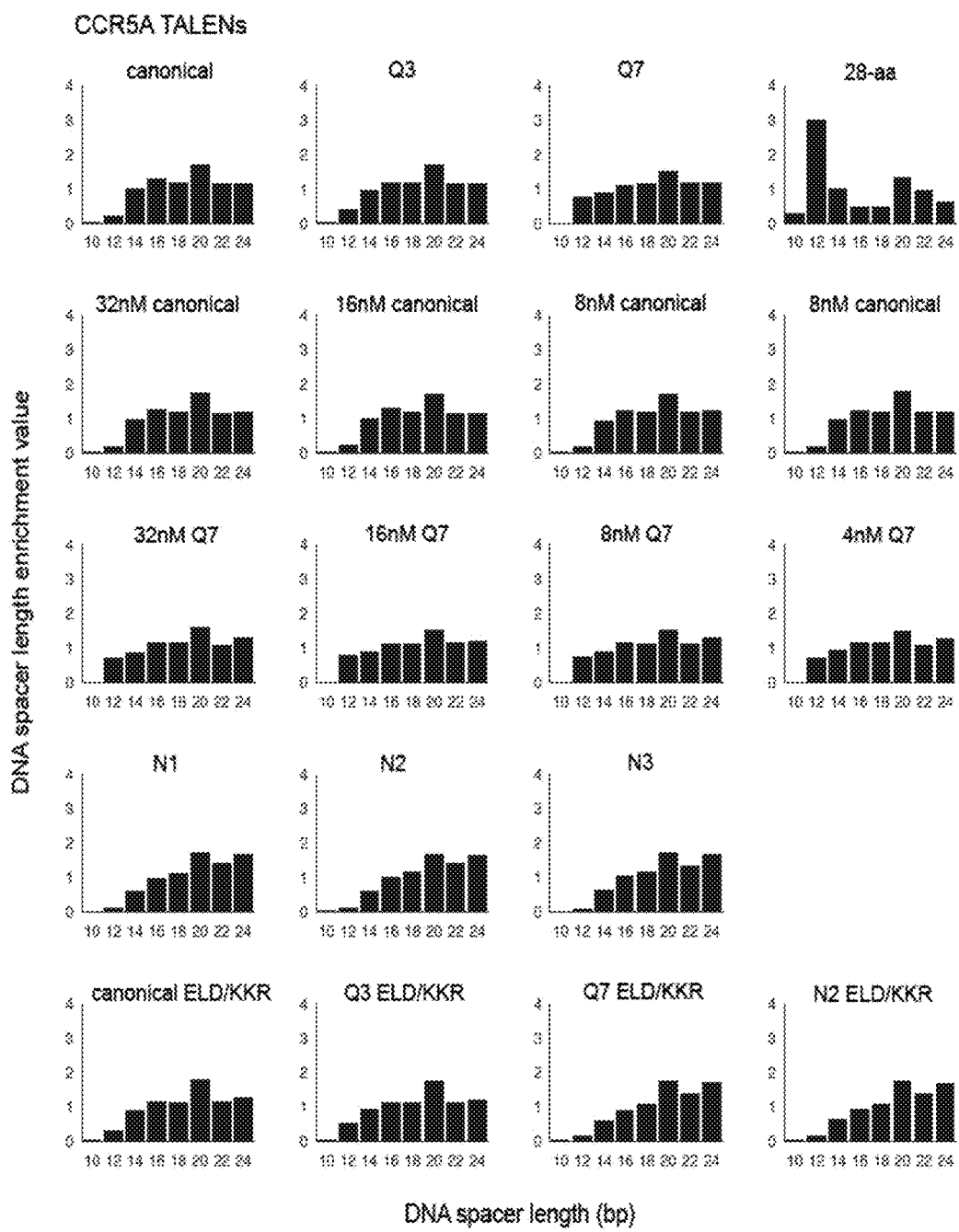
Figure 16B:
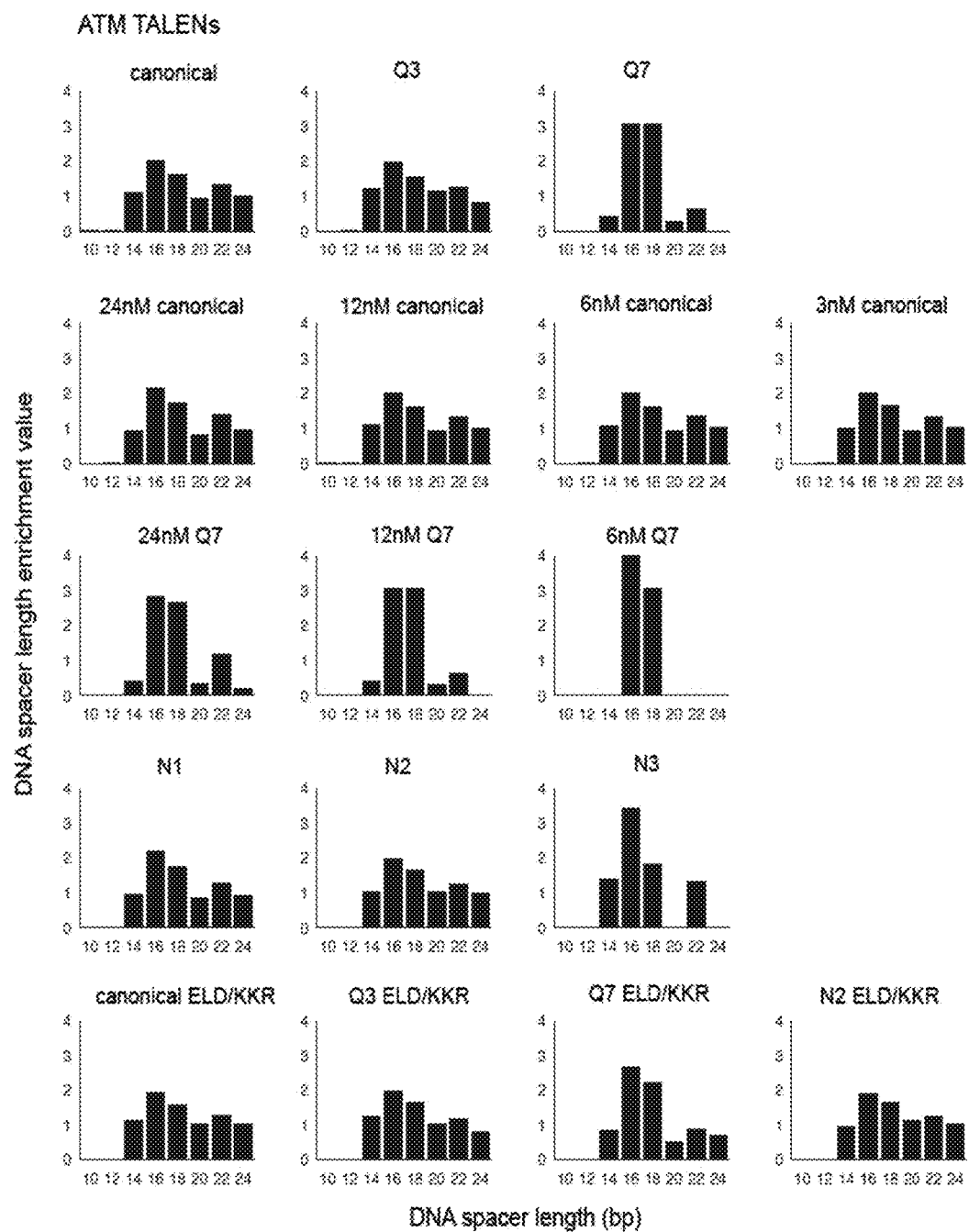

FIGS. 16A-B. Spacer-length preferences of TALENs. (A) For each selection with CCR5A TALENs containing various combinations of the canonical, Q3, Q7, or 28-aa C-terminal domains; N1, N2, or N3 N-terminal mutations; and the EL/KK or ELD/KKR FokI variants and at 4, 8, 16, or 32 nM, the DNA spacer-length enrichment values were calculated by dividing the abundance of DNA spacer lengths in post-selection sequences by the abundance of DNA spacer lengths in the preselection library sequences. (B) Same as (A) but for ATM TALENs.

Figure 17A:
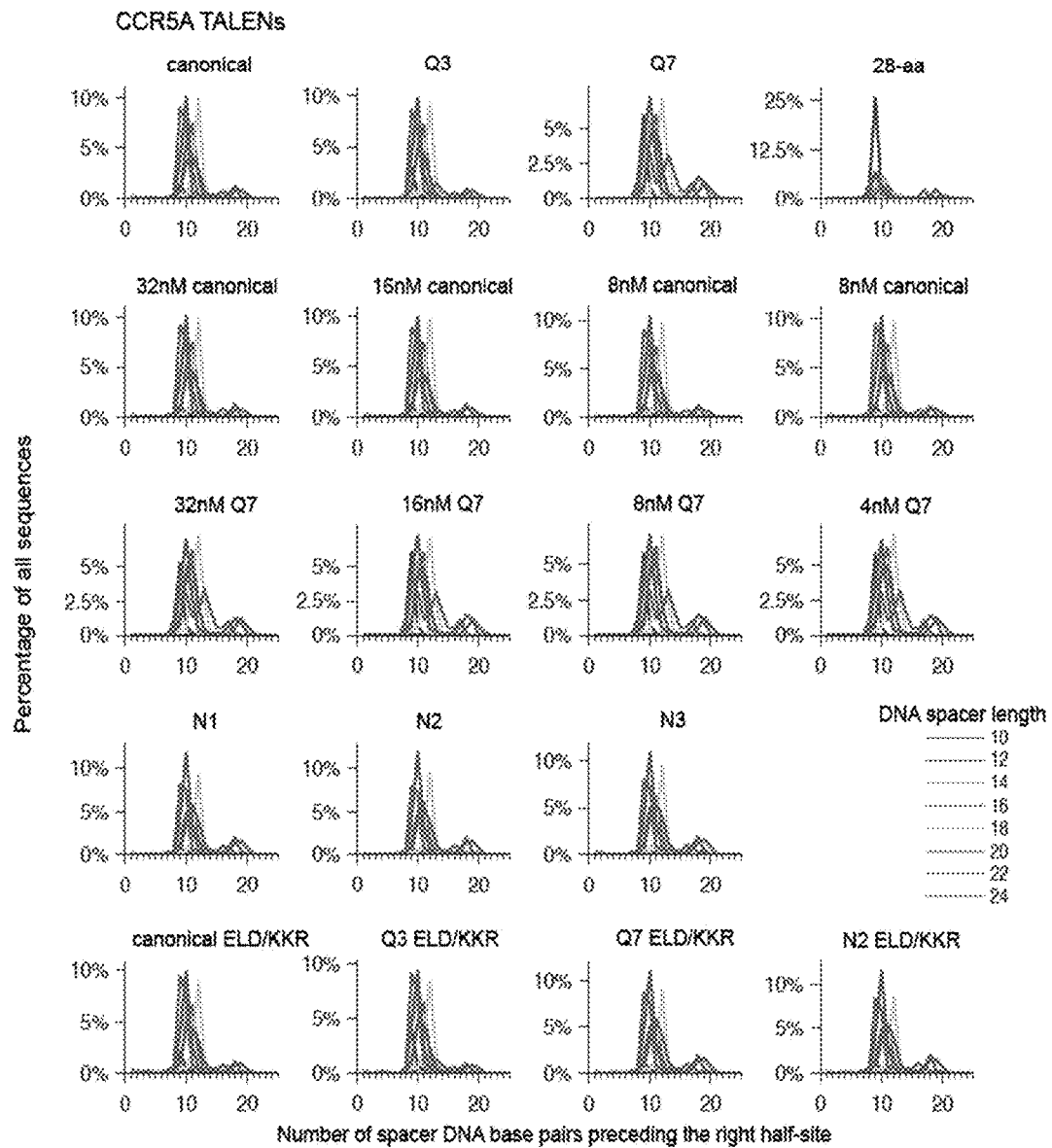
Figure 17B:
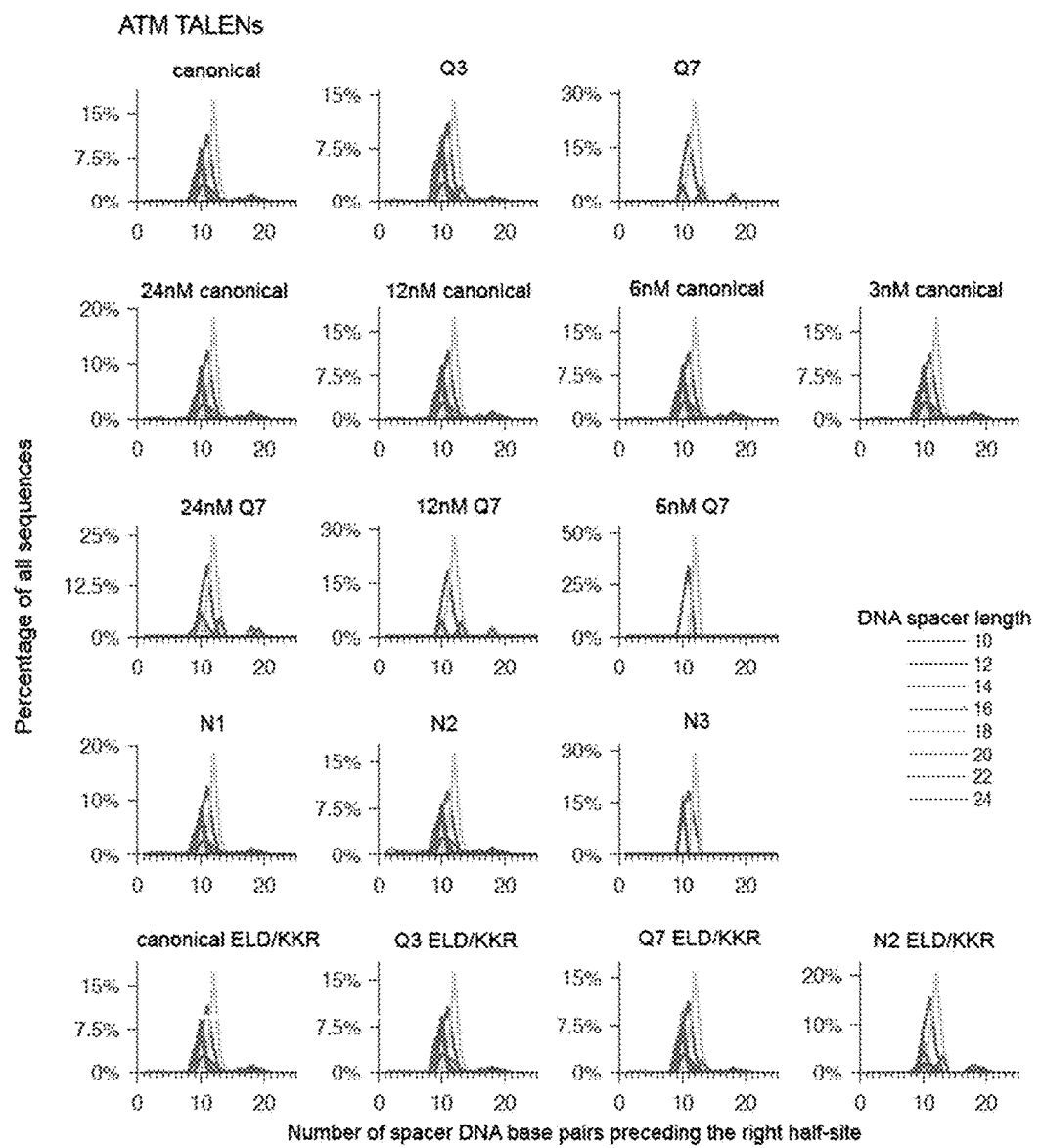

FIGS. 17A-B. DNA cleavage-site preferences of TALENs. (A) For each selection with CCR5A TALENs with various combinations of canonical, Q3, Q7, or 28-aa C-terminal domains; N1, N2, or N3 N-terminal mutations; and the EL/KK or ELD/KKR FokI variants and at 4, 8, 16, or 32 nM, histograms of the number of spacer DNA base pairs preceding the right half-site for each possible DNA spacer length, normalized to the total sequence counts of the entire selection, are shown. (B) Same as (A) for ATM TALENs.

Figure 18:
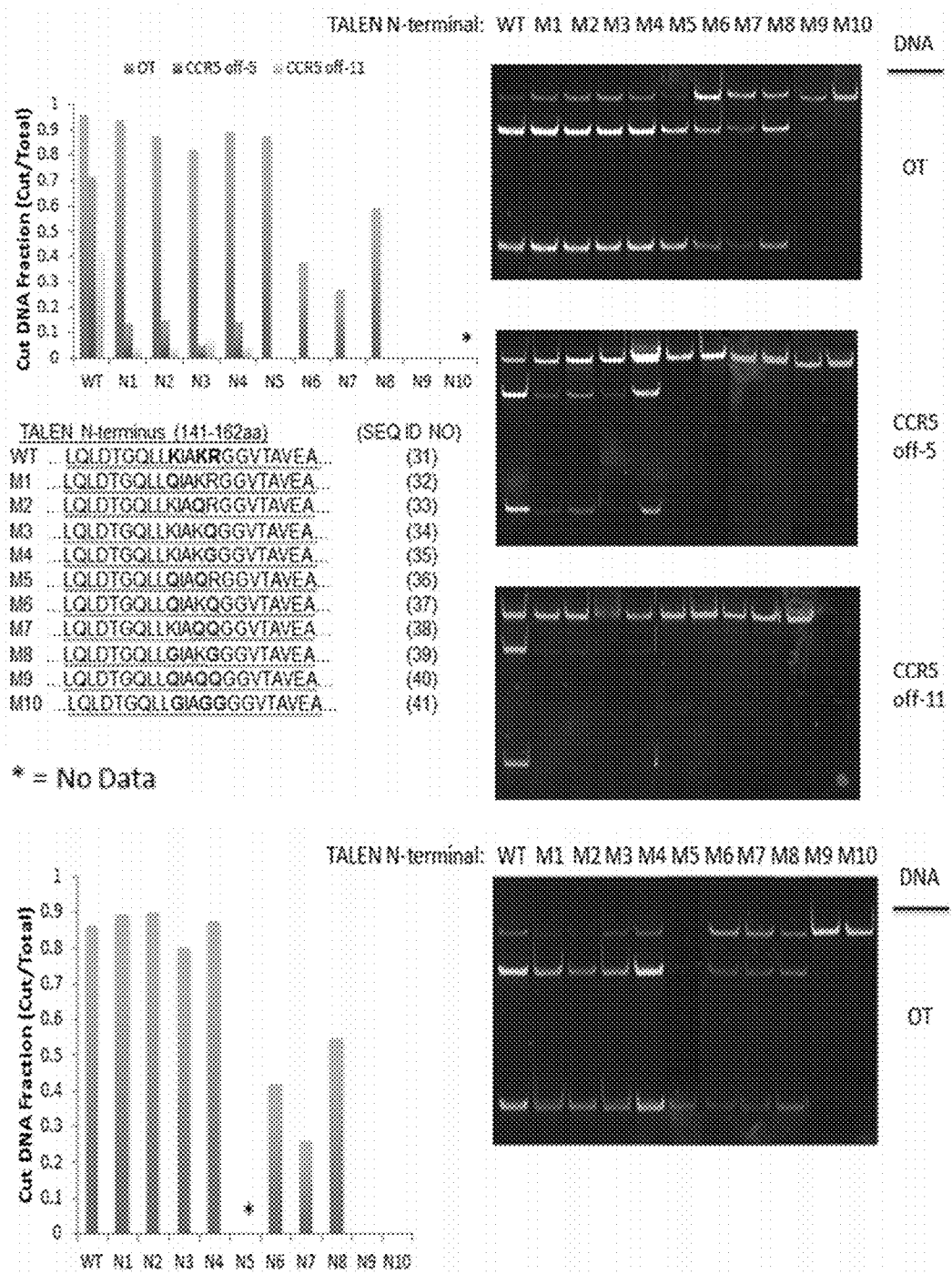

FIG. 18. DNA cleavage-site preferences of TALENs comprising N-terminal domains with different amino acid substitutions. Sequences in FIG. 18, from top to bottom, correspond to SEQ ID NOs: 31-41.

Figure 19:
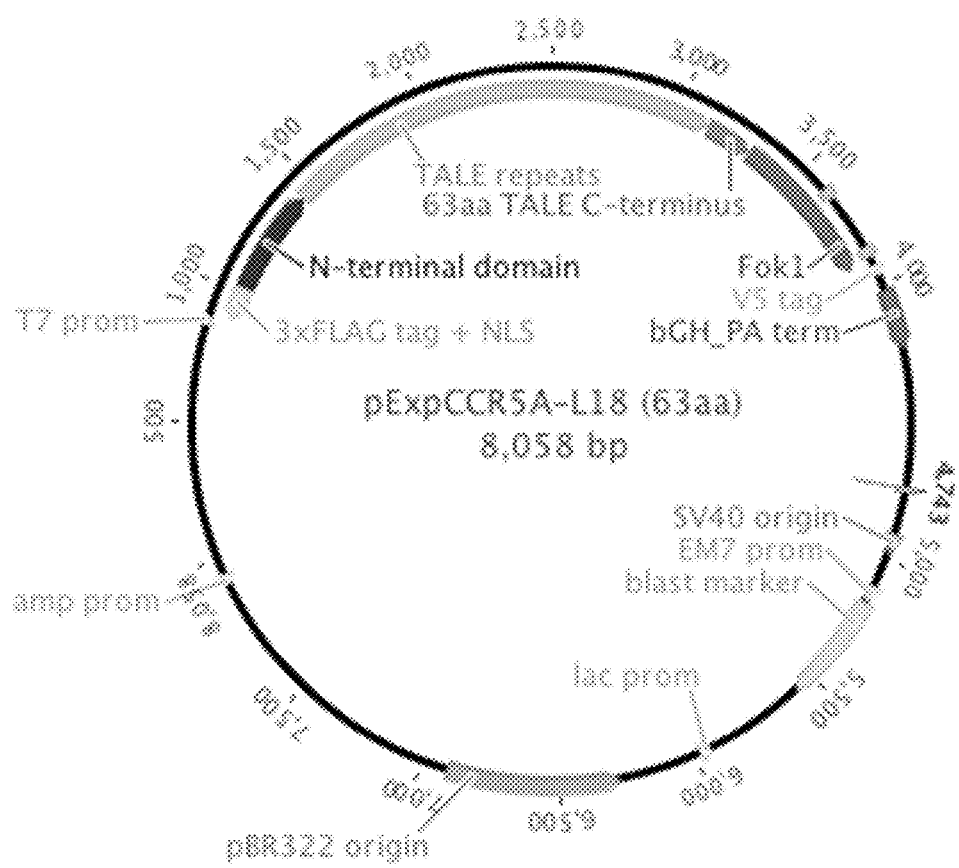

FIG. 19. Exemplary TALEN plasmid construct.

DEFINITIONS

As used herein and in the claims, the singular forms "a," "an," and "the" include the singular and the plural reference unless the context clearly indicates otherwise. Thus, for example, a reference to "an agent" includes a single agent and a plurality of agents.

The term "canonical sequence," as used herein, refers to a sequence of DNA, RNA, or amino acids that reflects the most common choice of base or amino acid at each position amongst known molecules of that type. For example, the canonical amino acid sequence of a protein domain may reflect the most common choice of amino acid resides at each position amongst all known domains of that type, or amongst the majority of known domains of that type. In some embodiments, a canonical sequence is a consensus sequence.

The terms "consensus sequence" and "consensus site," as used herein in the context of nucleic acid sequences, refers to a calculated sequence representing the most frequent nucleotide residue found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, bound with the highest affinity, and/or cleaved with the highest efficiency by a given nuclease.

The terms "conjugating," "conjugated," and "conjugation" refer to an association of two entities, for example, of two molecules such as two proteins, two domains (e.g., a binding domain and a cleavage domain), or a protein and an agent (e.g., a protein binding domain and a small molecule). The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "effective amount," as used herein, refers to an amount of a biologically active agent that is sufficient to elicit a desired biological response. For example, in some embodiments, an effective amount of a TALE nuclease may refer to the amount of the nuclease that is sufficient to induce cleavage of a target site specifically bound and cleaved by the nuclease, e.g., in a cell-free assay, or in a target cell, tissue, or organism. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term "engineered," as used herein refers to a molecule, complex, substance, or entity that has been designed, produced, prepared, synthesized, and/or manufactured by a human. Accordingly, an engineered product is a product that does not occur in nature. In some embodiments, an engineered molecule or complex, e.g., an engineered TALEN monomer, dimer, or multimer, is a TALEN that has been designed to meet particular requirements or to have particular desired features e.g., to specifically bind a target sequence of interest with minimal off-target binding, to have a specific minimal or maximal cleavage activity, and/or to have a specific stability.

As used herein, the term "isolated" refers to a molecule, complex, substance, or entity that has been (1) separated from at least some of the components with which it was associated when initially produced (whether in nature or in an experimental setting), and/or (2) produced, prepared, synthesized, and/or manufactured by a human. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "library," as used herein in the context of nucleic acids or proteins, refers to a population of two or more different nucleic acids or proteins, respectively. For example, a library of nuclease target sites comprises at least two nucleic acid molecules comprising different nuclease target sites. In some embodiments, a library comprises at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different nucleic acids or proteins. In some embodiments, the members of the library may comprise randomized sequences, for example, fully or partially randomized sequences. In some embodiments, the library comprises nucleic acid molecules that are unrelated to each other, e.g., nucleic acids comprising fully randomized sequences. In other embodiments, at least some members of the library may be related, for example, they may be variants or derivatives of a particular sequence, such as a consensus target site sequence.

The term "linker," as used herein, refers to a chemical group or a molecule linking two molecules or moieties, e.g., a binding domain and a cleavage domain of a nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The term "nuclease," as used herein, refers to an agent, for example a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease recognizes a single stranded target site, while in other embodiments, a nuclease recognizes a double-stranded target site, for example a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and a "cleavage domain" that catalyzes the cleavage of the phosphodiester bond within the nucleic acid backbone. In some embodiments, a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be combined to create nucleases that bind specific target sites, are well known to those of skill in the art. For example, transcriptional activator like elements can be used as binding domains to specifically bind a desired target site, and fused or conjugated to a cleavage domain, for example, the cleavage domain of FokI, to create an engineered nuclease cleaving the desired target site.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications' A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment of a disease or disorder. In some embodiments, a pharmaceutical composition comprises an active ingredient, e.g. a nuclease or a nucleic acid encoding a nuclease, and a pharmaceutically acceptable excipient.

The terms "prevention" or "prevent" refer to the prophylactic treatment of a subject who is at risk of developing a disease, disorder, or condition (e.g., at an elevated risk as compared to a control subject, or a control group of subject, or at an elevated risk as compared to the average risk of an age-matched and/or gender-matched subject), resulting in a decrease in the probability that the subject will develop the disease, disorder, or condition (as compared to the probability without prevention), and/or to the inhibition of further advancement of an already established disorder.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasms are also referred to as cancers.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

The term "randomized," as used herein in the context of nucleic acid sequences, refers to a sequence or residue within a sequence that has been synthesized to incorporate a mixture of free nucleotides, for example, a mixture of all four nucleotides A, T, G, and C. Randomized residues are typically represented by the letter N within a nucleotide sequence. In some embodiments, a randomized sequence or residue is fully randomized, in which case the randomized residues are synthesized by adding equal amounts of the nucleotides to be incorporated (e.g., 25% T, 25% A, 25% G, and 25% C) during the synthesis step of the respective sequence residue. In some embodiments, a randomized sequence or residue is partially randomized, in which case the randomized residues are synthesized by adding non-equal amounts of the nucleotides to be incorporated (e.g., 79% T, 7% A, 7% G, and 7% C) during the synthesis step of the respective sequence residue. Partial randomization allows for the generation of sequences that are templated on a given sequence, but have incorporated mutations at a desired frequency. For example, if a known nuclease target site is used as a synthesis template, partial randomization in which at each step the nucleotide represented at the respective residue is added to the synthesis at 79%, and the other three nucleotides are added at 7% each, will result in a mixture of partially randomized target sites being synthesized, which still represent the consensus sequence of the original target site, but which differ from the original target site at each residue with a statistical frequency of 21% for each residue so synthesized (distributed binomially). In some embodiments, a partially randomized sequence differs from the consensus sequence by more than 5%, more than 10%, more than 15%, more than 20%, more than 25%, or more than 30% on average, distributed binomially. In some embodiments, a partially randomized sequence differs from the consensus site by no more than 10%, no more than 15%, no more than 20%, no more than 25%, nor more than 30%, no more than 40%, or no more than 50% on average, distributed binomially.

The term "subject," as used herein, refers to an individual organism, for example, an individual mammal. In some embodiments, the subject is a human of either sex at any stage of development. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode.

The terms "target nucleic acid," and "target genome," as used herein in the context of nucleases, refer to a nucleic acid molecule or a genome, respectively, that comprises at least one target site of a given nuclease.

The term "target site," used herein interchangeably with the term "nuclease target site," refers to a sequence within a nucleic acid molecule that is bound and cleaved by a nuclease. A target site may be single-stranded or double-stranded. In the context of nucleases that dimerize, for example, nucleases comprising a FokI DNA cleavage domain, a target site typically comprises a left-half site (bound by one monomer of the nuclease), a right-half site (bound by the second monomer of the nuclease), and a spacer sequence between the half sites in which the cut is made. This structure ([left-half site]-[spacer sequence]-[right-half site]) is referred to herein as an LSR structure. In some embodiments, the left-half site and/or the right-half site is between 10-18 nucleotides long. In some embodiments, either or both half-sites are shorter or longer. In some embodiments, the left and right half sites comprise different nucleic acid sequences.

The term "Transcriptional Activator-Like Effector," (TALE) as used herein, refers to proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et.al. (February 2011). "A TALE nuclease architecture for efficient genome editing". *Nature Biotechnology* 29 (2): 143-8; Zhang, Feng; et.al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et.al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors". *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et.al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

DETAILED DESCRIPTION OF CERTAIN EMBODIMENTS OF THE INVENTION

Transcription activator-like effector nucleases (TALENs) are fusions of the FokI restriction endonuclease cleavage domain with a DNA-binding transcription activator-like effector (TALE) repeat array. TALENs can be engineered to reduce off-target cleavage activity and thus to specifically bind a target DNA sequence and can thus be used to cleave a target DNA sequence, e.g., in a genome, in vitro or in vivo. Such engineered TALENs can be used to manipulate genomes in vivo or in vitro, e.g., for gene knockouts or knock-ins via induction of DNA breaks at a target genomic site for targeted gene knockout through non-homologous end joining (NHEJ) or targeted genomic sequence replacement through homology-directed repair (HDR) using an exogenous DNA template.

TALENs can be designed to cleave any desired target DNA sequence, including naturally occurring and synthetic sequences. However, the ability of TALENs to distinguish target sequences from closely related off-target sequences has not been studied in depth. Understanding this ability and the parameters affecting it is of importance for the design of TALENs having the desired level of specificity for their therapeutic use and also for choosing unique target sequences to be cleaved in order to minimize the chance of off-target cleavage.

Some aspects of this disclosure are based on cleavage specificity data obtained from profiling 41 TALENs on $10^{12}$ potential off-target sites through in vitro selection and high-throughput sequencing. Computational analysis of the selection results predicted off-target substrates in the human genome, thirteen of which were modified by TALENs in human cells. Some aspect of this disclosure are based on the surprising findings that (i) TALEN repeats bind DNA relatively independently; (ii) longer TALENs are more tolerant of mismatches, yet are more specific in a genomic context; and (iii) excessive DNA-binding energy can lead to reduced TALEN specificity. Based on these findings, optimized TALENs were engineered with mutations designed to reduce non-specific DNA binding. Some of these engineered TALENs exhibit improved specificity, e.g., 34- to >116-fold greater specificity, in human cells compared to commonly used TALENs.

Figure 1A:
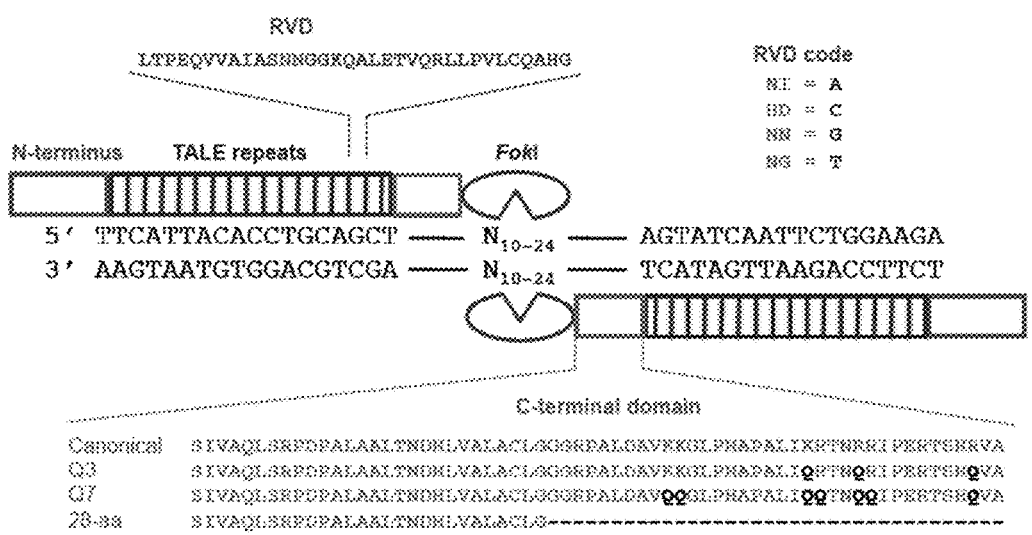
FIGS. 1A-B. TALEN architecture and selection scheme. (A) Architecture of a TALEN. A TALEN monomer contains an N-terminal domain followed by an array of TALE repeats (brown), a C terminal domain (green), and a FokI nuclease cleavage domain (purple). The 12th and 13th amino acids (the RVD (SEQ ID NO: 43), red) of each TALE repeat recognize a specific DNA base pair. Two different TALENs bind their corresponding half-sites, allowing FokI dimerization and DNA cleavage; ttcattacacctgcagct is SEQ ID NO: 44; agctgcaggtgtaatgaa is SEQ ID NO: 45; agtatcaattctg-gaagais SEQ ID NO: 46; and tcttccagaattgatact is SEQ ID NO: 47. The C-terminal domain variants used in this study are shown in green (SEQ ID NOs: 48-50, and 25, from top to bottom, respectively). (B) A single-stranded library of DNA oligonucleotides containing partially randomized left half-site (L), spacer (S), right half-site (R) and constant region (thick black line) was circularized, then concatemerized by rolling circle amplification. The resulting DNA libraries were incubated with an in vitro-translated TALEN of interest. Cleaved library members were blunted and ligated to adapter #1. The ligation products were amplified by PCR using one primer consisting of adapter #1 and the other primer consisting of adapter #2—constant sequence, which anneals to the constant regions. Amplicons 1½ target-sequence cassettes in length were isolated by gel purification and subjected to high-throughput DNA sequencing and computational analysis.

The ability to engineer site-specific changes in genomes represents a powerful research capability with significant therapeutic implications. TALENs are fusions of the FokI restriction endonuclease cleavage domain with a DNA-binding TALE repeat array (FIG. 1A). These arrays consist of multiple 34-amino acid TALE repeat sequences, each of which uses a repeat-variable di-residue (RVD), the amino acids at positions 12 and 13, to recognize a single DNA nucleotide.[1,2] Examples of RVDs that enable recognition of each of the four DNA base pairs are known, enabling arrays of TALE repeats to be constructed that can bind virtually any DNA sequence. TALENs can be engineered to be active only as heterodimers through the use of obligate heterodimeric FokI variants.[3,4] In this configuration, two distinct TALEN monomers are each designed to bind one target half-site and to cleave within the DNA spacer sequence between the two half-sites.

In cells, e.g., in mammalian cells, TALEN-induced double-strand breaks can result in targeted gene knockout through non-homologous end joining (NHEJ)[5] or targeted genomic sequence replacement through homology-directed repair (HDR) using an exogenous DNA template.[6,7] TALENs have been successfully used to manipulate genomes in a variety of organisms[8-11] and cell lines.[7,12,13]

TALEN-mediated DNA cleavage at off-target sites can result in unintended mutations at genomic loci. While SELEX experiments have characterized the DNA-binding specificities of monomeric TALE proteins,[5,7] the DNA cleavage specificities of active, dimeric nucleases can differ from the specificities of their component monomeric DNA-binding domains.[14] Full-genome sequencing of four TALEN-treated yeast strains[15] and two human cell lines[16] derived from a TALEN-treated cell revealed no evidence of TALE-induced genomic off-target mutations, consistent with other reports that observed no off-target genomic modification in Xenopus[17] and human cell lines.[18] In contrast, TALENs were observed to cleave off-target sites containing two to eleven mutations relative to the on-target sequence in vivo in zebrafish,[13,19] rats,[9] human primary fibroblasts,[20] and embryonic stem cells.[7] A systematic and comprehensive profile of TALEN specificity generated from measurements of TALEN cleavage on a large set of related mutant target sites has not been described before. Such a broad specificity profile is fundamental to understand and improve the potential of TALENs as research tools and therapeutic agents.

Some of the work described herein relates to experiments performed to profile the ability of 41 TALEN pairs to cleave $10^{12}$ off-target variants of each of their respective target sequences using a modified version of a previously described in vitro selection[14] for DNA cleavage specificity. These results from these experiments provide comprehensive profiles of TALEN cleavage specificities. The in vitro selection results were used to computationally predict off-target substrates in the human genome, 13 of which were confirmed to be cleaved by TALENs in human cells.

It was surprisingly found that, despite being less specific per base pair, TALENs designed to cleave longer target sites in general exhibit higher overall specificity than those that target shorter sites when considering the number of potential off-target sites in the human genome. The selection results also suggest a model in which excess non-specific TALEN binding energy gives rise to greater off-target cleavage relative to on-target cleavage. Based on this model, we engineered TALENs with substantially improved DNA cleavage specificity in vitro, and 30- to >150-fold greater specificity in human cells, than currently used TALEN constructs.

Figure 1B:
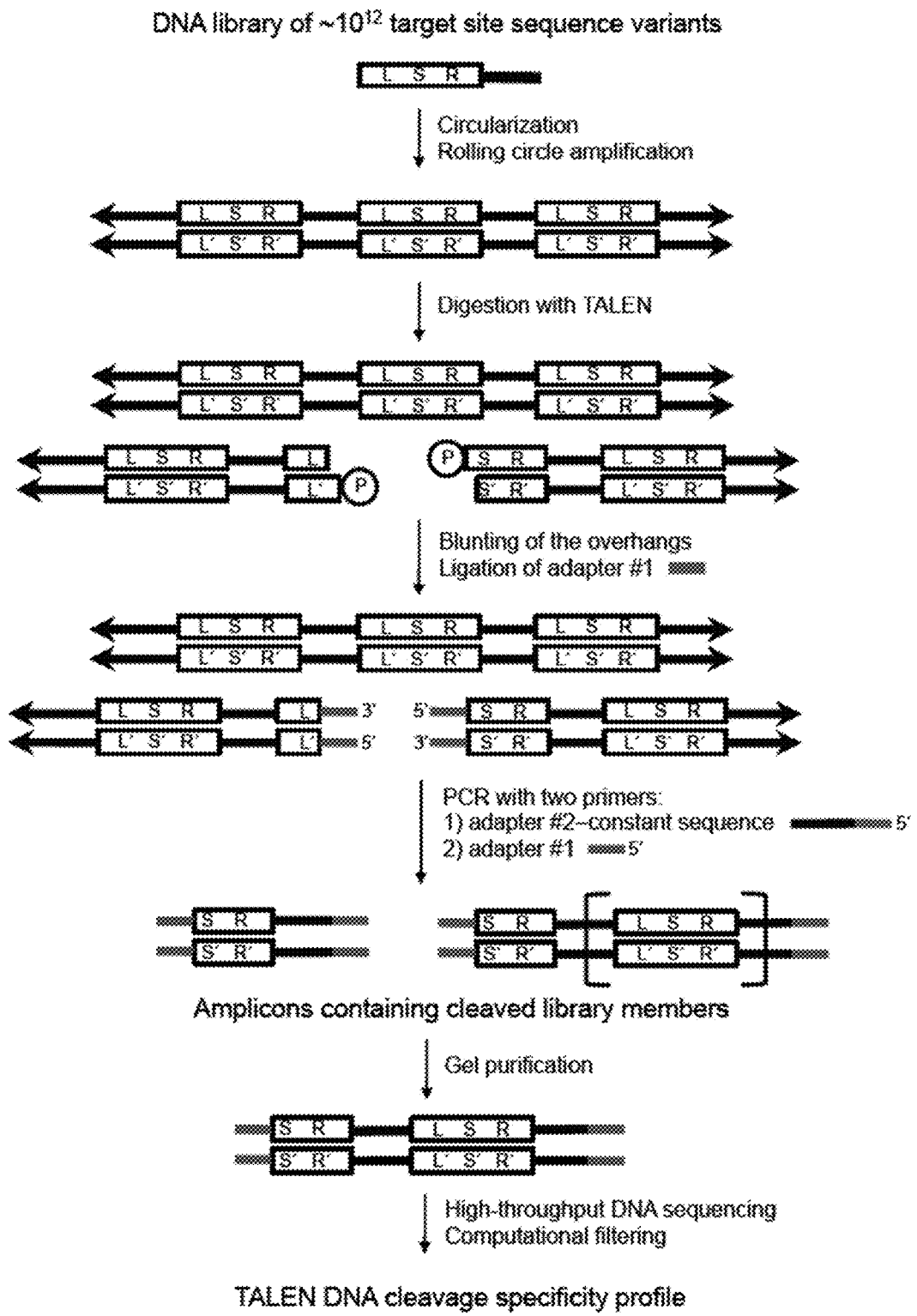

Some aspects of this disclosure are based on data obtained from profiling the specificity of 41 heterodimeric TALENs designed to target one of three distinct sequence, as described in more detail elsewhere herein. The profiling was performed using an improved version of an in vitro selection method[14] (also described in PCT Application Publication WO2013/066438 A2, the entire contents of which are incorporated herein by reference) with modifications that increase the throughput and sensitivity of the selection (FIG. 1B).

Briefly, TALENs were profiled against libraries of >$10^{12}$ DNA sequences and cleavage products were captured and analyzed to determine the specificity and off-target activity of each TALEN. The selection data accurately predicted the efficiency of off-target TALEN cleavage in vitro, and also indicated that TALENs are overall highly specific across the entire target sequence, but that some level of off-target cleavage occurs in conventional TALENs which can be undesirable in some scenarios of TALEN use. As a result of the experiments described herein, it was surprisingly found that that TALE repeats bind their respective DNA base pairs independently beyond a slightly increased tolerance for adjacent mismatches, which informed the recognition that TALEN specificity per base pair is independent of target-site length. It was experimentally validated that shorter TALENs have greater specificity per targeted base pair than longer TALENs, but that longer TALENs are more specific against the set of potential cleavage sites in the context of a whole genome than shorter TALENs for the tested TALEN lengths targeting 20- to 32-bp sites, as described in more detail elsewhere herein.

Some aspects of this disclosure are based on the surprising discovery that excess binding energy in longer TALENs reduces specificity by enabling the cleavage of off-target sequences without a corresponding increase in the efficiency of on-target cleavage efficiency. Some aspects of this disclosure are based on the surprising discovery that TALENs can be engineered to more specifically cleave their target sequences by reducing off-target binding energy without compromising on-target cleavage efficiency. The recognition that TALEN specificity can be improved by reducing non-specific DNA binding energy beyond what is required to enable efficient on-target cleavage served as the basis for the generation of engineered TALENs with improved target site specificity.

Typically, a TALEN monomer, e.g., a TALEN monomer as provided herein, comprises or is of the following structure:

[N-terminal domain]-[TALE repeat array]-[C-terminal domain]-[nuclease domain]

wherein each "-" individually indicates conjugation, either covalently or non-covalently, and wherein the conjugation can be direct, e.g., via direct bond, or indirect, e.g., via a linker domain. See also FIG. 1.

Some aspects of this disclosure provide TALENs with enhanced specificity as compared to TALENs that were previously used. In general, the sequence specificity of a TALEN is conferred by the TALE repeat array, which binds to a specific nucleotide sequence. TALE repeat arrays consist of multiple 34-amino acid TALE repeat sequences, each of which uses a repeat-variable di-residue (RVD), the amino acids at positions 12 and 13, to recognize a single DNA nucleotide. Some aspects of this disclosure provide that the specific binding of the TALE repeat array is sufficient for dimerization and nucleic acid cleavage, and that non-specific nucleic acid binding activity is due to the N-terminal and/or C-terminal domains of the TALEN.

Based on this recognition, improved TALENs have been engineered as provided herein. As it was discovered that non-specific binding via the N-terminal domain can occur through excess binding energy conferred by amino acid residues that are positively charged (cationic) at physiological pH, some of the improved TALENs provided herein have a decreased net charge and/or a decreased binding energy for binding their target nucleic acid sequence as compared to canonical TALENs. This decrease in charge leads to a decrease in off-target binding via the modified N-terminal and C-terminal domains. The portion of target recognition and binding, thus, is more narrowly confined to the specific recognition and binding activity of the TALE repeat array. The resulting TALENs, thus, exhibit an increase in the specificity of binding and, in turn, in the specificity of cleaving the target site by the improved TALEN as compared to a TALEN using non-modified domains.

In some embodiments, a TALEN is provided in which the net charge of the N-terminal domain is less than the net charge of the canonical N-terminal domain (SEQ ID NO: 1); and/or the net charge of the C-terminal domain is less than the net charge of the canonical C-terminal domain (SEQ ID NO: 22). In some embodiments, a TALEN is provided in which the binding energy of the N-terminal domain to a target nucleic acid molecule is less than the binding energy of the canonical N-terminal domain (SEQ ID NO: 1); and/or the binding energy of the C-terminal domain to a target nucleic acid molecule is less than the binding energy of the canonical C-terminal domain (SEQ ID NO: 22). In some embodiments, a modified TALEN N-terminal domain is provided the binding energy of which to the TALEN target nucleic acid molecule is less than the binding energy of the canonical N-terminal domain (SEQ ID NO: 1). In some embodiments, a modified TALEN C-terminal domain is provided the binding energy of which to the TALEN target nucleic acid molecule is less than the binding energy of the canonical C-terminal domain (SEQ ID NO: 22). In some embodiments, the binding energy of the N-terminal and/or of the C-terminal domain in the TALEN provided is decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or at least 99%.

In some embodiments, the canonical N-terminal domain and/or the canonical C-terminal domain is modified to replace an amino acid residue that is positively charged at physiological pH with an amino acid residue that is not charged or is negatively charged. In some embodiments, the modification includes the replacement of a positively charged residue with a negatively charged residue. In some embodiments, the modification includes the replacement of a positively charged residue with a neutral (uncharged) residue. In some embodiments, the modification includes the replacement of a positively charged residue with a residue having no charge or a negative charge. In some embodiments, the net charge of the modified N-terminal domain and/or of the modified C-terminal domain is less than or equal to +10, less than or equal to +9, less than or equal to +8, less than or equal to +7, less than or equal to +6, less than or equal to +5, less than or equal to +4, less than or equal to +3, less than or equal to +2, less than or equal to +1, less than or equal to 0, less than or equal to −1, less than or equal to −2, less than or equal to −3, less than or equal to −4, or less than or equal to −5, or less than or equal to −10. In some embodiments, the net charge of the modified N-terminal domain and/or of the modified C-terminal domain is between +5 and −5, between +2 and −7, between 0 and −5, between 0 and −10, between −1 and −10, or between −2 and −15. In some embodiments, the net charge of the modified N-terminal domain and/or of the modified C-terminal domain is negative. In some embodiments, the net charge of the modified N-terminal domain and of the modified C-terminal domain, together, is negative. In some embodiments, the net charge of the modified N-terminal domain and/or of the modified C-terminal domain is neutral or slightly positive (e.g., less than +2 or less than +1). In some embodiments, the net charge of the modified N-terminal domain and of the modified C-terminal domain, together, is neutral or slightly positive (e.g., less than +2 or less than +1).

In some embodiments, the modified N-terminal domain and/or the modified C-terminal domain comprise(s) an amino acid sequence that differs from the respective canonical domain sequence in that at least one cationic amino acid residue of the canonical domain sequence is replaced with an amino acid residue that exhibits no charge or a negative charge at physiological pH. In some embodiments, at least 1, at least 2, at least 3, at least 4, at least 5, at least 6, at least 7, at least 8, at least 9, at least 10, at least 11, at least 12, at least 13, at least 14, or at least 15 cationic amino acid(s) is/are replaced with an amino acid residue that exhibits no charge or a negative charge at physiological pH in the modified N-terminal domain and/or in the modified C-terminal domain. In some embodiments, 1, 2, 3, 4, 5, 6, 7, 8, 9, 10, 11, 12, 13, 14, 15 cationic amino acid(s) is/are replaced with an amino acid residue that exhibits no charge or a negative charge at physiological pH in the modified N-terminal domain and/or in the modified C-terminal domain.

In some embodiments, the cationic amino acid residue is arginine (R), lysine (K), or histidine (H). In some embodiments, the cationic amino acid residue is R or H. In some embodiments, the amino acid residue that exhibits no charge or a negative charge at physiological pH is glutamine (Q), Glycine (G), Asparagine (N), Threonine (T), Serine (S), Aspartic acid (D), or Glutamic Acid (E). In some embodiments, the amino acid residue that exhibits no charge or a negative charge at physiological pH is Q. In some embodiments, at least one lysine or arginine residue is replaced with a glutamine residue in the modified N-terminal domain and/or in the modified C-terminal domain.

In some embodiments, the C-terminal domain comprises one or more of the following amino acid replacements: K777Q, K778Q, K788Q, R789Q, R792Q, R793Q, R801Q. In some embodiments, the C-terminal domain comprises two or more of the following amino acid replacements: K777Q, K778Q, K788Q, R789Q, R792Q, R793Q, R801Q. In some embodiments, the C-terminal domain comprises three or more of the following amino acid replacements: K777Q, K778Q, K788Q, R789Q, R792Q, R793Q, R801Q. In some embodiments, the C-terminal domain comprises four or more of the following amino acid replacements: K777Q, K778Q, K788Q, R789Q, R792Q, R793Q, R801Q. In some embodiments, the C-terminal domain comprises five or more of the following amino acid replacements:

K777Q, K778Q, K788Q, R789Q, R792Q, R793Q, R801Q. In some embodiments, the C-terminal domain comprises six or more of the following amino acid replacements: K777Q, K778Q, K788Q, R789Q, R792Q, R793Q, R801Q. In some embodiments, the C-terminal domain comprises all seven of the following amino acid replacements: K777Q, K778Q, K788Q, R789Q, R792Q, R793Q, R801Q. In some embodiments, the C-terminal domain comprises a Q3 variant sequence (K788Q, R792Q, R801Q, see SEQ ID NO: 23). In some embodiments, the C-terminal domain comprises a Q7 variant sequence (K777Q, K778Q, K788Q, R789Q, R792Q, R793Q, R801Q, see SEQ ID NO: 24).

In some embodiments, the N-terminal domain is a truncated version of the canonical N-terminal domain. In some embodiments, the C-terminal domain is a truncated version of the canonical C-terminal domain. In some embodiments, the truncated N-terminal domain and/or the truncated C-terminal domain comprises less than 90%, less than 80%, less than 70%, less than 60%, less than 50%, less than 40%, less than 30%, or less than 25% of the residues of the canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues. In some embodiments, the modified N-terminal domain and/or the modified C-terminal domain is/are truncated and comprise one or more amino acid replacement(s). It will be apparent to those of skill in the art that it is desirable in some embodiments to adjust the DNA spacer length in TALENs using truncated domains, e.g., truncated C-terminal domains, in order to accommodate the truncation.

In some embodiments, the nuclease domain, also sometimes referred to as a nucleic acid cleavage domain is a non-specific cleavage domain, e.g., a FokI nuclease domain. In some embodiments, the nuclease domain is monomeric and must dimerize or multimerize in order to cleave a nucleic acid. Homo- or heterodimerization or multimerization of TALEN monomers typically occurs via binding of the monomers to binding sequences that are in sufficiently close proximity to allow dimerization, e.g., to sequences that are proximal to each other on the same nucleic acid molecule (e.g., the same double-stranded nucleic acid molecule).

The most commonly used domains, e.g., the most widely used N-terminal and C-terminal domains, are referred to herein as canonical domains. Exemplary sequences of a canonical N-terminal domain (SEQ ID NO: 1) and a canonical C-terminal domain (SEQ ID NO: 22) are provided herein. Exemplary sequences of FokI nuclease domains are also provided herein. In addition, exemplary sequences of TALE repeats forming a CCR5-binding TALE repeat array are provided. It will be understood that the sequences provided below are exemplary and provided for the purpose of illustrating some embodiments embraced by the present disclosure. They are not meant to be limiting and additional sequences useful according to aspects of this disclosure will be apparent to the skilled artisan based on this disclosure.

Canonical N-terminal domain:
(SEQ ID NO: 1)
VDLRTLGYSQQQQEKIKPKVRSTVAQHHEALVGHGFTHAHIVALSQHPAA
LGTVAVKYQDMIAALPEATHEAIVGVGKQWSGARALEALLTVAGELRGPP
LQLDTGQLLKIAKRGGVTAVEAVHAWRNALTGAPLN Modified N-terminal domain: N1
(SEQ ID NO: 2)
VDLRTLGYSQQQQEKIKPKVRSTVAQHHEALVGHGFTHAHIVALSQHPAA
LGTVAVKYQDMIAALPEATHEAIVGVGKQWSGARALEALLTVAGELRGPP
LQLDTGQLLQIAKRGGVTAVEAVHAWRNALTGAPLN Modified N-terminal domain: N2
(SEQ ID NO: 3)
VDLRTLGYSQQQQEKIKPKVRSTVAQHHEALVGHGFTHAHIVALSQHPAA
LGTVAVKYQDMIAALPEATHEAIVGVGKQWSGARALEALLTVAGELRGPP
LQLDTGQLLQIAQRGGVTAVEAVHAWRNALTGAPLN Modified N-terminal domain: N3
(SEQ ID NO: 4)
VDLRTLGYSQQQQEKIKPKVRSTVAQHHEALVGHGFTHAHIVALSQHPAA
LGTVAVKYQDMIAALPEATHEAIVGVGKQWSGARALEALLTVAGELRGPP
LQLDTGQLLQIAQQGGVTAVEAVHAWRNALTGAPLN TALE repeat array: L18 CCR5A
(SEQ ID NO: 5)
MTPDQVVAIASNGGGKQALETVQRLLPVLCQDH (SEQ ID NO: 6)
GLTPEQVVAIASHDGGKQALETVQRLLPVLCQAH (SEQ ID NO: 7)
GLTPDQVVAIASNIGGKQALETVQRLLPVLCQAH (SEQ ID NO: 8)
GLTPAQVVAIASNGGGKQALETVQRLLPVLCQDH (SEQ ID NO: 9)
GLTPDQVVAIASNGGGKQALETVQRLLPVLCQDH (SEQ ID NO: 10)
GLTPEQVVAIASNIGGKQALETVQRLLPVLCQAH (SEQ ID NO: 11)
GLTPDQVVAIASHDGGKQALETVQRLLPVLCQAH (SEQ ID NO: 12)
GLTPAQVVAIASNIGGKQALETVQRLLPVLCQDH (SEQ ID NO: 13)
GLTPDQVVAIASHDGGKQALETVQRLLPVLCQDH (SEQ ID NO: 14)
GLTPEQVVAIASHDGGKQALETVQRLLPVLCQAH (SEQ ID NO: 15)
GLTPDQVVAIASNGGGKQALETVQRLLPVLCQAH (SEQ ID NO: 16)
GLTPAQVVAIANNNGGKQALETVQRLLPVLCQDH (SEQ ID NO: 17)
GLTPDQVVAIASHDGGKQALETVQRLLPVLCQDH (SEQ ID NO: 18)
GLTPEQVVAIASNIGGKQALETVQRLLPVLCQAH (SEQ ID NO: 19)
GLTPDQVVAIANNNGGKQALETVQRLLPVLCQAH (SEQ ID NO: 20)
GLTPAQVVAIASHDGGKQALETVQRLLPVLCQDH (SEQ ID NO: 21)
GLTPEQVVAIASNGGGRPALE Canonical C-terminal domain:
(SEQ ID NO: 22)
SIVAQLSRPDPALAALTNDHLVALACLGGRPALDAVKKGLPHAPALIKRT
A NRRIPERTSHRV Modified C-terminal domain: Q3
(SEQ ID NO: 23)
SIVAQLSRPDPALAALTNDHLVALACLGGRPALDAVKKGLPHAPALIQRT
A NQRIPERTSHQV -continued
```
Modified C-terminal domain: Q7
                                          (SEQ ID NO: 24)
SIVAQLSRPDPALAALTNDHLVALACLGGRPALDAVQQGLPHAPALIQQI
NQQIPERTSHQVA Modified C-terminal domain: 28-aa
                                          (SEQ ID NO: 25)
SIVAQLSRPDPALAALTNDHLVALACLG FokI: homodimeric
                                          (SEQ ID NO: 26)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF*

FokI: EL
                                          (SEQ ID NO: 27)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMERYVEENQTRNKHLNPNEWWKVYPSSVIEFKFLFVSGHFKGNYKAQ

LTRLNHITNCNGAVLSVEELLIGGEMIKAGTLTLEEVRRKFNNGEINF*

FokI: KK
                                          (SEQ ID NO: 28)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVKENQTRNKHINPNEWWKVYPSSVIEFKFLFVSGHFKGNYKAQ

LTRLNHKTNCNGAVLSVEELLIGGEMIKAGTLTLEEVRRKFNNGEINF*

FokI: ELD
                                          (SEQ ID NO: 29)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMERYVEENQTRDKHLNPNEWWKVYPSSVIEFKFLFVSGHFKGNYKAQ

LTRLNHITNCNGAVLSVEELLIGGEMIKAGTLTLEEVRRKFNNGEINF*

FokI: KKR
                                          (SEQ ID NO: 30)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVKENQTRNKHINPNEWWKVYPSSVIEFKFLFVSGHFKGNYKAQ

LTRLNRKTNCNGAVLSVEELLIGGEMIKAGTLTLEEVRRKFNNGEINF*
```

In some embodiments, a TALEN is provided herein that comprises a canonical N-terminal domain, a TALE repeat array, a modified C-terminal domain, and a nuclease domain. In some embodiments, a TALEN is provided herein that comprises a modified N-terminal domain, a TALE repeat array, a canonical C-terminal domain, and a nuclease domain. In some embodiments, a TALEN is provided herein that comprises a modified N-terminal domain, a TALE repeat array, a modified C-terminal domain, and a nuclease domain. In some embodiments, the nuclease domain is a FokI nuclease domain. In some embodiments, the FokI nuclease domain is a homodimeric FokI domain, or a FokI-EL, FokI-KK, FokI-ELD, or FokI-KKR domain.

All possible combinations of the specific sequences of canonical and modified domains provided herein are embraced by this disclosure, including the following:

TABLE 1

Exemplary TALENs embraced by the present disclosure. The respective TALE repeat array employed will depend on the specific target sequence. Those of skill in the art will be able to design such sequence-specific TALE repeat arrays based on the instant disclosure and the knowledge in the art. Sequences for the different N-terminal, C-terminal, and Nuclease domains are provided above (See, SEQ ID NOs 1-4 and 22-30).

| TALEN | N-terminal domain | TALE repeat array | C-terminal domain | Nuclease domain |
|---|---|---|---|---|
| 1 | Canonical | Sequence-specific | Q3 | Homodimeric |
| 2 | Canonical | Sequence-specific | Q3 | EL |
| 3 | Canonical | Sequence-specific | Q3 | KK |
| 4 | Canonical | Sequence-specific | Q3 | ELD |
| 5 | Canonical | Sequence-specific | Q3 | KKR |
| 6 | Canonical | Sequence-specific | Q7 | Homodimeric |
| 7 | Canonical | Sequence-specific | Q7 | EL |
| 8 | Canonical | Sequence-specific | Q7 | KK |
| 9 | Canonical | Sequence-specific | Q7 | ELD |
| 10 | Canonical | Sequence-specific | Q7 | KKR |
| 11 | Canonical | Sequence-specific | Truncated (28aa) | Homodimeric |
| 12 | Canonical | Sequence-specific | Truncated (28aa) | EL |
| 13 | Canonical | Sequence-specific | Truncated (28aa) | KK |
| 14 | Canonical | Sequence-specific | Truncated (28aa) | ELD |
| 15 | Canonical | Sequence-specific | Truncated (28aa) | KKR |
| 16 | N1 | Sequence-specific | Canonical | Homodimeric |
| 17 | N1 | Sequence-specific | Canonical | EL |
| 18 | N1 | Sequence-specific | Canonical | KK |
| 19 | N1 | Sequence-specific | Canonical | ELD |
| 20 | N1 | Sequence-specific | Canonical | KKR |
| 21 | N1 | Sequence-specific | Q3 | Homodimeric |
| 22 | N1 | Sequence-specific | Q3 | EL |
| 23 | N1 | Sequence-specific | Q3 | KK |
| 24 | N1 | Sequence-specific | Q3 | ELD |
| 25 | N1 | Sequence-specific | Q3 | KKR |
| 26 | N1 | Sequence-specific | Q7 | Homodimeric |
| 27 | N1 | Sequence-specific | Q7 | EL |
| 28 | N1 | Sequence-specific | Q7 | KK |
| 29 | N1 | Sequence-specific | Q7 | ELD |
| 30 | N1 | Sequence-specific | Q7 | KKR |
| 31 | N1 | Sequence-specific | Truncated (28aa) | Homodimeric |
| 32 | N1 | Sequence-specific | Truncated (28aa) | EL |
| 33 | N1 | Sequence-specific | Truncated (28aa) | KK |
| 34 | N1 | Sequence-specific | Truncated (28aa) | ELD |
| 35 | N1 | Sequence-specific | Truncated (28aa) | KKR |
| 36 | N2 | Sequence-specific | Canonical | Homodimeric |
| 37 | N2 | Sequence-specific | Canonical | EL |
| 38 | N2 | Sequence-specific | Canonical | KK |
| 39 | N2 | Sequence-specific | Canonical | ELD |
| 40 | N2 | Sequence-specific | Canonical | KKR |
| 41 | N2 | Sequence-specific | Q3 | Homodimeric |
| 42 | N2 | Sequence-specific | Q3 | EL |
| 43 | N2 | Sequence-specific | Q3 | KK |
| 44 | N2 | Sequence-specific | Q3 | ELD |
| 45 | N2 | Sequence-specific | Q3 | KKR |
| 46 | N2 | Sequence-specific | Q7 | Homodimeric |
| 47 | N2 | Sequence-specific | Q7 | EL |
| 48 | N2 | Sequence-specific | Q7 | KK |
| 49 | N2 | Sequence-specific | Q7 | ELD |
| 50 | N2 | Sequence-specific | Q7 | KKR |
| 51 | N2 | Sequence-specific | Truncated (28aa) | Homodimeric |
| 52 | N2 | Sequence-specific | Truncated (28aa) | EL |
| 53 | N2 | Sequence-specific | Truncated (28aa) | KK |
| 54 | N2 | Sequence-specific | Truncated (28aa) | ELD |

TABLE 1-continued

Exemplary TALENs embraced by the present disclosure. The respective TALE repeat array employed will depend on the specific target sequence. Those of skill in the art will be able to design such sequence-specific TALE repeat arrays based on the instant disclosure and the knowledge in the art. Sequences for the different N-terminal, C-terminal, and Nuclease domains are provided above (See, SEQ ID NOs 1-4 and 22-30).

| TALEN | N-terminal domain | TALE repeat array | C-terminal domain | Nuclease domain |
|---|---|---|---|---|
| 55 | N2 | Sequence-specific | Truncated (28aa) | KKR |
| 56 | N3 | Sequence-specific | Canonical | Homodimeric |
| 57 | N3 | Sequence-specific | Canonical | EL |
| 58 | N3 | Sequence-specific | Canonical | KK |
| 59 | N3 | Sequence-specific | Canonical | ELD |
| 60 | N3 | Sequence-specific | Canonical | KKR |
| 61 | N3 | Sequence-specific | Q3 | Homodimeric |
| 62 | N3 | Sequence-specific | Q3 | EL |
| 63 | N3 | Sequence-specific | Q3 | KK |
| 64 | N3 | Sequence-specific | Q3 | ELD |
| 65 | N3 | Sequence-specific | Q3 | KKR |
| 66 | N3 | Sequence-specific | Q7 | Homodimeric |
| 67 | N3 | Sequence-specific | Q7 | EL |
| 68 | N3 | Sequence-specific | Q7 | KK |
| 69 | N3 | Sequence-specific | Q7 | ELD |
| 70 | N3 | Sequence-specific | Q7 | KKR |
| 71 | N3 | Sequence-specific | Truncated (28aa) | Homodimeric |
| 72 | N3 | Sequence-specific | Truncated (28aa) | EL |
| 73 | N3 | Sequence-specific | Truncated (28aa) | KK |
| 74 | N3 | Sequence-specific | Truncated (28aa) | ELD |
| 75 | N3 | Sequence-specific | Truncated (28aa) | KKR |
| 76 | Canonical | Sequence-specific | Canonical | EL |
| 77 | Canonical | Sequence-specific | Canonical | KK |
| 78 | Canonical | Sequence-specific | Canonical | ELD |
| 79 | Canonical | Sequence-specific | Canonical | KKR |
| 80 | Canonical | Sequence-specific | Truncated (28aa) | Homodimeric |
| 81 | Canonical | Sequence-specific | Truncated (28aa) | EL |
| 82 | Canonical | Sequence-specific | Truncated (28aa) | KK |
| 83 | Canonical | Sequence-specific | Truncated (28aa) | ELD |
| 84 | Canonical | Sequence-specific | Truncated (28aa) | KKR |

It will be understood by those of skill in the art that the exemplary sequences provided herein are for illustration purposes only and are not intended to limit the scope of the present disclosure. The disclosure also embraces the use of each of the inventive TALEN domains, e.g., the modified N-terminal domains, C-terminal domains, and nuclease domains described herein, in the context of other TALEN sequences, e.g., other modified or unmodified TALEN structures. Additional sequences satisfying the described principles and parameters that are useful in accordance to aspects of this disclosure will be apparent to the skilled artisan.

In some embodiments, the TALEN provided is a monomer. In some embodiments, the TALEN monomer can dimerize with another TALEN monomer to form a TALEN dimer. In some embodiments the formed dimer is a homodimer. In some embodiments, the dimer is a heterodimer.

In some embodiments, TALENs provided herein cleave their target sites with high specificity. For example, in some embodiments an improved TALEN is provided that has been engineered to cleave a desired target site within a genome while binding and/or cleaving less than 1, less than 2, less than 3, less than 4, less than 5, less than 6, less than 7, less than 8, less than 9 or less than 10 off-target sites at a concentration effective for the nuclease to cut its intended target site. In some embodiments, a TALEN is provided that has been engineered to cleave a desired unique target site that has been selected to differ from any other site within a genome by at least 3, at least 4, at least 5, at least 6, at least 7, at least 8, at least 9, or at least 10 nucleotide residues.

Some aspects of this disclosure provide nucleic acids encoding the TALENs provided herein. For example, nucleic acids are provided herein that encode the TALENs described in Table 1. In some embodiments, the nucleic acids encoding the TALEN are under the control of a heterologous promoter. In some embodiments, the encoding nucleic acids are included in an expression construct, e.g., a plasmid, a viral vector, or a linear expression construct. In some embodiments, the nucleic acid or expression construct is in a cell, tissue, or organism.

The map of an exemplary nucleic acid encoding a TALEN provided herein is illustrated in FIG. 19. An exemplary sequence of such a nucleic acid is provided below. It will be understood by those of skill in the art that the maps and sequences provided herein are exemplary and do not limit the scope of this disclosure.

As described elsewhere herein, TALENs, including the improved TALENs provided by this disclosure, can be engineered to bind (and cleave) virtually any nucleic acid sequence based on the sequence-specific TALE repeat array employed. In some embodiments, an improved TALEN provided herein binds a target sequence within a gene known to be associated with a disease or disorder. In some embodiments, TALENs provided herein may be used for therapeutic purposes. For example, in some embodiments, TALENs provided herein may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc. In some embodiments, the TALEN cleaves the target sequence upon dimerization. In some embodiments, a TALEN provided herein cleaves a target site within an allele that is associated with a disease or disorder. In some embodiments, the TALEN cleaves a target site the cleavage of which results in the treatment or prevention of a disease or disorder. In some embodiments, the disease is HIV/AIDS. In some embodiments, the disease is a proliferative disease. In some embodiments, the TALEN binds a CCR5 target sequence (e.g., a CCR5 sequence associated with HIV). In some embodiments, the TALEN binds an ATM target sequence (e.g., an ATM target sequence associated with ataxia telangiectasia). In some embodiments, the TALEN binds a VEGFA target sequence (e.g., a VEGFA sequence associated with a proliferative disease). In some embodiments, the TALEN binds a CFTR target sequence (e.g., a CFTR sequence associated with cystic fibrosis). In some embodiments, the TALEN binds a dystrophin target sequence (e.g., a dystrophin gene sequence associated with Duchenne muscular dystrophy). In some embodiments, the TALEN binds a target sequence associated with haemochromatosis, haemophilia, Charcot-Marie-Tooth disease, neurofibromatosis, phenylketonuria, polycystic kidney disease, sickle-cell disease, or Tay-Sachs disease. Suitable target genes, e.g., genes causing the listed diseases, are known to those of skill in the art. Additional genes and gene sequences associated with a disease or disorder will be apparent to those of skill in the art.

Some aspects of this disclosure provide isolated TALE effector domains, e.g., N- and C-terminal TALE effector domains, with decreased non-specific nucleic acid binding activity as compared to previously used TALE effector domains. The isolated TALE effector domains provided herein can be used in the context of suitable TALE effector molecules, e.g., TALE nucleases, TALE transcriptional activators, TALE transcriptional repressors, TALE recombinases, and TALE epigenome modification enzymes. Additional suitable TALE effectors in the context of which the isolated TALE domains can be used will be apparent to those of skill in the art based on this disclosure. In general, the isolated N- and C-terminal domains provided herein are engineered to optimize, e.g., minimize, excess binding energy conferred by amino acid residues that are positively charged (cationic) at physiological pH. Some of the improved N-terminal or C-terminal TALE domains provided herein have a decreased net charge and/or a decreased binding energy for binding a target nucleic acid sequence as compared to the respective canonical TALE domains. When used as part of a TALE effector molecule, e.g., a TALE nuclease, TALE transcriptional activator, TALE transcriptional repressor, TALE recombinase, or TALE epigenome modification enzyme, this decrease in charge leads to a decrease in off-target binding via the modified N-terminal and C-terminal domain(s). The portion of target recognition and binding, thus, is more narrowly confined to the specific recognition and binding activity of the TALE repeat array, as explained in more detail elsewhere herein. The resulting TALE effector molecule, thus, exhibits an increase in the specificity of binding and, in turn, in the specificity of the respective effect of the TALE effector (e.g., cleaving the target site by a TALE nuclease, activation of a target gene by a TALE transcriptional activator, repression of expression of a target gene by a TALE transcriptional repressor, recombination of a target sequence by a TALE recombinase, or epigenetic modification of a target sequence by a TALE epigenome modification enzyme) as compared to TALE effector molecules using unmodified domains.

In some embodiments, an isolated N-terminal TALE domain is provided in which the net charge is less than the net charge of the canonical N-terminal domain (SEQ ID NO: 1). In some embodiments, an isolated C-terminal TALE domain is provided in which the net charge is less than the net charge of the canonical C-terminal domain (SEQ ID NO: 22). In some embodiments, an isolated N-terminal TALE domain is provided in which the binding energy to a target nucleic acid molecule is less than the binding energy of the canonical N-terminal domain (SEQ ID NO: 1). In some embodiments, an isolated C-terminal TALE domain is provided in which the binding energy to a target nucleic acid molecule is less than the binding energy of the canonical C-terminal domain (SEQ ID NO: 22). In some embodiments, the binding energy of the isolated N-terminal and/or of the isolated C-terminal TALE domain provided herein is decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or at least 99%.

In some embodiments, the canonical N-terminal domain and/or the canonical C-terminal domain is modified to replace an amino acid residue that is positively charged at physiological pH with an amino acid residue that is not charged or is negatively charged to arrive at the isolated N-terminal and/or C-terminal domain provided herein. In some embodiments, the modification includes the replacement of a positively charged residue with a negatively charged residue. In some embodiments, the modification includes the replacement of a positively charged residue with a neutral (uncharged) residue. In some embodiments, the modification includes the replacement of a positively charged residue with a residue having no charge or a negative charge. In some embodiments, the net charge of the isolated N-terminal domain and/or of the isolated C-terminal domain provided herein is less than or equal to +10, less than or equal to +9, less than or equal to +8, less than or equal to +7, less than or equal to +6, less than or equal to +5, less than or equal to +4, less than or equal to +3, less than or equal to +2, less than or equal to +1, less than or equal to 0, less than or equal to −1, less than or equal to −2, less than or equal to −3, less than or equal to −4, or less than or equal to −5, or less than or equal to −10 at physiological pH. In some embodiments, the net charge of the isolated N-terminal domain and/or of the isolated C-terminal domain is between +5 and −5, between +2 and −7, between 0 and −5, between 0 and −10, between −1 and −10, or between −2 and −15 at physiological pH. In some embodiments, the net charge of the isolated N-terminal TALE domain and/or of the isolated C-terminal TALE domain is negative. In some embodiments, an isolated N-terminal TALE domain and an isolated C-terminal TALE domain are provided and the net charge of the isolated N-terminal TALE domain and of the isolated C-terminal TALE domain, together, is negative. In some embodiments, the net charge of the isolated N-terminal TALE domain and/or of the isolated C-terminal TALE domain is neutral or slightly positive (e.g., less than +2 or less than +1 at physiological pH). In some embodiments, an isolated N-terminal TALE domain and an isolated C-terminal TALE domain are provided, and the net charge of the isolated N-terminal TALE domain and of the isolated C-terminal TALE domain, together, is neutral or slightly positive (e.g., less than +2 or less than +1 at physiological pH).

In some embodiments, the isolated N-terminal domain and/or the isolated C-terminal domain provided herein comprise(s) an amino acid sequence that differs from the respective canonical domain sequence in that at least one cationic amino acid residue of the canonical domain sequence is replaced with an amino acid residue that exhibits no charge or a negative charge at physiological pH. In some embodiments, at least 1, at least 2, at least 3, at least 4, at least 5, at least 6, at least 7, at least 8, at least 9, at least 10, at least 11, at least 12, at least 13, at least 14, or at least 15 cationic amino acid(s) is/are replaced with an amino acid residue that exhibits no charge or a negative charge at physiological pH in the isolated N-terminal domain and/or in the isolated C-terminal domain provided. In some embodiments, 1, 2, 3, 4, 5, 6, 7, 8, 9, 10, 11, 12, 13, 14, 15 cationic amino acid(s) is/are replaced with an amino acid residue that exhibits no charge or a negative charge at physiological pH in the isolated N-terminal domain and/or in the isolated C-terminal domain.

In some embodiments, the cationic amino acid residue is arginine (R), lysine (K), or histidine (H). In some embodiments, the cationic amino acid residue is R or H. In some embodiments, the amino acid residue that exhibits no charge or a negative charge at physiological pH is glutamine (Q), glycine (G), asparagine (N), threonine (T), serine (S), aspartic acid (D), or glutamic acid (E). In some embodiments, the amino acid residue that exhibits no charge or a negative charge at physiological pH is Q. In some embodiments, at least one lysine or arginine residue is replaced with a glutamine residue in the isolated N-terminal domain and/or in the isolated C-terminal domain.

In some embodiments, an isolated C-terminal TALE domain is provided herein that comprises one or more of the following amino acid replacements: K777Q, K778Q, K788Q, R789Q, R792Q, R793Q, R801Q. In some embodiments, the isolated C-terminal domain comprises two or more of the following amino acid replacements: K777Q, K778Q, K788Q, R789Q, R792Q, R793Q, R801Q. In some embodiments, the isolated C-terminal domain comprises three or more of the following amino acid replacements: K777Q, K778Q, K788Q, R789Q, R792Q, R793Q, R801Q. In some embodiments, the isolated C-terminal domain comprises four or more of the following amino acid replacements: K777Q, K778Q, K788Q, R789Q, R792Q, R793Q, R801Q. In some embodiments, the isolated C-terminal domain comprises five or more of the following amino acid replacements: K777Q, K778Q, K788Q, R789Q, R792Q, R793Q, R801Q. In some embodiments, the isolated C-terminal domain comprises six or more of the following amino acid replacements: K777Q, K778Q, K788Q, R789Q, R792Q, R793Q, R801Q. In some embodiments, the isolated C-terminal domain comprises all seven of the following amino acid replacements: K777Q, K778Q, K788Q, R789Q, R792Q, R793Q, R801Q. In some embodiments, the isolated C-terminal domain comprises a Q3 variant sequence (K788Q, R792Q, R801Q, see SEQ ID NO: 23). In some embodiments, the isolated C-terminal domain comprises a Q7 variant sequence (K777Q, K778Q, K788Q, R789Q, R792Q, R793Q, R801Q, see SEQ ID NO: 24).

In some embodiments, an isolated N-terminal TALE domain is provided that is a truncated version of the canonical N-terminal domain. In some embodiments, an isolated C-terminal TALE domain is provided that is a truncated version of the canonical C-terminal domain. In some embodiments, the truncated N-terminal domain and/or the truncated C-terminal domain comprises less than 90%, less than 80%, less than 70%, less than 60%, less than 50%, less than 40%, less than 30%, or less than 25% of the residues of the canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues. In some embodiments, an isolated N-terminal TALE domain and/or an isolated C-terminal domain is provided herein that is/are truncated and comprise(s) one or more amino acid replacement(s). In some embodiments, the isolated N-terminal TALE domains comprise an amino acid sequence as provided in any of SEQ ID NOs 2-5. In some embodiments, the isolated C-terminal TALE domains comprise an amino acid sequence as provided in any of SEQ ID NOs 23-25.

It will be apparent to those of skill in the art that the isolated C- and N-terminal TALE domains provided herein may be used in the context of any TALE effector molecule, e.g., as part of a TALE nuclease, a TALE transcriptional activator, a TALE transcriptional repressor, a TALE recombinase, a TALE epigenome modification enzyme, or any other suitable TALE effector molecule. In some embodiments, a TALE domain provided herein is used in the context of a TALE molecule comprising or consisting essentially of the following structure

[N-terminal domain]-[TALE repeat array]-[C-terminal domain]-[effector domain]

or

[effector domain]-[N-terminal domain]-[TALE repeat array]-[C-terminal domain], wherein the effector domain may, in some embodiments, be a nuclease domain, a transcriptional activator or repressor domain, a recombinase domain, or an epigenetic modification enzyme domain.

It will also be apparent to those of skill in the art that it is desirable, in some embodiments, to adjust the DNA spacer length in TALE effector molecules comprising such a spacer, when using a truncated domain, e.g., truncated C-terminal domain as provided herein, in order to accommodate the truncation.

Some aspects of this disclosure provide compositions comprising a TALEN provided herein, e.g., a TALEN monomer. In some embodiments, the composition comprises the TALEN monomer and a different TALEN monomer that can form a heterodimer with the TALEN, wherein the dimer exhibits nuclease activity.

In some embodiments, the TALEN is provided in a composition formulated for administration to a subject, e.g., to a human subject. For example, in some embodiments, a pharmaceutical composition is provided that comprises the TALEN and a pharmaceutically acceptable excipient. In some embodiments, the pharmaceutical composition is formulated for administration to a subject. In some embodiments, the pharmaceutical composition comprises an effective amount of the TALEN for cleaving a target sequence in a cell in the subject. In some embodiments, the TALEN binds a target sequence within a gene known to be associated with a disease or disorder and wherein the composition comprises an effective amount of the TALEN for alleviating a symptom associated with the disease or disorder.

For example, some embodiments provide pharmaceutical compositions comprising a TALEN as provided herein, or a nucleic acid encoding such a nuclease, and a pharmaceutically acceptable excipient. Pharmaceutical compositions may optionally comprise one or more additional therapeutically active substances.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a composition provided herein is administered to a subject, for example, to a human subject, in order to effect a targeted genomic modification within the subject. In some embodiments, cells are obtained from the subject and contacted with a nuclease or a nuclease-encoding nucleic acid ex vivo, and re-administered to the subject after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with no more than routine experimentation. Subjects to which administration of the pharmaceutical compositions is contemplated include, but are not limited to, humans and/or other primates; mammals, including, but not limited to, cattle, pigs, horses, sheep, cats, dogs, mice, and/or rats; and/or birds, including commercially relevant birds such as chickens, ducks, geese, and/or turkeys.

The scope of this disclosure embraces methods of using the TALENs provided herein. It will be apparent to those of skill in the art that the TALENs provided herein can be used in any method suitable for the application of TALENs, including, but not limited to, those methods and applications known in the art. Such methods may include TALEN-mediated cleavage of DNA, e.g., in the context of genome manipulations such as, for example, targeted gene knockout through non-homologous end joining (NHEJ) or targeted genomic sequence replacement through homology-directed repair (HDR) using an exogenous DNA template, respectively. The improved features of the TALENs provided herein, e.g., the improved specificity of some of the TALENs provided herein, will typically allow for such methods and applications to be carried out with greater efficiency. All methods and applications suitable for the use of TALENs, and performed with the TALENs provided herein, are contemplated and are within the scope of this disclosure. For example, the instant disclosure provides the use of the TALENs provided herein in any method suitable for the use of TALENs as described in Boch, Jens (February 2011). "TALEs of genome targeting". Nature Biotechnology 29 (2): 135-6. doi:10.1038/nbt.1767. PMID 21301438; Boch, Jens; et.al. (December 2009). "Breaking the Code of DNA Binding Specificity of TAL-Type III Effectors". Science 326 (5959): 1509-12. Bibcode:2009Sci . . . 326.1509B. doi: 10.1126/science.1178811. PMID 19933107; Moscou, Matthew J.; Adam J. Bogdanove (December 2009). "A Simple Cipher Governs DNA Recognition by TAL Effectors". Science 326 (5959): 1501. Bibcode:2009Sci . . . 326.1501M. doi:10.1126/science.1178817. PMID 19933106; Christian, Michelle; et.al. (October 2010). "Targeting DNA Double-Strand Breaks with TAL Effector Nucleases". Genetics 186 (2): 757-61. doi:10.1534/genetics.110.120717. PMC 2942870. PMID 20660643; Li, Ting; et.al. (August 2010). "TAL nucleases (TALNs): hybrid proteins composed of TAL effectors and FokI DNA-cleavage domain". Nucleic Acids Research 39: 1-14. doi:10.1093/nar/gkq704. PMC 3017587. PMID 20699274; Mahfouz, Magdy M.; et.al. (February 2010). "De novo-engineered transcription activator-like effector (TALE) hybrid nuclease with novel DNA binding specificity creates double-strand breaks". PNAS 108 (6): 2623-8. Bibcode:2011PNAS..108.2623M. doi:10.1073/pnas.1019533108. PMC 3038751. PMID 21262818; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research. doi:10.1093/nar/gkr218; Miller, Jeffrey; et.al. (February 2011). "A TALE nuclease architecture for efficient genome editing". Nature Biotechnology 29 (2): 143-8. doi:10.1038/nbt.1755. PMID 21179091; Hockemeyer, D.; Wang, H.; Kiani, S.; Lai, C. S.; Gao, Q.; Cassady, J. P.; Cost, G. J.; Zhang, L. et al. (2011). "Genetic engineering of human pluripotent cells using TALE nucleases". Nature Biotechnology 29 (8). doi:10.1038/nbt.1927; Wood, A. J.; Lo, T. -W.; Zeitler, B.; Pickle, C. S.; Ralston, E. J.; Lee, A. H.; Amora, R.; Miller, J. C. et al. (2011). "Targeted Genome Editing Across Species Using ZFNs and TALENs". Science 333 (6040): 307. doi:10.1126/science.1207773. PMC 3489282. PMID 21700836; Tesson, L.; Usal, C.; Ménoret, S. V.; Leung, E.; Niles, B. J.; Remy, S. V.; Santiago, Y.; Vincent, A. I. et al. (2011). "Knockout rats generated by embryo microinjection of TALENs". Nature Biotechnology 29 (8): 695. doi:10.1038/nbt.1940; Huang, P.; Xiao, A.; Zhou, M.; Zhu, Z.; Lin, S.; Zhang, B. (2011). "Heritable gene targeting in zebrafish using customized TALENs". Nature Biotechnology 29 (8): 699. doi:10.1038/nbt.1939; Doyon, Y.; Vo, T. D.; Mendel, M. C.; Greenberg, S. G.; Wang, J.; Xia, D. F.; Miller, J. C.; Urnov, F. D. et al. (2010). "Enhancing zinc-finger-nuclease activity with improved obligate heterodimeric architectures". Nature Methods 8 (1): 74-79. doi:10.1038/nmeth.1539. PMID 21131970; Szczepek, M.; Brondani, V.; Büchel, J.; Serrano, L.; Segal, D. J.; Cathomen, T. (2007). "Structure-based redesign of the dimerization interface reduces the toxicity of zinc-finger nucleases". Nature Biotechnology 25 (7): 786. doi:10.1038/nbt1317. PMID 17603476; Guo, J.; Gaj, T.; Barbas Iii, C. F. (2010). "Directed Evolution of an Enhanced and Highly Efficient FokI Cleavage Domain for Zinc Finger Nucleases". Journal of Molecular Biology 400 (1): 96. doi:10.1016/j.jmb.2010.04.060. PMC 2885538. PMID 20447404; Mussolino, C.; Morbitzer, R.; Lutge, F.; Dannemann, N.; Lahaye, T.; Cathomen, T. (2011). "A novel TALE nuclease scaffold enables high genome editing activity in combination with low toxicity". Nucleic Acids Research. doi:10.1093/nar/gkr597; Zhang, Feng; et.al. (February 2011). "Efficient construction of sequence-specific TAL effectors for modulating mammalian transcription". Nature Biotechnology 29 (2): 149-53. doi:10.1038/nbt.1775. PMC 3084533. PMID 21248753; Morbitzer, R.; Elsaesser, J.; Hausner, J.; Lahaye, T. (2011). "Assembly of custom TALE-type DNA binding domains by modular cloning". Nucleic Acids Research. doi:10.1093/nar/gkr151; Li, T.; Huang, S.;

Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research. doi:10.1093/nar/gkr188; Geißler, R.; Scholze, H.; Hahn, S.; Streubel, J.; Bonas, U.; Behrens, S. E.; Boch, J. (2011). "Transcriptional Activators of Human Genes with Programmable DNA-Specificity". In Shiu, Shin-Han. PLoS ONE 6 (5): e19509. doi:10.1371/journal.pone.0019509; Weber, E.; Gruetzner, R.; Werner, S.; Engler, C.; Marillonnet, S. (2011). "Assembly of Designer TAL Effectors by Golden Gate Cloning". In Bendahmane, Mohammed. PLoS ONE 6 (5): e19722. doi:10.1371/journal.pone.0019722; Sander et al. Targeted gene disruption in somatic zebrafish cells using engineered TALENs. Nature Biotechnology Vol 29:697-98 (5 Aug. 2011) Sander, J. D.; Cade, L.; Khayter, C.; Reyon, D.; Peterson, R. T.; Joung, J. K.; Yeh, J. R. J. (2011). "Targeted gene disruption in somatic zebrafish cells using engineered TALENs". Nature Biotechnology 29 (8): 697. doi:10.1038/nbt.1934; the entire contents of each of which are incorporated herein by reference.

In some embodiments, the TALENs, TALEN domains, TALEN-encoding or TALEN domain-encoding nucleic acids, compositions, and reagents described herein are isolated. In some embodiments, the TALENs, TALEN domains, TALEN-encoding or TALEN domain-encoding nucleic acids, compositions, and reagents described herein are purified, e.g., at least 60%, at least 70%, at least 80%, at least 90%, or at least 95% pure.

Some aspects of this disclosure provide methods of cleaving a target sequence in a nucleic acid molecule using an inventive TALEN as described herein. In some embodiments, the method comprises contacting a nucleic acid molecule comprising the target sequence with a TALEN binding the target sequence under conditions suitable for the TALEN to bind and cleave the target sequence. In some embodiments, the TALEN is provided as a monomer. In some embodiments, the inventive TALEN monomer is provided in a composition comprising a different TALEN monomer that can dimerize with the first inventive TALEN monomer to form a heterodimer having nuclease activity. In some embodiments, the inventive TALEN is provided in a pharmaceutical composition. In some embodiments, the target sequence is in a cell. In some embodiments, the target sequence is in the genome of a cell. In some embodiments, the target sequence is in a subject. In some embodiments, the method comprises administering a composition, e.g., a pharmaceutical composition, comprising the TALEN to the subject in an amount sufficient for the TALEN to bind and cleave the target site.

Some aspects of this disclosure provide methods of preparing engineered TALENs. In some embodiments, the method comprises replacing at least one amino acid in the canonical N-terminal TALEN domain and/or the canonical C-terminal TALEN domain with an amino acid having no charge or a negative charge at physiological pH; and/or truncating the N-terminal TALEN domain and/or the C-terminal TALEN domain to remove a positively charged fragment; thus generating an engineered TALEN having an N-terminal domain and/or a C-terminal domain of decreased net charge. In some embodiments, the at least one amino acid being replaced comprises a cationic amino acid or an amino acid having a positive charge at physiological pH. In some embodiments, the amino acid replacing the at least one amino acid is a cationic amino acid or a neutral amino acid. In some embodiments, the truncated N-terminal TALEN domain and/or the truncated C-terminal TALEN domain comprises less than 90%, less than 80%, less than 70%, less than 60%, less than 50%, less than 40%, less than 30%, or less than 25% of the residues of the respective canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues.

In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 amino acid residues. In some embodiments, the method comprises replacing at least 2, at least 3, at least 4, at least 5, at least 6, at least 7, at least 8, at least 9, at least 10, at least 11, at least 12, at least 13, at least 14, or at least 15 amino acids in the canonical N-terminal TALEN domain and/or in the canonical C-terminal TALEN domain with an amino acid having no charge or a negative charge at physiological pH. In some embodiments, the amino acid being replaced is arginine (R) or lysine (K). In some embodiments, the amino acid residue having no charge or a negative charge at physiological pH is glutamine (Q) or glycine (G). In some embodiments, the method comprises replacing at least one lysine or arginine residue with a glutamine residue.

In some embodiments, the improved TALENs provided herein are designed and/or generated by recombinant technology. In some embodiments, designing and/or generating comprises designing a TALE repeat array that specifically binds a desired target sequence, or a half-site thereof.

Some aspects of this disclosure provide kits comprising an engineered TALEN as provided herein, or a composition (e.g., a pharmaceutical composition) comprising such a TALEN. In some embodiments, the kit comprises an excipient and instructions for contacting the TALEN with the excipient to generate a composition suitable for contacting a nucleic acid with the TALEN. In some embodiments, the excipient is a pharmaceutically acceptable excipient.

Typically, the kit will comprise a container housing the components of the kit, as well as written instructions stating how the components of the kit should be stored and used.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1

Materials and Methods

Oligonucleotides, PCR and DNA Purification

All oligonucleotides were purchased from Integrated DNA Technologies (IDT). Oligonucleotide sequences are listed in Table 10. PCR was performed with 0.4 µL of 2 U/µL Phusion Hot Start II DNA polymerase (Thermo-Fisher) in 50 µL with 1×HF Buffer, 0.2 mM dNTP mix (0.2 mM dATP, 0.2 mM dCTP, 0.2 mM dGTP, 0.2 mM dTTP) (NEB), 0.5 µM to 1 µM of each primer and a program of: 98° C., 1 min; 35 cycles of [98° C., 15 s; 62° C., 15 s; 72° C., 1 min] unless otherwise noted. Many DNA reactions were purified with a QIAquick PCR Purification Kit (Qiagen) referred to below as Q-column purification or MinElute PCR Purification Kit (Qiagen) referred to below as M-column purification.

TALEN Construction

The canonical TALEN plasmids were constructed by the FLASH method[12] with each TALEN targeting 10-18 base pairs. N-terminal mutations were cloned by PCR with Q5 Hot Start Master Mix (NEB) [98° C., 22 s; 62° C., 15 s; 72° C., 7 min]) using phosphorylated TAL-N1fwd (for N1), phosphorylated TAL-N2fwd (for N2), or phosphorylated TAL-N3fwd (for N3) and phosphorylated TALNrev as primers. 1 µL DpnI (NEB) was added and the reaction was incubated at 37° C. for 30 min then M-column purified. ~25 ng of eluted DNA was blunt-end ligated intramolecularly in 10 µL 2× Quick Ligase Buffer, 1 µL of Quick Ligase (NEB) in a total volume of 20 µL at room temperature (~21° C.) for 15 min. 1 µL of this ligation reaction was transformed into Top10 chemically competent cells (Invitrogen). C-terminal domain mutations were cloned by PCR using TAL-Cifwd and TAL-Cirev primers, then Q-column purified. ~1 ng of this eluted DNA was used as the template for PCR with TALCifwd and either TAL-Q3 (for Q3) or TAL-Q7 (for Q7) for primers, then Q-column purified. ~1 ng of this eluted DNA was used as the template for PCR with TAL-Cifwd and TAL-Ciirev for primers, then Qcolumn purified. ~1 µg of this DNA fragment was digested with HpaI and BamHI in 1× NEBuffer 4 and cloned into ~2 µg of desired TALEN plasmid pre-digested with HpaI and BamHI.

In Vitro TALEN Expression

TALEN proteins, all containing a 3×FLAG tag, were expressed by in vitro transcription/translation. 800 ng of TALEN-encoding plasmid or no plasmid ("empty lysate" control) was added to an in vitro transcription/translation reaction using the TNT® Quick Coupled Transcription/Translation System, T7 Variant (Promega) in a final volume of 20 µL at 30° C. for 1.5 h. Western blots were used to visualize protein using the anti-FLAG M2 monoclonal antibody (Sigma-Aldrich). TALEN concentrations were calculated by comparison to standard curve of 1 ng to 16 ng N-terminally FLAG-tagged bacterial alkaline phosphatase (Sigma-Aldrich).

In Vitro Selection for DNA Cleavage

Pre-selection libraries were prepared with 10 pmol of oligo libraries containing partially randomized target half-site sequences (CCR5A, ATM, or CCR5B) and fully randomized 10- to 24-bp spacer sequences (Table 10). Oligonucleotide libraries were separately circularized by incubation with 100 units of CircLigase II ssDNA Ligase (Epicentre) in 1× CircLigase II Reaction Buffer (33 mM Tris-acetate, 66 mM potassium acetate, 0.5 mM dithiothreitol, pH 7.5) supplemented with 2.5 mM MnCl2 in 20 µL total for 16 h at 60° C. then incubated at 80° C. for 10 min. 2.5 µL of each circularization reaction was used as a substrate for rolling-circle amplification at 30° C. for 16 h in a 50-µL reaction using the Illustra TempliPhi 100 Amplification Kit (GE Healthcare). The resulting concatemerized libraries were quantified with Quant-iT™ PicoGreen® dsDNA Kit (Invitrogen) and libraries with different spacer lengths were combined in an equimolar ratio.

For selections on the CCR5B sequence libraries, 500 ng of pre-selection library was digested for 2 h at 37° C. in 1× NEBuffer 3 with in vitro transcribed/translated TALEN plus empty lysate (30 µL total). For all CCR5B TALENs, in vitro transcribed/translated TALEN concentrations were quantified by Western blot (during the blot, TALENs were stored for 16 h at 4° C.) and then TALEN was added to 40 nM final concentration per monomer. For selections on CCR5A and ATM sequence libraries, the combined pre-selection library was further purified in a 300,000 MWCO spin column (Sartorius) with three 500-µL washes in 1× NEBuffer 3. 125 ng pre-selection library was digested for 30 min at 37° C. in 1× NEBuffer 3 with a total 24 µL of fresh in vitro transcribed/translated TALENs and empty lysate. For all CCR5A and ATM TALENs, 6 µL of in vitro transcription/translation left TALEN and 6 µL of right TALEN were used, corresponding to a final concentration in a cleavage reaction of 16 nM ±2 nM or 12 nM ±1.5 nM for CC5A or ATM TALENs, respectively. These TALEN concentrations were quantified by Western blot performed in parallel with digestion.

For all selections, the TALEN-digested library was incubated with 1 µL of 100 µg/µL RNase A (Qiagen) for 2 min and then Q-column purified. 50 µL of purified DNA was incubated with 3 µL of 10 mM dNTP mix (10 mM dATP, 10 mM dCTP, 10 mM dGTP, 10 mM dTTP) (NEB), 6 µL of 10× NEBuffer 2, and 1 µL of 5 U/µL Klenow Fragment DNA Polymerase (NEB) for 30 min at room temperature and Q-column purified. 50 µL of the eluted DNA was ligated with 2 pmol of heated and cooled #1 adapters containing barcodes corresponding to each sample (selections with different TALEN concentrations or constructs) (Table 10A). Ligation was performed in 1× T4 DNA Ligase Buffer (50 mM Tris-HCl, 10 mM MgCl2, 1 mM ATP, 10 mM DTT, pH 7.5) with 1 µL of 400 U/µL T4 DNA ligase (NEB) in 60 µL total volume for 16 h at room temperature, then Q-column purified.

6 µL of the eluted DNA was amplified by PCR in 150 µL total reaction volume (divided into 3×50 µL reactions) for 14 to 22 cycles using the #2A adapter primers in Table 10A. The PCR products were purified by Q-column. Each DNA sample was quantified with Quant-iT™ PicoGreen® dsDNA Kit (Invitrogen) and then pooled into an equimolar mixture. 500 ng of pooled DNA was run a 5% TBE 18-well Criterion PAGE gel (BioRad) for 30 min at 200 V and DNAs of length ~230 bp (corresponding to 1.5 target site repeats plus adapter sequences) were isolated and purified by Qcolumn. ~2 ng of eluted DNA was amplified by PCR for 5 to 8 cycles with #2B adapter primers (Table 10A) and purified by M-column.

10 µL of eluted DNA was purified using 12 µL of AMPure XP beads (Agencourt) and quantified with an Illumina/Universal Library Quantification Kit (Kapa Biosystems). DNA was prepared for high-throughput DNA sequencing according to Illumina instructions and sequenced using a MiSeq DNA Sequencer (Illumina) using a 12 pM final solution and 156-bp paired-end reads. To prepare the pre-selection library for sequencing, the pre-selection library was digested with 1 µL to 4 µL of appropriate restriction enzyme (CCR5A=Tsp45I, ATM=Acc65I, CCR5B=AvaI (NEB)) for 1 h at 37° C. then ligated as described above with 2 pmol of heated and cooled #1 library adapters (Table 10A). Pre-selection library DNA was prepared as described above using #2A library adapter primers and #2B library adapter primers in place of #2A adapter primers and #2B adapter primers, respectively (Table 10A). The resulting pre-selection library DNA was sequenced together with the TALEN-digested samples.

Discrete In Vitro TALEN Cleavage Assays

Discrete DNA substrates for TALEN digestion were constructed by combining pairs of oligonucleotides as specified in Table 9B with restriction cloning14 into pUC19 (NEB). Corresponding cloned plasmids were amplified by PCR (59° C. annealing for 15 s) for 24 cycles with pUC19Ofwd and pUC19Orev primers (Table 10B) and Q-column purified. 50 ng of amplified DNAs were digested in 1× NEBuffer 3 with 3 µL each of in vitro transcribed/translated TALEN left and right monomers (corresponding to a ~16 nM to ~12 nM final TALEN concentration), and 6 µL of empty lysate in a total reaction volume of 120 µL. The digestion reaction was incubated for 30 min at 37° C., then incubated with 1 µL of 100 µg/µL RNase A (Qiagen) for 2 min and purified by M-column. The entire 10 µL of eluted DNA with glycerol added to 15% was analyzed on a 5% TBE 18-well Criterion PAGE gel (Bio-Rad) for 45 min at 200 V, then stained with 1× SYBR Gold (Invitrogen) for 10 min. Bands were visualized and quantified on an AlphaImager HP (Alpha Innotech).

Cellular TALEN Cleavage Assays

TALENs were cloned into mammalian expression vectors12 and the resulting TALEN vectors transfected into U2OS-EGFP cells as previously described.[12] Genomic DNA was isolated after 2 days as previously described.[12] For each assay, 50 ng of isolated genomic DNA was amplified by PCR [98° C., 15 s 67.5° C., 15 s; 72° C., 22 s] for 35 cycles with pairs of primers with or without 4% DMSO as specified in Table 10C. The relative DNA content of the PCR reaction for each genomic site was quantified with Quant-iT™ PicoGreen® dsDNA Kit (Invitrogen) and then pooled into an equimolar mixture, keeping no-TALEN and all TALEN-treated samples separate. DNA corresponding to 150 to 350 bp was purified by PAGE as described above.

44 µL of eluted DNA was incubated with 5 µL of 1× T4 DNA Ligase Buffer and 1 µL of 10 U/µL Polynucleotide kinase (NEB) for 30 min at 37° C. and Q-column purified. 43 µL of eluted DNA was incubated with 1 µL of 10 mM dATP (NEB), 5 µL of 10× NEBuffer 2, and 1 µL of 5 U/µL DNA Klenow Fragment (3'→5' exo-) (NEB) for 30 min at 37° C. and purified by M-column. 10 µL of eluted DNA was ligated as above with 10 pmol of heated and cooled G (genomic) adapters (Table 10A). 8 µL of eluted DNA was amplified by PCR for 6 to 8 cycles with G-B primers containing barcodes corresponding to each sample. Each sample DNA was quantified with Quant-iT™ PicoGreen® dsDNA Kit (Invitrogen) and then pooled into an equimolar mixture. The combined DNA was subjected to high throughput sequencing using a MiSeq as described above.

Data Analysis

Illumina sequencing reads were filtered and parsed with scripts written in Unix Bash as outlined in the Algorithms section. The source code is available upon request. Specificity scores were calculated as previously described.[14] Statistical analysis on the distribution of number of mutations in various TALEN selections in Table 3 was performed as previously described.[14] Statistical analysis of modified sites in Table 7 was performed as previously described.[14]

Algorithms

All scripts were written in bash or MATLAB.

Computational Filtering of Pre-selection Sequences and Selected Sequences

For Pre-selection Sequences
1) Search for 16 bp constant sequence (CCR5A=CGTCACGCTCACCACT (SEQ ID NO: 166), CCR5B=CCTCGGGACTCCACGCT (SEQ ID NO: 167), ATM=GGTACCCCACTCCGCGT (SEQ ID NO: 168)) immediately after first 4 bases read (random bases), accepting only sequences with the 16 bp constant sequence allowing for one mutation.
2) Search for 9 bp final sequence at a position at least the minimum possible full site length away and up to the max full site length away from constant sequence to confirm the presence of a full site, accept only sequences with this 9 bp final sequence. (Final sequence: CCR5A=CGTCACGCT, CCR5B=CCTCGGGAC, ATM=GGTACGTGC)
3) Search for best instances of each half site in the full site, accept any sequences with proper left and right half-site order of left then right.
4) Determine DNA spacer sequence between the two half sites, the single flanking nucleotide to left of the left half-site and single flanking nucleotide to right of the right half-site (sequence between half sites and constant sequences).
5) Filter by sequencing read quality scores, accepting sequences with quality scores of A or better across three fourths of the half site positions.

For Selected Sequences
1) Output to separate files all sequence reads and position quality scores of all sequences starting with correct 5 bp barcodes corresponding to different selection conditions.
2) Search for the initial 16 bp sequence immediately after the 5 bp barcode repeated at a position at least the minimum possible full site length away and up to the max full site length away from initial sequence to confirm the presence of a full site with repeated sequence, accept only sequences with a 16 bp repeat allowing for 1 mutation.
3) Search for 16 bp constant sequence within the full site, accept only sequences with a constant sequence allowing for one mutation. Parse sequence to start with constant sequence plus 5' sequence to second instance of repeated sequence then initial sequence after barcode to constant sequence resulting in constant sequences sandwiching the equivalent of one full site:
CONSTANT-LFLANK-LHS-SPACER-RHS-RFLANK-CONSTANT
LFLANK=Left Flank Sequence (designed as a single random base)
LHS=Left Half Site Sequence
RHS=Right Half Site Sequence
RFLANK=Right Flank Sequence (designed as a single random base)
CONSTANT=Constant Sequence (CCR5A=CGTCACGCTCACCACT (SEQ ID NO: 166), CCR5B=CCTCGGGACTCCACGCT (SEQ ID NO: 167), ATM=GGTACCCCACTCCGCGT (SEQ ID NO: 168))
4) Search for best instances of each half site in the full site, accept any sequences with proper left and right half-site order of left then right.
5) With half site positions determine corresponding spacer (sequence between the two half sites), left flank and right flank sequences (sequence between half sites and constant sequences).

6) Determine sequence end by taking sequence from the start of read after the 5 bp barcode sequence to the beginning of the constant sequence.

SEQUENCESTART-RHS-RFLANK-CONSTANT

7) Filter by sequencing read quality scores, accepting sequences with quality scores of A or better across three fourths of the half site positions.
8) Selected sequences were filtered by sequence end, by accepting only sequences with sequence ends in the spacer that were 2.5-fold more abundant than the amount of sequence end background calculated as the mean of the number of sequences with ends zero to five base pairs into each half-site from the spacer side (sequence end background number was calculated for both half sites with the closest half site to the sequence end utilized as sequence end background for comparison).

Computational Search for Genomic Off-Target Sites Related to the CCR5B Target Site 1) The Patmatch program[39] was used to search the human genome (GRCh37/hg19 build) for pattern sequences as follows: CCR5B left half-site sequence (L16, L13 or L10) NNNNNNNNN . . . CCR5B right half-site sequence (R16, R13 or R10)[M,0,0] where number of Ns varied from 12 to 25 and M (indicating mutations allowed) varied from 0 to 14.
2) The number of output off-target sites were de-cumulated since the program outputs all sequences with X or fewer mutations, resulting in the number of off-target sites in the human genome that are a specific number of mutations away from the target site.

Identification of Indels in Sequences of Genomic Sites

1) For each sequence the primer sequence was used to identify the genomic site.
2) Sequences containing the reference genomic sequence corresponding to 8 bp to the left of the target site and reference genomic sequence 8 bp (or 6 bp for genomic sites at the very end of sequencing reads) to the right of the full target site were considered target site sequences.
3) Any target site sequences corresponding to the same size as the reference genomic site were considered unmodified and any sequences not the reference size were aligned with ClustalW[40] to the reference genomic site.
4) Aligned sequences with more than two insertions or two deletions in the DNA spacer sequence between the two half-site sequences were considered indels.

Results

Specificity Profiling of TALENs targeting CCR5 and ATM

We profiled the specificity of 41 heterodimeric TALEN pairs (hereafter referred to as TALENs) in total, comprising TALENs targeting left and right half-sites of various lengths and TALENs with different domain variants. Each of the 41 TALENs was designed to target one of three distinct sequences, which we refer to as CCR5A, CCR5B, or ATM, in two different human genes, CCR5 and ATM (FIG. 7). We used an improved version of a previously described in vitro selection method[14] with modifications that increase the throughput and sensitivity of the selection (FIG. 1B).

Briefly, preselection libraries of >$10^{12}$ DNA sequences each were digested with 3 nM to 40 nM of an in vitro translated TALEN. These concentrations correspond to ~20 to ~200 dimeric TALEN molecules per human cell nucleus,[21] a relatively low level of cellular protein expression.[22,23] Cleaved library members contained a free 5' monophosphate that was captured by adapter ligation and isolated by gel purification (FIG. 1B). In the control sample, all members of the pre-selection library were cleaved by a restriction endonuclease at a constant sequence to enable them to be captured by adapter ligation and isolated by gel purification. High-throughput sequencing of TALEN-treated or control samples surviving this selection process and computational analysis revealed the abundance of all TALEN-cleaved sequences as well as the abundance of the corresponding sequences before selection. The enrichment value for each library member surviving selection was calculated by dividing its post-selection sequence abundance by its preselection abundance. The pre-selection DNA libraries were sufficiently large that they each contain, in theory, at least ten copies of all possible DNA sequences with six or fewer mutations relative to the on-target sequence.

For all 41 TALENs tested, the DNA that survived the selection contained significantly fewer mean mutations in the targeted half-sites than were present in the pre-selection libraries (Table 3 and 4). For example, the mean number of mutations in DNA sequences surviving selection after treatment with TALENs targeting 18-bp left and right half-sites was 4.06 for CCR5A and 3.18 for ATM sequences, respectively, compared to 7.54 and 6.82 mutations in the corresponding pre-selection libraries (FIGS. 2A and 2B). For all selections, the on-target sequences were enriched by 8- to 640-fold (Table 5). To validate our selection results in vitro, we assayed the ability of the CCR5B TALENs targeting 13-bp left and right half-sites (L13+R13) to cleave each of 16 diverse off-target substrates (FIGS. 2E and 2F). The resulting discrete in vitro cleavage efficiencies correlated well with the observed enrichment values (FIG. 2G).

To determine the specificity at each position in the TALEN target site for all four possible base pairs, a specificity score was calculated as the difference between preselection and post-selection base pair frequencies, normalized to the maximum possible change of the pre-selection frequency from complete specificity (defined as 1.0) to complete anti-specificity (defined as −1.0). For all TALENs tested, the targeted base pair at every position in both half-sites is preferred, with the sole exception of the base pair closest to the spacer for some ATM TALENs at the right-half site (FIG. 2C, 2D and FIGS. 8 through 13). The 5' T nucleotide recognized by the N-terminal domain is highly specified, and the 5' DNA end (the N-terminal TALEN end) generally exhibits higher specificity than the 3' DNA end; both observations are consistent with previous reports.[24,25] Taken together, these results show that the selection data accurately predicts the efficiency of off-target TALEN cleavage in vitro, and that TALENs are overall highly specific across the entire target sequence.

TALEN Off-Target Cleavage in Cells

To test if off-target cleavage activities reported by the selection are relevant to off-target cleavage in cells, we used the in vitro selection results to train a machine-learning algorithm to generate potential TALEN off-target sites in the human genome.[26] This computational step was necessary because the preselection libraries cover all sequences with six or fewer mutations, while almost all potential off-target sites in the human genome for CCR5 and ATM sequences differ at more than six positions relative to the target sequence. The algorithm calculates the posterior probability of each nucleotide in each position of a target to occur in a sequence that was cleaved by the TALENs in opposition to sequences from the target library that were not observed to be cleaved.[27] These posterior probabilities were then used to score the likelihood that the TALEN used to train the algorithm would cleave every possible target sequence in the human genome with monomer spacing of 10 to 30 bps. Using the machine-learning algorithm, we identified 36 CCR5A and 36 ATM TALEN off-target sites that differ from the on-target sequence at seven to fourteen positions (Table 6).

The 72 best-scoring genomic off-target sites for CCR5A and ATM TALENs were amplified from genomic DNA purified from human U2OS-EGFP cells12 expressing either CCR5A or ATM TALENs.[3] Sequences containing insertions or deletions of three or more base pairs in the DNA spacer of the potential genomic off-target sites and present in significantly greater numbers in the TALEN-treated samples versus the untreated control sample were considered TALEN-induced modifications. Of the 35 CCR5A off-target sites that we successfully amplified, we identified six off-target sites with TALEN-induced modifications; likewise, of the 31 ATM off-target sites that we successfully amplified, we observed seven off-target sites with TALEN-induced modifications (FIG. 3 and Table 7). The inspection of modified on-target and off-target sites yielded a prevalence of deletions ranging from three to dozens of base pairs (FIG. 3), consistent with previously described characteristics of TALEN-induced genomic modification.[28]

These results collectively indicate that the in vitro selection data, processed through a machine-learning algorithm, can predict bona fide off-target substrates that undergo TALEN-induced modification in human cells. TALE Repeats Productively Bind Base Pairs with Relative Independence The extensive number of quantitatively characterized off-target substrates in the selection data enabled us to assess whether mutations at one position in the target sequence affect the ability of TALEN repeats to productively bind other positions. We generated an expected enrichment value for every possible double-mutant sequence for the L13+R13 CCR5B TALENs assuming independent contributions from the two corresponding single-mutation enrichments. In general, the predicted enrichment values closely resembled the actual observed enrichment values for each double-mutant sequence (FIG. 14A), suggesting that component single mutations independently contributed to the overall cleavability of double-mutant sequences. The difference between the observed and predicted double-mutant enrichment values was relatively independent of the distance between the two mutations, except that two neighboring mismatches were slightly better tolerated than would be expected (FIG. 14B).

Figure 4A:
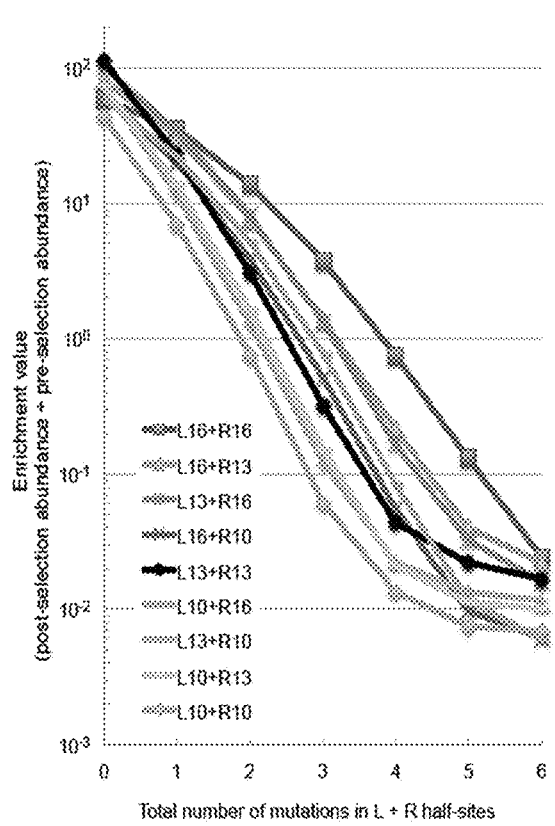

To determine the potential interdependence of more than two mutations, we evaluated the relationship between selection enrichment values and the number of mutations in the post-selection target for the L13+R13 CCR5B TALEN (FIG. 4A, black line). For 0 to 5 mutations, enrichment values closely followed a simple exponential function of the mean number of mutations (m) (Table 8). This relationship is consistent with a model in which each successive mutation reduces the binding energy by a constant amount ($\Delta G$), resulting in an exponential decrease in TALEN binding (Keq(m)) such that Keq(m)~$e\Delta G^*m$. The observed exponential relationship therefore suggests that the mean reduction in binding energy from a typical mismatch is independent of the number of mismatches already present in the TALEN:DNA interaction. Collectively, these results indicate that TALE repeats bind their respective DNA base pairs independently beyond a slightly increased tolerance for adjacent mismatches.

Longer TALENs are Less Specific Per Recognized Base Pair

The independent binding of TALE repeats simplistically predicts that TALEN specificity per base pair is independent of target-site length. To experimentally characterize the relationship between TALE array length and off-target cleavage, we constructed TALENs targeting 10, 13, or 16 bps (including the 5' T) for both the left (L10, L13, L16) and right (R10, R13, R16) half-sites. TALENs representing all nine possible combinations of left and right CCR5B TALENs were subjected to in vitro selection. The results revealed that shorter TALENs have greater specificity per targeted base pair than longer TALENs (Table 3). For example, sequences cleaved by the L10+R10 TALEN contained a mean of 0.032 mutations per recognized base pair, while those cleaved by the L16+R16 TALEN contained a mean of 0.067 mutations per recognized base pair. For selections with the longest CCR5B TALENs targeting 16+16 base pairs or CCR5A and ATM TALENs targeting 18+18 bp, the mean selection enrichment values do not follow a simple exponential decrease as function of mutation number (FIG. 4A and Table 8).

We hypothesized that excess binding energy from the larger number of TALE repeats in longer TALENs reduces specificity by enabling the cleavage of sequences with more mutations, without a corresponding increase in the cleavage of sequences with fewer mutations, because the latter are already nearly completely cleaved. Indeed, the in vitro cleavage efficiencies of discrete DNA sequences for these longer TALENs are independent of the presence of a small number of mutations in the target site (FIGS. 5C-5F), suggesting there is nearly complete binding and cleavage of sequences containing few mutations. Likewise, higher TALEN concentrations also result in decreased enrichment values of sequences with few mutations while increasing the enrichment values of sequences with many mutations (Table 5). These results together support a model in which excessive TALEN binding arising from either long TALE arrays or high TALEN concentrations decreases observed TALEN DNA cleavage specificity of each recognized base pair.

Longer TALENs Induce Less Off-Target Cleavage in a Genomic Context

Figure 4B:
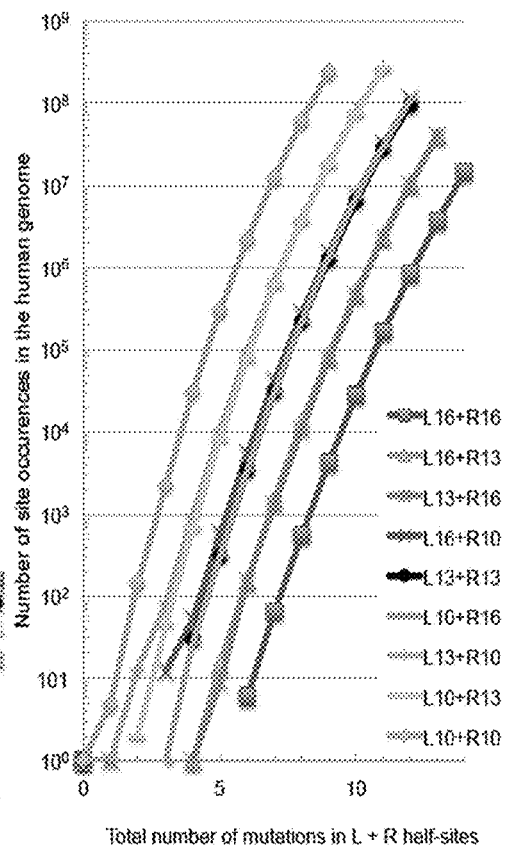
Figure 5F:
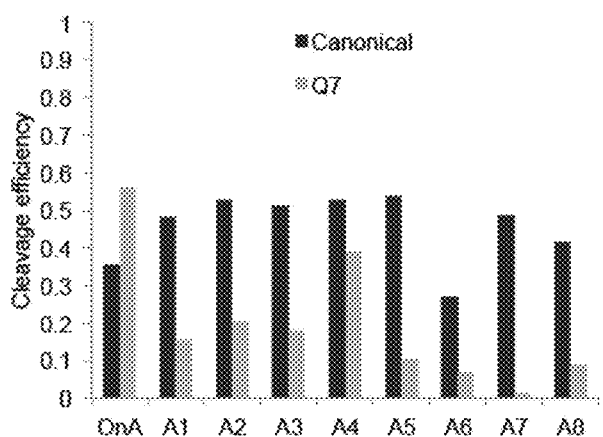

Although longer TALENs are more tolerant of mismatched sequences (FIG. 4A) than shorter TALENs, in the human genome there are far fewer closely related off-target sites for a longer target site than for a shorter target site (FIG. 4B). Since off-target site abundance and cleavage efficiency both contribute to the number of off-target cleavage events in a genomic context, we calculated overall genome cleavage specificity as a function of TALEN length by multiplying the extrapolated mean enrichment value of mutant sequences of a given length with the number of corresponding mutant sequences in the human genome. The decrease in potential off-target site abundance resulting from the longer target site length is large enough to outweigh the decrease in specificity per recognized base pair observed for longer TALENs (FIG. 4C). As a result, longer TALENs are predicted to be more specific against the set of potential cleavage sites in the human genome than shorter TALENs for the tested TALEN lengths targeting 20- to 32-bp sites.

Engineering TALENs with Improved Specificity

The findings above suggest that TALEN specificity can be improved by reducing non-specific DNA binding energy beyond what is needed to enable efficient on-target cleavage. The most widely used 63-aa C-terminal domain between the TALE repeat array and the FokI nuclease domain contains ten cationic residues. We speculated that reducing the cationic charge of the canonical TALE C-terminal domain would decrease non-specific DNA binding[29] and improve TALEN specificity.

We constructed two C-terminal domain variants in which three ("Q3", K788Q, R792Q, R801Q) or seven ("Q7", K777Q, K778Q, K788Q, R789Q, R792Q, R793Q, R801Q) cationic Arg or Lys residues in the canonical 63-aa C-terminal domain were mutated to Gln. We performed in vitro selections on CCR5A and ATM TALENs containing the canonical, engineered Q3, and engineered Q7 C-terminal domains, as well as a previously reported 28-aa truncated C-terminal domain[5] with a theoretical net charge identical to that of the Q7 C-terminal domain (−1).

The on-target sequence enrichment values for the CCR5A and ATM selections increased substantially as the net charge of the C-terminal domain decreased (FIGS. 5A and 5B). For example, the ATM selections resulted in on-target enrichment values of 510, 50, and 20 for the Q7, Q3, and canonical 63-aa C-terminal variants, respectively. These results suggest that the TALEN variants in which cationic residues in the C-terminal domain have been partially replaced by neutral residues or completely removed are substantially more specific in vitro than the TALENs that containing the canonical 63-aa C-terminal domain. Similarly, mutating one, two, or three cationic residues in the TALEN N-terminus to Gln also increased cleavage specificity (Table 5, and FIGS. 8-11).

In order to confirm the greater DNA cleavage specificity of Q7 over canonical 63-aa C-terminal domains in vitro, a representative collection of 16 off-target DNA substrates were digested in vitro with TALENs containing either canonical or engineered Q7 C-terminal domains. ATM and CCR5A TALENs with the canonical 63-aa C-terminal domain TALEN demonstrate comparable in vitro cleavage activity on target sites with zero, one, or two mutations (FIGS. 5C-5F). In contrast, for 11 of the 16 off-target substrates tested, the engineered Q7 TALEN variants showed substantially higher (~4-fold or greater) discrimination against off-target DNA substrates with one or two mutations than the canonical 63-aa C-terminal domain TALENs, even though the Q7 TALENs cleaved their respective on-target sequences with comparable or greater efficiency than TALENs with the canonical 63-aa C-terminal domains (FIGS. 5C-5F). Overall, the discrete cleavage assays are consistent with the selection results and indicate that TALENs with engineered Q7 C-terminal domains are substantially more specific than TALENs with canonical 63-aa C-terminal domains in vitro.

Improved Specificity of Engineered TALENs in Human Cells

To determine if the increased specificity of the engineered TALENs observed in vitro also applies in human cells, TALEN-induced modification rates of the on-target and top 36 predicted off-target sites were measured for CCR5A and ATM TALENs containing all six possible combinations of the canonical 63-aa, Q3, or Q7 C-terminal domains and the EL/KK or ELD/KKR FokI domains (12 TALENs total).

Figure 6:
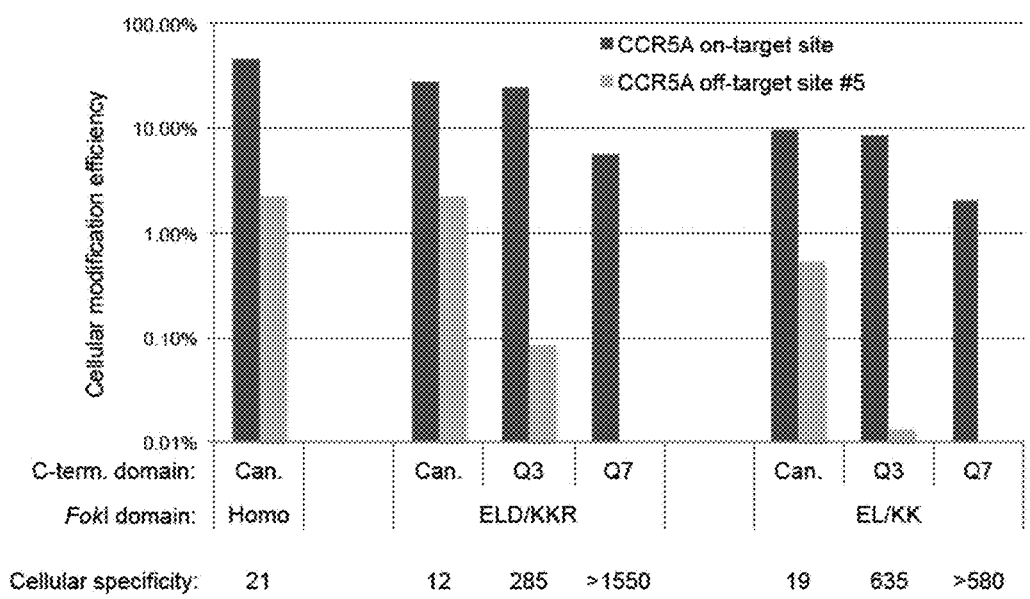
FIG. 6. Specificity of engineered TALENs in human cells. The cellular modification efficiency of canonical and engineered TALENs expressed as a percentage of indels consistent with TALEN-induced modification out of total sequences is shown for the on-target CCR5A sequence and for CCR5A off-target site #5, the most highly cleaved off-target substrate tested. Cellular specificity, defined as the ratio of on-target to off-target modification, is shown below each pair of bars.
Figure 8A:
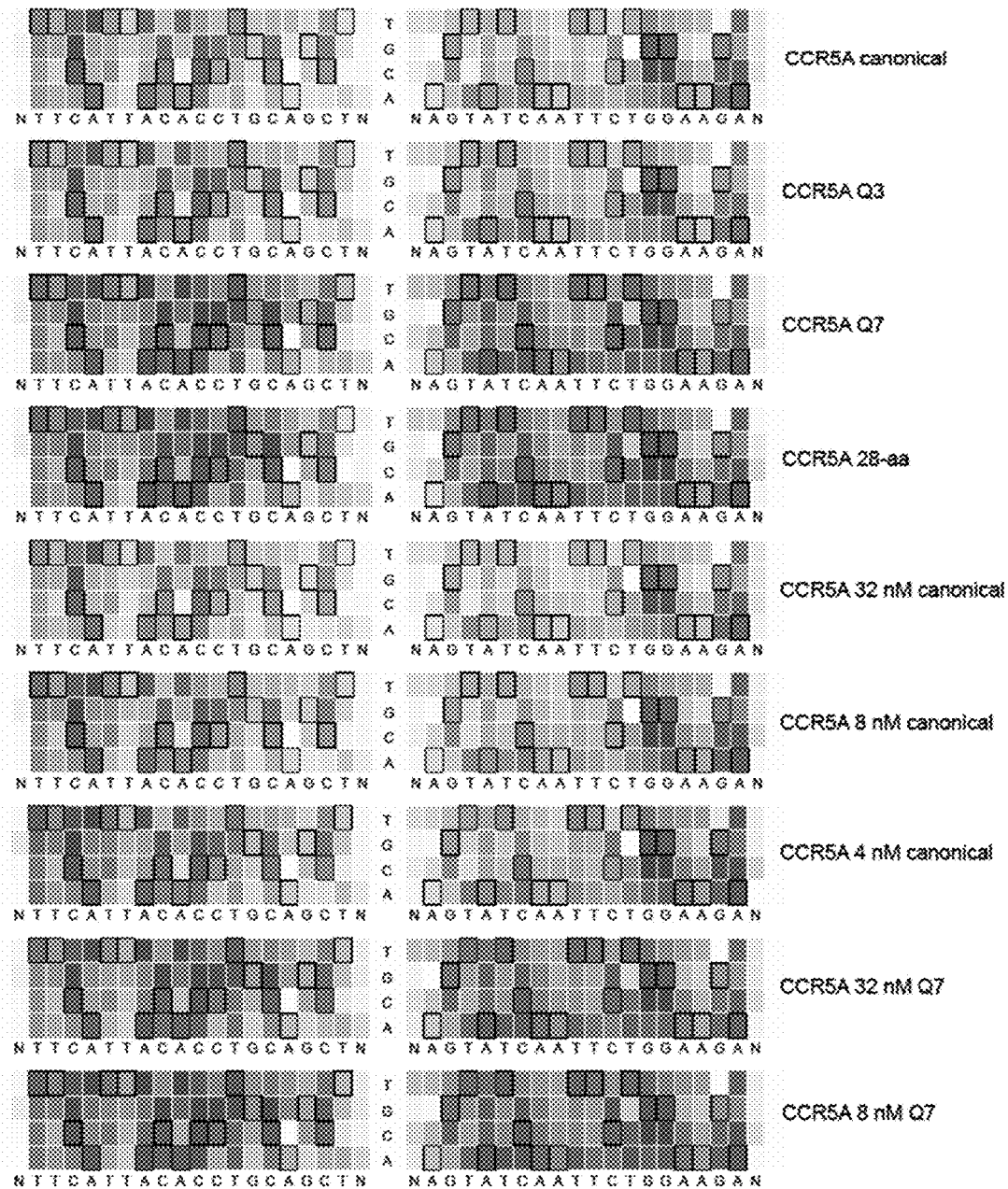
FIGS. 8A-B. Specificity profiles from all CCR5A TALEN selections as heat maps. Specificity scores for every targeted base pair in selections of CCR5A TALENs are shown. Specificity scores for the L18+R18 CCR5A TALEN at all positions in the target half-sites plus a single flanking position. The colors range from a maximum specificity score of 1.0 to white (score of 0, no specificity) to a maximum negative score of −1.0. Boxed bases represent the intended target base. The titles to the right indicate if the TALEN used in the selection differs from the canonical TALEN architecture, which contains a canonical C-terminal domain, wild-type N-terminal domain, and EL/KK FokI variant. Selections correspond to conditions listed in Table 2. (A) Specificity profiles of canonical, Q3, Q7, 28-aa, 32 nM canonical, 8 nM canonical, 4 nM canonical, 32 nM Q7 and 8 nM Q7 CCR5A TALEN selections. (B) Specificity profiles of 4 nM Q7, N1, N2, N3, canonical ELD/KKR, Q3 ELD/KKR, Q7 ELD/KKR and N2 ELD/KKR CCR5A TALEN selections. When not specified, TALEN concentration was 16 nM. Nttcattacacctgcagctn corresponds to SEQ ID NO: 51 and nagtatcaattctggaagan corresponds to SEQ ID NO: 52.
Figure 8B:
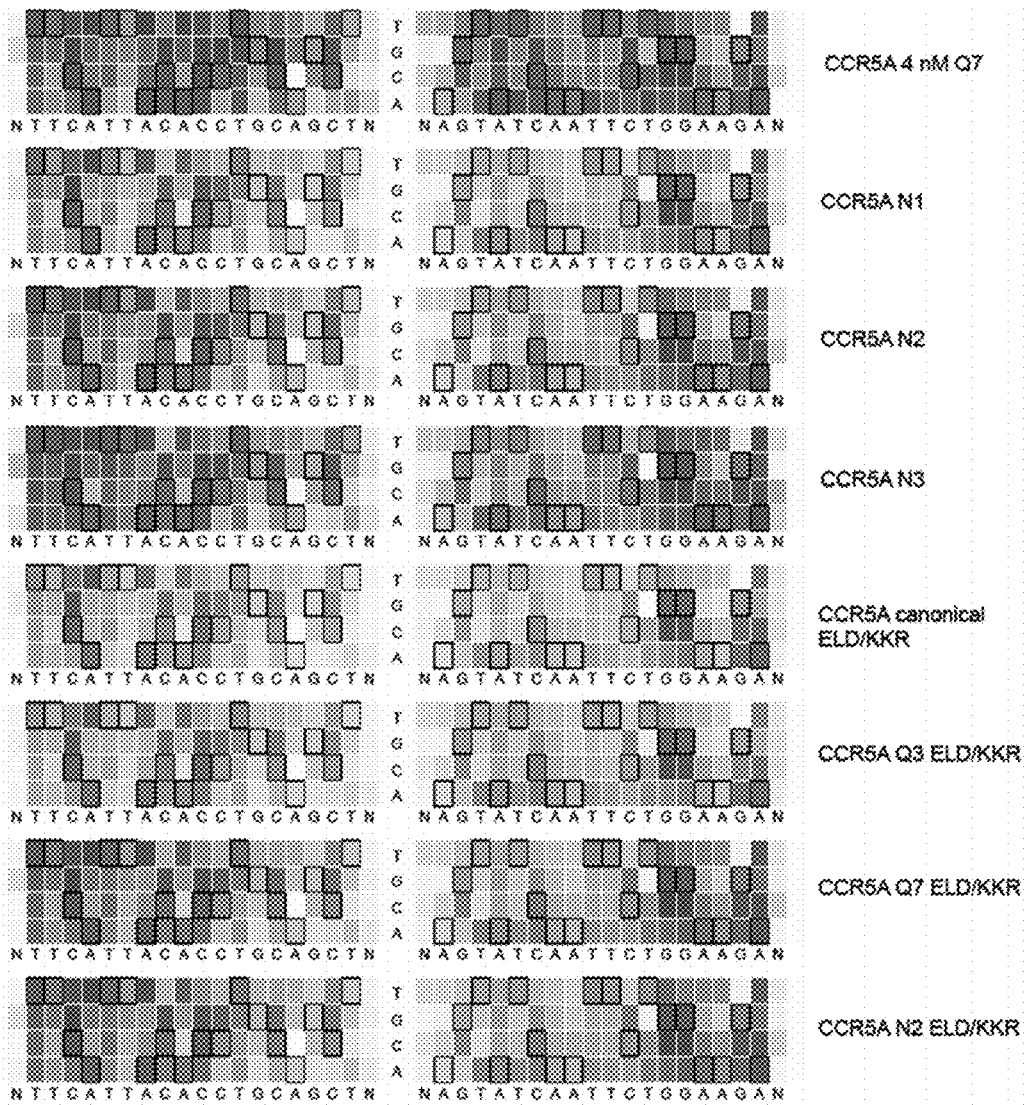
Figure 9A:
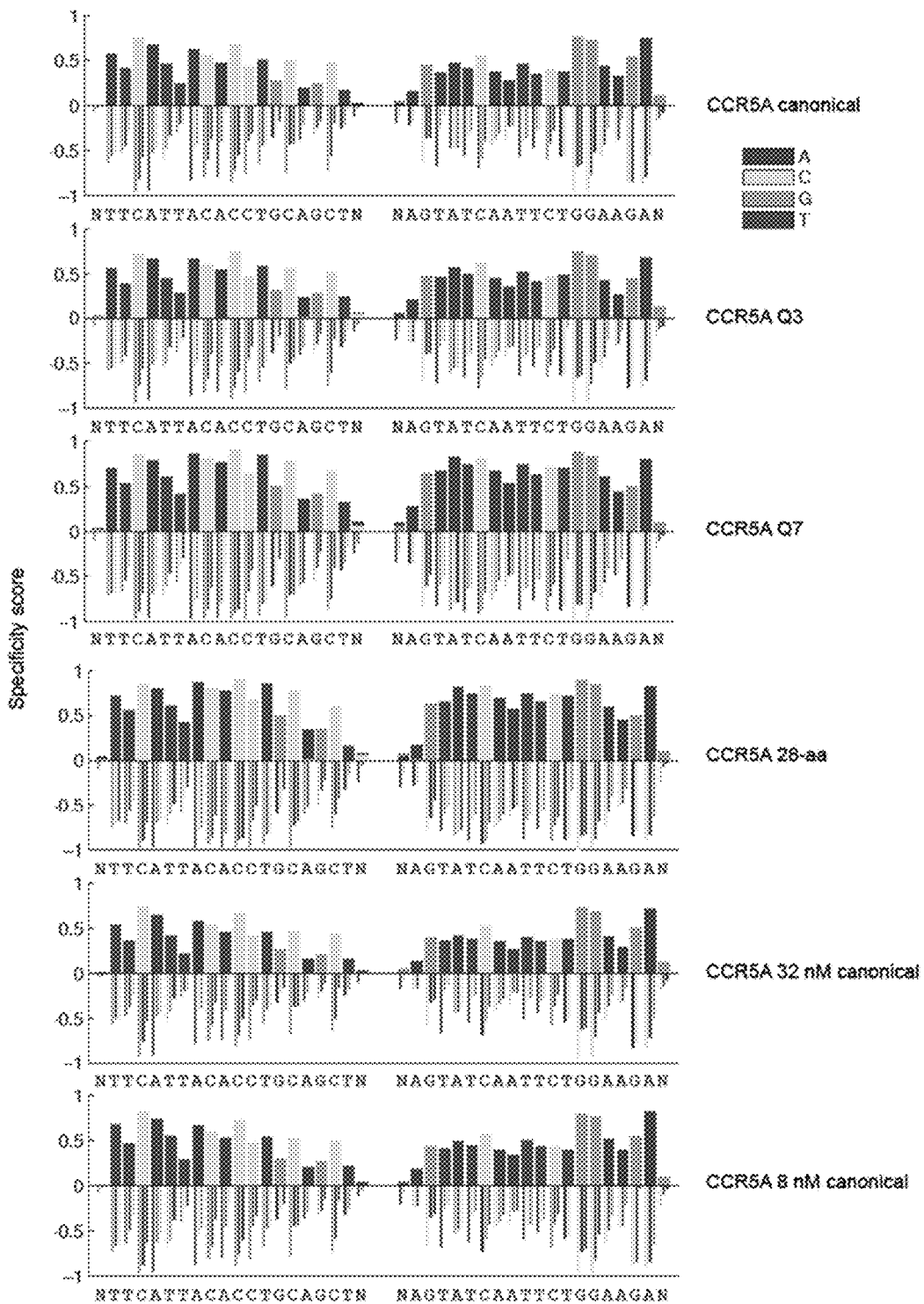
FIGS. 9A-C. Specificity profiles from all CCR5A TALEN selections as bar graphs. Specificity scores for every targeted base pair in selections of CCR5A TALENs are shown. Positive specificity scores, up to complete specificity at a specificity score of 1.0, signify enrichment of that base pair over the other possibilities at that position. Negative specificity scores, down to complete antispecificity of −1.0, represents enrichment against that base pair. Specified positions were plotted as stacked bars above the X-axis (multiple specified base pairs at the same position were plotted over each other with the shortest bar in front, and not end-to-end) while anti-specified base pairs were plotted as narrow, grouped bars. The titles to the right indicate if the TALEN used in the selection differs from the canonical TALEN architecture, which contains a canonical C-terminal domain, wild-type N-terminal domain, and EL/KK FokI variant. Selections correspond to conditions listed in Table 2. (A) Specificity profiles of canonical, Q3, Q7, 28-aa, 32 nM canonical, and 8 nM canonical CCR5A TALEN selections. (B) Specificity profiles of 4 nM canonical, 32 nM Q7, 8 nM Q7, 4 nM Q7, N1, and N2 CCR5A TALEN selections. (C) Specificity profiles of N3, canonical ELD/KKR, Q3 ELD/KKR, Q7 ELD/KKR, and N2 ELD/KKR CCR5A TALEN selections. When not specified, TALEN concentration was 16 nM. nttcattacacctgcagctn corresponds to SEQ ID NO: 51, nagtatcaattctggaagan corresponds to SEQ ID NO: 52, ntgaattgggatgctgtttn corresponds to SEQ ID NO: 53; and ntttattttactgtctttan corresponds to SEQ ID NO: 54.
Figure 9B:
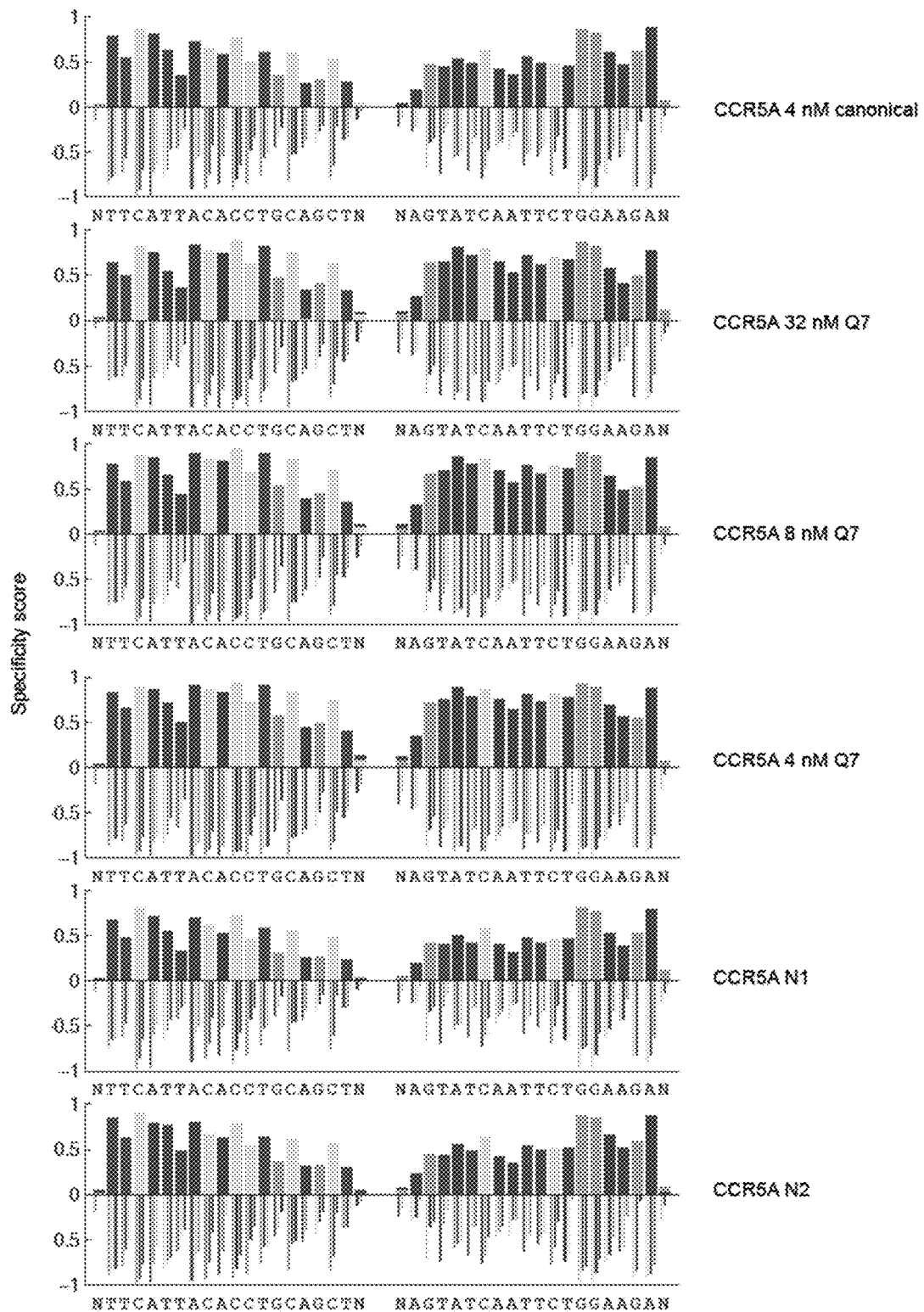
Figure 9C:
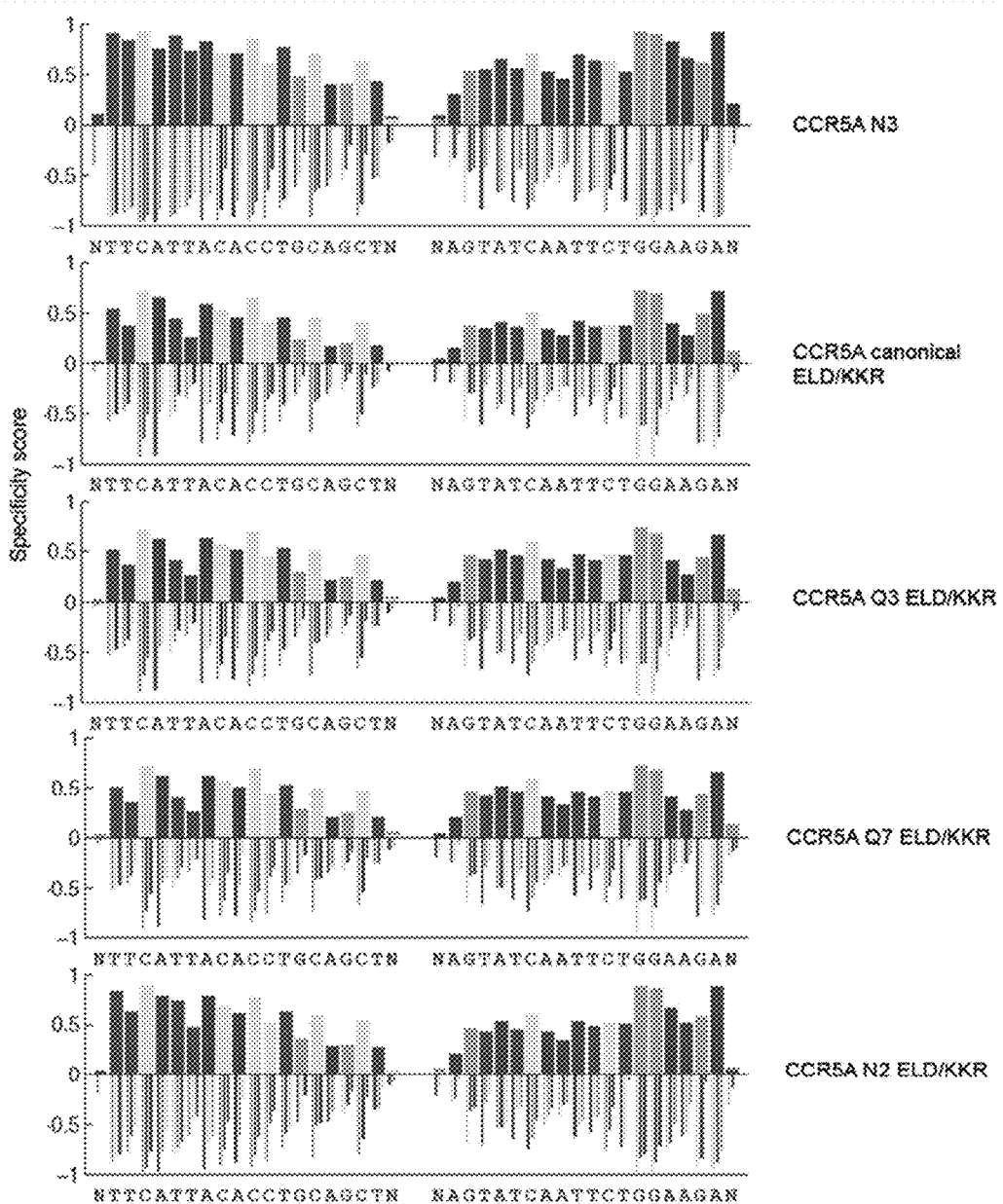

For both FokI variants, the TALENs with Q3 C-terminal domains demonstrate significant on-target activities ranging from 8% to 24% modification, comparable to the activity of TALENs with the canonical 63-aa C-terminal domains. TALENs with canonical 63-aa or Q3 C-terminal domains and the ELD/KKR FokI domain are both more active in modifying the CCR5A and ATM on-target site in cells than the corresponding TALENs with the Q7 C-terminal domain by ~5-fold (FIG. 6 and Table 7).

Consistent with the improved specificity observed in vitro, the engineered Q7 TALENs are more specific than the Q3 variants, which in turn are more specific than the canonical 63-aa C-terminal domain TALENs. Compared to the canonical 63-aa C-terminal domains, TALENs with Q3 C-terminal domains demonstrate a mean increase in cellular specificity (defined as the ratio of the cellular modification percentage for on-target to off-target sites) of more than 13-fold and more than 9-fold for CCR5A and ATM sites, respectively, with the ELD/KKR FokI domain (Table 7). These mean improvements can only be expressed as lower limits due to the absence or near-absence of observed cleavage events by the engineered TALENs for many off-target sequences. For the most abundantly cleaved off-target site (CCR5A off-target site #5), the Q3 C-terminal domain is 34-fold more specific (FIG. 6), and the Q7 C-terminal domain is >116-fold more specific, than the canonical 63-aa C-terminal domain.

Together, these results reveal that for targeting the CCR5 and ATM sequences, replacing the canonical 63-aa C-terminal domain with the engineered Q3 C-terminal domain results in comparable activity for the on-target site in cells, a 34-fold improvement in specificity in cells for the most readily cleaved off-target site, and a consistent increase in specificity for other off-target sites. When less activity is required, the engineered Q7 C-terminal domain offers additional gains in specificity.

Engineering N-Terminal Domains for Improved TALEN DNA Cleavage Specificity

The model of TALEN binding and specificity described herein predicts that reducing excess TALEN binding energy will increase TALEN DNA cleavage specificity. To further test this prediction and potentially further augment TALEN specificity, we mutated one ("N1", K150Q), two ("N2", K150Q and K153Q), or three ("N3", K150Q, K153Q, and R154Q) Lys or Arg residues to Gln in the N-terminal domain of TALENs targeting CCR5A and ATM. These N-terminal residues have been shown in previous studies to bind non-specifically to DNA, and mutations at these specific residues to neutralize the cationic charge decrease non-specific DNA binding energy.[33] We hypothesized the reduction in non-specific binding energy from these N-terminal mutations would decrease excess TALEN binding energy resulting in increased specificity. In vitro selections on these three TALEN variants revealed that the less cationic N-terminal TALENs indeed exhibit greater enrichment values of on-target cleavage (Table 5).

Figure 10A:
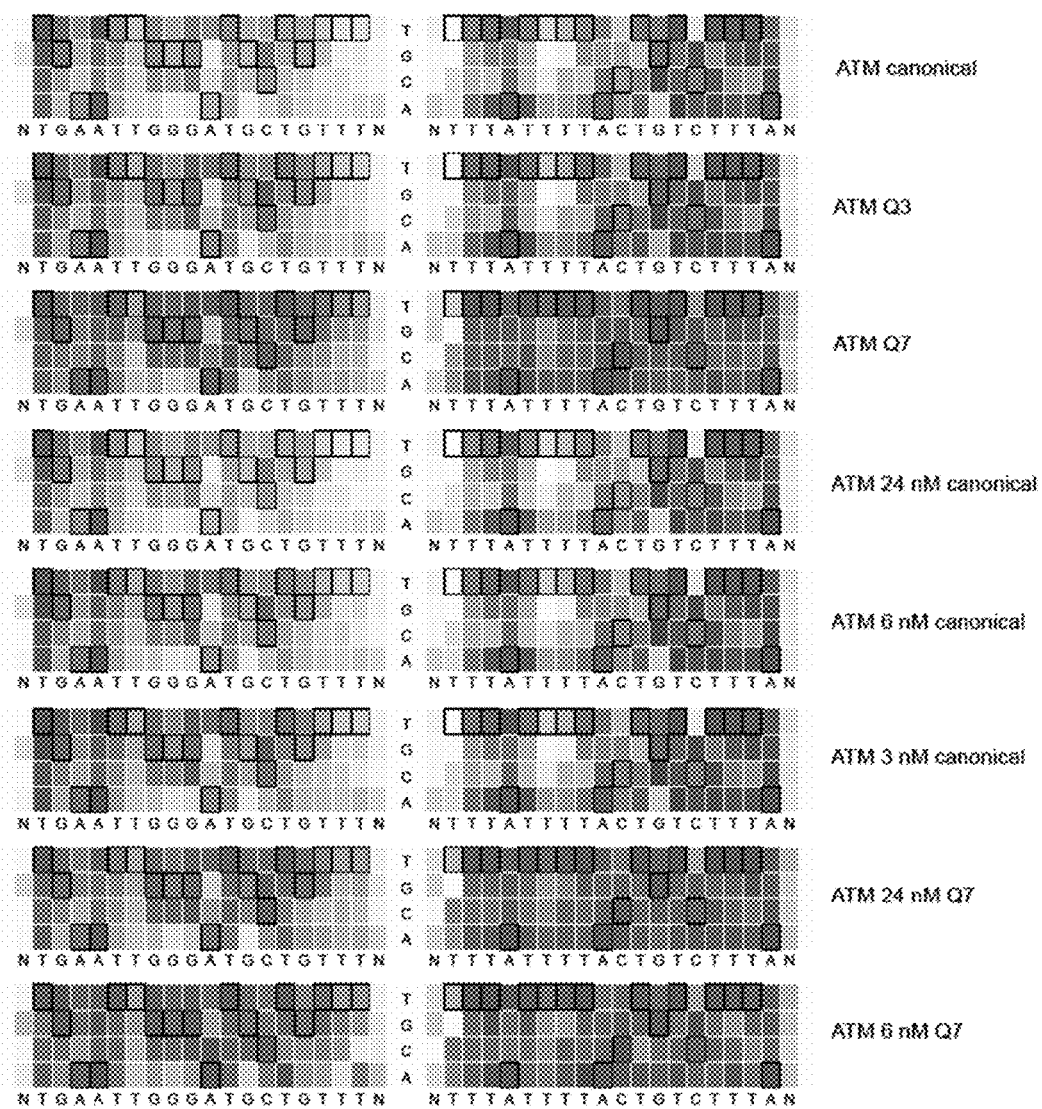
FIGS. 10A-B. Specificity profiles from all ATM TALEN selections as heat maps. Specificity scores for every targeted base pair in selections of ATM TALENs are shown. Specificity scores for the L18+R18 ATM TALEN at all positions in the target half-sites plus a single flanking position. The colors range from a maximum specificity score of 1.0 to white (score of 0, no specificity) to a maximum negative score of −1.0. Boxed bases represent the intended target base. The titles to the right indicate if the TALEN used in the selection differs from the canonical TALEN architecture, which contains a canonical C-terminal domain, wild type N-terminal domain, and EL/KK FokI variant. Selections correspond to conditions listed in Table 2. (A) Specificity profiles of (12 nM) canonical, Q3, (12 nM) Q7, 24 nM canonical, 6 nM canonical, 3 nM canonical, 24 nM Q7, and 6 nM Q7 ATM TALEN selections. (B) Specificity profiles of N1, N2, N3, canonical ELD/KKR, Q3 ELD/KKR, Q7 ELD/KKR, and N2 ELD/KKR ATM TALEN selections. When not specified, TALEN concentration was 12 nM. ntgaattgggatgctgtttn corresponds to SEQ ID NO: 53; and ntttattttactgtctttan corresponds to SEQ ID NO: 54.
Figure 10B:
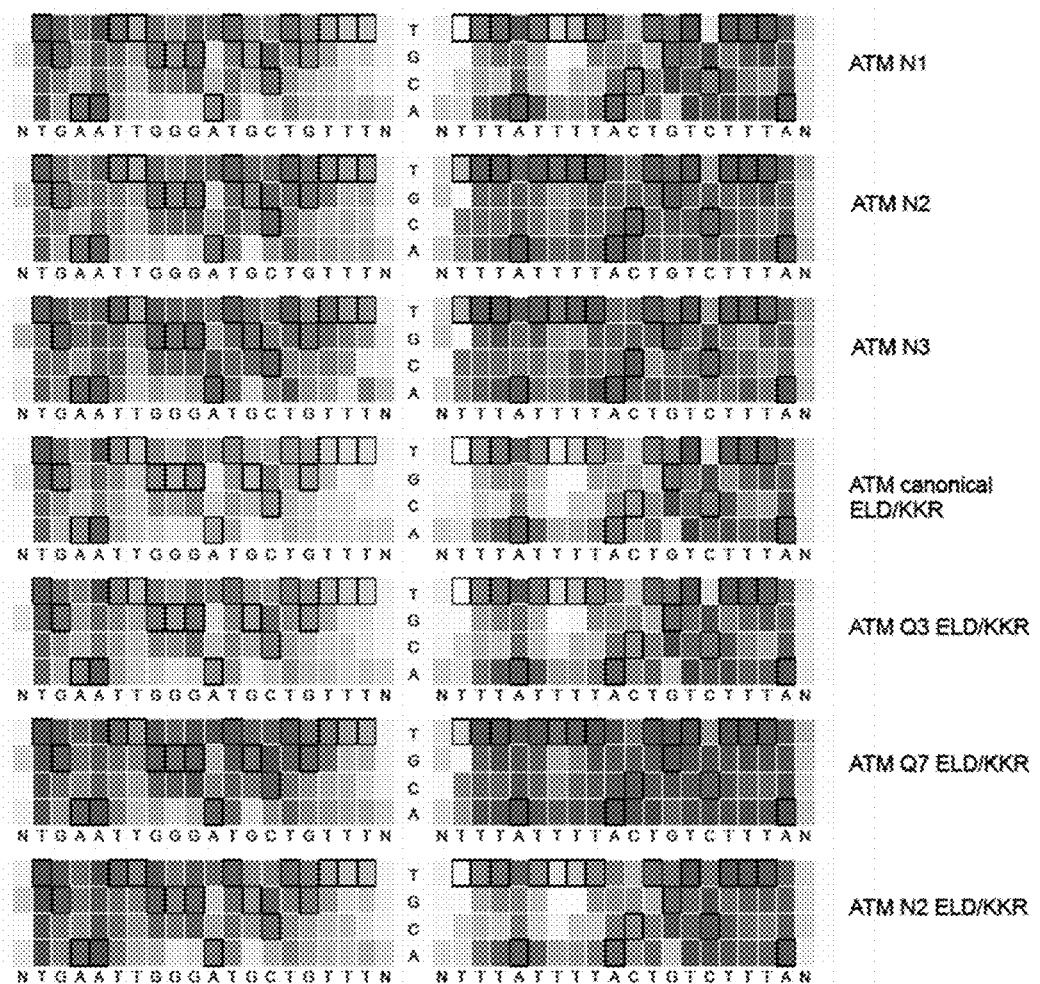
Figure 11A:
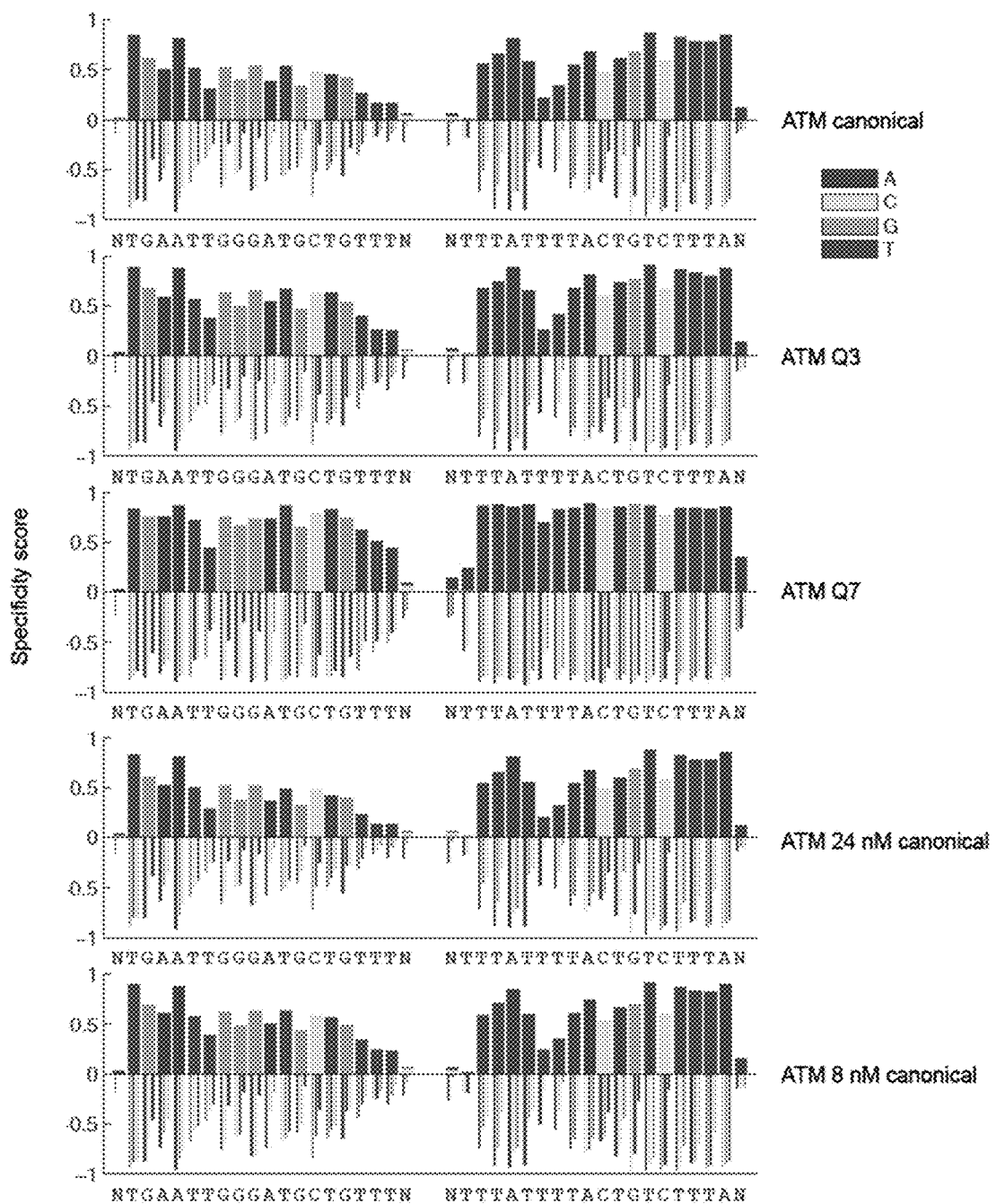
FIGS. 11A-C. Specificity profiles from all ATM TALEN selections as bar graphs. Specificity scores for every targeted base pair in selections of ATM TALENs are shown. Positive specificity scores, up to complete specificity at a specificity score of 1.0, signify enrichment of that base pair over the other possibilities at that position. Negative specificity scores, down to complete antispecificity of −1.0, represents enrichment against that base pair. Specified positions were plotted as stacked bars above the X-axis (multiple specified base pairs at the same position were plotted over each other with the shortest bar in front, and not end-to-end) while anti-specified base pairs were plotted as narrow, grouped bars. The titles to the right indicate if the TALEN used in the selection differs from the canonical TALEN architecture, which contains a canonical C-terminal domain, wild-type N-terminal domain, and EL/KK FokI variant. Selections correspond to conditions listed in Table 2. (A) Specificity profiles of canonical, Q3, Q7, 32 nM canonical, and 8 nM canonical ATM TALEN selections. (B) Specificity profiles of 3 nM canonical, 24 nM Q7, 6 nM Q7, N1, N2, and N3 ATM TALEN selections. (C) Specificity profiles of canonical ELD/KKR, Q3 ELD/KKR, Q7 ELD/KKR, and N2 ELD/KKR ATM TALEN selections. When not specified, TALEN concentration was 12 nM. ntgaattgggatgctgtttn corresponds to SEQ ID NO: 53; and ntttattttactgtctttan corresponds to SEQ ID NO: 54.
Figure 11B:
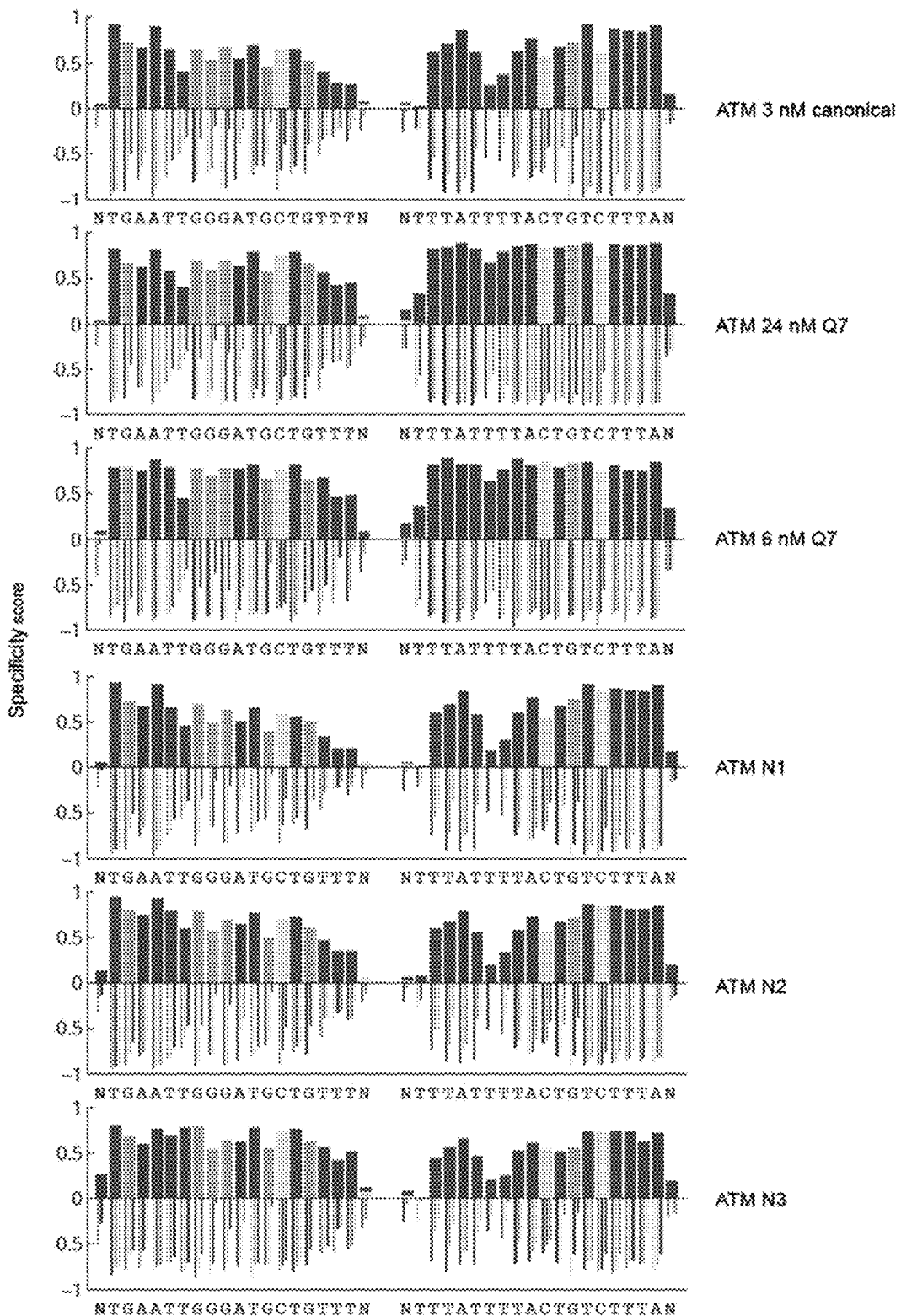
Figure 11C:
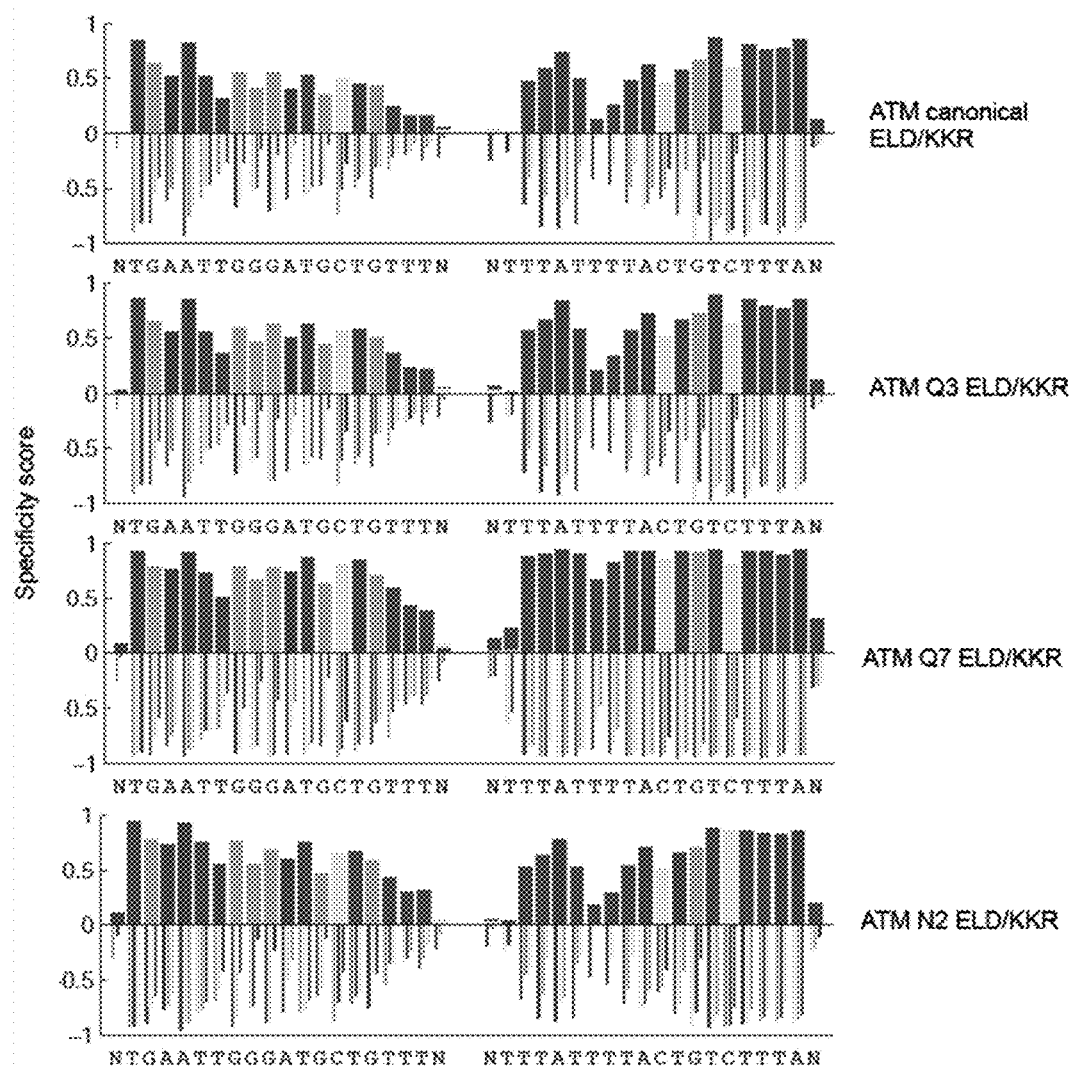
Figure 12:
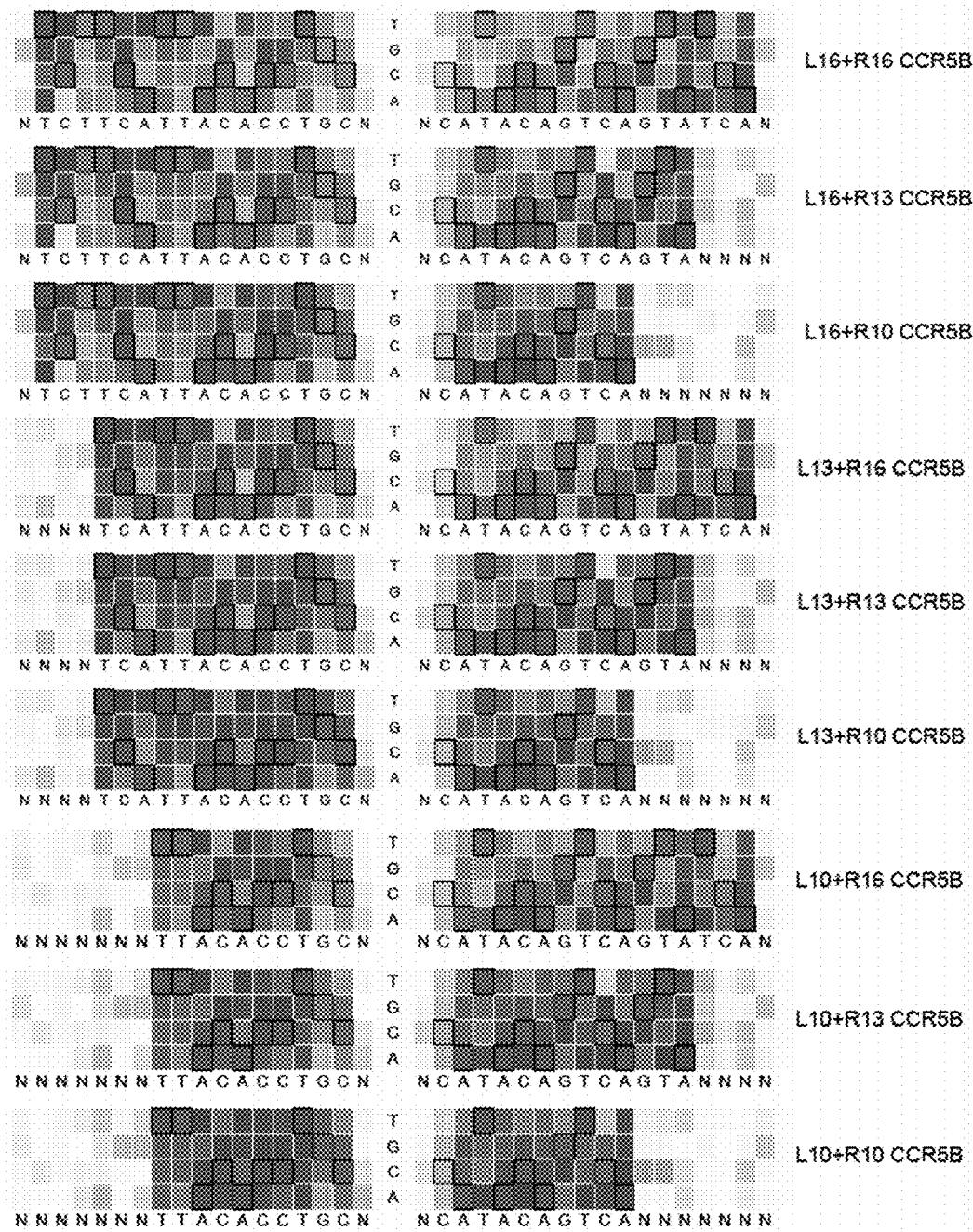
FIG. 12. Specificity profiles from all CCR5B TALEN selections as heat maps. Specificity scores for every targeted base pair in selections of CCR5B TALENs are shown. Specificity scores for CCR5B TALENs targeting all possible combinations of the left (L10, L13, L16) and right (R10, R13, R16) half-sites at all positions in the target half-sites plus a single flanking position. The colors range from a maximum specificity score of 1.0) to white (score of 0, no specificity) to a maximum negative score of −1.0. Boxed bases represent the intended target base. The titles to the right notes the targeted left (L) and right (R) target half-sites for the CCR5B TALEN used in the selection. Selections correspond to conditions listed in Table 2. Sequences in the left column correspond, from top to bottom, to SEQ ID NOs: 160, 160, 160, 161, 161, 161, 162, 162, and 162. Sequences in the right column correspond, from top to bottom, to SEQ ID NOs: 163, 164, 165, 163, 164, 165, 163, 164, and 165.
Figure 13A:
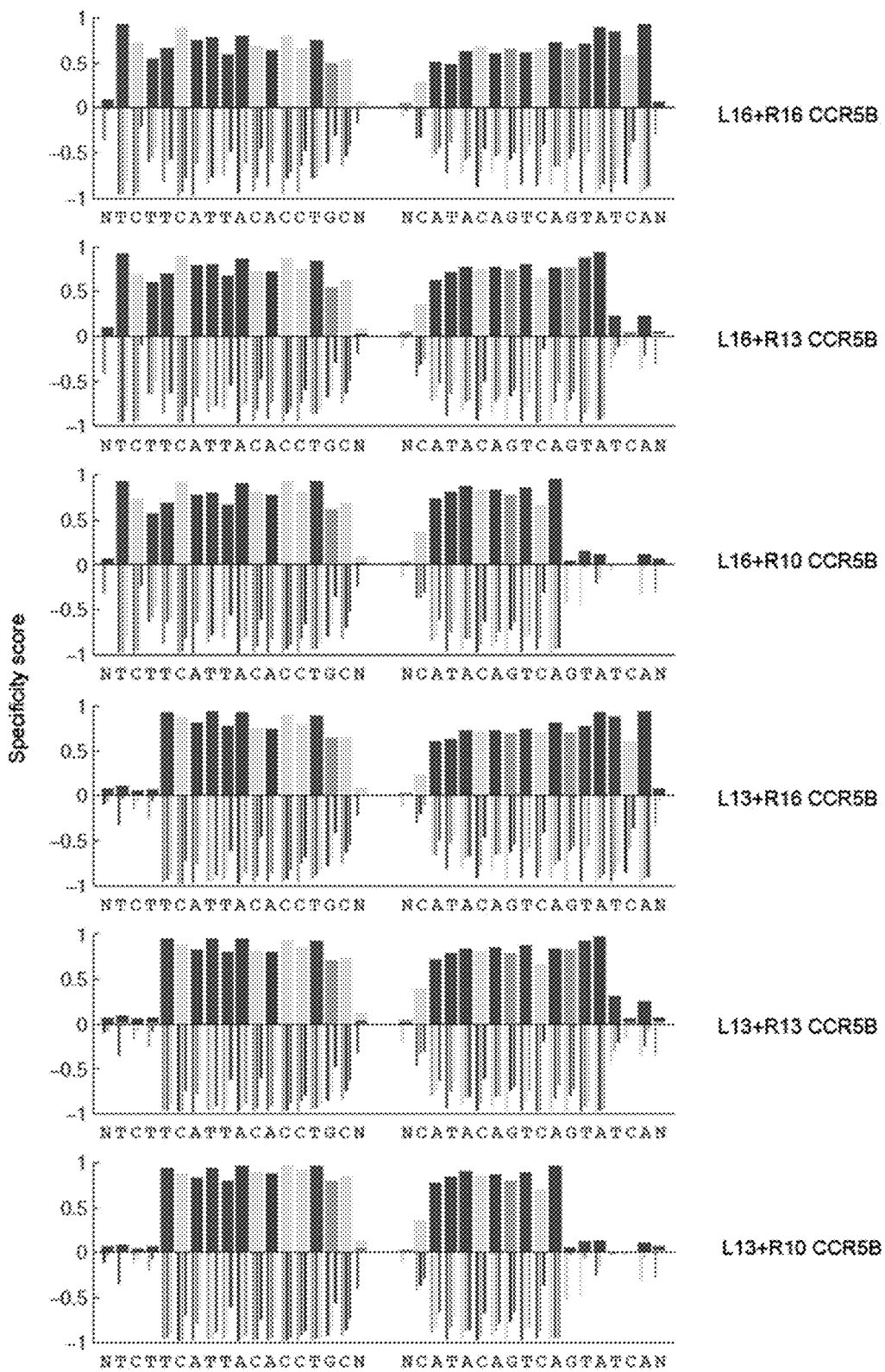
FIGS. 13A-B. Specificity profiles from all CCR5B TALEN selections as bar graphs (A-B). Specificity scores for every targeted base pair in selections of CCR5B TAL-ENs are shown. Positive specificity scores, up to complete specificity at a specificity score of 1.0, signify enrichment of that base pair over the other possibilities at that position.
Figure 13B:
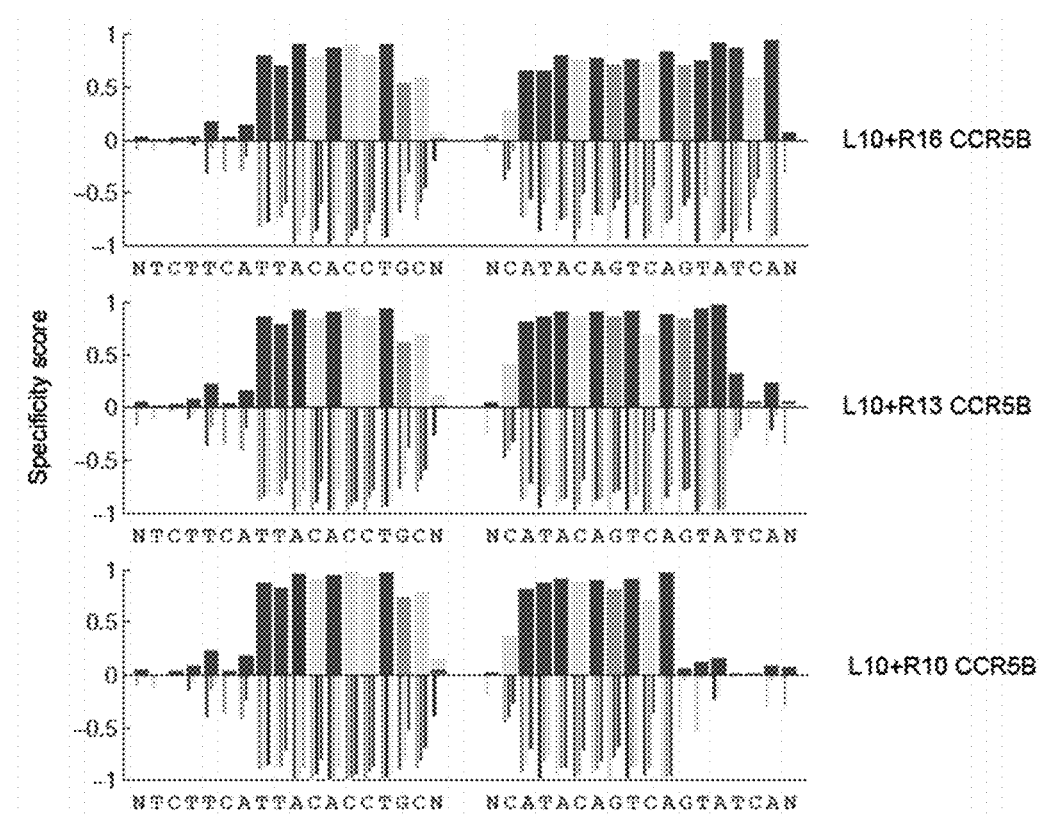

Effects of N-Terminal and C-Terminal Domains and TALEN Concentration on Specificity All TALEN constructs tested specifically recognize the intended base pair across both half-sites (FIGS. 8 to 13), except that some of the ATM TALENs do not specifically interact with the base pair adjacent to the spacer (targeted by the most C-terminal TALE repeat) (FIGS. 10 and 11). To compare the broad specificity profiles of canonical TALENs with those containing engineered C-terminal or N-terminal domains, the specificity scores of each target base pair from selections using CCR5A and ATM TALENs with the canonical, Q3, or Q7 C-terminal domains and N1, N2, or N3 N-terminal domains were subtracted by the corresponding specificity scores from selections on the canonical TALEN (canonical 63-aa C-terminal domain, wild-type N-terminal domain).

The results are shown in FIG. 15. Mutations in the C-terminal domain that increase specificity did so most strongly in the middle and at the C-terminal end of each half-site. Likewise, the specificity-increasing mutations in the N-terminus tended to increase specificity most strongly at positions near the TALEN N-terminus (5' DNA end) although mutations in the N-terminus of ATM TALEN targeting the right half-site did not significantly alter specificity. These results are consistent with a local binding compensation model in which weaker binding at either terminus demands increased specificity in the TALE repeats near this terminus. To characterize the effects of TALEN concentration on specificity, the specificity scores from selections of ATM and CCR5A TALENs performed at three different concentrations ranging from 3 nM to 16 nM were each subtracted by the specificity scores of corresponding selections performed at the highest TALEN concentration assayed, 24 nM for ATM, or 32 nM for CCR5A. The results (FIG. 15) indicate that specificity scores increase fairly uniformly across the half-sites as the concentration of TALEN is decreased.

DNA Spacer-Length and Cut-Site Preferences

To assess the spacer-length preference of various TALEN architectures (C-terminal mutations, N-terminal mutations, and FokI variants) and various TALEN concentrations, the enrichment values of library members with 10- to 24-base pair spacer lengths in each of the selections with CCR5A and ATM TALEN with various combinations of the canonical, Q3, Q7, or 28-aa C-terminal domains; N1, N2, or N3 N-terminal mutations; and the EL/KK or ELD/KKR FokI variants at 4 nM to 32 nM CCR5A and ATM TALEN were calculated (FIG. 16). All of the tested concentrations, N-terminal variants, C-terminal variants, and FokI variants demonstrated a broad DNA spacer-length preference ranging from 14- to 24-base pairs with three notable exceptions. First, the CCR5A 28-aa C-terminal domain exhibited a much narrower DNA spacer-length preference than the broader DNA spacer-length preference of the canonical C-terminal domain, consistent with previous reports.[34-36] Second, the CCR5A TALENs containing Q7 C-terminal domains showed an increased tolerance for 12-base spacers compared to the canonical C-terminal domain variant (FIG. 16). This slightly broadened spacer-length preference may reflect greater conformational flexibility in the Q7 C-terminal domain, perhaps resulting from a smaller number of non-specific protein:DNA interactions along the TALEN: DNA interface. Third, the ATM TALENs with Q7 C-terminal domains and the ATM TALENs with N3 mutant N-terminal domains showed a narrowed spacer preference.

These more specific TALENs (Table 5) with lower DNA-binding affinity may have faster off-rates that are competitive with the rate of cleavage of non-optimal DNA spacer lengths, altering the observed spacer-length preference. While previous reports have focused on the length of the TALEN C-terminal domain as a primary determinant of DNA spacer-length preference, these results suggest the net charge of the C-terminal domain as well as overall DNA-binding affinity can also affect TALEN spacer-length preference.

We also characterized the location of TALEN DNA cleavage within the spacer. We created histograms reporting the number of spacer DNA bases observed preceding the right half-site in each of the sequences from the selections with CCR5A and ATM TALEN with various combinations of the canonical, Q3, Q7, or 28-aa C-terminal domains; N1, N2, or N3 N-terminal mutations; and the EL/KK or ELD/KKR FokI variants (FIG. 17). The peaks in the histogram were interpreted to represent the most likely locations of DNA cleavage within the spacer. The cleavage positions are dependent on the length of the DNA spacer between the TALEN binding half-sites, as might be expected from conformational constraints imposed by the TALEN C-terminal domain and DNA spacer lengths.

Discussion

The in vitro selection of 41 TALENs challenged with $10^{12}$ closed related off-target sequences and subsequent analysis inform our understanding of TALEN specificity through four key findings: (i) TALENs are highly specific for their intended target base pair at all positions with specificity increasing near the N-terminal TALEN end of each TALE repeat array (corresponding to the 5' end of the bound DNA); (ii) longer TALENs are more specific in a genomic context while shorter TALENs have higher specificity per nucleotide; (iii) TALE repeats each bind their respective base pair relatively independently; and (iv) excess DNA-binding affinity leads to increased TALEN activity against off-target sites and therefore decreased specificity.

The observed decrease in specificity for TALENs with more TALE repeats or more cationic residues in the C-terminal domain or N-terminus are consistent with a model in which excess TALEN binding affinity leads to increased promiscuity. Excess binding energy could also explain the previously reported promiscuity at the 5' terminal T of TALENs with longer C-terminal domains[30] and is also consistent with a report of higher TALEN protein concentrations resulting in more off-target site cleavage in vivo.[9] While decreasing TALEN protein expression in cells in theory could reduce off-target cleavage, the Kd values of some TALEN constructs for their target DNA sequences are likely already comparable to, or below, the theoretical minimum protein concentration in a human cell nucleus, ~0.2 nM.[21]

The difficulty of improving the specificity of such TALENs by lowering their expression levels, coupled with the need to maintain sufficient TALEN concentrations to effect desired levels of on-target cleavage, highlight the value of engineering TALENs with higher intrinsic specificity such as those described in this work. Our findings suggest that mutant C-terminal domains with reduced non-specific DNA binding may be used to fine-tune the DNA-binding affinity of TALENs such that on-target sequences are cleaved efficiently but with minimal excess binding energy, resulting in better discrimination between on-target and off-target sites. Since TALENs targeting up to 46 total base pairs have been shown to be active in cells,[15] the results presented here are consistent with the notion that specificity may be even further improved by engineering TALENs with a combination of mutant N-terminal and C-terminal domains that impart reduced non-specific DNA binding, a greater number of TALE repeats to contribute additional on-target DNA binding, and the more specific (but lower-affinity) NK RVD to recognize G.[25,31]

Our study has identified more bona fide TALEN genomic off-target sites than other studies using methods such as SELEX or integrase-deficient lentiviral vectors (IDLVs).[32] Our model and the resulting improved TALENs would have been difficult to derive from cellular off-target cleavage methods, which are intrinsically limited by the small number of sequences closely related to a target sequence of interest that are present in a genome, or from SELEX experiments with monomeric TALE repeat arrays,[5] which do not measure DNA cleavage activity and therefore does not characterize active, dimeric TALENs. In contrast, each TALEN in this study was evaluated for its ability to cleave any of $10^{12}$ close variants of its on-target sequence, a library size several orders of magnitude greater than the number of different sequences in a mammalian genome. This dense coverage of off-target sequence space enabled the elucidation of detailed relationships between DNA-cleavage specificity and target base pair position, TALE repeat length, TALEN concentration, mismatch location, and engineered TALEN domain composition.

Example 2

A number of TALENs were generated in which at least one cationic amino acid residue of the canonical N-terminal domain sequence was replaced with an amino acid residue that exhibits no charge or a negative charge at physiological pH. The TALENs comprised substitutions of glycine (G) and/or glutamine (Q) in their N-terminal domains (see FIG. 18). An evaluation of the cutting preferences of the engineered TALENs demonstrated that mutations to glycine (G) are equivalent to glutamine (Q). Mutating the positively charged amino acids in the TALEN N-terminal domain (K150Q, K153Q, and R154Q) result in similar decreases in binding affinity and off-target cleavage for mutations to either Q or G. For example, TALENs comprising the M3 and M4 N-terminus, which comprises the same amino acid (R154) mutated to either Q or G, respectively, demonstrated roughly equivalent amounts of cleavage. Similarly TALENs comprising the M6 and M8 N-terminus, varying only in whether Q or G substitutions were introduced at positions K150 and R154, and TALENs comprising the M9 and M10 N-terminus, varying only in whether Q or G substitutions were introduced at positions K150, K153, and R154, showed similar cleavage activity.

Example 3

A plasmid was generated for cloning and expression of engineered TALENs as provided herein. A map of the plasmid is shown in FIG. 19. The plasmid allows for the modular cloning of N-terminal and C-terminal domains, e.g., engineered domains as provided herein, and for TALE repeats, thus generating a recombinant nucleic acid encoding the desired engineered TALEN. The plasmid also encodes amino acid tags, e.g., an N-terminal FLAG tag and a C-terminal V5 tag, which can, optionally be utilized for purification or detection of the encoded TALEN. Use of these tags is optional and one of skill in the art will understand that the TALEN-encoding sequences will have to be cloned in-frame with the tag-encoding sequences in order to result in a tagged TALEN protein being encoded.

An exemplary sequence of a cloning vector as illustrated in FIG. 19 is provided below. Those of skill in the art will understand that the sequence below is illustrative of an exemplary embodiment and does not limit this disclosure.

>pExpCCR5A-L18(63aa)
(SEQ ID NO: 42)
GACGGATCGGGAGATCTCCCGATCCCCTATGGTCGACTCTCAGTACAATC

TGCTCTGATGCCGCATAGTTAAGCCAGTATCTGCTCCCTGCTTGTGTGTT

-continued

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGACTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCTGGCTAACTAGAGAACCCACTGCTTACTG

GCTTATCGAAATTAATACGACTCACTATAGGGAGACCCAAGCTGGCTAGC

ACCATGGACTACAAAGACCATGACGGTGATTATAAAGATCATGACATCGA

TTACAAGGATGACGATGACAAGATGGCCCCCAAGAAGAAGAGGAAGGTGG

GCATTCACCGCGGGGTACCTATGGTGGACTTGAGGACACTCGGTTATTCG

CAACAGCAACAGGAGAAAATCAAGCCTAAGGTCAGGAGCACCGTCGCGCA

ACACCACGAGGCGCTTGTGGGGCATGGCTTCACTCATGCGCATATTGTCG

CGCTTTCACAGCACCCTGCGGCGCTTGGGACGGTGGCTGTCAAATACCAA

GATATGATTGCGGCCCTGCCCGAAGCCACGCACGAGGCAATTGTAGGGGT

CGGTAAACAGTGGTCGGGAGCGCGAGCACTTGAGGCGCTGCTGACTGTGG

CGGGTGAGCTTAGGGGGCCTCCGCTCCAGCTCGACACCGGGCAGCTGCTG

AAGATCGCGAAGAGAGGGGGAGTAACAGCGGTAGAGGCAGTGCACGCCTG

GCGCAATGCGCTCACCGGGGCCCCCTTGAACCTGACCCCAGACCAGGTAG

TCGCAATCGCGTCAAACGGAGGGGGAAAGCAAGCCCTGGAAACCGTGCAA

AGGTTGTTGCCGGTCCTTTGTCAAGACCACGGCCTTACACCGGAGCAAGT

CGTGGCCATTGCATCCCACGACGGTGGCAAACAGGCTCTTGAGACGGTTC

AGAGACTTCTCCCAGTTCTCTGTCAAGCCCACGGGCTGACTCCCGATCAA

GTTGTAGCGATTGCGTCGAACATTGGAGGGAAACAAGCATTGGAGACTGT

CCAACGGCTCCTTCCCGTGTTGTGTCAAGCCCACGGTTTGACGCCTGCAC

AAGTGGTCGCCATCGCCTCGAATGGCGGCGGTAAGCAGGCGCTGGAAACA

GTACAGCGCCTGCTGCCTGTACTGTGCCAGGATCATGGACTGACCCCAGA

CCAGGTAGTCGCAATCGCGTCAAACGGAGGGGGAAAGCAAGCCCTGGAAA

CCGTGCAAAGGTTGTTGCCGGTCCTTTGTCAAGACCACGGCCTTACACCG

GAGCAAGTCGTGGCCATTGCAAGCAACATCGGTGGCAAACAGGCTCTTGA

GACGGTTCAGAGACTTCTCCCAGTTCTCTGTCAAGCCCACGGGCTGACTC

CCGATCAAGTTGTAGCGATTGCGTCGCATGACGGAGGGAAACAAGCATTG

-continued

```
GAGACTGTCCAACGGCTCCTTCCCGTGTTGTGTCAAGCCCACGGTTTGAC
GCCTGCACAAGTGGTCGCCATCGCCTCCAATATTGGCGGTAAGCAGGCGC
TGGAAACAGTACAGCGCCTGCTGCCTGTACTGTGCCAGGATCATGGACTG
ACCCCAGACCAGGTAGTCGCAATCGCGTCACATGACGGGGGAAAGCAAGC
CCTGGAAACCGTGCAAAGGTTGTTGCCGGTCCTTTGTCAAGACCACGGCC
TTACACCGGAGCAAGTCGTGGCCATTGCATCCCACGACGGTGGCAAACAG
GCTCTTGAGACGGTTCAGAGACTTCTCCCAGTTCTCTGTCAAGCCCACGG
GCTGACTCCCGATCAAGTTGTAGCGATTGCGTCCAACGGTGGAGGGAAAC
AAGCATTGGAGACTGTCCAACGGCTCCTTCCCGTGTTGTGTCAAGCCCAC
GGTTTGACGCCTGCACAAGTGGTCGCCATCGCCAACAACAACGGCGGTAA
GCAGGCGCTGGAAACAGTACAGCGCCTGCTGCCTGTACTGTGCCAGGATC
ATGGACTGACCCCAGACCAGGTAGTCGCAATCGCGTCACATGACGGGGGA
AAGCAAGCCCTGGAAACCGTGCAAAGGTTGTTGCCGGTCCTTTGTCAAGA
CCACGGCCTTACACCGGAGCAAGTCGTGGCCATTGCAAGCAACATCGGTG
GCAAACAGGCTCTTGAGACGGTTCAGAGACTTCTCCCAGTTCTCTGTCAA
GCCCACGGGCTGACTCCCGATCAAGTTGTAGCGATTGCGAATAACAATGG
AGGGAAACAAGCATTGGAGACTGTCCAACGGCTCCTTCCCGTGTTGTGTC
AAGCCCACGGTTTGACGCCTGCACAAGTGGTCGCCATCGCCAGCCATGAT
GGCGGTAAGCAGGCGCTGGAAACAGTACAGCGCCTGCTGCCTGTACTGTG
CCAGGATCATGGACTGACACCCGAACAGGTGGTCGCCATTGCTTCTAATG
GGGGAGGACGGCCAGCCTTGGAGTCCATCGTAGCCCAATTGTCCAGGCCC
GATCCCGCGTTGGCTGCGTTAACGAATGACCATCTGGTGGCGTTGGCATG
TCTTGGTGGACGACCCGCGCTCGATGCAGTCAAAAAGGGTCTGCCTCATG
CTCCCGCATTGATCAAAAGAACCAACCGGCGGATTCCCGAGAGAACTTCC
CATCGAGTCGCGGGATCCCAACTAGTCAAAAGTGAACTGGAGGAGAAGAA
ATCTGAACTTCGTCATAAATTGAAATATGTGCCTCATGAATATATTGAAT
TAATTGAAATTGCCAGAAATTCCACTCAGGATAGAATTCTTGAAATGAAG
GTAATGGAATTTTTTATGAAAGTTTATGGATATAGAGGTAAACATTTGGG
TGGATCAAGGAAACCGGACGGAGCAATTTATACTGTCGGATCTCCTATTG
ATTACGGTGTGATCGTGGATACTAAAGCTTATAGCGGAGGTTATAATCTG
CCAATTGGCCAAGCAGATGAAATGGAGCGATATGTCGAAGAAAATCAAAC
ACGAAACAAACATATCAACCCTAATGAATGGTGGAAAGTCTATCCATCTT
CTGTAACGGAATTTAAGTTTTTATTTGTGAGTGGTCACTTTAAAGGAAAC
TACAAAGCTCAGCTTACACGATTAAATCATATCACTAATTGTAATGGAGC
TGTTCTTAGTGTAGAAGAGCTTTTAATTGGTGGAGAAATGATTAAAGCCG
GCACATTAACCTTAGAGGAAGTGAGACGGAAATTTAATAACGGCGAGATA
AACTTTTAAGGGCCCTTCGAAGGTAAGCCTATCCCTAACCCTCTCCTCGG
TCTCGATTCTACGCGTACCGGTCATCATCACCATCACCATTGAGTTTAAA
CCCGCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTC
```

-continued

```
ATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGA
GGCGGAAAGAACCAGCTGGGGCTCTAGGGGGTATCCCCACGCGCCCTGTA
GCGGCGCATTAAGCGCGGCGGGTGTGGTGGTTACGCGCAGCGTGACCGCT
ACACTTGCCAGCGCCCTAGCGCCCGCTCCTTTCGCTTTCTTCCCTTCCTT
TCTCGCCACGTTCGCCGGCTTTCCCCGTCAAGCTCTAAATCGGGGCATCC
CTTTAGGGTTCCGATTTAGTGCTTTACGGCACCTCGACCCCAAAAAACTT
GATTAGGGTGATGGTTCACGTAGTGGGCCATCGCCCTGATAGACGGTTTT
TCGCCCTTTGACGTTGGAGTCCACGTTCTTTAATAGTGGACTCTTGTTCC
AAACTGGAACAACACTCAACCCTATCTCGGTCTATTCTTTTGATTTATAA
GGGATTTTGGGGATTTCGGCCTATTGGTTAAAAAATGAGCTGATTTAACA
AAAATTTAACGCGAATTAATTCTGTGGAATGTGTGTCAGTTAGGGTGTGG
AAAGTCCCCAGGCTCCCCAGGCAGGCAGAAGTATGCAAAGCATGCATCTC
AATTAGTCAGCAACCAGGTGTGGAAAGTCCCCAGGCTCCCCAGCAGGCAG
AAGTATGCAAAGCATGCATCTCAATTAGTCAGCAACCATAGTCCCGCCCC
TAACTCCGCCCATCCCGCCCCTAACTCCGCCCAGTTCCGCCCATTCTCCG
CCCCATGGCTGACTAATTTTTTTTATTTATGCAGAGGCCGAGGCCGCCTC
TGCCTCTGAGCTATTCCAGAAGTAGTGAGGAGGCTTTTTTGGAGGCCTAG
GCTTTTGCAAAAAGCTCCCGGGAGCTTGTATATCCATTTTCGGATCTGAT
CAGCACGTGTTGACAATTAATCATCGGCATAGTATATCGGCATAGTATAA
TACGACAAGGTGAGGAACTAAACCATGGCCAAGCCTTTGTCTCAAGAAGA
ATCCACCCTCATTGAAAGAGCAACGGCTACAATCAACAGCATCCCCATCT
CTGAAGACTACAGCGTCGCCAGCGCAGCTCTCTAGCGACGGCCGCATC
TTCACTGGTGTCAATGTATATCATTTTACTGGGGGACCTTGTGCAGAACT
CGTGGTGCTGGGCACTGCTGCTGCTGCGGCAGCTGGCAACCTGACTTGTA
TCGTCGCGATCGGAAATGAGAACAGGGGCATCTTGAGCCCCTGCGGACGG
TGTCGACAGGTGCTTCTCGATCTGCATCCTGGGATCAAAGCGATAGTGAA
GGACAGTGATGGACAGCCGACGGCAGTTGGGATTCGTGAATTGCTGCCCT
CTGGTTATGTGTGGGAGGGCTAAGCACTTCGTGGCCGAGGAGCAGGACTG
ACACGTGCTACGAGATTTCGATTCCACCGCCGCCTTCTATGAAAGGTTGG
GCTTCGGAATCGTTTTCCGGGACGCCGGCTGGATGATCCTCCAGCGCGGG
GATCTCATGCTGGAGTTCTTCGCCCACCCCAACTTGTTTATTGCAGCTTA
TAATGGTTACAAATAAAGCAATAGCATCACAAATTTCACAAATAAAGCAT
TTTTTTCACTGCATTCTAGTTGTGGTTTGTCCAAACTCATCAATGTATCT
TATCATGTCTGTATACCGTCGACCTCTAGCTAGAGCTTGGCGTAATCATG
GTCATAGCTGTTTCCTGTGTGAAATTGTTATCCGCTCACAATTCCACACA
ACATACGAGCCGGAAGCATAAAGTGTAAAGCCTGGGGTGCCTAATGAGTG
AGCTAACTCACATTAATTGCGTTGCGCTCACTGCCCGCTTTCCAGTCGGG
AAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTG
```

-continued

```
CGCTCGGTCGTTCGGCTGCGGCGAGCGGTATCAGCTCACTCAAAGGCGGT

AATACGGTTATCCACAGAATCAGGGGATAACGCAGGAAAGAACATGTGAG

CAAAAGGCCAGCAAAAGGCCAGGAACCGTAAAAAGGCCGCGTTGCTGGCG

TTTTTCCATAGGCTCCGCCCCCCTGACGAGCATCACAAAAATCGACGCTC

AAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACC

GGATACCTGTCCGCCTTTCTCCCTTCGGGAAGCGTGGCGCTTTCTCAATG

CTCACGCTGTAGGTATCTCAGTTCGGTGTAGGTCGTTCGCTCCAAGCTGG

GCTGTGTGCACGAACCCCCGTTCAGCCCGACCGCTGCGCCTTATCCGGT

AACTATCGTCTTGAGTCCAACCCGGTAAGACACGACTTATCGCCACTGGC

AGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTA

TTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTG

TTTGCAAGCAGCAGATTACGCGCAGAAAAAAGGATCTCAAGAAGATCCT

TTGATCTTTTCTACGGGGTCTGACGCTCAGTGGAACGAAAACTCACGTTA

AGGGATTTTGGTCATGAGATTATCAAAAGGATCTTCACCTAGATCCTTT

TAAATTAAAAATGAAGTTTTAAATCAATCTAAAGTATATATGAGTAAACT

TGGTCTGACAGTTACCAATGCTTAATCAGTGAGGCACCTATCTCAGCGAT

CTGTCTATTTCGTTCATCCATAGTTGCCTGACTCCCCGTCGTGTAGATAA

CTACGATACGGGAGGGCTTACCATCTGGCCCCAGTGCTGCAATGATACCG

CGAGACCCACGCTCACCGGCTCCAGATTTATCAGCAATAAACCAGCCAGC

CGGAAGGGCCGAGCGCAGAAGTGGTCCTGCAACTTTATCCGCCTCCATCC

AGTCTATTAATTGTTGCCGGGAAGCTAGAGTAAGTAGTTCGCCAGTTAAT

AGTTTGCGCAACGTTGTTGCCATTGCTACAGGCATCGTGGTGTCACGCTC

GTCGTTTGGTATGGCTTCATTCAGCTCCGGTTCCCAACGATCAAGGCGAG

TTACATGATCCCCATGTTGTGCAAAAAAGCGGTTAGCTCCTTCGGTCCT

CCGATCGTTGTCAGAAGTAAGTTGGCCGCAGTGTTATCACTCATGGTTAT

GGCAGCACTGCATAATTCTCTTACTGTCATGCCATCCGTAAGATGCTTTT

CTGTGACTGGTGAGTACTCAACCAAGTCATTCTGAGAATAGTGTATGCGG

CGACCGAGTTGCTCTTGCCCGGCGTCAATACGGGATAATACCGCGCCACA

TAGCAGAACTTTAAAAGTGCTCATCATTGGAAAACGTTCTTCGGGGCGAA

AACTCTCAAGGATCTTACCGCTGTTGAGATCCAGTTCGATGTAACCCACT

CGTGCACCCAACTGATCTTCAGCATCTTTTACTTTCACCAGCGTTTCTGG

GTGAGCAAAAACAGGAAGGCAAAATGCCGCAAAAAAGGGAATAAGGGCGA

CACGGAAATGTTGAATACTCATACTCTTCCTTTTTCAATATTATTGAAGC

ATTTATCAGGGTTATTGTCTCATGAGCGGATACATATTTGAATGTATTTA

GAAAAATAAACAAATAGGGGTTCCGCGCACATTTCCCCGAAAAGTGCCAC

CTGACGTC
```

REFERENCES

1. Moscou, M. J. & Bogdanove, A. J. A simple cipher governs DNA recognition by TAL effectors. Science 326, 1501 (2009).
2. Boch, J. et al. Breaking the code of DNA binding specificity of TAL-type III effectors. Science 326, 1509-1512 (2009).
3. Doyon, Y. et al. Enhancing zinc-finger-nuclease activity with improved obligate heterodimeric architectures. Nat Methods 8, 74-79 (2011).
4. Cade, L. et al. Highly efficient generation of heritable zebrafish gene mutations using homo- and heterodimeric TALENs. Nucleic Acids Res 40, 8001-8010 (2012).
5. Miller, J. C. et al. A TALE nuclease architecture for efficient genome editing. Nat Biotechnol 29, 143-148 (2011).
6. Bedell, V. M. et al. In vivo genome editing using a high-efficiency TALEN system. Nature 491, 114-118 (2012).
7. Hockemeyer, D. et al. Genetic engineering of human pluripotent cells using TALE nucleases. Nat Biotechnol 29, 731-734 (2011).
8. Cermak, T. et al. Efficient design and assembly of custom TALEN and other TAL effector-based constructs for DNA targeting. Nucleic Acids Res 39, e82 (2011).
9. Tesson, L. et al. Knockout rats generated by embryo microinjection of TALENs. Nat Biotechnol 29, 695-696 (2011).
10. Moore, F. E. et al. Improved somatic mutagenesis in zebrafish using transcription activator-like effector nucleases (TALENs). PLoS One 7, e37877 (2012).
11. Wood, A. J. et al. Targeted genome editing across species using ZFNs and TALENs. Science 333, 307 (2011).
12. Reyon, D. et al. FLASH assembly of TALENs for high-throughput genome editing. Nat Biotechnol 30, 460-465 (2012).
13. Mussolino, C. et al. A novel TALE nuclease scaffold enables high genome editing activity in combination with low toxicity. Nucleic Acids Res 39, 9283-9293 (2011).
14. Pattanayak, V., Ramirez, C. L., Joung, J. K. & Liu, D. R. Revealing off-target cleavage specificities of zinc-finger nucleases by in vitro selection. Nat Methods 8, 765-770 (2011).
15. Li, T. et al. Modularly assembled designer TAL effector nucleases for targeted gene knockout and gene replacement in eukaryotes. Nucleic Acids Res 39, 6315-6325 (2011).
16. Ding, Q. et al. A TALEN Genome-Editing System for Generating Human Stem Cell-Based Disease Models. Cell Stem Cell (2012).
17. Lei, Y. et al. Efficient targeted gene disruption in *Xenopus* embryos using engineered transcription activator-like effector nucleases (TALENs). Proc Natl Acad Sci USA 109, 17484-17489 (2012).
18. Kim, Y. et al. A library of TAL effector nucleases spanning the human genome. Nat Biotechnol 31, 251-258 (2013).
19. Dahlem, T. J. et al. Simple methods for generating and detecting locus-specific mutations induced with TALENs in the zebrafish genome. PLoS Genet 8, e1002861 (2012).
20. Osborn, M. J. et al. TALEN-based Gene Correction for Epidermolysis Bullosa. Molecular Therapy (2013).
21. Maul, G. G. & Deaven, L. Quantitative determination of nuclear pore complexes in cycling cells with differing DNA content. J Cell Biol 73, 748-760 (1977).

22. Huang, B. et al. Counting low-copy number proteins in a single cell. Science 315, 81-84 (2007).
23. Beck, M. et al. The quantitative proteome of a human cell line. Mol Syst Biol 7, 549 (2011).
24. Meckler, J. F. et al. Quantitative analysis of TALE-DNA interactions suggests polarity effects. Nucleic Acids Res (2013).
25. Christian, M. L. et al. Targeting G with TAL effectors: a comparison of activities of TALENs constructed with NN and NK repeat variable di-residues. PLoS One 7, e45383 (2012).
26. Sander, J. D. et al. Abstraction of zinc finger nuclease cleavage profiles reveals an expanded landscape of off-target mutations. Submitted (2013).
27. Witten, I. H. & Frank, E. Data mining: practical machine learning tools and techniques, Edn. 2nd. (Morgan Kaufman, San Francisco; 2005).
28. Kim, Y., Kweon, J. & Kim, J. S. TALENs and ZFNs are associated with different mutation signatures. Nat Methods 10, 185 (2013).
29. McNaughton, B. R., Cronican, J. J., Thompson, D. B. & Liu, D. R. Mammalian cell penetration, siRNA transfection, and DNA transfection by supercharged proteins. Proc Natl Acad Sci USA 106, 6111-6116 (2009).
30. Sun, N., Liang, J., Abil, Z. & Zhao, H. Optimized TAL effector nucleases (TALENs) for use in treatment of sickle cell disease. Mol Biosyst 8, 1255-1263 (2012).
31. Cong, L., Zhou, R., Kuo, Y. C., Cunniff, M. & Zhang, F. Comprehensive interrogation of natural TALE DNA-binding modules and transcriptional repressor domains. Nat Commun 3, 968 (2012).
32. Gabriel, R. et al. An unbiased genome-wide analysis of zinc-finger nuclease specificity. Nat Biotechnol 29, 816-823 (2011).
33. Gao, H., Wu, X., Chai, J. & Han, Z. Crystal structure of a TALE protein reveals an extended N-terminal DNA binding region. Cell Res 22, 1716-1720 (2012).
34. Li, T. et al. Modularly assembled designer TAL effector nucleases for targeted gene knockout and gene replacement in eukaryotes. Nucleic Acids Res 39, 6315-6325 (2011).
35. Miller, J. C. et al. A TALE nuclease architecture for efficient genome editing. Nat Biotechnol 29, 143-148 (2011).
36. Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).
37. Pattanayak, V., Ramirez, C. L., Joung, J. K. & Liu, D. R. Revealing off-target cleavage specificities of zinc-finger nucleases by in vitro selection. Nat Methods 8, 765-770 (2011).
38. Sander, J. D. et al. Abstraction of zinc finger nuclease cleavage profiles reveals an expanded landscape of off-target mutations. Submitted (2013).
39. Yan, T. et al. PatMatch: a program for finding patterns in peptide and nucleotide sequences. Nucleic Acids Res 33, W262-266 (2005).
40. Larkin, M. A. et al. Clustal W and Clustal X version 2.0. Bioinformatics 23, 2947-2948 (2007).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

TABLES

TABLE 2

TALEN constructs and concentrations used in the selections. For each selection using TALENs targeting the CCR5A target sequence (A), ATM target sequence (B) and CCR5B target sequence (C), the selection name, the target DNA site, the TALEN N-terminal domain, the TALEN C-terminal domain, the TALEN FokI domain, and the TALEN concentration (conc.) are shown.

| Selection name | Target site | Left + Right half-site | Site length | N-terminal domain | C-terminal domain | FokI domain | TALEN conc. (nM) |
|---|---|---|---|---|---|---|---|
| A |  |  |  |  |  |  |  |
| CCR5A 32 nM canonical | CCR5A | L18 + R18 | 36 | canonical | Canonical | EL/KK | 32 |
| CCR5A 16 nM canonical (or CCR5A 32 canonical) | CCR5A | L18 + R18 | 36 | canonical | Canonical | EL/KK | 16 |
| CCR5A 8 nM canonical | CCR5A | L18 + R18 | 36 | canonical | Canonical | EL/KK | 8 |
| CCR5A 4 nM canonical | CCR5A | L18 + R18 | 36 | canonical | Canonical | EL/KK | 4 |
| CCR5A Q3 | CCR5A | L18 + R18 | 36 | canonical | Q3 | EL/KK | 16 |
| CCR5A 32 nM Q7 | CCR5A | L18 + R18 | 36 | canonical | Q7 | EL/KK | 32 |
| CCR5A 16 nM Q7 (or CCR5A Q7) | CCR5A | L18 + R18 | 36 | canonical | Q7 | EL/KK | 16 |
| CCR5A 8 nM Q7 | CCR5A | L18 + R18 | 36 | canonical | Q7 | EL/KK | 8 |
| CCR5A 4 nM Q7 | CCR5A | L18 + R18 | 36 | canonical | Q7 | EL/KK | 4 |
| CCR5A 28-aa | CCR5A | L18 + R18 | 36 | canonical | 28-aa | EL/KK | 16 |
| CCR5A N1 | CCR5A | L18 + R18 | 36 | N1 | Canonical | EL/KK | 16 |
| CCR5A N2 | CCR5A | L18 + R18 | 36 | N2 | Canonical | EL/KK | 16 |
| CCR5A N3 | CCR5A | L18 + R18 | 36 | N3 | Canonical | EL/KK | 16 |
| CCR5A canonical ELD/KKR | CCR5A | L18 + R18 | 36 | canonical | Canonical | ELD/KKR | 16 |
| CCR5A Q3 ELD/KKR | CCR5A | L18 + R18 | 36 | canonical | Q3 | ELD/KKR | 16 |
| CCR5A Q7 ELD/KKR | CCR5A | L18 + R18 | 36 | canonical | Q7 | ELD/KKR | 16 |
| CCR5A N2 ELD/KKR | CCR5A | L18 + R18 | 36 | N2 | Canonical | ELD/KKR | 16 |
| B |  |  |  |  |  |  |  |
| ATM 32 nM canonical | ATM | L18 + R18 | 36 | canonical | Canonical | EL/KK | 24 |
| ATM 16 nM canonical (or ATM canonical) | ATM | L18 + R18 | 36 | canonical | Canonical | EL/KK | 12 |
| ATM 8 nM canonical | ATM | L18 + R18 | 36 | canonical | Canonical | EL/KK | 6 |
| ATM 4 nM canonical | ATM | L18 + R18 | 36 | canonical | Canonical | EL/KK | 3 |
| ATM Q3 | ATM | L18 + R18 | 36 | canonical | Q3 | EL/KK | 12 |
| ATM 32 nM Q7 | ATM | L18 + R18 | 36 | canonical | Q7 | EL/KK | 24 |
| ATM 16 nM Q7 (or ATM Q7) | ATM | L18 + R18 | 36 | canonical | Q7 | EL/KK | 12 |
| ATM 8 nM Q7 | ATM | L18 + R18 | 36 | canonical | Q7 | EL/KK | 6 |
| ATM 4 nM Q7 | ATM | L18 + R18 | 36 | canonical | Q7 | EL/KK | 3 |
| ATM 28-aa | ATM | L18 + R18 | 36 | canonical | 28aa | EL/KK | 12 |
| ATM N1 | ATM | L18 + R18 | 36 | N1 | Canonical | EL/KK | 12 |
| ATM N2 | ATM | L18 + R18 | 36 | N2 | Canonical | EL/KK | 12 |
| ATM N3 | ATM | L18 + R18 | 36 | N3 | Canonical | EL/KK | 12 |
| ATM canonical ELD/KKR | ATM | L18 + R18 | 36 | canonical | Canonical | ELD/KKR | 12 |
| ATM Q3 ELD/KKR | ATM | L18 + R18 | 36 | canonical | Q3 | ELD/KKR | 12 |
| ATM Q7 ELD/KKR | ATM | L18 + R18 | 36 | canonical | Q7 | ELD/KKR | 12 |
| ATM N2 ELD/KKR | ATM | L18 + R18 | 36 | N2 | Canonical | ELD/KKR | 12 |
| C |  |  |  |  |  |  |  |
| L16 + R16 CCR5B | CCR5B | L16 + R16 | 32 | canonical | Canonical | EL/KK | 10 |
| L16 + R13 CCR5B | CCR5B | L16 + R13 | 29 | canonical | Canonical | EL/KK | 10 |
| L16 + R10 CCR5B | CCR5B | L16 + R10 | 26 | canonical | Canonical | EL/KK | 10 |
| L13 + R16 CCR5B | CCR5B | L13 + R16 | 29 | canonical | Canonical | EL/KK | 10 |

TABLE 2-continued

TALEN constructs and concentrations used in the selections. For each selection using TALENs targeting the CCR5A target sequence (A), ATM target sequence (B) and CCR5B target sequence (C), the selection name, the target DNA site, the TALEN N-terminal domain, the TALEN C-terminal domain, the TALEN FokI domain, and the TALEN concentration (conc.) are shown.

| Selection name | Target site | Left + Right half-site | Site length | N-terminal domain | C-terminal domain | FokI domain | TALEN conc. (nM) |
|---|---|---|---|---|---|---|---|
| L13 + R13 CCR5B | CCR5B | L13 + R13 | 26 | canonical | Canonical | EL/KK | 10 |
| L13 + R10 CCR5B | CCR5B | L13 + R10 | 23 | canonical | Canonical | EL/KK | 10 |
| L10 + R16 CCR5B | CCR5B | L10 + R16 | 26 | canonical | Canonical | EL/KK | 10 |
| L10 + R13 CCR5B | CCR5B | L10 + R13 | 23 | canonical | Canonical | EL/KK | 10 |
| L10 + R10 CCR5B | CCR5B | L10 + R10 | 20 | canonical | Canonical | EL/KK | 10 |

TABLE 3

Statistics of sequences selected by TALEN digestion. Statistics are shown for each TALEN selection on the CCR5A target sequence (A), ATM target sequence (B), and CCR5B target sequences (C). Seq. counts: total counts of high-throughput sequenced and computationally filtered selection sequences. Mean mut.: mean mutations in selected sequences. Stdev. mut.: standard deviation of mutations in selected sequences. Mut./bp: mean mutation normalized to target site length (bp). P-value vs. library: P-values between the TALEN selection sequence distributions to the corresponding pre-selection library sequence distributions (Supplementary Table 4) were determined as previously reported.5 P-value vs. other TALENs: all pair-wise comparisons between all TALEN digestions were calculated and P-values between 0.01 and 0.5 are shown. Note that for the 3 nM Q7 ATM and the 28-aa ATM selection not enough sequences were obtained to interpret, although these selections were performed.

| Selection name | Seq. count | Mean mut. | Stdev mut. | Mut./bp | P-value vs. library | P-value vs. other TALENs |
|---|---|---|---|---|---|---|
| A | | | | | | |
| CCR5A 32 nM canonical | 53883 | 4.327 | 1.483 | 0.120 | 3.3E−10 | vs. CCR5A canonical ELD/KKR = 0.260 |
| CCR5A 16 nM canonical | 28940 | 4.061 | 1.438 | 0.113 | 5.4E−10 | vs. CCR5A Q3 ELD/KKR = 0.028 |
| CCR5A 8 nM canonical | 29568 | 3.751 | 1.394 | 0.104 | 3.3E−10 | |
| CCR5A 4 nM canonical | 34355 | 3.347 | 1.355 | 0.093 | 1.5E−10 | |
| CCR5A Q3 | 51694 | 3.841 | 1.380 | 0.107 | 1.7E−10 | |
| CCR5A 32 nM Q7 | 48473 | 2.718 | 1.197 | 0.076 | 4.4E−11 | |
| CCR5A 16 nM Q7 | 56593 | 2.559 | 1.154 | 0.071 | 3.1E−11 | |
| CCR5A 8 nM Q7 | 43895 | 2.303 | 1.157 | 0.064 | 3.0E−11 | |
| CCR5A 4 nM Q7 | 43737 | 2.018 | 1.234 | 0.056 | 2.1E−11 | |
| CCR5A 28-aa | 47395 | 2.614 | 1.203 | 0.073 | 4.0E−11 | |
| CCR5A N1 | 64257 | 3.721 | 1.379 | 0.103 | 1.1E−10 | vs. CCR5A 8 nM canonical = 0.039 |
| CCR5A N2 | 45467 | 3.148 | 1.306 | 0.087 | 8.2E−11 | |
| CCR5A N3 | 24064 | 2.474 | 1.493 | 0.069 | 8.1E−11 | |
| CCR5A canonical ELD/KKR | 46998 | 4.336 | 1.491 | 0.120 | 4.0E−10 | |
| CCR5A Q3 ELD/KKR | 56978 | 4.098 | 1.415 | 0.114 | 2.2E−10 | |
| CCR5A Q7 ELD/KKR | 54903 | 3.234 | 1.330 | 0.090 | 7.3E−11 | |
| CCR5A N2 ELD/KKR | 79632 | 3.286 | 1.341 | 0.091 | 5.2E−11 | |
| B | | | | | | |
| ATM 24 nM canonical | 89571 | 3.262 | 1.360 | 0.091 | 6.54E−11 | vs. ATM canonical ELD/KKR = 0.012 |
| ATM 12 nM canonical (or ATM canonical) | 96703 | 3.181 | 1.307 | 0.088 | 5.36E−11 | |
| ATM 6 nM canonical | 78852 | 2.736 | 1.259 | 0.076 | 3.63E−11 | |
| ATM 3 nM canonical | 82527 | 2.552 | 1.258 | 0.071 | 2.71E−11 | |
| ATM Q3 | 96582 | 2.551 | 1.248 | 0.071 | 2.31E−11 | vs. ATM 4 nM canonical = 0.222 |
| ATM 24 nM Q7 | 10166 | 1.885 | 2.125 | 0.052 | 2.06E−10 | |
| ATM 12 nM Q7 | 4662 | 1.626 | 2.083 | 0.045 | 5.31E−10 | |

TABLE 3-continued

Statistics of sequences selected by TALEN digestion. Statistics are shown for each TALEN selection on the CCR5A target sequence (A), ATM target sequence (B), and CCR5B target sequences (C). Seq. counts: total counts of high-throughput sequenced and computationally filtered selection sequences. Mean mut.: mean mutations in selected sequences. Stdev. mut.: standard deviation of mutations in selected sequences. Mut./bp: mean mutation normalized to target site length (bp). P-value vs. library: P-values between the TALEN selection sequence distributions to the corresponding pre-selection library sequence distributions (Supplementary Table 4) were determined as previously reported.5 P-value vs. other TALENs: all pair-wise comparisons between all TALEN digestions were calculated and P-values between 0.01 and 0.5 are shown. Note that for the 3 nM Q7 ATM and the 28-aa ATM selection not enough sequences were obtained to interpret, although these selections were performed.

| Selection name | Seq. count | Mean mut. | Stdev mut. | Mut./bp | P-value vs. library | P-value vs. other TALENs |
|---|---|---|---|---|---|---|
| (or ATM Q7) | | | | | | |
| ATM 6 nM Q7 | 1290 | 1.700 | 2.376 | 0.047 | 7.16E−09 | vs. ATM 16 nM Q7 = 0.035 |
| ATM N1 | 84402 | 2.627 | 1.318 | 0.073 | 2.92E−11 | |
| ATM N2 | 62470 | 2.317 | 1.516 | 0.064 | 2.69E−11 | |
| ATM N3 | 1605 | 2.720 | 2.363 | 0.076 | 2.69E−08 | |
| ATM canonical ELD/KKR | 107970 | 3.279 | 1.329 | 0.091 | 5.48E−11 | |
| ATM Q3 ELD/KKR | 104099 | 2.846 | 1.244 | 0.079 | 3.15E−11 | |
| ATM Q7 ELD/KKR | 21108 | 1.444 | 1.56 | 0.040 | 3.02E−11 | |
| ATM N2 ELD/KKR | 70185 | 2.45 | 1.444 | 0.06805 | 2.82E−11 | |

C

| Selection name | Seq. count | Mean mut. | Stdev mut. | Mut./bp | P-value vs. library |
|---|---|---|---|---|---|
| L16 + R16 CCR5B | 34904 | 2.134 | 1.168 | 0.067 | 4.7E−11 |
| L16 + R13 CCR5B | 38229 | 1.581 | 1.142 | 0.055 | 2.7E−11 |
| L16 + R10 CCR5B | 37801 | 1.187 | 0.949 | 0.046 | 2.2E−11 |
| L13 + R16 CCR5B | 46608 | 1.505 | 1.090 | 0.052 | 1.7E−11 |
| L13 + R13 CCR5B | 53973 | 0.996 | 1.025 | 0.038 | 8.8E−12 |
| L13 + R10 CCR5B | 60550 | 0.737 | 0.884 | 0.032 | 7.4E−12 |
| L10 + R16 CCR5B | 36927 | 1.387 | 0.971 | 0.053 | 3.0E−11 |
| L10 + R13 CCR5B | 58170 | 0.839 | 0.882 | 0.036 | 9.1E−12 |
| L10 + R10 CCR5B | 57331 | 0.646 | 0.779 | 0.032 | 1.0E−11 |

TABLE 4

Statistics of sequences from pre-selection libraries. For each preselection library containing a distribution of mutant sequences of the CCR5A target sequence, ATM target sequence and CCR5B target sequences. Seq. counts: total counts of high-throughput sequenced and the computationally filtered selection sequences. Mean mut.: mean mutations of sequences. Stdev. mut.: standard deviation of sequences. Mut./bp: mean mutation normalized to target site length (bp).

| Library name | Target site | Left + Right half-site | Site length | Seq. count | Mean mut. | Stdev mut. | Mut./bp |
|---|---|---|---|---|---|---|---|
| CCR5A Library | CCR5A | L18 + R18 | 36 | 158643 | 7.539 | 2.475 | 0.209 |
| ATM Library | ATM | L18 + R18 | 36 | 212661 | 6.820 | 2.327 | 0.189 |
| CCR5B Library | CCR5B | L16 + R16 | 32 | 280223 | 6.500 | 2.441 | 0.203 |
| CCR5B Library | CCR5B | L16 + R13 | 29 | 280223 | 5.914 | 2.336 | 0.204 |
| CCR5B Library | CCR5B | L16 + R10 | 26 | 280223 | 5.273 | 2.218 | 0.203 |
| CCR5B Library | CCR5B | L13 + R16 | 29 | 280223 | 5.969 | 2.340 | 0.206 |
| CCR5B Library | CCR5B | L13 + R13 | 26 | 280223 | 5.383 | 2.230 | 0.207 |
| CCR5B Library | CCR5B | L13 + R10 | 23 | 280223 | 4.742 | 2.106 | 0.206 |
| CCR5B Library | CCR5B | L10 + R16 | 26 | 280223 | 5.396 | 2.217 | 0.208 |
| CCR5B Library | CCR5B | L10 + R13 | 23 | 280223 | 4.810 | 2.100 | 0.209 |
| CCR5B Library | CCR5B | L10 + R10 | 20 | 280223 | 4.169 | 1.971 | 0.208 |

TABLE 5

Enrichment values of sequences as a function of number of mutations.
For each TALEN selection on the CCR5A target sequence (A), ATM
target sequence (B) and CCR5B target sequence (C), enrichment
values calculated by dividing the fractional abundance of post-selection
sequences from a TALEN digestion by the fractional abundance of pre-
selection sequences as a function of total mutations (Mut.) in the half-sites.

| Selection | _____ Enrichment value _____ | | | | | | | | |
|---|---|---|---|---|---|---|---|---|---|
| | 0 Mut. | 1 Mut. | 2 Mut. | 3 Mut. | 4 Mut. | 5 Mut. | 6 Mut. | 7 Mut. | 8 Mut. |
| A | | | | | | | | | |
| CCR5A 32 nM canonical | 9.879 | 9.191 | 8.335 | 6.149 | 4.205 | 2.269 | 1.005 | 0.325 | 0.085 |
| CCR5A 16 nM canonical | 12.182 | 13.200 | 10.322 | 7.195 | 4.442 | 2.127 | 0.748 | 0.216 | 0.052 |
| CCR5A 8 nM canonical | 19.673 | 17.935 | 13.731 | 8.505 | 4.512 | 1.756 | 0.531 | 0.116 | 0.028 |
| CCR5A 4 nM canonical | 36.737 | 29.407 | 19.224 | 9.958 | 4.047 | 1.242 | 0.302 | 0.058 | 0.014 |
| CCR5A Q3 | 18.550 | 16.466 | 12.024 | 8.070 | 4.632 | 1.938 | 0.572 | 0.126 | 0.026 |
| CCR5A 32 nM Q7 | 60.583 | 54.117 | 31.082 | 11.031 | 2.640 | 0.469 | 0.073 | 0.013 | 0.006 |
| CCR5A 16 nM Q7 | 62.294 | 64.689 | 35.036 | 10.538 | 2.163 | 0.322 | 0.046 | 0.010 | 0.006 |
| CCR5A 8 nM Q7 | 97.020 | 91.633 | 38.634 | 8.974 | 1.485 | 0.189 | 0.029 | 0.010 | 0.007 |
| CCR5A 4 nM Q7 | 197.239 | 130.497 | 38.361 | 6.535 | 0.896 | 0.120 | 0.025 | 0.019 | 0.017 |
| CCR5A 28-aa | 70.441 | 62.213 | 33.481 | 10.488 | 2.317 | 0.402 | 0.064 | 0.012 | 0.006 |
| CCR5A N1 | 19.038 | 16.052 | 13.858 | 8.788 | 4.546 | 1.697 | 0.499 | 0.115 | 0.025 |
| CCR5A N2 | 41.715 | 35.752 | 22.638 | 10.424 | 3.777 | 0.989 | 0.194 | 0.038 | 0.007 |
| CCR5A N3 | 173.897 | 86.392 | 31.503 | 8.770 | 1.853 | 0.350 | 0.089 | 0.036 | 0.027 |
| CCR5A canonical ELD/KKR | 8.101 | 10.012 | 8.220 | 6.147 | 4.119 | 2.291 | 1.019 | 0.330 | 0.083 |
| CCR5A Q3 ELD/KKR | 14.664 | 12.975 | 9.409 | 6.819 | 4.544 | 2.235 | 0.797 | 0.198 | 0.041 |
| CCR5A Q7 ELD/KKR | 37.435 | 32.922 | 21.033 | 10.397 | 3.867 | 1.087 | 0.238 | 0.046 | 0.010 |
| CCR5A N2 ELD/KKR | 35.860 | 31.459 | 20.135 | 10.189 | 3.983 | 1.155 | 0.260 | 0.050 | 0.013 |
| B | | | | | | | | | |
| ATM 24 nM canonical | 19.900 | 16.881 | 12.162 | 6.318 | 2.629 | 0.884 | 0.226 | 0.057 | 0.015 |
| ATM 12 nM canonical | 20.472 | 17.645 | 12.724 | 6.549 | 2.606 | 0.803 | 0.189 | 0.039 | 0.007 |
| ATM 6 nM canonical | 41.141 | 29.522 | 17.153 | 6.551 | 1.872 | 0.431 | 0.062 | 0.017 | 0.006 |
| ATM 3 nM canonical | 56.152 | 37.152 | 18.530 | 6.196 | 1.562 | 0.308 | 0.056 | 0.015 | 0.008 |
| ATM Q3 | 50.403 | 36.687 | 19.031 | 6.245 | 1.513 | 0.294 | 0.057 | 0.016 | 0.010 |
| ATM 24 nM Q7 | 353.148 | 90.350 | 13.475 | 1.531 | 0.186 | 0.128 | 0.116 | 0.118 | 0.103 |
| ATM 12 nM Q7 | 513.385 | 89.962 | 11.310 | 0.860 | 0.190 | 0.093 | 0.115 | 0.092 | 0.111 |
| ATM 6 nM Q7 | 644.427 | 82.074 | 7.650 | 0.677 | 0.170 | 0.205 | 0.163 | 0.164 | 0.071 |
| ATM N1 | 57.218 | 35.388 | 17.808 | 6.124 | 1.644 | 0.383 | 0.076 | 0.023 | 0.011 |
| ATM N2 | 119.240 | 53.618 | 18.977 | 4.742 | 0.992 | 0.233 | 0.076 | 0.044 | 0.037 |
| ATM N3 | 201.158 | 55.468 | 15.244 | 3.187 | 0.764 | 0.307 | 0.154 | 0.173 | 0.267 |
| ATM canonical ELD/KKR | 19.356 | 15.692 | 11.855 | 6.403 | 2.706 | 0.899 | 0.224 | 0.054 | 0.011 |
| ATM Q3 ELD/KKR | 32.816 | 25.151 | 16.172 | 6.727 | 2.095 | 0.506 | 0.095 | 0.018 | 0.004 |
| ATM Q7 ELD/KKR | 447.509 | 93.166 | 13.505 | 1.543 | 0.170 | 0.053 | 0.049 | 0.045 | 0.045 |
| ATM N2 ELD/KKR | 90.625 | 45.525 | 18.683 | 5.369 | 1.267 | 0.274 | 0.075 | 0.035 | 0.027 |
| C | | | | | | | | | |
| L16 + R16 CCR5B | 59.422 | 35.499 | 13.719 | 3.770 | 0.737 | 0.132 | 0.024 | 0.011 | 0.008 |
| L16 + R13 CCR5B | 80.852 | 31.434 | 7.754 | 1.380 | 0.218 | 0.040 | 0.022 | 0.016 | 0.017 |
| L16 + R10 CCR5B | 64.944 | 20.056 | 3.867 | 0.515 | 0.056 | 0.010 | 0.006 | 0.006 | 0.007 |
| L13 + R16 CCR5B | 101.929 | 34.255 | 8.131 | 1.299 | 0.167 | 0.033 | 0.016 | 0.011 | 0.014 |
| L13 + R13 CCR5B | 113.102 | 22.582 | 3.037 | 0.315 | 0.044 | 0.022 | 0.017 | 0.017 | 0.016 |
| L13 + R10 CCR5B | 74.085 | 11.483 | 1.270 | 0.121 | 0.022 | 0.013 | 0.011 | 0.013 | 0.008 |
| L10 + R16 CCR5B | 60.186 | 22.393 | 5.286 | 0.777 | 0.084 | 0.012 | 0.006 | 0.006 | 0.008 |
| L10 + R13 CCR5B | 74.204 | 13.696 | 1.673 | 0.152 | 0.021 | 0.011 | 0.010 | 0.009 | 0.010 |
| L10 + R10 CCR5B | 43.983 | 7.018 | 0.740 | 0.061 | 0.013 | 0.007 | 0.007 | 0.008 | 0.005 |

A

| CCR5A Site OnCCR5 | Score | Mut. | Left half-site | Spacer length | Right half-site | Gene |
|---|---|---|---|---|---|---|
| A | 0.008 | 0 | TTCATTACACCTGCAGCT | 18 | AGTATCAATTCTGGAAGA | CCR5 |
| OffC-1 | 0.747 | 9 | TaCATcACAtaTGCAaaT | 29 | tGTATCAtTTCTGGgAGA | ARL17A & LRRC37A |
| OffC-2 | 0.747 | 9 | TaCATcACAtaTGCAaaT | 29 | tGTATCAtTTCTGGgAGA | ARL17A & LRRC37A |
| OffC-3 | 0.747 | 9 | TaCATcACAtaTGCAaaT | 29 | tGTATCAtTTCTGGgAGA | ARL17A & LRRC37A |
| OffC-4 | 0.747 | 11 | TcCATaACACaTctttCT | 10 | tGcATCAtTcCTGGAAGA | ZSCAN5A |
| OffC-5 | 0.804 | 11 | TcCAaTACctCTGCcaCA | 14 | AGgAgCAAcTCTGGgAGA | |
| OffC-6 | 0.818 | 10 | TTCAgTcCAtCTGaAaac | 16 | gGTATCAtTTCTGGAgGA | KL |
| OffC-7 | 0.834 | 14 | TaCAaaACcCtTGCcaaa | 27 | taTATCAATTtgGGgAGA | |
| OffC-8 | 0.837 | 12 | TcCAagACACCTGCttac | 26 | tcTATCAATTtgGGgAGA | |
| OffC-9 | 0.874 | 10 | TTCATaACAtCTtaAaaT | 27 | AaTAcCAAcTCTGGAtGA | ZEB2 |
| OffC-10 | 0.89 | 12 | TcCAaaACAtCTGaAaaT | 25 | tGgATCAAaTtgGGAAGA | |
| OffC-11 | 0.896 | 12 | TTCAgaACACaTGactac | 21 | tGTATCAgTTaTGGAtGA | GABPA |
| OffC-12 | 0.904 | 13 | TcCATaAtAtCTtCctCT | 28 | gGgATtAATTgGGAgGA | |
| OffC-13 | 0.905 | 11 | TgCAaTAtACCTGttgaT | 16 | ctcATCAATTCTGGgtGA | |
| OffC-14 | 0.906 | 12 | TTCATaACACtccacctT | 16 | gGTATCAAaTCTGGgGA | SYN3 |
| OffC-15 | 0.906 | 12 | TcCATgACACaaaagaCT | 26 | gGTATCtAtcCTGGAAtA | SPOCK3 |
| OffC-16 | 0.906 | 9 | TTCcTTcCACCaGtgtCc | 28 | AGcATCAATcCTGGAAGA | |
| OffC-17 | 0.907 | 10 | TTaATaACAtCTcCAaCT | 24 | gGcAcCAAaTCTGGAtGA | ATP13A5 |
| OffC-18 | 0.909 | 13 | TcCATcACcCCTcCctCc | 10 | gGTgcCAgcTCTGGAgGA | TBC1D7 |
| OffC-19 | 0.909 | 8 | TTCATTACtCCTcCtttCT | 30 | ctTATCAcTTtTGGAAGA | |
| OffC-20 | 0.912 | 10 | TgCATTACAcaTtatGtg | 17 | AGcAgCAcTTCTGGAAGA | |
| OffC-21 | 0.913 | 11 | TTCAaaACACaTaCAtCT | 28 | AacAaCAtTcCTGtAAGA | PRKAG2 |
| OffC-22 | 0.913 | 10 | TcCATTACcaCTGCAGaT | 25 | gacATCAgTTaTGGAtGA | |
| OffC-23 | 0.925 | 13 | TTCcagAcCcCCTtCcTCa | 13 | gacATCAAaTCTGGgAGA | |
| OffC-24 | 0.927 | 12 | TTCcaaACACCcGCttCc | 26 | taTATCctTTCTGGAAtA | |
| OffC-25 | 0.93 | 12 | TgaAaTACACCTGCctaT | 13 | gGccTCAAggCTGGAtGA | IL15 |
| OffC-26 | 0.93 | 12 | TgCcaaACctCTGtcaCc | 22 | AGgATCAcTTCTGGAAGA | |
| OffC-27 | 0.931 | 12 | TgCcaaACctCTGtcaCc | 22 | AGgATCAcTTCTGGAAGA | |
| OffC-28 | 0.931 | 8 | TTtATTACACtTcCAGaT | 19 | gaTATCctTTCTGGAAGA | ADIPOR2 |
| OffC-29 | 0.932 | 13 | TaCAaaAaACtTtCtGag | 27 | tGTATCAATTtgGGgAGA | FBXL17 |
| OffC-30 | 0.932 | 11 | TcCAaaACACCcaCAGac | 19 | gGTATagATTgTGGAAGA | ZNF365 |
| OffC-31 | 0.934 | 13 | TTCATTcCACaTcCccac | 25 | gtTATCAAcatgGGAAGA | MYO18B |
| OffC-32 | 0.934 | 11 | TTCAaTAtgCCaaCAGCT | 11 | AGctTCAATctgGGAgGA | |
| OffC-33 | 0.934 | 12 | TTCAaTACACtTGtctaT | 12 | tGTgTCAtTTCTGGgttA | |
| OffC-34 | 0.935 | 11 | TTCAacACACCTtCAaaa | 12 | tGTgTCAtTaaTGGAAGA | |
| OffC-35 | 0.935 | 10 | TTCAaaACAtCTGacatT | 10 | AaTAgaAATTCTGGAAGA | |
| OffC-36 | 0.935 | 11 | cTCcTaAtACCTGCAaaT | 21 | gaTATtatTTCTGGAgGA | |

40

B

| ATM Site | Score | Mut. | Left half-site | Spacer length | Right half-site | Gene |
|---|---|---|---|---|---|---|
| OnATM | 0.000 | 0 | TGAATTGGGATGCTGTTT | 18 | TTTATTTTACTGTCTTTA | ATM |
| OffA-1 | 0.595 | 7 | TGAATaGGaAaataTaTTT | 20 | TTTATTTTACTGTtTTTA | |
| OffA-2 | 0.697 | 9 | TGgATTcaGATacCTcTTT | 10 | TTTATTTTttTaTtTTTA | |
| OffA-3 | 0.697 | 9 | TGgATTcaGATacCTcTTT | 10 | TTTATTTTttTaTtTTTA | |
| OffA-4 | 0.697 | 9 | TGgATTcaGATacCTcTTT | 10 | TTTATTTTttTaTtTTTA | |
| OffA-5 | 0.697 | 9 | TGgATTcaGATacCTcTTT | 10 | TTTATTTTttTaTtTTTA | |
| OffA-6 | 0.697 | 9 | TGgATTcaGATacCTcTTT | 10 | TTTATTTTttTaTtTTTA | |
| OffA-7 | 0.697 | 9 | TGgATTcaGATacCTcTTT | 10 | TTTATTTTttTaTtTTTA | |
| OffA-8 | 0.7 | 8 | TGcATaGGaATGCTaaTT | 10 | TTTATTTTACTaTtTaTA | MGAT4C |
| OffA-9 | 0.708 | 10 | TGAATTaaaATcCTGcTT | 19 | gTTATaTgACTaTtTTTA | BRCA2 |
| OffA-10 | 0.711 | 10 | TccATTaaaATaCTaTTT | 18 | TTTATTTTAtTaTtTTTA | CPNE4 |
| OffA-11 | 0.715 | 10 | TGAATTGaGAgaagcaTT | 16 | TTTATTTTAtTaTtTTTA | |
| OffA-12 | 0.725 | 10 | TGAAgTGGGATacCTGTTa | 29 | ggTATATTAtaaTtTTTA | |
| OffA-13 | 0.729 | 9 | TGAATTatGAaGCTacTT | 17 | TTTATTgTAaTaTtTTTA | NAALADL2 |
| OffA-14 | 0.731 | 9 | TGAATaaGgATGCTaTTa | 25 | TTTATTTatttTaTtTTTA | |
| OffA-15 | 0.744 | 10 | TGAATgGGGAcaCaGcca | 29 | TTTATTTTAtTaTtTTTA | |
| OffA-16 | 0.752 | 9 | TaAATgGaaATGCTGTTc | 24 | aTTATTTTAtTGTtTTTt | |
| OffA-17 | 0.761 | 9 | gGAAaTGGGAtaCTGagT | 15 | TTTATgTTACTaTtTcTA | |
| OffA-18 | 0.781 | 11 | TGgATcGaagTGaTtaTT | 23 | TTTATTTTAtTaTtTTTA | CIDEC |
| OffA-19 | 0.792 | 11 | TGAATTGaGATtCacagc | 23 | TTTATTTTttTaTtTTTA | |
| OffA-20 | 0.803 | 8 | TGAATaGGaAatCTGaTT | 10 | TTTATTTTAtTaTtaTTA | THSD7B |
| OffA-21 | 0.807 | 12 | TaAATTaaaATaCTccag | 23 | aTTATTTTAaTGTtTTTA | ARID1B |
| OffA-22 | 0.811 | 10 | TGAATaGGaAaATtcTTT | 12 | TTTATTTattTaTtTTTA | |
| OffA-23 | 0.811 | 9 | TagATTGaaATGCTGTTT | 15 | TTTtTaTTAtTaTtTTTA | KLHL4 |

-continued

B

| ATM Site | Score | Mut. | Left half-site | Spacer length | Right half-site | Gene |
|---|---|---|---|---|---|---|
| OffA-24 | 0.816 | 10 | TGAcTaGaaATGaTGaTT | 25 | TTTATTTTctTaTtTTTA | |
| OffA-25 | 0.817 | 12 | TGAATTtaaAaaaTGTcc | 13 | aTTATTTTAtTaTtTTTA | |
| OffA-26 | 0.817 | 12 | TGAATTtaaAaaaTGTcc | 13 | aTTATTTTAtTaTtTTTA | |
| OffA-27 | 0.817 | 10 | TGgATccaGATaCTcTTT | 10 | TTTATTTTttTaTtTTTA | |
| OffA-28 | 0.819 | 7 | TGgAgTGaGATcCTGTTT | 21 | TTTATTTTAtTGTtaTTA | |
| OffA-29 | 0.824 | 8 | TGAAcTtGGATGaTaTaT | 24 | TTTATTTgAtTaTCTTTA | |
| OffA-30 | 0.832 | 9 | TGtATTGGGATaCcaTTT | 26 | TcTATTTTAtTaTtTTTt | |
| OffA-31 | 0.833 | 9 | TcAATTGGGATGaTcaTa | 23 | TTTATTcTAtTtTtTTTA | |
| OffA-32 | 0.835 | 9 | TGAAagGGaAaGtTGgaT | 23 | TTTATTTTACTaTtTTTA | |
| OffA-33 | 0.841 | 9 | TGgtTTGGGATcCTGTgt | 27 | TTTATgTTttTaTtTTTA | PTCHD2 |
| OffA-34 | 0.841 | 9 | TGAAaTGGGATGagcTTg | 28 | TTTATTTTAtTaTtTTaA | |
| OffA-35 | 0.844 | 10 | TGAATTGGGATaCTGTag | 29 | cTTAaaTaAaTaTtTTTA | ST6GALNAC3 |
| OffA-36 | 0.844 | 10 | TGAATTGtGgTatTGccT | 18 | TTTATggTttTGTCTTTA | |

Table 6. Predicted off-target sites in the human genome. (A) Using a machine learning "classifier" algorithm trained on the output of the in vitro CCR5A TALEN selection,6 mutant sequences of the target site allowing for spacer lengths of 10 to 30 base pairs were scored. The resulting 36 predicted off-targets sites with the best scores for the CCR5A TALENs are shown with classifier scores, mutation numbers, left and right half-site sequences (mutations from on-target in lower case), the length of the spacer between half-sites in base pairs, and the gene (including introns) in which the predicted off-target sites occurs, if it lies within a gene. (B) Same as (A) for ATM TALENs. Sequences correspond to SEQ ID NOs: 44, 169-204 (left half-site column of Table 6A); SEQ ID NOs: 46, 205-240 (right half-site column of Table 6A); SEQ ID NOs: 128, 242-276 (left half-site column of Table 6B); and SEQ ID NOs: 137, 277-312 (right half-site column of Table 6B).

TABLE 7

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

A

| C-terminal domain<br>FokI domain | No TALEN<br>No TALEN | Q7<br>EL/KK | Q7<br>ELD/KKR | Q3<br>EL/KK | Q3<br>ELD/KKR | Canonical<br>EL/KK | Canonical<br>ELD/KKR | Canonical<br>Homo |
|---|---|---|---|---|---|---|---|---|
| CCR5A Sites | | | | | | | | |
| OnC | | | | | | | | |
| Indels | 5 | 147 | 705 | 1430 | 3731 | 641 | 2004 | 3943 |
| Total | 23644 | 7192 | 12667 | 16843 | 15381 | 8546 | 7267 | 8422 |
| % Modified | 0.021% | 2.044% | 5.566% | 8.490% | 24.257% | 9.841% | 27.577% | 46.818% |
| P-value | | 1.3E−33 | 2.5E−160 | <1.0E−200 | <1.0E−200 | 5.9E−200 | <1.0E−200 | <1.0E−200 |
| Specificity | | | | | | | | |
| OffC-1 | | | | | | | | |
| Indels | 0 | 0 | 1 | 1 | 0 | 0 | 1 | 1 |
| Total | 51248 | 38975 | 79858 | 35491 | 77804 | 34227 | 87497 | 42498 |
| % Modified | <0.006% | <0.006% | <0.006% | <0.006% | <0.006% | <0.006% | <0.006% | <0.006% |
| P-value | | | | | | | | |
| Specificity | | | | | | | | |
| OffC-2 | | | | | | | | |
| Indels | 0 | 0 | 0 | 0 | 0 | 0 | 10 | 0 |
| Total | 124356 | 96280 | 157387 | 93337 | 159817 | 85603 | 163332 | 114663 |
| Modified | <0.006% | <0.006% | <0.006% | <0.006% | <0.006% | <0.006% | 0.006% | <0.006% |
| P-value | | | | | | | 1.6E−03 | |
| Specificity | | >307 | >835 | >1274 | >3639 | >1476 | >4137 | >7023 |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffC-3 | | | | | | | | |
|---|---|---|---|---|---|---|---|---|
| Indels | 5 | 0 | 4 | 1 | 0 | 0 | 6 | 3 |
| Total | 93085 | 75958 | 130027 | 72919 | 131132 | 57192 | 136796 | 90039 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-4 | | | | | | | | |
| Indels | 0 | 1 | 0 | 0 | 0 | 0 | 0 | 0 |
| Total | 45377 | 44674 | 52876 | 35133 | 53909 | 26034 | 42284 | 40452 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-5 | | | | | | | | |
| Indels | 0 | 0 | 0 | 3 | 22 | 134 | 385 | 395 |
| Total | 27009 | 28172 | 26035 | 22432 | 25800 | 25273 | 17045 | 17077 |
| Modified | <0.006% | <0.006% | <0.006% | 0.013% | 0.085% | 0.527% | 2.209% | 2.261% |
| P-value | | | | | 2.7E−06 | 4.5E−31 | 4.9E−87 | 2.8E−89 |
| Specificity | | >576 | >1450 | 635 | 285 | 19 | 12 | 21 |
| OffC-6 | | | | | | | | |
| Indels | 0 | 0 | 0 | 0 | 0 | 0 | 0 | 0 |
| Total | 10766 | 12309 | 10886 | 9240 | 10558 | 10500 | 5943 | 6560 |
| Modified | <0.009% | <0.008% | <0.009% | <0.011% | <0.009% | <0.010% | <0.017% | <0.015% |
| P-value | | | | | | | | |
| Specificity | | | | | | | | |
| OffC-7 | | | | | | | | |
| Total | 0 | 0 | 0 | 0 | 0 | 0 | 0 | 0 |
| Modified | 15626 | 28825 | 22138 | 31742 | 19577 | 11902 | 33200 | 15400 |
| P-value | <0.006% | <0.006% | <0.006% | <0.006% | <0.006% | <0.008% | <0.006% | <0.006% |
| Specificity | | | | | | | | |
| OffC-9 | | | | | | | | |
| Indels | 0 | 0 | 0 | 1 | 0 | 0 | 0 | 0 |
| Total | 40603 | 39765 | 47974 | 51595 | 44002 | 34520 | 25211 | 30771 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-10 | | | | | | | | |
| Indels | 0 | 0 | 0 | 0 | 0 | 0 | 0 | 0 |
| Total | 4142 | 9591 | 5187 | 1413 | 7975 | 4378 | 2215 | 3779 |
| Modified | <0.024% | <0.010% | <0.019% | <0.071% | <0.013% | <0.023% | <0.045% | <0.026% |
| P-value | | | | | | | | |
| Specificity | | | | | | | | |
| OffC-11 | | | | | | | | |
| Indels | 0 | 0 | 0 | 0 | 0 | 0 | 0 | 0 |
| Total | 71180 | 55455 | 65015 | 44847 | 70907 | 50967 | 65257 | 60191 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-12 | | | | | | | | |
| Indels | 0 | 0 | 0 | 0 | 0 | 0 | 0 | 0 |
| Total | 3242 | 1784 | 30274 | 14006 | 4897 | 19830 | 9747 | 12910 |
| Modified | <0.031% | <0.056% | <0.006% | <0.007% | <0.020% | <0.006% | <0.010% | <0.008% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffC-13 | | | | | | | | |
|---|---|---|---|---|---|---|---|---|
| Indels | 0 | 0 | 0 | 0 | 0 | 0 | 0 | 0 |
| Total | 65518 | 52459 | 53413 | 38156 | 61600 | 47922 | 57211 | 78546 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-14 | | | | | | | | |
| Indels | 0 | 0 | 0 | 0 | 0 | 0 | 2 | 0 |
| Total | 34607 | 7217 | 26301 | 8339 | 29845 | 1081 | 9471 | 19026 |
| Modified | <0.006% | <0.014% | <0.006% | <0.012% | <0.006% | <0.093% | 0.021% | <0.006% |
| P-value | | | | | | | | |
| Specificity | | | | | | | | |
| OffC-15 | | | | | | | | |
| Indels | 0 | 0 | 0 | 0 | 0 | 0 | 16 | 2 |
| Total | 4989 | 4880 | 6026 | 9370 | 9156 | 7371 | 6967 | 4662 |
| Modified | <0.020% | <0.020% | <0.017% | <0.011% | <0.011% | <0.014% | 0.230% | 0.043% |
| P-value | | | | | | | 6.3E−05 | |
| Specificity | | >100 | >335 | >796 | >2221 | >725 | 120 | 1091 |
| OffC-16 | | | | | | | | |
| Indels | 0 | 1 | 1 | 1 | 14 | 1 | 12 | 0 |
| Total | 36228 | 34728 | 34403 | 34866 | 44362 | 38384 | 38536 | 32636 |
| Modified | <0.006% | <0.006% | <0.006% | <0.006% | 0.032% | <0.006% | 0.031% | <0.006% |
| P-value | | | | | 1.8E−04 | | 5.3E−04 | |
| Specificity | | >307 | >835 | >1274 | 769 | >1476 | 886 | >7023 |
| OffC-17 | | | | | | | | |
| Indels | 0 | 0 | 0 | 0 | 0 | 0 | 0 | 0 |
| Total | 32112 | 23901 | 31273 | 33968 | 27437 | 29670 | 27133 | 31299 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-18 | | | | | | | | |
| Indels | 0 | 0 | 0 | 0 | 0 | 0 | 0 | 0 |
| Total | 9437 | 9661 | 13505 | 14900 | 13848 | 12720 | 6624 | 12804 |
| Modified | <0.011% | <0.010% | <0.007% | <0.007% | <0.007% | <0.008% | <0.015% | <0.008% |
| P-value | | | | | | | | |
| Specificity | | | | | | | | |
| OffC-19 | | | | | | | | |
| Indels | 1 | 1 | 1 | 2 | 2 | 2 | 1 | 0 |
| Total | 22869 | 11479 | 22702 | 15258 | 20733 | 17449 | 14638 | 28478 |
| Modified | <0.006% | 0.009% | <0.006% | 0.013% | 0.010% | 0.011% | 0.007% | <0.006% |
| P-value | | | | | | | | |
| Specificity | | | | | | | | |
| OffC-20 | | | | | | | | |
| Indels | 0 | 0 | 0 | 0 | 0 | 1 | 0 | 0 |
| Total | 23335 | 26164 | 30782 | 15261 | 20231 | 21184 | 14144 | 18972 |
| Modified | <0.006% | <0.006% | <0.006% | <0.007% | <0.006% | <0.006% | <0.007% | <0.006% |
| P-value | | | | | | | | |
| Specificity | | | | | | | | |
| OffC-21 | | | | | | | | |
| Indels | 0 | 0 | 0 | 0 | 0 | 0 | 0 | 0 |
| Total | 34302 | 27573 | 31694 | 24451 | 25826 | 27192 | 18110 | 21161 |
| Modified | <0.006% | <0.006% | <0.006% | <0.006% | <0.006% | <0.006% | <0.006% | <0.006% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffC-22 | | | | | | | | |
|---|---|---|---|---|---|---|---|---|
| Indels | 1 | 0 | 0 | 0 | 0 | 0 | 0 | 0 |
| Total | 81037 | 86687 | 74274 | 79004 | 93477 | 92089 | 75359 | 104857 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-23 | | | | | | | | |
| Indels | 0 | 0 | 0 | 0 | 0 | 0 | 0 | 0 |
| Total | 18812 | 19337 | 23034 | 25603 | 25023 | 28615 | 17172 | 21033 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-24 | | | | | | | | |
| Indels | 0 | 0 | 1 | 0 | 0 | 0 | 0 | 1 |
| Total | 23538 | 21673 | 24594 | 27687 | 18343 | 29113 | 21709 | 26610 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-25 | | | | | | | | |
| Indels | 0 | 0 | 0 | 0 | 0 | 0 | 0 | 0 |
| Total | 28941 | 25326 | 25871 | 10641 | 21422 | 20171 | 18946 | 18711 |
| Modified | <0.006% | <0.006% | <0.006% | <0.009% | <0.006% | <0.006% | <0.006% | <0.006% |
| P-value | | | | | | | | |
| Specificity | | | | | | | | |
| OffC-26 | | | | | | | | |
| Indels | 0 | 0 | 1 | 0 | 0 | 0 | 0 | 0 |
| Total | 71831 | 48494 | 62650 | 45801 | 60175 | 65137 | 28795 | 64632 |
| Modified | <0.006% | <0.006% | <0.006% | <0.006% | <0.006% | <0.006% | <0.006% | <0.006% |
| P-value | | | | | | | | |
| Specificity | | | | | | | | |
| OffC-27 | | | | | | | | |
| Indels | 0 | 0 | 0 | 0 | 0 | 0 | 0 | 0 |
| Total | 12181 | 2423 | 11258 | 7188 | 5126 | 4003 | 2116 | 4503 |
| % Modified | <0.008% | <0.041% | <0.009% | <0.014% | <0.020% | <0.025% | <0.047% | <0.022% |
| P-value | | | | | | | | |
| Specificity | | | | | | | | |
| OffC-28 | | | | | | | | |
| Indels | 0 | 0 | 0 | 0 | 6 | 1 | 12 | 5 |
| Total | 10651 | 6410 | 16179 | 13980 | 13022 | 7232 | 7379 | 8998 |
| % Modified | <0.009% | <0.016% | <0.006% | <0.007% | 0.046% | 0.014% | 0.163% | 0.056% |
| P-value | | | | | 1.4E−02 | | 5.3E−04 | |
| Specificity | | >131 | >835 | >1187 | 526 | 712 | 170 | 843 |
| OffC-29 | | | | | | | | |
| Indels | 0 | 0 | 0 | 0 | 0 | 0 | 0 | 0 |
| Total | 4262 | 3766 | 4228 | 6960 | 3234 | 1516 | 2466 | 1810 |
| % Modified | <0.023% | <0.027% | <0.024% | <0.014% | <0.031% | <0.066% | <0.041% | <0.055% |
| P-value | | | | | | | | |
| Specificity | | | | | | | | |
| OffC-30 | | | | | | | | |
| Indels | 0 | 0 | 0 | 0 | 0 | 0 | 0 | 0 |
| Total | 11840 | 12257 | 9617 | 34097 | 20507 | 5029 | 22248 | 6285 |
| % Modified | <0.008% | <0.008% | <0.010% | <0.006% | <0.006% | <0.020% | <0.006% | <0.016% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffC-31 | | | | | | | | |
|---|---|---|---|---|---|---|---|---|
| Indels | 0 | 0 | 0 | 0 | 0 | 0 | 0 | 0 |
| Total | 64522 | 67791 | 50085 | 50056 | 56241 | 48287 | 72230 | 100410 |
| % Modified | <0.006% | <0.006% | <0.006% | <0.006% | <0.006% | <0.006% | <0.006% | <0.006% |
| P-value | | | | | | | | |
| Specificity | | | | | | | | |
| OffC-32 | | | | | | | | |
| Indels | 0 | 0 | 0 | 0 | 0 | 0 | 0 | 0 |
| Total | 1944 | 6888 | 9330 | 3207 | 4591 | 6699 | 13607 | 19115 |
| % Modified | <0.051% | <0.015% | <0.011% | <0.031% | <0.022% | <0.015% | <0.007% | <0.006% |
| P-value | | | | | | | | |
| Specificity | | | | | | | | |
| OffC-33 | | | | | | | | |
| Indels | 0 | 0 | 0 | 0 | 0 | 0 | 0 | 0 |
| Total | 34475 | 27039 | 18547 | 33467 | 15745 | 17075 | 4 | 18844 |
| % Modified | <0.006% | <0.006% | <0.006% | <0.006% | <0.006% | <0.006% | <25.000% | <0.006% |
| P-value | | | | | | | | |
| Specificity | | | | | | | | |
| OffC-34 | | | | | | | | |
| Indels | 0 | 0 | 0 | 0 | 0 | 0 | 0 | 0 |
| Total | 9052 | 18858 | 13647 | 11796 | 6945 | 6114 | 4979 | 9072 |
| % Modified | <0.011% | <0.006% | <0.007% | <0.006% | <0.014% | <0.016% | <0.020% | <0.011% |
| P-value | | | | | | | | |
| Specificity | | | | | | | | |
| OffC-35 | | | | | | | | |
| Indels | 0 | 0 | 0 | 0 | 0 | 0 | 0 | 0 |
| Total | 23839 | 22290 | 25133 | 24190 | 10 | 10459 | 22554 | 11897 |
| % Modified | <0.006% | <0.006% | <0.006% | <0.006% | <10.000% | <0.010% | <0.006% | <0.008% |
| P-value | | | | | | | | |
| Specificity | | | | | | | | |
| OffC-36 | | | | | | | | |
| Indels | 1 | 0 | 0 | 1 | 2 | 1 | 19 | 5 |
| Total | 23412 | 24394 | 23427 | 24132 | 19723 | 28369 | 12461 | 18052 |
| Modified | <0.006% | <0.006% | <0.006% | <0.006% | <0.010% | <0.006% | 0.152% | 0.028% |
| P-value | | | | | | | 2.6E−05 | |
| Specificity | | >307 | >835 | >1274 | 2392 | >1476 | 181 | 1690 |

B

| C-term. Domain: | No TALEN | Q7 | Q7 | Q3 | Q3 | Canonical | Canonical | Canonical |
|---|---|---|---|---|---|---|---|---|
| FokI Domain: | No TALEN | EL/KK | ELD/KKR | EL/KK | ELD/KKR | EL/KK | ELD/KKR | Homo |
| ATM Sites | | | | | | | | |
| On-A | | | | | | | | |
| Indels | 3 | 0 | 46 | 104 | 309 | 1289 | 410 | 909 |
| Total | 6888 | 1869 | 2520 | 1198 | 1808 | 19025 | 2533 | 5003 |
| Modified | 0.03% | 0.00% | 1.83% | 8.66% | 17.09% | 6.78% | 16.19% | 18.17% |
| P-value | | 0 | 2.2E−11 | 3.2E−26 | 4.9E−81 | 6.4E−276 | 4.5E−105 | 1.5E−228 |
| Specificity | | | | | | | | |
| OffA-1 | | | | | | | | |
| Indels | 0 | 0 | 1 | 0 | 1 | 0 | 13 | 34 |
| Total | 52490 | 45383 | 34195 | 32325 | 47589 | 39704 | 50349 | 44056 |
| Modified | <0.006% | <0.006% | <0.006% | <0.006% | <0.006% | <0.006% | 0.0026% | 0.077% |
| P-value | | | | | | | 3.1E−04 | 5.5E−09 |
| Specificity | | >0 | >274 | >1302 | >2564 | >1016 | 627 | 235 |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffA-2 | | | | | | | | |
|---|---|---|---|---|---|---|---|---|
| Indels | 0 | 0 | 0 | 0 | 0 | 0 | 0 | 0 |
| Total | 8777 | 11846 | 11362 | 12273 | 20704 | 3776 | 5650 | 5025 |
| Modified | <0.011% | <0.008% | <0.009% | <0.008% | <0.006% | <0.026% | <0.018% | <0.020% |
| P-value | | | | | | | | |
| Specificity | | | | | | | | |
| OffA-3 | | | | | | | | |
| Indels | 0 | 0 | 0 | 0 | 1 | 0 | 0 | 0 |
| Total | 47338 | 14352 | 21253 | 17777 | 26512 | 19483 | 43728 | 29469 |
| Modified | <0.006% | <0.007% | <0.006% | <0.006% | <0.006% | <0.006% | <0.006% | <0.006% |
| P-value | | | | | | | | |
| Specificity | | | | | | | | |
| OffA-4 | | | | | | | | |
| Indels | 0 | 0 | 0 | 0 | 0 | 0 | 0 | 0 |
| Total | 12292 | 532 | 1383 | 2597 | 861 | 2598 | 1356 | 3573 |
| Modified | <0.008% | <0.188% | <0.072% | <0.039% | <0.116% | <0.038% | 0.074% | <0.028% |
| P-value | | | | | | | | |
| Specificity | | | | | | | | |
| OffA-5 | | | | | | | | |
| Indels | 0 | 0 | 0 | 0 | 0 | 0 | 0 | 0 |
| Total | 60859 | 22846 | 25573 | 19054 | 25315 | 31754 | 66622 | 60925 |
| Modified | <0.006% | <0.006% | <0.006% | <0.006% | <0.006% | <0.006% | <0.006% | <0.006% |
| P-value | | | | | | | | |
| Specificity | | | | | | | | |
| OffA-6 | | | | | | | | |
| Indels | 0 | 0 | 0 | 0 | 0 | 0 | 0 | 0 |
| Total | 60859 | 22846 | 25573 | 19054 | 25315 | 31754 | 66622 | 60925 |
| Modified | <0.006% | <0.006% | <0.006% | <0.006% | <0.006% | <0.006% | <0.006% | <0.006% |
| P-value | | | | | | | | |
| Specificity | | | | | | | | |
| OffA-7 | | | | | | | | |
| Indels | 0 | 0 | 0 | 0 | 0 | 0 | 0 | 0 |
| Total | 60859 | 22846 | 25573 | 19054 | 25315 | 31754 | 66622 | 60925 |
| Modified | <0.006% | <0.006% | <0.006% | <0.006% | <0.006% | <0.006% | <0.006% | <0.006% |
| P-value | | | | | | | | |
| Specificity | | | | | | | | |
| OffA-8 | | | | | | | | |
| Indels | 0 | 0 | 0 | 0 | 0 | 0 | 0 | 0 |
| Total | 9170 | 1614 | 5934 | 3215 | 2450 | 12750 | 10120 | 13003 |
| Modified | <0.011% | <0.062% | <0.017% | <0.031% | <0.041% | <0.008% | <0.010% | <0.008% |
| P-value | | | | | | | | |
| Specificity | | | | | | | | |
| OffA-9 | | | | | | | | |
| Indels | 0 | 0 | 0 | 0 | 0 | 0 | 0 | 3 |
| Total | 8753 | 12765 | 9504 | 10114 | 11086 | 10676 | 9013 | 11110 |
| Modified | <0.011% | <0.008% | <0.011% | <0.010% | <0.009% | <0.009% | <0.011% | 0.027% |
| P-value | | | | | | | | |
| Specificity | | | | | | | | |
| OffA-10 | | | | | | | | |
| Indels | 1 | 0 | 0 | 2 | 2 | 3 | 5 | 7 |
| Total | 8151 | 16888 | 8804 | 7061 | 8891 | 32138 | 14889 | 40120 |
| Modified | 0.012% | <0.006% | <0.011% | 0.028% | 0.022% | 0.009% | 0.034% | 0.017% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffA-11 | | | | | | | | |
|---|---|---|---|---|---|---|---|---|
| Indels | 0 | 0 | 1 | 0 | 0 | 0 | 9 | 76 |
| Total | 41343 | 32352 | 26834 | 28709 | 26188 | 32519 | 24894 | 19586 |
| Modified | <0.006% | <0.006% | <0.006% | <0.006% | <0.006% | <0.006% | 0.036% | 0.388% |
| P-value | | | | | | | 2.7E−03 | 2.5E−18 |
| Specificity | | >0 | >274 | >1302 | >2564 | >1016 | 448 | 47 |
| OffA-12 | | | | | | | | |
| Indels | 0 | 0 | 0 | 0 | 0 | 0 | 0 | 0 |
| Total | 13186 | 2326 | 13961 | 12911 | 21134 | 9220 | 7792 | 8068 |
| Modified | <0.008% | <0.043% | <0.007% | <0.008% | <0.006% | <0.011% | <0.013% | <0.012% |
| P-value | | | | | | | | |
| Specificity | | | | | | | | |
| OffA-13 | | | | | | | | |
| Indels | 0 | 0 | 0 | 0 | 0 | 2 | 9 | 0 |
| Total | 32704 | 32015 | 12312 | 23645 | 26315 | 24078 | 36111 | 22364 |
| Modified | <0.006% | <0.006% | <0.006% | <0.006% | <0.006% | 0.008% | 0.025% | <0.006% |
| P-value | | | | | | | 2.7E−03 | |
| Specificity | | >0 | >225 | >1302 | >2564 | 616 | 649 | >2725 |
| OffA-15 | | | | | | | | |
| Indels | 0 | 0 | 0 | 0 | 1 | 0 | 0 | 0 |
| Total | 14654 | 15934 | 12313 | 6581 | 13053 | 18996 | 10916 | 21519 |
| Modified | <0.007% | <0.006% | <0.008% | <0.015% | 0.008% | <0.006% | <0.009% | <0.006% |
| P-value | | | | | | | | |
| Specificity | | | | | | | | |
| OffA-16 | | | | | | | | |
| Indels | 1 | 0 | 0 | 0 | 0 | 0 | 0 | 12 |
| Total | 65190 | 35639 | 37252 | 30378 | 31469 | 22590 | 13594 | 20922 |
| Modified | <0.006% | <0.006% | <0.006% | <0.006% | <0.006% | <0.006% | <0.007% | 0.057% |
| P-value | | | | | | | | 7.9E−04 |
| Specificity | | >0 | >274 | >1302 | >2564 | >1016 | >2200 | 317 |
| OffA-17 | | | | | | | | |
| Indels | 0 | 0 | 0 | 0 | 0 | 0 | 0 | 6 |
| Total | 1972 | 606 | 1439 | 2113 | 2862 | 728 | 597 | 636 |
| Modified | <0.051% | <0.165% | <0.069% | <0.047% | <0.035% | <0.137% | <0.168% | 0.943% |
| P-value | | | | | | | | 1.4E−02 |
| Specificity | | >0 | >26 | >183 | >489 | >49 | >97 | 19 |
| OffA-18 | | | | | | | | |
| Indels | 0 | 0 | 0 | 0 | 0 | 0 | 0 | 0 |
| Total | 5425 | 995 | 1453 | 1831 | 3132 | 1934 | 1534 | 5816 |
| Modified | <0.018% | <0.101% | <0.069% | <0.055% | <0.032% | <0.052% | <0.065% | <0.017% |
| P-value | | | | | | | | |
| Specificity | | | | | | | | |
| OffA-19 | | | | | | | | |
| Indels | 1 | 2 | 0 | 1 | 1 | 1 | 1 | 3 |
| Total | 31094 | 41252 | 33213 | 29518 | 32337 | 25904 | 27575 | 38711 |
| Modified | <0.006% | <0.006% | <0.006% | <0.006% | <0.006% | <0.006% | <0.006% | <0.008% |
| P-value | | | | | | | | |
| Specificity | | | | | | | | |
| OffA-21 | | | | | | | | |
| Indels | 0 | 0 | 0 | 0 | 0 | 0 | 0 | 0 |
| Total | 15297 | 9710 | 16719 | 12119 | 15483 | 21692 | 16558 | 15418 |
| Modified | <0.007% | <0.010% | <0.006% | <0.008% | <0.006% | <0.006% | <0.006% | <0.006% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffA-22 | | | | | | | | |
|---|---|---|---|---|---|---|---|---|
| Indels | 27 | 41 | 38 | 46 | 32 | 50 | 55 | 57 |
| Total | 9406 | 11150 | 11516 | 10269 | 13814 | 14057 | 11685 | 14291 |
| Modified | 0.287% | 0.368% | 0.330% | 0.448% | 0.232% | 0.356% | 0.471% | 0.399% |
| P-value | | | | | | | | |
| Specificity | | | | | | | | |
| OffA-23 | | | | | | | | |
| Indels | 1 | 0 | 0 | 0 | 0 | 0 | 10 | 20 |
| Total | 5671 | 9363 | 2203 | 7011 | 7078 | 12068 | 3484 | 8619 |
| Modified | 0.018% | <0.011% | <0.045% | <0.014% | <0.014% | <0.008% | 0.287% | 0.232% |
| P-value | | | | | | | 3.5E−03 | 9.1E−05 |
| Specificity | | >0 | >40 | >609 | >1210 | >818 | 56 | 78 |
| OffA-24 | | | | | | | | |
| Indels | 4 | 0 | 0 | 1 | 0 | 1 | 0 | 2 |
| Total | 17288 | 7909 | 14261 | 29936 | 6943 | 6333 | 14973 | 19953 |
| Modified | 0.023% | <0.013% | <0.007% | <0.006% | <0.014% | 0.016% | <0.007% | 0.010% |
| P-value | | | | | | | | |
| Specificity | | | | | | | | |
| OffA-25 | | | | | | | | |
| Indels | 0 | 0 | 0 | 0 | 0 | 0 | 0 | 0 |
| Total | 20089 | 45320 | 50758 | 108581 | 11574 | 20948 | 123827 | 74151 |
| Modified | <0.006% | <0.006% | <0.006% | <0.006% | <0.009% | <0.006% | <0.006% | <0.006% |
| P-value | | | | | | | | |
| Specificity | | | | | | | | |
| OffA-27 | | | | | | | | |
| Indels | 0 | 0 | 0 | 0 | 1 | 0 | 0 | 0 |
| Total | 47338 | 14352 | 21253 | 17777 | 26512 | 19483 | 43728 | 29469 |
| Modified | <0.006% | <0.007% | <0.006% | <0.006% | <0.006% | <0.006% | <0.006% | <0.006% |
| P-value | | | | | | | | |
| Specificity | | | | | | | | |
| OffA-29 | | | | | | | | |
| Indels | 0 | 0 | 0 | 0 | 0 | 0 | 0 | 0 |
| Total | 5174 | 12618 | 36909 | 18063 | 16486 | 17934 | 9999 | 35072 |
| Modified | <0.019% | <0.008% | <0.006% | <0.006% | <0.006% | <0.006% | <0.010% | <0.006% |
| P-value | | | | | | | | |
| Specificity | | | | | | | | |
| OffA-30 | | | | | | | | |
| Indels | 4 | 4 | 0 | 7 | 4 | 4 | 0 | 3 |
| Total | 45082 | 56531 | 35333 | 88651 | 69652 | 20362 | 29180 | 21350 |
| Modified | 0.009% | 0.007% | <0.006% | 0.008% | <0.006% | 0.020% | <0.006% | 0.014% |
| P-value | | | | | | | | |
| Specificity | | | | | | | | |
| OffA-32 | | | | | | | | |
| Indels | 0 | 0 | 0 | 0 | 0 | 0 | 0 | 0 |
| Total | 13405 | 6721 | 14013 | 7513 | 14135 | 22376 | 6407 | 13720 |
| Modified | <0.007% | <0.015% | <0.007% | <0.013% | <0.007% | <0.006% | <0.016% | <0.007% |
| P-value | | | | | | | | |
| Specificity | | | | | | | | |
| OffA-33 | | | | | | | | |
| Indels | 0 | 0 | 0 | 0 | 1 | 1 | 0 | 4 |
| Total | 108222 | 46866 | 157329 | 48611 | 92559 | 152094 | 201408 | 225805 |
| Modified | <0.006% | <0.006% | <0.006% | <0.006% | <0.006% | <0.006% | <0.006% | <0.006% |
| P-value | | | | | | | | |
| Specificity | | | | | | | | |

TABLE 7-continued

Cellular modification induced by TALENs at on-target and predicted off-target genomic sites. (A) Results from sequencing CCR5A on-target and each predicted genomic off-target site that amplified from genomic DNA isolated from human cells treated with either no TALEN or TALENs containing canonical, Q3 or Q7 C-terminal domains, and either EL/KK heterodimeric, ELD/KKR heterodimeric, or homodimeric (Homo) FokI domains. Indels: the number of observed sequences containing insertions or deletions consistent with TALEN-induced cleavage. Total: total number of sequence counts. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/16,400), whichever value was more conservative (larger). P-values: calculated as previously reported5 between each TALEN-treated sample and the untreated control sample. P-values less than 0.05 are shown. Specificity: the ratio of ontarget to off-target genomic modification frequency for each site. (B) Same as (A) for the ATM target sites.

| OffA-34 | | | | | | | | |
|---|---|---|---|---|---|---|---|---|
| Indels | 0 | 0 | 0 | 0 | 0 | 0 | 0 | 2 |
| Total | 3889 | 3158 | 2903 | 2235 | 2112 | 3022 | 2322 | 2481 |
| Modified | <0.026% | <0.032% | <0.034% | <0.045% | <0.047% | <0.033% | <0.043% | 0.061% |
| P-value | | | | | | | | |
| Specificity | | | | | | | | |
| OffA-35 | | | | | | | | |
| Indels | 0 | 0 | 0 | 1 | 0 | 0 | 0 | 33 |
| Total | 46462 | 37431 | 38043 | 31033 | 44803 | 37257 | 41073 | 47273 |
| Modified | <0.006% | <0.006% | <0.006% | <0.006% | <0.006% | <0.006% | <0.006% | 0.070% |
| P-value | | | | | | | | 9.2E−09 |
| Specificity | | >0 | >274 | >1302 | >2564 | >1016 | >2428 | 260 |
| OffA-36 | | | | | | | | |
| Indels | 0 | 0 | 2 | 0 | 0 | 0 | 0 | 0 |
| Total | 27115 | 17075 | 45425 | 35059 | 22298 | 19610 | 12620 | 27170 |
| Modified | <0.006% | <0.006% | <0.006% | <0.006% | <0.006% | <0.006% | <0.006% | <0.006% |
| P-value | | | | | | | | |
| Specificity | | | | | | | | |

TABLE 8

Exponential fitting of enrichment values as function of mutation number. Enrichment values of post-selection sequences as function of mutation were normalized relative to on-target enrichment (=1.0 by definition). Normalized enrichment values of sequences with zero to four mutations were fit to an exponential function, a*eb, with R2 reported using the non-linear least squares method.

| TALEN selection | a | b | $R^2$ |
|---|---|---|---|
| L13 + R10 CCR5B | 1.00 | −1.88 | 0.999937 |
| L10 + R10 CCR5B | 1.00 | −1.85 | 0.999901 |
| L10 + R13 CCR5B | 1.00 | −1.71 | 0.999822 |
| L13 + R13 CCR5B | 1.00 | −1.64 | 0.999771 |
| L13 + R16 CCR5B | 1.00 | −1.15 | 0.998286 |
| L16 + R10 CCR5B | 1.00 | −1.24 | 0.998252 |
| L10 + R16 CCR5B | 1.01 | −1.08 | 0.996343 |
| L16 + R13 CCR5B | 1.01 | −1.04 | 0.995844 |
| L16 + R16 CCR5B | 1.03 | −0.70 | 0.977880 |
| L18 + R18 ATM | 1.08 | −0.36 | 0.913087 |
| L18 + R18 CCR5A | 1.13 | −0.21 | 0.798923 |

TABLE 9

Exponential fitting and extrapolation of enrichment values as function of mutation number. Enrichment values of all sequences from all nine of the CCR5B selections as function of mutation number were normalized relative to enrichment values of sequences with the lowest mutation number in the range shown (=1.0 by definition). Normalized enrichment values of sequences from the range of mutations specified were fit to an exponential function, a*e$^b$, with $R^2$ reported utilizing the non-linear least squares method. These exponential decrease, b, were used to extrapolate all mean enrichment values beyond five mutations.

| TALEN selection | Range | a | b | $R^2$ |
|---|---|---|---|---|
| L16 + R16 CCR5B | 3-5 | 1.00 | −1.638 | 0.99998 |
| L16 + R13 CCR5B | 2-4 | 1.00 | −1.733 | 0.99998 |
| L16 + R10 CCR5B | 2-4 | 1.00 | −2.023 | 0.99999 |
| L13 + R16 CCR5B | 2-4 | 1.00 | −1.844 | 0.99997 |
| L13 + R13 CCR5B | 1-3 | 1.00 | −2.014 | 0.99998 |
| L13 + R10 CCR5B | 1-3 | 1.00 | −2.205 | 0.99999 |
| L10 + R16 CCR5B | 2-4 | 1.00 | −1.929 | 0.99995 |
| L10 + R13 CCR5B | 1-3 | 1.00 | −2.110 | 0.99998 |
| L10 + R10 CCR5B | 1-3 | 1.00 | −2.254 | 0.99999 |

TABLE 10

A

| oligo-nucleotide name | oligonucleotide sequence (5',>3') |
|---|---|
| TAL-Nrev | 5Phos/CAGCAGCTGCCCGGT |
| TAL-N1fwd | 5Phos/cAGATCGCGAAGAGAGGGGGAGTAACAGCGGTAG |

TABLE 10-continued

| | |
|---|---|
| TAL-N2fwd | 5Phos/cAGATCGCGcAGAGAGGGGGAGTAACAGCGGTAG |
| TAL-N3fwd | 5Phos/cAGATCGCGcAGcagGGGGGAGTAACAGCGGTAG |
| TAL-Cifwd | ATC GTA GCC CAA TTG TCC A |
| TAL-Cirev | GTTGGTTCTTTGGATCAATGCG |
| TAL-Q3 | AAGTTCTCTCGGGAATCCGTTGGTTGGTTCTTTGGATCA |
| TAL-Q7 | GAAGTTCTCTCGGGAATTTGTTGGTTGGTTTGTTGGATCAATGCGGGAGCAT<br>GAGGCAGACCTTGTTGGACTGCATC |
| TAL-Ciirev | CTTTTGACTAGTTGGGATCCCGCGACTTGATGGGAAGTTCTCTCGGGAAT |
| CCR5A Library10 | 5Phos/CACCACTCT%T%C%A%T%T%A%C%A%C%C%T%G%C%A%G%C%T%NNNNNNNNNN<br>A%G%T%A%C%A%A%T%T%C%T%G%G%A%A%G%A%NCGTCACGCT |
| CCR5A Library12 | 5Phos/CACCACTCT%T%C%A%T%T%A%C%A%C%C%T%G%C%A%G%C%T%NNNNNNNNNN<br>NNA%G%T%A%C%A%A%T%T%C%T%G%G%A%A%G%A%NCGTCACGCT |
| CCR5A Library14 | 5Phos/CACCACTCT%T%C%A%T%T%A%C%A%C%C%T%G%C%A%G%C%T%NNNNNNNNNN<br>NNNNA%G%T%A%C%A%A%T%T%C%T%G%G%A%A%G%A%NCGTCACGCT |
| CCR5A Library16 | 5Phos/CACCACTCT%T%C%A%T%T%A%C%A%C%C%T%G%C%A%G%C%T%NNNNNNNNNN<br>NNNNNNA%G%T%A%C%A%A%T%T%C%T%G%G%A%A%G%A%NCGTCACGCT |
| CCR5A Library18 | 5Phos/CACCACTCT%T%C%A%T%T%A%C%A%C%C%T%G%C%A%G%C%T%NNNNNNNNNN<br>NNNNNNNNA%G%T%A%C%A%A%T%T%C%T%G%G%A%A%G%A%NCGTCACGCT |
| CCR5A Library20 | 5Phos/CACCACTCT%T%C%A%T%T%A%C%A%C%C%T%G%C%A%G%C%T%NNNNNNNNNN<br>NNNNNNNNNNA%G%T%A%C%A%A%T%T%C%T%G%G%A%A%G%A%NCGTCACGCT |
| CCR5A Library22 | 5Phos/CACCACTCT%T%C%A%T%T%A%C%A%C%C%T%G%C%A%G%C%T%NNNNNNNNNN<br>NNNNNNNNNNNNA%G%T%A%C%A%A%T%T%C%T%G%G%A%A%G%A%NCGTCACGCT |
| CCR5A Library24 | 5Phos/CACCACTCT%T%C%A%T%T%A%C%A%C%C%T%G%C%A%G%C%T%NNNNNNNNNN<br>NNNNNNNNNNNNNNA%G%T%A%C%A%A%T%T%C%T%G%G%A%A%G%A%NCGTCACGCT |
| CCR5B Library10 | 5Phos/CCACGCTNT%C%T%T%C%A%T%T%A%C%A%C%C%T%G%C%NNNNNNNNNNC%A%<br>T%A%C%A%G%T%C%A%G%T%A%T%C%A%NCCTCGGGACT |
| CCR5B Library12 | 5Phos/CCACGCTNT%C%T%T%C%A%T%T%A%C%A%C%C%T%G%C%NNNNNNNNNNNNC%<br>A%T%A%C%A%G%T%C%A%G%T%A%T%C%A%NCCTCGGGACT |
| CCR5B Library14 | 5Phos/CCACGCTNT%C%T%T%C%A%T%T%A%C%A%C%C%T%G%C%NNNNNNNNNNNNNN<br>C%A%T%A%C%A%G%T%C%A%G%T%A%T%C%A%NCCTCGGGACT |
| CCR5B Library16 | 5Phos/CCACGCTNT%C%T%T%C%A%T%T%A%C%A%C%C%T%G%C%NNNNNNNNNNNNNN<br>NNC%A%T%A%C%A%G%T%C%A%G%T%A%T%C%A%NCCTCGGGACT |
| CCR5B Library18 | 5Phos/CCACGCTNT%C%T%T%C%A%T%T%A%C%A%C%C%T%G%C%NNNNNNNNNNNNNN<br>NNNNC%A%T%A%C%A%G%T%C%A%G%T%A%T%C%A%NCCTCGGGACT |
| CCR5B Library20 | 5Phos/CCACGCTNT%C%T%T%C%A%T%T%A%C%A%C%C%T%G%C%NNNNNNNNNNNNNN<br>NNNNNNC%A%T%A%C%A%G%T%C%A%G%T%A%T%C%A%NCCTCGGGACT |
| CCR5B Library22 | 5Phos/CCACGCTNT%C%T%T%C%A%T%T%A%C%A%C%C%T%G%C%NNNNNNNNNNNNNN<br>NNNNNNNNC%A%T%A%C%A%G%T%C%A%G%T%A%T%C%A%NCCTCGGGACT |
| CCR5B Library24 | 5Phos/CCACGCTNT%C%T%T%C%A%T%T%A%C%A%C%C%T%G%C%NNNNNNNNNNNNNN<br>NNNNNNNNNNC%A%T%A%C%A%G%T%C%A%G%T%A%T%C%A%NCCTCGGGACT |
| ATM Library10 | 5Phos/CCACGCTNT%G%A%A%T%T%G%G%G%A%T%G%C%T%G%T%T%T%NNNNNNNNNN<br>T%T%T%A%T%T%T%T%A%C%T%G%T%C%T%T%T%A%GGTACCCCA |
| ATM Library12 | 5Phos/CCACGCTNT%G%A%A%T%T%G%G%G%A%T%G%C%T%G%T%T%T%NNNNNNNNNN<br>NNT%T%T%A%T%T%T%T%A%C%T%G%T%C%T%T%T%A%GGTACCCCA |
| ATM Library14 | 5Phos/CCACGCTNT%G%A%A%T%T%G%G%G%A%T%G%C%T%G%T%T%T%NNNNNNNNNN<br>NNNNT%T%T%A%T%T%T%T%A%C%T%G%T%C%T%T%T%A%GGTACCCCA |
| ATM Library16 | 5Phos/CCACGCTNT%G%A%A%T%T%G%G%G%A%T%G%C%T%G%T%T%T%NNNNNNNNNN<br>NNNNNNT%T%T%A%T%T%T%T%A%C%T%G%T%C%T%T%T%A%GGTACCCCA |
| ATM Library18 | 5Phos/CCACGCTNT%G%A%A%T%T%G%G%G%A%T%G%C%T%G%T%T%T%NNNNNNNNNN<br>NNNNNNNNT%T%T%A%T%T%T%T%A%C%T%G%T%C%T%T%T%A%GGTACCCCA |
| ATM Library20 | 5Phos/CCACGCTNT%G%A%A%T%T%G%G%G%A%T%G%C%T%G%T%T%T%NNNNNNNNNN<br>NNNNNNNNNNT%T%T%A%T%T%T%T%A%C%T%G%T%C%T%T%T%A%GGTACCCCA |

TABLE 10-continued

| | |
|---|---|
| ATM Library22 | 5Phos/CCACGCTNT%G%A%A%T%T%G%G%G%A%T%G%C%T%G%T%T%T%NNNNNNNNNN NNNNNNNNNNNNNNT%T%T%A%T%T%T%T%A%C%T%G%T%C%T%T%T%A%GGTACCCCA |
| ATM Library24 | 5Phos/CCACGCTNT%G%A%A%T%T%G%G%G%A%T%G%C%T%G%T%T%T%NNNNNNNNNN NNNNNNNNNNNNNNT%T%T%A%T%T%T%T%A%C%T%G%T%C%T%T%T%A%GGTACCCCA |
| #1 adapter-fwd**1 | AATGATACGGCGACCACCGAGATCTACACTCTTTCCCTACACGACGCTCTTCCGATCTACTGT |
| #1 adapter-rev**1 | ACAGTAGATCGGAAGAGCGTCGTGTAGGGAAAGAGTGTAGATCTCGGTGG |
| #1 adapter-fwd**2 | AATGATACGGCGACCACCGAGATCTACACTCTTTCCCTACACGACGCTCTTCCGATCTCTGAA |
| #1 adapter-rev**2 | TTCAGAGATCGGAAGAGCGTCGTGTAGGGAAAGAGTGTAGATCTCGGTGG |
| #1 adapter-fwd**3 | AATGATACGGCGACCACCGAGATCTACACTCTTTCCCTACACGACGCTCTTCCGATCTTGCAA |
| #1 adapter-rev**3 | TTGCAATGATCGGAAGAGCGTCGTGTAGGGAAAGAGTGTAGATCTCGGTGG |
| #1 adapter-fwd**4 | AATGATACGGCGACCACCGAGATCTACACTCTTTCCCTACACGACGCTCTTCCGATCTTGACT |
| #1 adapter-rev**4 | AGTCAAGATCGGAAGAGCGTCGTGTAGGGAAAGAGTGTAGATCTCGGTGG |
| #1 adapter-fwd**5 | AATGATACGGCGACCACCGAGATCTACACTCTTTCCCTACACGACGCTCTTCCGATCTGCATT |
| #1 adapter-rev**5 | AATGCAGATCGGAAGAGCGTCGTGTAGGGAAAGAGTGTAGATCTCGGTGG |
| #1 adapter-fwd**6 | AATGATACGGCGACCACCGAGATCTACACTCTTTCCCTACACGACGCTCTTCCGATCTCATGA |
| #1 adapter-rev**6 | TCATGAGATCGGAAGAGCGTCGTGTAGGGAAAGAGTGTAGATCTCGGTGG |
| #1 adapter-fwd**7 | AATGATACGGCGACCACCGAGATCTACACTCTTTCCCTACACGACGCTCTTCCGATCTATGCT |
| #1 adapter-rev**7 | AGCATAGATCGGAAGAGCGTCGTGTAGGGAAAGAGTGTAGATCTCGGTGG |
| #1 adapter-fwd**8 | AATGATACGGCGACCACCGAGATCTACACTCTTTCCCTACACGACGCTCTTCCGATCTCTAGT |
| #1 adapter-rev**8 | ACTAGAGACGGAAGAGCGTCGTGTAGGGAAAGAGTGTAGATCTCGGTGG |
| #1 adapter-fwd**9 | AATGATACGGCGACCACCGAGATCTACACTCTTTCCCTACACGACGCTCTTCCGATCTGCTAA |
| #1 adapter-rev**9 | TTAGCAGATCGGAAGAGCGTCGTGTAGGGAAAGAGTGTAGATCTCGGTGG |
| #1 adapter-fwd**10 | AATGATACGGCGACCACCGAGATCTACACTCTTTCCCTACACGACGCTCTTCCGATCTCAGTA |
| #1 adapter-rev**10 | TACTGAGATCGGAAGAGCGTCGTGTAGGGAAAGAGTGTAGATCTCGGTGG |
| #1 adapter-fwd**11 | TACTGAGATCGGAAGAGCGTCGTGTAGGGAAAGAGTGTAGATCTCGGTGG |
| #1 adapter-rev**11 | AATGATACGGCGACCACCGAGATCTACACTCTTTCCCTACACGACGCTCTTCCGATCTGTACT |
| #1 adapter-fwd**12 | AGTACAGATCGGAAGAGCGTCGTGTAGGGAAAGAGTGTAGATCTCGGTGG |
| #1 adapter-rev**12 | AATGATACGGCGACCACCGAGATCTACACTCTTTCCCTACACGACGCTCTTCCGATCTACTGT |
| #1 adapter-fwd**13 | ACAGTAGATCGGAAGAGCGTCGTGTAGGGAAAGAGTGTAGATCTCGGTGG |
| #1 adapter-rev**13 | AATGATACGGCGACCACCGAGATCTACACTCTTTCCCTACACGACGCTCTTCCGATCTGCTAA |
| #1 adapter-fwd**14 | TTAGCAGATCGGAAGAGCGTCGTGTAGGGAAAGAGTGTAGATCTCGGTGG |
| #1 adapter-rev**14 | AATGATACGGCGACCACCGAGATCTACACTCTTTCCCTACACGACGCTCTTCCGATCTCAGTA |
| #1 adapter-fwd**15 | AATGATACGGCGACCACCGAGATCTACACTCTTTCCCTACACGACGCTCTTCCGATCTGTACT |

TABLE 10-continued

| | |
|---|---|
| #1 adapter-rev**15 | AGTACAGATCGGAAGAGCGTCGTGTAGGGAAAGAGTGTAGATCTCGGTGG |
| #1 adapter-fwd**16 | AATGATACGGCGACCACCGAGATCTACACTCTTTCCCTACACGACGCTCTTCCGATCTACTGT |
| #1 adapter-rev**16 | ACAGTAGATCGGAAGAGCGTCGTGTAGGGAAAGAGTGTAGATCTCGGTGG |
| #2A primer-fwd | AATGATACGGCGACCAC |
| #2A primer-rev*CCR5A | GTTCAGACGTGTGCTCTTCCGATCTNNNNAGTGGTGAGCGTGACG |
| #2A primer-rev*ATM | GTTCAGACGTGTGCTCTTCCGATCTNNNNACGCGGAGTGGGGTACC |
| #2A primer-rev*CCR5B | CAGACGTGTGCTCTTCCGATCNNNNAGCGTGGAGTCCCGAGG |
| #2B primer-fwd | AATGATACGGCGACCAC |
| #2B primer-rev**1 | CAAGCAGAAGACGGCATACGAGATTGTTGACTGTGACTGGAGTTCAGACGTGTGCTCTTC |
| #2B primer-rev**2 | CAAGCAGAAGACGGCATACGAGATACGGAACTGTGACTGGAGTTCAGACGTGTGCTCTTC |
| #2B primer-rev**3 | CAAGCAGAAGACGGCATACGAGATTCTAACATGTGACTGGAGTTCAGACGTGTGCTCTTC |
| #2B primer-rev**4 | CAAGCAGAAGACGGCATACGAGATCGGGACGGGTGACTGGAGTTCAGACGTGTGCTCTTC CAAGCAGAAGACGGCATACGAGATCGTGATGTGACTGGAGTTCAGACGTGTGCTCTTCCG |
| #1 Lib. adapter-fwd*CCR5A | GTACCCAGATCGGAAGAGCACACGTCTGAACTCCAGTCACACAGTGATCTCGTATGCCGTCTTCTGCTTG |
| #1 Lib. adapter-rev*CCR5A | GTGACTGGAGTTCAGACGTGTGCTCTTCCGATCTG |
| #1 Lib. adapter-fwd*ATM | GTACGATGCGATCGGAAGAGCACACGTCTGAACTCCAGTCACTTAGGCATCTCGTATGCCGTCTTCTGCTTG |
| #1 Lib. adapter-rev*ATM | GTGACTGGAGTTCAGACGTGTGCTCTTCCGATCGCATC |
| #1 Lib. adapter-fwd*CCR5B | TCGGGAACGTGATCGGAAGAGCACACGTCTGAACTCCAGTCACCGTCTAATCTCGTATGCCGTCTTCTGCTTG |
| #1 Lib. adapter-rev*CCR5B | GTGACTGGAGTTCAGACGTGTGCTCTTCCGATCACGTT |
| #2A Lib. primer-rev | CAAGCAGAAGACGGCATACGA |
| #2A Lib. primer-fwd*CCR5A | AATGATACGGCGACCACCGAGATCTACACTCTTTCCCTACACGACGCTCTTCCGATCTNNNNCGTCACGCTCACCACT |
| #2A Lib. primer-fwd*ATM | AATGATACGGCGACCACCGAGATCTACACTCTTTCCCTACACGACGCTCTTCCGATCTNNNNGGTACCCCACTCCGCGT |
| #2A Lib. primer-fwd*CCR5B | AATGATACGGCGACCACCGAGATCTACACTCTTTCCCTACACGACGCTCTTCCGATCTNNNNCCTCGGGACTCCACGCT |
| #2B Lib. primer-rev | CAAGCAGAAGACGGCATACGA |
| #2B Lib. primer-fwd | AATGATACGGCGACCAC |
| G adapter-fwd | ACACTCTTTCCCTACACGACGCTCTTCCGATCT |
| G adapter-rev | /5Phos GATCGGAAGAGCACACGTCTGAACTCCA |
| G-B primer-fwd | AATGATACGGCGACCACCGAGATCTACACTCTTTCCCTACACGAC |
| G-B primer-rev**1 | CAAGCAGAAGACGGCATACGAGATGTGCGGACGTGACTGGAGTTCAGACGTGTGCT |
| G-B primer-rev**3 | CAAGCAGAAGACGGCATACGAGATCGTTTCACGTGACTGGAGTTCAGACGTGTGCT |
| G-B primer-rev**3 | CAAGCAGAAGACGGCATACGAGATAAGGCCACGTGACTGGAGTTCAGACGTGTGCT |
| G-B primer-rev**4 | CAAGCAGAAGACGGCATACGAGATTCCGAAACGTGACTGGAGTTCAGACGTGTGCT |
| G-B primer-rev**5 | CAAGCAGAAGACGGCATACGAGATTACGTACGGTGACTGGAGTTCAGACGTGTGCT |
| G-B primer-rev**6 | CAAGCAGAAGACGGCATACGAGATATCCACTCGTGACTGGAGTTCAGACGTGTGCT |

TABLE 10-continued

| | |
|---|---|
| G-B primer-rev**7 | CAAGCAGAAGACGGCATACGAGATAAAGGAATGTGACTGGAGTTCAGACGTGTGCT |
| G-B primer-rev**8 | CAAGCAGAAGACGGCATACGAGATATATCAGTGTGACTGGAGTTCAGACGTGTGCT |
| CCR5AonCfwd | CGACGGTCTAGAGTCTTCATTACACCTGCAGCTCTCATTTTCCATACAGT |
| CCR5Amut1fwd | CGACGGTGTAGAGTCTTCATTACAtCTGCAcCTCTCATTTTCCATACAGT |
| CCR5Amut2fwd | CGACGGTCTAGAGTCTTCAaTACACCTGtAGCTCTCATTTTCCATACAGT |
| CCR5Amut3fwd | CGACGGTCTAGAGTCTTCgTTACACCTGCAtCTCTCATTTTCCATACAGT |
| CCR5Amut4fwd | CGACGGTCTAGAGTCTTaATTgCACCTGCAGCTCTCATTTTCCATACAGT |
| CCR5AonCrev | CCGACGAAGCTTTTCTTCCAGAATTGATACTGACTGTATGGAAAATGA |
| CCR5Amut1rev | CCGACGAAGCTTTTCTTaCAGAATTcATACTGACTGTATGGAAAATGA |
| CCR5Amut2rev | CCGACGAAGCTTTTCcTCCAGAgTTGATACTGACTGTATGGAAAATGA |
| CCR5Amut3rev | CCGACGAAGCTTTTCTTCCtGAATTGATAaTGACTGTATGGAAAATGA |
| CCR5Amut4rev | CCGACGAAGCTTTTCTTCCAGcATTGtTACTGACTGTATGGAAAATGA |
| ATMonAfwd | CGACGGTCTAGATTTGAATTGGGATGCTGTTTTTAGGTATTCTATTCAAATT |
| ATMmut1fwd | CGACGGTCTAGATTTGAATTGGGtTGCTGTTTTTAGGTATTCTATTCAAATT |
| ATMmut2fwd | CGACGGTCTAGATTTGAATTGcGATGCTGTTTTTAGGTATTCTATTCAAATT |
| ATMmut3fwd | CGACGGTCTAGATTTGAgTTGGGATGCTGTTTTTAGGTATTCTATTCAAATT |
| ATMmut4fwd | CGACGGTCTAGATTTGAATTGGGATGCTGaTTTTAGGTATTCTATTCAAATT |
| ATMonArev | CCGACGAAGCTTAATAAAGACAGTAAAATAAATTTGAATAGAATACCTAAAA |
| ATmut1rev | CCGACGAAGCTTAATAAAGACAGTgAAATAAATTTGAATAGAATACCTAAAA |
| ATmut2rev | CCGACGAAGCTTAATAAAGAtAGTAAAATAAATTTGAATAGAATACCTAAAA |
| ATmut3rev | CCGACGAAGCTTAATAAAGACAGTAAgATAAATTTGAATAGAATACCTAAAA |
| ATmut4rev | CCGACGAAGCTTAATAAcGACAGTAAAATAAATTTGAATAGAATACCTAAAA |
| CCR5BonBfwd | CGACGGTCTAGAAAGGTCTTCATTACACCTGCAGCTCTCATTTTCCATACAGTCA |
| CCR5Bmut1fwd | CGACGGTCTAGAGTCTTCATTACACCTGtAGCTCTCATTTTC |
| CCR5Bmut2fwd | CGACGGTCTAGAGTCTTCATaACACCTGCAGCTCTCATTTTC |
| CCR5Bmut3fwd | CGACGGTCTAGAGTCTTCATTACACCcGCAGCTCTCATTTTC |
| CCR5Bmut4fwd | CGACGGTCTAGAGTCTTCATaACACCTGtAGCTCTCATTTTC |
| CCR5Bmut5fwd | CGACGGTCTAGAGTCTTCATTAtACCTaCAGCTCTCATTTTC |
| CCR5Bmut6fwd | CGACGGTCTAGAGTCTTCATTgCACCcGCAGCTCTCATTTTC |
| CCR5BonBrev | CCGACGAAGCTTTCTTCCAGAATTGATACTGACTGTATGGAAAATGAGAGCT |
| CCR5Bmut1rev | CCGACGAAGCTTTCTTCCAGAATTGATACTaACTGTATGGAAAATGAGAGCT |
| CCR5Bmut2rev | CCGACGAAGCTTTCTTCCAGAATTGATACTGACTGTATcGAAAATGAGAGCT |
| CCR5Bmut3rev | CCGACGAAGCTTTCTTCCAGAATTGATACTGACTGaATGGAAAATGAGAGCT |
| CCR5Bmut4rev | CCGACGAAGCTTTCTTCCAGAATTGATACcGACTGTATGGAAAATGAGAGCT |
| CCR5Bmut5rev | CCGACGAAGCTTTCTTCCAGAATTGATACTaACTGTATcGAAAATGAGAGCT |
| CCR5Bmut6rev | CCGACGAAGCTTTCTTCCAGAATTGATACTGAaTGtGGAAAATGAGAGCT |
| CCR5Bmut7rev pUC19Ofwd | CCGACGAAGCTTTCTTCCAGAATTGATACTGAtaGTATGGAAAATGAGAGCT GCGACACGGAAATGTTGAATACTCAT |
| pUC19Orev | CAGCGAGTCAGTGAGCGA |

TABLE 10-continued

B

| DNA substrate name | Oligonucleotide Combination |
|---|---|
| A1 | ATMmut1fwd + ATMonArev |
| A2 | ATMmut2fwd + ATMonArev |
| A3 | ATMonAfwd + ATMmut1rev |
| A4 | ATMonAfwd + ATMmut2rev |
| A5 | ATMmut2fwd + ATMmut2rev |
| A6 | ATMmut3fwd + ATMmut3rev |
| A7 | ATMmut1fwd + ATMmut1rev |
| A8 | ATMmut4fwd + ATMmut4rev |
| C1 | CCR5Amut1fwd + CCR5AonCrev |
| C2 | CCR5Amut2fwd + CCR5AonCrev |
| C3 | CCR5Amut3fwd + CCR5AonCrev |
| C4 | CCR5Amut4fwd + CCR5AonCrev |
| C5 | CCR5AonAfwd + CCR5Amut1rev |
| C6 | CCR5AonAfwd + CCR5Amut2rev |
| C7 | CCR5AonAfwd + CCR5Amut3rev |
| C8 | CCR5AonAfwd + CCR5Amut4rev |
| B1 | CCR5Bmut1fwd + CCR5BonBrev |
| B2 | CCR5Bmut2fwd + CCR5BonBrev |
| B3 | CCR5Bmut3fwd + CCR5BonBrev |
| B4 | CCR5BonBfwd + CCR5Bmut1rev |
| B5 | CCR5BonBfwd + CCR5Bmut2rev |
| B6 | CCR5BonBfwd + CCR5Bmut3rev |
| B7 | CCR5BonBfwd + CCR5Bmut4rev |
| B8 | CCR5Bmut4fwd + CCR5BonBrev |
| B9 | CCR5Bmut5fwd + CCR5BonBrev |
| B10 | CCR5Bmut6fwd + CCR5BonBrev |
| B11 | CCR5BonBfwd + CCR5Bmut5rev |
| B12 | CCR5BonBfwd + CCR5Bmut6rev |
| B13 | CCR5BonBfwd + CCR5Bmut7rev |
| B14 | CCR5Bmut1fwd + CCR5Bmut1rev |
| B15 | CCR5Bmut2fwd + CCR5Bmut2rev |
| B16 | CCR5Bmut3fwd + CCR5Bmut3rev |

C

| Site | Fwd primer | Rev primer | PCR |
|---|---|---|---|
| OnCCR5A | TCACTTGGGTGGTGGCTGTG | GACCATGACAAGCAGCGGCA | |
| OffC-1 | AGTCCAAGACCAGCCTGGGG | AAGAACCTGTTGTCTAATCCAGCA | |
| OffC-2 | GAACCTGTTGTCTAATCCAGCGTC | CTGCAAAGAAGGCCAGGCA | |
| OffC-3 | AGTCCAAGACCAGCCTGGGG | AAGAACCTGTTGTCTAATCCAGCA | |

TABLE 10-continued

| | | | |
|---|---|---|---|
| OffC-4 | TGACCTGTTTGTTCAGGTCTTCC | CCATATGGTCCCTGTCGCAA | |
| OffC-5 | TCCAGTTGCTGTCCCTTCAGA | ACAGGGAGAGCCACCAATGC | |
| OffC-6 | GCCCGGCCTGTCCTGTATTT | CACCCACACATGCACTTCCC | |
| OffC-7 | TGGCTATTCTAGTTCTTTTGCAT | CCATGCCCTAGGGATTTGTGGA | |
| OffC-8 | CGCTGAAGGCTGTCACCCTAA | TGGACCTAAGAGTCCTGCCCAT | |
| OffC-9 | CCACCACCACACAACTTCACA | CAGCTGGCGAGAACTGCAAA | ND |
| OffC-10 | TTCCAGGTCCTTTGCACAAATA | GCAAGGTCGTTGGATAGAAGTTGA | |
| OffC-11 | CACCGAAAGCAACCCATCC | TGATCTGCCCACCCCAGACT | |
| OffC-12 | TCATTCTCACCATCTGGAATTGG | TCTGGCTGGACTGCTCTGGTT | |
| OffC-13 | TGGCATGTGGATCAGTACCCA | TAGAACATGCCCGCGAACAG | |
| OffC-14 | CTGACGTCCATGTCAACGGG | TTTGAATTCCCCCTCCCCAT | |
| OffC-15 | GCTCCTTTCTGAGAAGCACCCAT | GGCAGATGGTGGCAGGTCTT | |
| OffC-16 | ATGAGGGCTTGGATTGGCTG | CCACCTCCCCCACTGCAATA | |
| OffC-17 | GGAGGCCTTCATTGTGTCACG | AACTCCACCTGGGTGCCCTA | |
| OffC-18 | CGTGGTCCCCCAGAAATCAC | GGAGCAGGAGTTGGTGGCAT | |
| OffC-19 | GATTGCATAGGTTAGCATTGCC | GCCCCTGTTGGTTGACTCCC | |
| OffC-20 | TTCCAGCGAATGGAAAGTGCT | AAGCCCAGGAATAAGGGCCA | |
| OffC-21 | AAGCATGCTCACACTGTGGTGTA | TTGCTTGAGGCGGAAGTTGC | |
| OffC-22 | TGACCCTCCAGCAAAGGTGA | CCCCAGGACTGAGCATGAG | |
| OffC-23 | GCTTTGCTTGCACTGTGCCTT | GGGGACAGACTGTGAGGGCT | |
| OffC-24 | TCAAAAGGATGTGATCTGCCACA | GGCCTCTTTGAGGGCCAGTT | |
| OffC-25 | CCAGGGCTCAATTCTTAGACCG | AAAAGAGCAGGGCTGCCATC | |
| OffC-26 | TGTTCATGCCTGCACAGTGG | TGGATGTGCCCTCTACCACA | |
| OffC-27 | TTTGGCAAGGAATTCACAGTTC | TCATGCCTGCACAGTGGTTG | |
| OffC-28 | GGAGGATGTCTTTGTGGTAGGGG | CGCTGCCAAGCAAACTCAAA | |
| OffC-29 | TCCCCCAACTTCACTGTTTTT | GCAATGAGCATGTGGACACCA | |
| OffC-30 | TTCTCTGTTTCCAGTGATTTCAGA | GTCGCAAAACAGCCAGTTGC | +DMSO |
| OffC-31 | TGGCTTGGTTAATGGACAATGG | CCTGCAAGGAGCAAGGCTTC | +DMSO |
| OffC-32 | TGGGCTTCGTGACTTAAAGAG | GGACAAGAGGGCCAGGGTTT | |
| OffC-33 | TCTTAAACATGTGGAACCCAGTCAT | TGAAAACCCACAGAGTGGGAGA | |
| OffC-34 | GCAGATTCATTAGCGTTTGTGGC | TGCATGGGTGTAAATGTAGCAGAAA | |
| OffC-35 | CCAAGGATCAATACCTTTGGAGGA | GCCCTCCCTTGAATCAGGCT | |
| OffC-36 | TTCCCCTAACCAGGGGCAGT | GTGGTGAGTGGGTGTGGCAG | |
| OnATM | AGCGCCTGATTCGAGATCCT | AGCGCCTGATTCGAGATCCT | |
| OffA-1 | CCTGCCATTGAATTCCAGCCT | TGTCTGCCTTTCCTGTCCCC | |
| OffA-2 | GACTGCCACTGCACTCCCAC | GGATACCCTTGCCTCCCCAC | |
| OffA-3 | CCTCCCATTTTCCTTCCTCCA | CTGGGAGACACAGGTGGCAG | |
| OffA-4 | TCCTCCAATTTTCCTTCCTCCA | CTGGGAGACACAGGTGGCAG | |
| OffA-5 | CTGGGAGACACAGGTGGCAG | AGGACCAATGGGCCAATCT | |
| OffA-6 | CTGGGAGACACAGGTGGCAG | AGGACCAATGGGCCAATCT | |

TABLE 10-continued

| | | | |
|---|---|---|---|
| OffA-7 | CTGGGAGACACAGGTGGCAG | AGGACCAATGGGGCCAATCT | |
| OffA-8 | GCATGCCAAAGAAATTGTAGGC | TTCCCCCTGTCATGGTCTTCA | |
| OffA-9 | GCATCTCTGCATTCCTCAGAAGTGG | AGAAACTGAGCAAGCCTCAGTCAA | |
| OffA-10 | GGGATACCAAAGAGCTTTTGTTTTGTT | CAGAGGCTGCATGATGCCTAATA | |
| OffA-11 | TGCAGCTACGGATGAAAACCAT | TCAGAATACCTCCCCGCCAG | |
| OffA-12 | GCATAAAGCACAGGATGGGAGA | TCCCTCTTTAACGGTTATGTTGGC | |
| OffA-13 | TGGGTTAAGTAATTTCGAAAGGAGAA | ATGTGCCCCACACATTGCC | +DMSO |
| OffA-14 | GAGTGAGCCACTGCACCCAG | CGTGTGGTGGTGGCACAAG | ND |
| OffA-15 | CCTCCCTCTGGCTCCCTCCC | ACCAGGGCCTGTTGGGGGTT | |
| OffA-16 | TGCTCCCTGACCTTCCTGAGA | CCATTGGAATGAGAACCTTCTGG | |
| OffA-17 | GGTGGAACAATCCACCTGTATTAGC | GAATGTGACACCACCACCGC | |
| OffA-18 | GGCTTTGCAAACATAAACACTCA | CCTTCTGAGCAGCTGGGACAA | |
| OffA-19 | CACTGGAACCCAGGAGGTGG | CCTCCCATTGGAGCCTTGGT | |
| OffA-20 | CAGCCTGCCTGGGTGACAG | CATCTGAGCTCAAAACTGCTGC | +DMSO |
| OffA-21 | GCCACTGCATTGCATTTTCC | TGAGGGAGGTCTGTTTCCTG | ND |
| OffA-22 | GGGAGGATCTCTCGAGTCCAGG | CCTTGCCTGACTTGCCCTGT | |
| OffA-23 | TGTTTAGTAATTAAGACCCTGGCTTTC | GCGACAGGTACAAAGCAGTCCAT | |
| OffA-24 | GCCCTTTGATTTCATCTGTTTCCC | CATTGCTGCCATTGCACTCC | |
| OffA-25 | AAACTGGCACATGTACTCCT | ACATGATTTGATTTTTCATGTGTTT | ND |
| OffA-26 | GGGTGGAAGGTGAGAGGAGATT | CGCAGATGGGCATGTTATTG | |
| OffA-27 | CCTCCCATTTTCCTTCCTCCA | GACTGCCACTGCACTCCCAC | ND |
| OffA-28 | AGCCAAGATTGCACCATTGC | GTCCCTGACGGAGGCTGAGA | |
| OffA-29 | TGGTTGGATTTTGGCTCTGTCAC | TGTCAATATCAATACCCTGCTTTCCTC | |
| OffA-30 | TGGTTACTTTTAAAGGGTCATGATGGA | AAAAATGGATGCAAAGCCAAA | +DMSO |
| OffA-31 | GGGACACAGAGCCAAACCGT | TGTGCACATGTACCCTAAAACT | ND |
| OffA-32 | CAGTCATTGTTTCTAGGTAGGGGA | TTGGCAATTTGGGTGCAACA | |
| OffA-33 | TGGATAACCTGCAGATTTGTTTCTG | TGAGCCCAGGAGTTTCAGGC | |
| OffA-34 | TCGTGTGTGTGTGTTTGCTTCA | CAGTGGTTCGGAAACAGCA | |
| OffA-35 | TGGGAATGTAAATCTGACTGGCTG | CTGGAACTCTGGGCATGGCT | |
| OffA-36 | GCTGCAATTGCTTTTTGGCA | TGGACCCCTCCCTTACACC | |

Oligonucleotides used in this study.
(A) All oligonucleotides were purchased from Integrated DNA Technologies (SEQ ID NO: 313-447 from top to bottom). '/5Phos/' indicates 5' phosphorylated oligonucleotides.
A % symbol indicates that the preceding nucleotide was incorporated as a mixture of phosphoramidites consisting of 79 mol% of the phosphoramidite corresponding to the preceding nucleotide and 7 mol% of each of the other three canonical phosphoramidites.
An (*) indicates that the oligonucleotide primer was specific to a selection sequence (either CCR5A, ATM or CCR5B).
An (**) indicates that the oligonucleotide adapter or primer had a unique sequence identifier to distinguish between different samples (selection conditions or cellular TALEN treatment).
(B) Combinations of oligonucleotides used to construct discrete DNA substrates used in TALEN digestion assays.
(C) Primer pairs for PCR amplifying on-target and off-target genomic sites.
+DMSO: DMSO was used in the PCR;
ND: no correct DNA product was detected from the PCR reaction.
Sequences correspond to SEQ ID NOs: 472-545 (Fwd primers from top to bottom); and SEQ ID NOs: 546-619 (Rev primers from top to bottom).

What is claimed is:

1. An isolated Transcription Activator-Like Effector (TALE) domain, wherein (i) the isolated TALE domain is an N-terminal TALE domain comprising the amino acid sequence of SEQ ID NO: 2, SEQ ID NO: 3, or SEQ ID NO: 4, or a functional truncated version thereof, and the net charge of the isolated N-terminal domain is less than the net charge of the canonical N-terminal domain as set forth in SEQ ID NO: 1 at physiological pH; or (ii) wherein the isolated TALE domain is a C-terminal TALE domain comprising an amino acid sequence that differs from the canonical C-terminal domain of SEQ ID NO: 22, in that it comprises one or more of the following amino acid replacements: K37Q, K38Q, K48Q, R49Q, R52Q, R53Q, R57Q, and R61Q, or a functional truncated version thereof, and the net charge of the C-terminal domain is less than the net charge of the canonical C-terminal domain as set forth in SEQ ID NO: 22 at physiological pH.

2. An isolated N-terminal or C-terminal TALE domain, wherein
(i) the isolated TALE domain is an N-terminal TALE domain and the binding energy of the N-terminal domain to a target nucleic acid molecule is smaller than the binding energy of the canonical N-terminal domain as set forth in SEQ ID NO: 1; or
(ii) the isolated TALE domain is a C-terminal TALE domain and the binding energy of the C-terminal domain to a target nucleic acid molecule is smaller than the binding energy of the canonical C-terminal domain as set forth in SEQ ID NO: 22.

3. The isolated TALE domain of claim 1, wherein the net charge of the C-terminal domain is less than or equal to +6, less than or equal to +5, less than or equal to +4, less than or equal to +3, less than or equal to +2, less than or equal to +1, less than or equal to 0, less than or equal to −1, less than or equal to −2, less than or equal to −3, less than or equal to −4, or less than or equal to −5.

4. The isolated TALE domain of claim 1, wherein the C-terminal domain comprises an amino acid sequence that differs from the canonical C-terminal domain of SEQ ID NO: 22 in that at least one cationic amino acid residue of the canonical C-terminal domain sequence is replaced with an amino acid residue that exhibits no charge or a negative charge at physiological pH.

5. The isolated TALE domain of claim 1, wherein the N-terminal domain comprises an amino acid sequence that differs from the canonical N-terminal domain of SEQ ID NO: 1 in that at least one cationic amino acid residue of the canonical N-terminal domain sequence is replaced with an amino acid residue that exhibits no charge or a negative charge at physiological pH.

6. The isolated TALE domain of claim 1, wherein at least 1, at least 2, at least 3, at least 4, at least 5, at least 6, at least 7, at least 8, at least 9, at least 10, at least 11, at least 12, at least 13, at least 14, or at least 15 cationic amino acid(s) in the isolated TALE domain is/are replaced with an amino acid residue that exhibits no charge or a negative charge at physiological pH.

7. The isolated TALE domain of claim 4, wherein the at least one cationic amino acid residue is arginine (R) or lysine (K).

8. The isolated TALE domain of claim 4, wherein the amino acid residue that exhibits no charge or a negative charge at physiological pH is glutamine (Q) or glycine (G).

9. The isolated TALE domain of claim 1, wherein the N-terminal domain is a truncated version of the canonical N-terminal domain.

10. The isolated TALE domain of claim 1, wherein the C-terminal domain is a truncated version of the canonical C-terminal domain.

11. The isolated TALE domain of claim 10, wherein the truncated domain comprises less than 90%, less than 80%, less than 70%, less than 60%, less than 50%, less than 40%, less than 30%, or less than 25% of the residues of the canonical domain.

12. The isolated TALE domain of claim 10, wherein the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues.

13. The isolated TALE domain of claim 10, wherein the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues.

14. The isolated TALE domain of claim 1, wherein the isolated TALE domain is comprised in a TALE molecule comprising the structure

[N-terminal domain]-[TALE repeat array]-[C-terminal domain]-[effector domain]

or

[effector domain]-[N-terminal domain]-[TALE repeat array]-[C-terminal domain].

15. The isolated TALE domain of claim 14, wherein the effector domain comprises a nuclease domain, a transcriptional activator or repressor domain, a recombinase domain, or an epigenetic modification enzyme domain.

16. The isolated TALE domain of claim 14, wherein the TALE molecule binds a target sequence within a gene known to be associated with a disease or disorder.

* * * * *

SEQUENCE LISTING

<160> NUMBER OF SEQ ID NOS: 619

<210> SEQ ID NO 1
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 1

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn
    130                 135

<210> SEQ ID NO 2
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 2

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn
    130                 135

<210> SEQ ID NO 3
<211> LENGTH: 136

<212> TYPE: PRT
<213> ORGANISM: Artificial Sequence
<220> FEATURE:
<223> OTHER INFORMATION: Synthetic Polypeptide

<400> SEQUENCE: 3

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Gln Ile Ala
            100                 105                 110

Gln Arg Gly Gly Val Thr Ala Val Glu Ala Val His Ala Trp Arg Asn
        115                 120                 125

Ala Leu Thr Gly Ala Pro Leu Asn
    130                 135

<210> SEQ ID NO 4
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 4

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Gln Ile Ala
            100                 105                 110

Gln Gln Gly Gly Val Thr Ala Val Glu Ala Val His Ala Trp Arg Asn
        115                 120                 125

Ala Leu Thr Gly Ala Pro Leu Asn
    130                 135

<210> SEQ ID NO 5
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 5

Met Thr Pro Asp Gln Val Val Ala Ile Ala Ser Asn Gly Gly Lys
1               5                   10                  15

Gln Ala Leu Glu Thr Val Gln Arg Leu Leu Pro Val Leu Cys Gln Asp
            20                  25                  30

His

<210> SEQ ID NO 6
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 6

Gly Leu Thr Pro Glu Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 7
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 7

Gly Leu Thr Pro Asp Gln Val Val Ala Ile Ala Ser Asn Ile Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 8
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 8

Gly Leu Thr Pro Ala Gln Val Val Ala Ile Ala Ser Asn Gly Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 9
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 9

Gly Leu Thr Pro Asp Gln Val Val Ala Ile Ala Ser Asn Gly Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 10
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 10

Gly Leu Thr Pro Glu Gln Val Val Ala Ile Ala Ser Asn Ile Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 11
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 11

Gly Leu Thr Pro Asp Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 12
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 12

Gly Leu Thr Pro Ala Gln Val Val Ala Ile Ala Ser Asn Ile Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 13
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 13

Gly Leu Thr Pro Asp Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 14
<211> LENGTH: 34
<212> TYPE: PRT

```
<213> ORGANISM: Artificial Sequence
<220> FEATURE:
<223> OTHER INFORMATION: Synthetic Polypeptide

<400> SEQUENCE: 14

Gly Leu Thr Pro Glu Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 15
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 15

Gly Leu Thr Pro Asp Gln Val Val Ala Ile Ala Ser Asn Gly Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 16
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 16

Gly Leu Thr Pro Ala Gln Val Val Ala Ile Ala Asn Asn Asn Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 17
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 17

Gly Leu Thr Pro Asp Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 18
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 18

Gly Leu Thr Pro Glu Gln Val Val Ala Ile Ala Ser Asn Ile Gly Gly
```

```
                1               5                   10                  15
Lys Gln Ala Leu Glu Thr Val Gln Arg Leu Leu Pro Val Leu Cys Gln
            20                  25                  30
Ala His

<210> SEQ ID NO 19
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 19

Gly Leu Thr Pro Asp Gln Val Val Ala Ile Ala Asn Asn Asn Gly Gly
1               5                   10                  15

Lys Gln Ala Leu Glu Thr Val Gln Arg Leu Leu Pro Val Leu Cys Gln
            20                  25                  30

Ala His

<210> SEQ ID NO 20
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 20

Gly Leu Thr Pro Ala Gln Val Val Ala Ile Ala Ser His Asp Gly Gly
1               5                   10                  15

Lys Gln Ala Leu Glu Thr Val Gln Arg Leu Leu Pro Val Leu Cys Gln
            20                  25                  30

Asp His

<210> SEQ ID NO 21
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 21

Gly Leu Thr Pro Glu Gln Val Val Ala Ile Ala Ser Asn Gly Gly Gly
1               5                   10                  15

Arg Pro Ala Leu Glu
            20

<210> SEQ ID NO 22
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 22

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
            20                  25                  30

Leu Asp Ala Val Lys Lys Gly Leu Pro His Ala Pro Ala Leu Ile Lys
        35                  40                  45

Arg Thr Asn Arg Arg Ile Pro Glu Arg Thr Ser His Arg Val Ala
```

<210> SEQ ID NO 23
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 23

```
Ser Ile Val Ala Gln Leu Ser Arg Pro Asp Pro Ala Leu Ala Ala Leu
1               5                   10                  15
Thr Asn Asp His Leu Val Ala Leu Ala Cys Leu Gly Gly Arg Pro Ala
            20                  25                  30
Leu Asp Ala Val Lys Lys Gly Leu Pro His Ala Pro Ala Leu Ile Gln
        35                  40                  45
Arg Thr Asn Gln Arg Ile Pro Glu Arg Thr Ser His Gln Val Ala
    50                  55                  60
```

<210> SEQ ID NO 24
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 24

```
Ser Ile Val Ala Gln Leu Ser Arg Pro Asp Pro Ala Leu Ala Ala Leu
1               5                   10                  15
Thr Asn Asp His Leu Val Ala Leu Ala Cys Leu Gly Gly Arg Pro Ala
            20                  25                  30
Leu Asp Ala Val Gln Gln Gly Leu Pro His Ala Pro Ala Leu Ile Gln
        35                  40                  45
Gln Thr Asn Gln Gln Ile Pro Glu Arg Thr Ser His Gln Val Ala
    50                  55                  60
```

<210> SEQ ID NO 25
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 25

```
Ser Ile Val Ala Gln Leu Ser Arg Pro Asp Pro Ala Leu Ala Ala Leu
1               5                   10                  15
Thr Asn Asp His Leu Val Ala Leu Ala Cys Leu Gly
            20                  25
```

<210> SEQ ID NO 26
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 26

```
Gly Ser Gln Leu Val Lys Ser Glu Leu Glu Lys Lys Ser Glu Leu
1               5                   10                  15
Arg His Lys Leu Lys Tyr Val Pro His Glu Tyr Ile Glu Leu Ile Glu
            20                  25                  30
Ile Ala Arg Asn Ser Thr Gln Asp Arg Ile Leu Glu Met Lys Val Met
```

-continued

```
                35                  40                  45
Glu Phe Phe Met Lys Val Tyr Gly Tyr Arg Gly Lys His Leu Gly Gly
 50                  55                  60

Ser Arg Lys Pro Asp Gly Ala Ile Tyr Thr Val Gly Ser Pro Ile Asp
 65                  70                  75                  80

Tyr Gly Val Ile Val Asp Thr Lys Ala Tyr Ser Gly Gly Tyr Asn Leu
                 85                  90                  95

Pro Ile Gly Gln Ala Asp Glu Met Gln Arg Tyr Val Glu Glu Asn Gln
                100                 105                 110

Thr Arg Asn Lys His Ile Asn Pro Asn Glu Trp Trp Lys Val Tyr Pro
            115                 120                 125

Ser Ser Val Thr Glu Phe Lys Phe Leu Phe Val Ser Gly His Phe Lys
        130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195
```

<210> SEQ ID NO 27
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 27

```
Gly Ser Gln Leu Val Lys Ser Glu Leu Glu Glu Lys Lys Ser Glu Leu
 1               5                  10                  15

Arg His Lys Leu Lys Tyr Val Pro His Glu Tyr Ile Glu Leu Ile Glu
                20                  25                  30

Ile Ala Arg Asn Ser Thr Gln Asp Arg Ile Leu Glu Met Lys Val Met
            35                  40                  45

Glu Phe Phe Met Lys Val Tyr Gly Tyr Arg Gly Lys His Leu Gly Gly
 50                  55                  60

Ser Arg Lys Pro Asp Gly Ala Ile Tyr Thr Val Gly Ser Pro Ile Asp
 65                  70                  75                  80

Tyr Gly Val Ile Val Asp Thr Lys Ala Tyr Ser Gly Gly Tyr Asn Leu
                 85                  90                  95

Pro Ile Gly Gln Ala Asp Glu Met Glu Arg Tyr Val Glu Glu Asn Gln
                100                 105                 110

Thr Arg Asn Lys His Leu Asn Pro Asn Glu Trp Trp Lys Val Tyr Pro
            115                 120                 125

Ser Ser Val Thr Glu Phe Lys Phe Leu Phe Val Ser Gly His Phe Lys
        130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
```

<210> SEQ ID NO 28
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 28

```
Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Lys Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Lys Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195
```

<210> SEQ ID NO 29
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 29

```
Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95
```

Pro Ile Gly Gln Ala Asp Glu Met Glu Arg Tyr Val Glu Asn Gln
            100                 105                 110

Thr Arg Asp Lys His Leu Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
            195

<210> SEQ ID NO 30
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 30

Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Lys Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn Arg Lys Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
            195

<210> SEQ ID NO 31
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 31

Leu Gln Leu Asp Thr Gly Gln Leu Leu Lys Ile Ala Lys Arg Gly Gly
1               5                   10                  15

Thr Val Thr Ala Val Glu Ala
            20

<210> SEQ ID NO 32
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 32

Leu Gln Leu Asp Thr Gly Gln Leu Leu Gln Ile Ala Lys Arg Gly Gly
1               5                   10                  15

Thr Val Thr Ala Val Glu Ala
            20

<210> SEQ ID NO 33
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 33

Leu Gln Leu Asp Thr Gly Gln Leu Leu Lys Ile Ala Gln Arg Gly Gly
1               5                   10                  15

Thr Val Thr Ala Val Glu Ala
            20

<210> SEQ ID NO 34
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 34

Leu Gln Leu Asp Thr Gly Gln Leu Leu Lys Ile Ala Lys Gln Gly Gly
1               5                   10                  15

Thr Val Thr Ala Val Glu Ala
            20

<210> SEQ ID NO 35
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 35

Leu Gln Leu Asp Thr Gly Gln Leu Leu Lys Ile Ala Lys Gly Gly Gly
1               5                   10                  15

Thr Val Thr Ala Val Glu Ala
            20

<210> SEQ ID NO 36
<211> LENGTH: 23
<212> TYPE: PRT
<213> ORGANISM: Artificial Sequence
<220> FEATURE:
<223> OTHER INFORMATION: Synthetic Polypeptide

```
<400> SEQUENCE: 36

Leu Gln Leu Asp Thr Gly Gln Leu Leu Gln Ile Ala Gln Arg Gly Gly
1               5                   10                  15

Thr Val Thr Ala Val Glu Ala
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 37

Leu Gln Leu Asp Thr Gly Gln Leu Leu Gln Ile Ala Lys Gln Gly Gly
1               5                   10                  15

Thr Val Thr Ala Val Glu Ala
            20

<210> SEQ ID NO 38
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 38

Leu Gln Leu Asp Thr Gly Gln Leu Leu Lys Ile Ala Gln Gln Gly Gly
1               5                   10                  15

Thr Val Thr Ala Val Glu Ala
            20

<210> SEQ ID NO 39
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 39

Leu Gln Leu Asp Thr Gly Gln Leu Leu Gly Ile Ala Lys Gly Gly Gly
1               5                   10                  15

Thr Val Thr Ala Val Glu Ala
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 40

Leu Gln Leu Asp Thr Gly Gln Leu Leu Gln Ile Ala Gln Gln Gly Gly
1               5                   10                  15

Thr Val Thr Ala Val Glu Ala
            20

<210> SEQ ID NO 41
<211> LENGTH: 23
<212> TYPE: PRT
<213> ORGANISM: Artificial Sequence
<220> FEATURE:
<223> OTHER INFORMATION: Synthetic Polypeptide
```

<400> SEQUENCE: 41

Leu Gln Leu Asp Thr Gly Gln Leu Leu Gly Ile Ala Gly Gly Gly Gly
1               5                   10                  15

Thr Val Thr Ala Val Glu Ala
            20

<210> SEQ ID NO 42
<211> LENGTH: 8058
<212> TYPE: DNA
<213> ORGANISM: Artificial Sequence
<220> FEATURE:
<223> OTHER INFORMATION: Synthetic Polynucleotide

<400> SEQUENCE: 42

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| accatggact | acaaagacca | tgacggtgat | tataaagatc | atgacatcga | ttacaaggat | 960 |
| gacgatgaca | agatggcccc | caagaagaag | aggaaggtgg | gcattcaccg | cggggtacct | 1020 |
| atggtggact | tgaggacact | cggttattcg | caacagcaac | aggagaaaat | caagcctaag | 1080 |
| gtcaggagca | ccgtcgcgca | acaccacgag | gcgcttgtgg | ggcatggctt | cactcatgcg | 1140 |
| catattgtcg | cgctttcaca | gcaccctgcg | gcgcttggga | cggtggctgt | caaataccaa | 1200 |
| gatatgattg | cggccctgcc | cgaagccacg | cacgaggcaa | ttgtaggggt | cggtaaacag | 1260 |
| tggtcgggag | cgcgagcact | tgaggcgctg | ctgactgtgg | cgggtgagct | taggggcct | 1320 |
| ccgctccagc | tcgacaccgg | gcagctgctg | aagatcgcga | agagagggg | agtaacagcg | 1380 |
| gtagaggcag | tgcacgcctg | gcgcaatgcg | ctcaccgggg | cccccttgaa | cctgaccca | 1440 |
| gaccaggtag | tcgcaatcgc | gtcaaacgga | gggggaaagc | aagccctgga | aaccgtgcaa | 1500 |
| aggttgttgc | cggtcctttg | tcaagaccac | ggccttacac | cggagcaagt | cgtggccatt | 1560 |
| gcatcccacg | acggtggcaa | acaggctctt | gagacggttc | agagacttct | cccagttctc | 1620 |
| tgtcaagccc | acgggctgac | tcccgatcaa | gttgtagcga | ttgcgtcgaa | cattggaggg | 1680 |
| aaacaagcat | ggagactgt | ccaacggctc | cttccgtgt | tgtgtcaagc | ccacggtttg | 1740 |
| acgcctgcac | aagtggtcgc | catcgcctcg | aatggcggcg | gtaagcaggc | gctggaaaca | 1800 |

```
gtacagcgcc tgctgcctgt actgtgccag gatcatggac tgaccccaga ccaggtagtc    1860
gcaatcgcgt caaacggagg gggaaagcaa gccctggaaa ccgtgcaaag gttgttgccg    1920
gtcctttgtc aagaccacgg ccttacaccg gagcaagtcg tggccattgc aagcaacatc    1980
ggtggcaaac aggctcttga gacggttcag agacttctcc cagttctctg tcaagcccac    2040
gggctgactc ccgatcaagt tgtagcgatt gcgtcgcatg acggagggaa acaagcattg    2100
gagactgtcc aacggctcct tcccgtgttg tgtcaagccc acggtttgac gcctgcacaa    2160
gtggtcgcca tcgcctccaa tattggcggt aagcaggcgc tggaaacagt acagcgcctg    2220
ctgcctgtac tgtgccagga tcatggactg accccagacc aggtagtcgc aatcgcgtca    2280
catgacgggg gaaagcaagc cctggaaacc gtgcaaaggt tgttgccggt cctttgtcaa    2340
gaccacggcc ttacaccgga gcaagtcgtg gccattgcat cccacgacgg tgcaaacag    2400
gctcttgaga cggttcagag acttctccca gttctctgtc aagcccacgg ctgactccc    2460
gatcaagttg tagcgattgc gtccaacggt ggagggaaac aagcattgga gactgtccaa    2520
cggctccttc ccgtgttgtg tcaagcccac ggtttgacgc ctgcacaagt ggtcgccatc    2580
gccaacaaca acggcggtaa caggcgctg gaaacagtac agcgcctgct gcctgtactg    2640
tgccaggatc atggactgac cccagaccag gtagtcgcaa tcgcgtcaca tgacggggga    2700
aagcaagccc tggaaaccgt gcaaaggttg ttgccggtcc tttgtcaaga ccacggcctt    2760
acaccggagc aagtcgtggc cattgcaagc aacatcggtg caaacaggc tcttgagacg    2820
gttcagagac ttctcccagt tctctgtcaa gcccacgggc tgactcccga tcaagttgta    2880
gcgattgcga taacaatgg agggaaacaa gcattgagga ctgtccaacg gctccttccc    2940
gtgttgtgtc aagcccacgg tttgacgcct gcacaagtgg tcgccatcgc cagccatgat    3000
ggcggtaagc aggcgctgga aacagtacag cgcctgctgc ctgtactgtg ccaggatcat    3060
ggactgacac ccgaacaggt ggtcgccatt gcttctaatg ggggaggacg gccagccttg    3120
gagtccatcg tagcccaatt gtccaggccc gatcccgcgt tggctgcgtt aacgaatgac    3180
catctggtgg cgttggcatg tcttggtgga cgacccgcgc tcgatgcagt caaaaagggt    3240
ctgcctcatg ctcccgcatt gatcaaaaga accaaccggc ggattcccga gagaacttcc    3300
catcgagtcg cgggatccca actagtcaaa agtgaactgg aggagaagaa atctgaactt    3360
cgtcataaat tgaaatatgt gcctcatgaa tatattgaat taattgaaat tgccagaaat    3420
tccactcagg atagaattct tgaaatgaag gtaatggaat tttttatgaa agtttatgga    3480
tatagaggta acatttggg tggatcaagg aaaccggacg gagcaattta tactgtcgga    3540
tctcctattg attacggtgt gatcgtggat actaaagctt atagcggagg ttataatctg    3600
ccaattggcc aagcagatga atggagcga tatgtcgaag aaaatcaaac acgaaacaaa    3660
catatcaacc ctaatgaatg gtggaaagtc tatccatctt ctgtaacgga atttaagttt    3720
ttatttgtga gtggtcactt taaaggaaac tacaaagctc agcttacacg attaaatcat    3780
atcactaatt gtaatggagc tgttcttagt gtagaagagc ttttaattgg tggagaaatg    3840
attaaagccg gcacattaac cttagaggaa gtgagacgga aatttaataa cggcgagata    3900
aacttttaag ggcccttcga aggtaagcct atccctaacc ctctcctcgg tctcgattct    3960
acgcgtaccg gtcatcatca ccatcaccat tgagtttaaa cccgctgatc agcctcgact    4020
gtgccttcta gttgccagcc atctgttgtt tgccctcccc ccgtgccttc cttgaccctg    4080
gaaggtgcca ctcccactgt cctttcctaa taaaatgagg aaattgcatc gcattgtctg    4140
agtaggtgtc attctattct ggggggtggg gtggggcagg acagcaaggg ggaggattgg    4200
```

```
gaagacaata gcaggcatgc tggggatgcg gtgggctcta tggcttctga ggcggaaaga    4260
accagctggg gctctagggg gtatcccac gcgccctgta gcggcgcatt aagcgcggcg    4320
ggtgtggtgg ttacgcgcag cgtgaccgct acacttgcca gcgccctagc gcccgctcct    4380
ttcgctttct tcccttcctt tctcgccacg ttcgccggct ttccccgtca agctctaaat    4440
cggggcatcc ctttagggtt ccgatttagt gctttacggc acctcgaccc caaaaaactt    4500
gattagggtg atggttcacg tagtgggcca tcgccctgat agacggtttt tcgccctttg    4560
acgttggagt ccacgttctt taatagtgga ctcttgttcc aaactggaac aacactcaac    4620
cctatctcgg tctattcttt tgatttataa gggattttgg ggatttcggc ctattggtta    4680
aaaaatgagc tgatttaaca aaatttaac gcgaattaat tctgtggaat gtgtgtcagt    4740
tagggtgtgg aaagtcccca ggctccccag gcaggcagaa gtatgcaaag catgcatctc    4800
aattagtcag caaccaggtg tggaaagtcc ccaggctccc cagcaggcag aagtatgcaa    4860
agcatgcatc tcaattagtc agcaaccata gtcccgcccc taactccgcc catcccgccc    4920
ctaactccgc ccagttccgc ccattctccg ccccatggct gactaatttt ttttatttat    4980
gcagaggccg aggccgcctc tgcctctgag ctattccaga gtagtgagg aggcttttttt    5040 ggaggcctag gcttttgcaa aaagctcccg ggagcttgta tatccatttt cggatctgat    5100
cagcacgtgt tgacaattaa tcatcggcat agtatatcgg catagtataa tacgacaagg    5160
tgaggaacta aaccatggcc aagcctttgt ctcaagaaga atccaccctc attgaaagag    5220
caacggctac aatcaacagc atccccatct ctgaagacta cagcgtcgcc agcgcagctc    5280
tctctagcga cggccgcatc ttcactggtg tcaatgtata tcattttact gggggaccttt    5340 gtgcagaact cgtggtgctg ggcactgctg ctgctgcggc agctggcaac ctgacttgta    5400
tcgtcgcgat cggaaatgag aacagggggca tcttgagccc ctgcggacgg tgtcgacagg    5460
tgcttctcga tctgcatcct gggatcaaag cgatagtgaa ggacagtgat ggacagccga    5520
cggcagttgg gattcgtgaa ttgctgccct ctggttatgt gtgggagggc taagcacttc    5580
gtggccgagg agcaggactg acacgtgcta cgagatttcg attccaccgc cgccttctat    5640
gaaaggttgg gcttcggaat cgttttccgg gacgccggct ggatgatcct ccagcgcggg    5700
gatctcatgc tggagttctt cgcccacccc aacttgttta ttgcagctta taatggttac    5760
aaataaagca atagcatcac aaatttcaca ataaagcat ttttttcact gcattctagt    5820
tgtggtttgt ccaaactcat caatgtatct tatcatgtct gtataccgtc gacctctagc    5880
tagagcttgg cgtaatcatg gtcatagctg tttcctgtgt gaaattgtta tccgctcaca    5940
attccacaca acatacgagc cggaagcata aagtgtaaag cctggggtgc ctaatgagtg    6000
agctaactca cattaattgc gttgcgctca ctgcccgctt tccagtcggg aaacctgtcg    6060
tgccagctgc attaatgaat cggccaacgc gcggggagag cggtttgcg tattgggcgc    6120 tcttccgctt cctcgctcac tgactcgctg cgctcggtcg ttcggctgcg gcgagcggta    6180
tcagctcact caaaggcggt aatacggtta tccacagaat caggggataa cgcaggaaag    6240
aacatgtgag caaaaggcca gcaaaaggcc aggaaccgta aaaaggccgc gttgctggcg    6300 ttttttccata ggctccgccc ccctgacgag catcacaaaa atcgacgctc aagtcagagg    6360
tggcgaaacc cgacaggact ataaagatac caggcgtttc cccctggaag ctccctcgtg    6420
cgctctcctg ttccgaccct gccgcttacc ggatacctgt ccgcctttct cccttcggga    6480
agcgtggcgc tttctcaatg ctcacgctgt aggtatctca gttcggtgta ggtcgttcgc    6540
```

```
tccaagctgg gctgtgtgca cgaaccccc gttcagcccg accgctgcgc cttatccggt    6600
aactatcgtc ttgagtccaa cccggtaaga cacgacttat cgccactggc agcagccact    6660
ggtaacagga ttagcagagc gaggtatgta ggcggtgcta cagagttctt gaagtggtgg    6720
cctaactacg gctacactag aaggacagta tttggtatct gcgctctgct gaagccagtt    6780
accttcggaa aaagagttgg tagctcttga tccggcaaac aaaccaccgc tggtagcggt    6840 ggttttttg tttgcaagca gcagattacg cgcagaaaaa aaggatctca agaagatcct    6900
ttgatctttt ctacggggtc tgacgctcag tggaacgaaa actcacgtta agggattttg    6960
gtcatgagat tatcaaaaag gatcttcacc tagatccttt taaattaaaa atgaagtttt    7020
aaatcaatct aaagtatata tgagtaaact tggtctgaca gttaccaatg cttaatcagt    7080
gaggcaccta tctcagcgat ctgtctattt cgttcatcca tagttgcctg actccccgtc    7140
gtgtagataa ctacgatacg ggagggctta ccatctggcc ccagtgctgc aatgataccg    7200
cgagacccac gctcaccggc tccagattta tcagcaataa accagccagc cggaagggcc    7260
gagcgcagaa gtggtcctgc aactttatcc gcctccatcc agtctattaa ttgttgccgg    7320
gaagctagag taagtagttc gccagttaat agtttgcgca acgttgttgc cattgctaca    7380
ggcatcgtgg tgtcacgctc gtcgtttggt atggcttcat tcagctccgg ttcccaacga    7440
tcaaggcgag ttacatgatc ccccatgttg tgcaaaaaag cggttagctc cttcggtcct    7500
ccgatcgttg tcagaagtaa gttggccgca gtgttatcac tcatggttat ggcagcactg    7560
cataattctc ttactgtcat gccatccgta agatgctttt ctgtgactgg tgagtactca    7620
accaagtcat tctgagaata gtgtatgcgg cgaccgagtt gctcttgccc ggcgtcaata    7680
cgggataata ccgcgccaca tagcagaact ttaaaagtgc tcatcattgg aaaacgttct    7740
tcggggcgaa aactctcaag gatcttaccg ctgttgagat ccagttcgat gtaacccact    7800
cgtgcaccca actgatcttc agcatctttt actttcacca gcgtttctgg gtgagcaaaa    7860
acaggaaggc aaaatgccgc aaaaaaggga ataagggcga cacggaaatg ttgaatactc    7920
atactcttcc tttttcaata ttattgaagc atttatcagg gttattgtct catgagcgga    7980
tacatatttg aatgtattta gaaaaataaa caaataggggg ttccgcgcac atttccccga    8040
aaagtgccac ctgacgtc                                                 8058
```

<210> SEQ ID NO 43
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 43

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 44
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 44

```
ttcattacac ctgcagct                                                    18
```

<210> SEQ ID NO 45
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 45

```
agctgcaggt gtaatgaa                                                    18
```

<210> SEQ ID NO 46
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 46

```
agtatcaatt ctggaaga                                                    18
```

<210> SEQ ID NO 47
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 47

```
tcttccagaa ttgatact                                                    18
```

<210> SEQ ID NO 48
<211> LENGTH: 64
<212> TYPE: PRT
<213> ORGANISM: Artificial Sequence
<220> FEATURE:
<223> OTHER INFORMATION: Synthetic Polypeptide

<400> SEQUENCE: 48

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Gly Arg Pro
            20                  25                  30

Ala Leu Asp Ala Val Lys Lys Gly Leu Pro His Ala Pro Ala Leu Ile
        35                  40                  45

Lys Arg Thr Asn Arg Arg Ile Pro Glu Arg Thr Ser His Arg Val Ala
    50                  55                  60

<210> SEQ ID NO 49
<211> LENGTH: 64
<212> TYPE: PRT
<213> ORGANISM: Artificial Sequence
<220> FEATURE:
<223> OTHER INFORMATION: Synthetic Polypeptide

<400> SEQUENCE: 49

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Gly Arg Pro
            20                  25                  30

Ala Leu Asp Ala Val Lys Lys Gly Leu Pro His Ala Pro Ala Leu Ile
        35                  40                  45

Gln Arg Thr Asn Gln Arg Ile Pro Glu Arg Thr Ser His Gln Val Ala
        50                  55                  60

<210> SEQ ID NO 50
<211> LENGTH: 64
<212> TYPE: PRT
<213> ORGANISM: Artificial Sequence
<220> FEATURE:
<223> OTHER INFORMATION: Synthetic Polypeptide

<400> SEQUENCE: 50

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Gly Arg Pro
            20                  25                  30

Ala Leu Asp Ala Val Gln Gln Gly Leu Pro His Ala Pro Ala Leu Ile
        35                  40                  45

Gln Gln Thr Asn Gln Gln Ile Pro Glu Arg Thr Ser His Gln Val Ala
    50                  55                  60

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 51
nttcattaca cctgcagctn                                            20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 52
nagtatcaat tctggaagan                                            20

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature

```
<222> LOCATION: (20)..(20)
<223> OTHER INFORMATION: n is a, c, g, or t

<400> SEQUENCE: 53
ntgaattggg atgctgtttn                                           20

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 54
ntttatttta ctgtctttan                                           20

<210> SEQ ID NO 55
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 55
tcattacacc tgc                                                  13

<210> SEQ ID NO 56
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 56
tcattacacc tgt                                                  13

<210> SEQ ID NO 57
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 57
tcataacacc tgc                                                  13

<210> SEQ ID NO 58
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 58
tcattacacc cgc                                                  13

<210> SEQ ID NO 59
<211> LENGTH: 13
<212> TYPE: DNA
```

```
<213> ORGANISM: Artificial Sequence
<220> FEATURE:
<223> OTHER INFORMATION: Synthetic Polynucleotide

<400> SEQUENCE: 59
tcattacacc tgc                                                          13

<210> SEQ ID NO 60
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 60
tcattacacc tgc                                                          13

<210> SEQ ID NO 61
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 61
tcattacacc tgc                                                          13

<210> SEQ ID NO 62
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 62
tcattacacc tgc                                                          13

<210> SEQ ID NO 63
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 63
tcataacacc tgt                                                          13

<210> SEQ ID NO 64
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 64
tcattatacc tac                                                          13

<210> SEQ ID NO 65
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 65
tcattgcacc cgc                                                          13
```

<210> SEQ ID NO 66
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 66
tcattacacc tgc                                               13

<210> SEQ ID NO 67
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 67
tcattacacc tgc                                               13

<210> SEQ ID NO 68
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 68
tcattacacc tgc                                               13

<210> SEQ ID NO 69
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 69
tcattacacc tgt                                               13

<210> SEQ ID NO 70
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 70
tcataacacc tgc                                               13

<210> SEQ ID NO 71
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 71
tcattacacc tgt                                               13

<210> SEQ ID NO 72
<211> LENGTH: 13
<212> TYPE: DNA
<213> ORGANISM: Artificial Sequence
<220> FEATURE:

<223> OTHER INFORMATION: Synthetic Polynucleotide

<400> SEQUENCE: 72
catacagtca gta                                                              13

<210> SEQ ID NO 73
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 73
catacagtca gta                                                              13

<210> SEQ ID NO 74
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 74
catacagtca gta                                                              13

<210> SEQ ID NO 75
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 75
catacagtca gta                                                              13

<210> SEQ ID NO 76
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 76
catacagtaa gta                                                              13

<210> SEQ ID NO 77
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 77
gatacagtca gta                                                              13

<210> SEQ ID NO 78
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 78
cattcagtca gta                                                              13

```
<210> SEQ ID NO 79
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 79
catacagtcg gta                                                        13

<210> SEQ ID NO 80
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 80
catacagtca gta                                                        13

<210> SEQ ID NO 81
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 81
catacagtca gta                                                        13

<210> SEQ ID NO 82
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 82
catacagtca gta                                                        13

<210> SEQ ID NO 83
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 83
gatacagtaa gta                                                        13

<210> SEQ ID NO 84
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 84
cacacattca gta                                                        13

<210> SEQ ID NO 85
<211> LENGTH: 13
<212> TYPE: DNA
<213> ORGANISM: Artificial Sequence
<220> FEATURE:
<223> OTHER INFORMATION: Synthetic Polynucleotide
```

<400> SEQUENCE: 85
catactatca gta					13

<210> SEQ ID NO 86
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 86
catacagtaa gta					13

<210> SEQ ID NO 87
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 87
gatacagtca gta					13

<210> SEQ ID NO 88
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 88
cattcagtca gta					13

<210> SEQ ID NO 89
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 89
ttcattacac ctgcagctct cattttccat acagtcagta tcaattctgg aaga					54

<210> SEQ ID NO 90
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 90
ttcattacac ctgcagctct catacagtca gtatcaattc tggaaga					47

<210> SEQ ID NO 91
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 91
ttcattacac ctgcagtcag tatcaattct ggaaga					36

<210> SEQ ID NO 92
<211> LENGTH: 18

```
<212> TYPE: DNA
<213> ORGANISM: Artificial Sequence
<220> FEATURE:
<223> OTHER INFORMATION: Synthetic Polynucleotide

<400> SEQUENCE: 92
ttcattacac ctggaaga                                                   18

<210> SEQ ID NO 93
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 93
tacatcacat atgcaaattg actcaaaatg gatcatagac ctaaatgtgt atcatttctg     60
ggaga                                                                 65

<210> SEQ ID NO 94
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 94
tacatcacat atgcaaattg actcaaaatg gatcaaccta atgtgtatc atttctggga      60 ga                                                                    62

<210> SEQ ID NO 95
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 95
tacatcacat atgcaaattg actcaaaatg gacctaaatg tgtatcattt ctgggaga      58

<210> SEQ ID NO 96
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 96
tccaatacct ctgccacacc caggcattgg ccaggagcaa ctctgggaga               50

<210> SEQ ID NO 97
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 97
tccaatacct ctgccacacc caggagcaac tctgggaga                            39

<210> SEQ ID NO 98
<211> LENGTH: 40
<212> TYPE: DNA
<213> ORGANISM: Artificial Sequence
<220> FEATURE:
```

<223> OTHER INFORMATION: Synthetic Polynucleotide

<400> SEQUENCE: 98
tccaatacct ctggcattgg ccaggagcaa ctctgggaga                    40

<210> SEQ ID NO 99
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 99
tccaatacct ctgggaga                                             18

<210> SEQ ID NO 100
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 100
tccatgacac aaaagacttc cctgatttct tctaaggcat cactggtatc tatcctggaa    60
ta                                                                  62

<210> SEQ ID NO 101
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 101
tccatgacac aaaagacttc cctgatttct tctaaggctg gtatctatcc tggaata         57

<210> SEQ ID NO 102
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 102
ttccttccac cagtgtccac agtcttcaca ctgatcacca atcccagca tcaatcctgg    60 aaga                                                                64

<210> SEQ ID NO 103
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 103
ttccttccac cagtgtccac agtccaccaa atcccagcat caatcctgga aga            53

<210> SEQ ID NO 104
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 104
tttattacac ttccagatct tttattttaa gttaccagat atcctttctg gaaga          55

<210> SEQ ID NO 105
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 105
tttattacac ttccagatat cctttctgga aga          33

<210> SEQ ID NO 106
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 106
tttattacac ttccagatct tttatatcct ttctggaaga          40

<210> SEQ ID NO 107
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 107
tttattacac ttccagatct tttatccttt ctggaaga          38

<210> SEQ ID NO 108
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 108
ctcctaatac ctgcaaatta taaggacact atttgacttg atattatttc tggagga          57

<210> SEQ ID NO 109
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 109
ctcctaatac ctgcaaatta taaggacact gacttgatat tatttctgga gga          53

<210> SEQ ID NO 110
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 110
ttcattacac ctgcagct          18

<210> SEQ ID NO 111
<211> LENGTH: 18
<212> TYPE: DNA

```
<213> ORGANISM: Artificial Sequence
<220> FEATURE:
<223> OTHER INFORMATION: Synthetic Polynucleotide

<400> SEQUENCE: 111
ttcattacat ctgcacct                                                  18

<210> SEQ ID NO 112
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 112
ttcaatacac ctgtagct                                                  18

<210> SEQ ID NO 113
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 113
ttcattacac ccgcagca                                                  18

<210> SEQ ID NO 114
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 114
ttaattgcac ctgcagct                                                  18

<210> SEQ ID NO 115
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 115
ttcattacac ctgcagct                                                  18

<210> SEQ ID NO 116
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 116
ttcattacac ctgcagct                                                  18

<210> SEQ ID NO 117
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 117
ttcattacac ctgcagct                                                  18
```

<210> SEQ ID NO 118
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 118
ttcattacac ctgcagct                                                 18

<210> SEQ ID NO 119
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 119
agtatcaatt ctggaaga                                                 18

<210> SEQ ID NO 120
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 120
agtatcaatt ctggaaga                                                 18

<210> SEQ ID NO 121
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 121
agtatcaatt ctggaaga                                                 18

<210> SEQ ID NO 122
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 122
agtatcaatt ctggaaga                                                 18

<210> SEQ ID NO 123
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 123
agtatcaatt ctggaaga                                                 18

<210> SEQ ID NO 124
<211> LENGTH: 18
<212> TYPE: DNA
<213> ORGANISM: Artificial Sequence
<220> FEATURE:

<223> OTHER INFORMATION: Synthetic Polynucleotide

<400> SEQUENCE: 124
agtatgaatt ctgtaaga                                                   18

<210> SEQ ID NO 125
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 125
agtatcaact ctggagga                                                   18

<210> SEQ ID NO 126
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 126
attatcaatt caggaaga                                                   18

<210> SEQ ID NO 127
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 127
agtaacaatg ctggaaga                                                   18

<210> SEQ ID NO 128
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 128
tgaattggga tgctgttt                                                   18

<210> SEQ ID NO 129
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 129
tgaattgggt tgctgttt                                                   18

<210> SEQ ID NO 130
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 130
tgaattgcga tgctgttt                                                   18

<210> SEQ ID NO 131
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 131
tgaattggga tgctgttt                                                18

<210> SEQ ID NO 132
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 132
tgaattggga tgctgttt                                                18

<210> SEQ ID NO 133
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 133
tgaattgcga tgctgttt                                                18

<210> SEQ ID NO 134
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 134
tgagttggga tgctgttt                                                18

<210> SEQ ID NO 135
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 135
tgaattgggt tgctgttt                                                18

<210> SEQ ID NO 136
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 136
tgaattggga tgctattt                                                18

<210> SEQ ID NO 137
<211> LENGTH: 18
<212> TYPE: DNA
<213> ORGANISM: Artificial Sequence
<220> FEATURE:
<223> OTHER INFORMATION: Synthetic Polynucleotide

```
<400> SEQUENCE: 137
tttattttac tgtcttta                                                    18

<210> SEQ ID NO 138
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 138
tttattttac tgtcttta                                                    18

<210> SEQ ID NO 139
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 139
tttattttac tgtcttta                                                    18

<210> SEQ ID NO 140
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 140
tttatttcac tgtcttta                                                    18

<210> SEQ ID NO 141
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 141
tttattttac tatcttta                                                    18

<210> SEQ ID NO 142
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 142
tttattttac tatcttta                                                    18

<210> SEQ ID NO 143
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 143
tttatgttac tgtcttta                                                    18

<210> SEQ ID NO 144
<211> LENGTH: 18
```

```
<212> TYPE: DNA
<213> ORGANISM: Artificial Sequence
<220> FEATURE:
<223> OTHER INFORMATION: Synthetic Polynucleotide

<400> SEQUENCE: 144
tttatttgac tgtcttta                                                 18

<210> SEQ ID NO 145
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 145
tttattttac tgtcctta                                                 18

<210> SEQ ID NO 146
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 146
ttcattacac ctgcagct                                                 18

<210> SEQ ID NO 147
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 147
tcttcattac acctgc                                                   16

<210> SEQ ID NO 148
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 148
tcattacacc tgc                                                      13

<210> SEQ ID NO 149
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 149
ttacacctgc                                                          10

<210> SEQ ID NO 150
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 150
```

```
tcttcattac acctgcagct ctcattttcc atacagtcag tatcaattct ggaaga      56
```

<210> SEQ ID NO 151
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 151

```
tcttccagaa ttgatactga ctgtatggaa aatgagagct gcaggtgtaa tgaaga      56
```

<210> SEQ ID NO 152
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 152

```
tcttccagaa ttgatact                                                18
```

<210> SEQ ID NO 153
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 153

```
tgatactgac tgtatg                                                  16
```

<210> SEQ ID NO 154
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 154

```
tactgactgt atg                                                     13
```

<210> SEQ ID NO 155
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 155

```
tgactgtatg                                                         10
```

<210> SEQ ID NO 156
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 156

```
tgaattggga tgctgttt                                                18
```

<210> SEQ ID NO 157
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 157
tgaattggga tgctgttttt aggtattcta ttcaaattta ttttactgtc ttta        54

<210> SEQ ID NO 158
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 158
taaagacagt aaaataaatt tgaatagaat acctaaaaac agcatcccaa ttca        54

<210> SEQ ID NO 159
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 159
taaagacagt aaaataaa                                                 18

<210> SEQ ID NO 160
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 160
ntcttcatta cacctgcn                                                 18

<210> SEQ ID NO 161
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 161
nnnntcatta cacctgcn                                                 18

<210> SEQ ID NO 162
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 162
nnnnnnntta cacctgcn                                                18

<210> SEQ ID NO 163
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 163
ncatacagtc agtatcan                                                18

<210> SEQ ID NO 164
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(18)
<223> OTHER INFORMATION: n is a, c, g, or t

<400> SEQUENCE: 164
ncatacagtc agtannnn                                                18

<210> SEQ ID NO 165
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 165
ncatacagtc annnnnnn                                                18

<210> SEQ ID NO 166
<211> LENGTH: 16
<212> TYPE: DNA
<213> ORGANISM: Homo sapiens

<400> SEQUENCE: 166
```
cgtcacgctc accact                                              16

<210> SEQ ID NO 167
<211> LENGTH: 17
<212> TYPE: DNA
<213> ORGANISM: Homo sapiens

<400> SEQUENCE: 167
cctcgggact ccacgct                                             17

<210> SEQ ID NO 168
<211> LENGTH: 17
<212> TYPE: DNA
<213> ORGANISM: Homo sapiens

<400> SEQUENCE: 168 ggtacccac tccgcgt                                              17

<210> SEQ ID NO 169
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 169
tacatcacat atgcaaat                                            18

<210> SEQ ID NO 170
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 170
tacatcacat atgcaaat                                            18

<210> SEQ ID NO 171
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 171
tacatcacat atgcaaat                                            18

<210> SEQ ID NO 172
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 172
tccataacac atctttct                                            18

<210> SEQ ID NO 173
<211> LENGTH: 18
<212> TYPE: DNA
<213> ORGANISM: Artificial Sequence
<220> FEATURE:
<223> OTHER INFORMATION: Synthetic Polynucleotide

```
<400> SEQUENCE: 173
tccaatacct ctgccaca                                                  18

<210> SEQ ID NO 174
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 174
ttcagtccat ctgaaaac                                                  18

<210> SEQ ID NO 175
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 175
tacaaaaccc ttgccaaa                                                  18

<210> SEQ ID NO 176
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 176
tccaagacac ctgcttac                                                  18

<210> SEQ ID NO 177
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 177
ttcataacat cttaaaat                                                  18

<210> SEQ ID NO 178
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 178
tccaaaacat ctgaaaat                                                  18

<210> SEQ ID NO 179
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 179
ttcagaacac atgactac                                                  18

<210> SEQ ID NO 180
<211> LENGTH: 18
```

-continued

```
<212> TYPE: DNA
<213> ORGANISM: Artificial Sequence
<220> FEATURE:
<223> OTHER INFORMATION: Synthetic Polynucleotide

<400> SEQUENCE: 180
tccataatat cttcctct                                                 18

<210> SEQ ID NO 181
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 181
tgcaatatac ctgttgat                                                 18

<210> SEQ ID NO 182
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 182
ttcataacac tccacctt                                                 18

<210> SEQ ID NO 183
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 183
tccatgacac aaaagact                                                 18

<210> SEQ ID NO 184
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 184
ttccttccac cagtgtcc                                                 18

<210> SEQ ID NO 185
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 185
ttaataacat ctccaact                                                 18

<210> SEQ ID NO 186
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 186
```

```
tccatcaccc ctccctcc                                          18
```

<210> SEQ ID NO 187
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 187

```
ttcattactc ctccttct                                          18
```

<210> SEQ ID NO 188
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 188

```
tgcattacac attatgtg                                          18
```

<210> SEQ ID NO 189
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 189

```
ttcaaaacac atacatct                                          18
```

<210> SEQ ID NO 190
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 190

```
tccattacca ctgcagat                                          18
```

<210> SEQ ID NO 191
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 191

```
ttccagaccc cttcctca                                          18
```

<210> SEQ ID NO 192
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 192

```
ttccaaacac ccgcttcc                                          18
```

<210> SEQ ID NO 193
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 193
tgaaatacac ctgcctat                                                18

<210> SEQ ID NO 194
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 194
tgccaaacct ctgtcacc                                                18

<210> SEQ ID NO 195
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 195
tgccaaacct ctgtcacc                                                18

<210> SEQ ID NO 196
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 196
tttattacac ttccagat                                                18

<210> SEQ ID NO 197
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 197
tacaaaaaac tttctgag                                                18

<210> SEQ ID NO 198
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 198
tccaaaacac ccacagac                                                18

<210> SEQ ID NO 199
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 199
ttcattccac atccccac                                                18

<210> SEQ ID NO 200
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 200
ttcaatatgc caacagct                                                 18

<210> SEQ ID NO 201
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 201
ttcaatacac ttgtctat                                                 18

<210> SEQ ID NO 202
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 202
ttcaacacac cttcaaaa                                                 18

<210> SEQ ID NO 203
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 203
ttcaaaacat ctgacatt                                                 18

<210> SEQ ID NO 204
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 204
ctcctaatac ctgcaaat                                                 18

<210> SEQ ID NO 205
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 205
tgtatcattt ctgggaga                                                 18

<210> SEQ ID NO 206
<211> LENGTH: 18
<212> TYPE: DNA
<213> ORGANISM: Artificial Sequence
<220> FEATURE:
<223> OTHER INFORMATION: Synthetic Polynucleotide

```
<400> SEQUENCE: 206
tgtatcattt ctgggaga                                                 18

<210> SEQ ID NO 207
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 207
tgtatcattt ctgggaga                                                 18

<210> SEQ ID NO 208
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 208
tgcatcattc ctggaaga                                                 18

<210> SEQ ID NO 209
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 209
aggagcaact ctgggaga                                                 18

<210> SEQ ID NO 210
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 210
ggtatcattt ctgagga                                                  18

<210> SEQ ID NO 211
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 211
tatatcaatt tggggaga                                                 18

<210> SEQ ID NO 212
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 212
tctatcaatt tggggaga                                                 18

<210> SEQ ID NO 213
```

```
<210> SEQ ID NO 213
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 213
aataccaact ctggatga                                                 18

<210> SEQ ID NO 214
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 214
tggatcaaat tgggaaga                                                 18

<210> SEQ ID NO 215
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 215
tgtatcagtt atggatga                                                 18

<210> SEQ ID NO 216
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 216
gggattaatt tgggagga                                                 18

<210> SEQ ID NO 217
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 217
ctcatcaatt ctgggtga                                                 18

<210> SEQ ID NO 218
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 218
ggtatcaaat ctggggga                                                 18

<210> SEQ ID NO 219
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 219
```
ggtatctatc ctggaata                                              18

<210> SEQ ID NO 220
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 220
agcatcaatc ctggaaga                                              18

<210> SEQ ID NO 221
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 221
ggcaccaaat ctggatga                                              18

<210> SEQ ID NO 222
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 222
ggtgccagct ctggagga                                              18

<210> SEQ ID NO 223
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 223
cttatcactt ttggaaga                                              18

<210> SEQ ID NO 224
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 224
agcagcactt ctggaaga                                              18

<210> SEQ ID NO 225
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 225
aacaacattc ctgtaaga                                              18

<210> SEQ ID NO 226
<211> LENGTH: 18
<212> TYPE: DNA

```
<213> ORGANISM: Artificial Sequence
<220> FEATURE:
<223> OTHER INFORMATION: Synthetic Polynucleotide

<400> SEQUENCE: 226
gacatcagtt atggatga                                              18

<210> SEQ ID NO 227
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 227
gacatcaaat ctgggaga                                              18

<210> SEQ ID NO 228
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 228
tatatccttt ctggaata                                              18

<210> SEQ ID NO 229
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 229
ggcctcaagg ctggatga                                              18

<210> SEQ ID NO 230
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 230
aggatcactt ctggaaga                                              18

<210> SEQ ID NO 231
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 231
aggatcactt ctggaaga                                              18

<210> SEQ ID NO 232
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 232
gatatccttt ctggaaga                                              18
```

<210> SEQ ID NO 233
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 233
tgtatcaatt tggggaga                                                 18

<210> SEQ ID NO 234
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 234
ggtatagatt gtggaaga                                                 18

<210> SEQ ID NO 235
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 235
gttatcaaca tgggaaga                                                 18

<210> SEQ ID NO 236
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 236
agcttcaatc tgggagga                                                 18

<210> SEQ ID NO 237
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 237
tgtgtcattt ctgggtta                                                 18

<210> SEQ ID NO 238
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 238
tgtgtcatta atggaaga                                                 18

<210> SEQ ID NO 239
<211> LENGTH: 18
<212> TYPE: DNA
<213> ORGANISM: Artificial Sequence
<220> FEATURE:

<223> OTHER INFORMATION: Synthetic Polynucleotide

<400> SEQUENCE: 239
aatagaaatt ctggaaga                                                   18

<210> SEQ ID NO 240
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 240
gatattattt ctggagga                                                   18

<210> SEQ ID NO 241
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 241
tgaataggaa atatattt                                                   18

<210> SEQ ID NO 242
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 242
tggattcaga tactcttt                                                   18

<210> SEQ ID NO 243
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 243
tggattcaga tactcttt                                                   18

<210> SEQ ID NO 244
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 244
tggattcaga tactcttt                                                   18

<210> SEQ ID NO 245
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 245
tggattcaga tactcttt                                                   18

```
<210> SEQ ID NO 246
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 246
tggattcaga tactcttt                                                 18

<210> SEQ ID NO 247
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 247
tggattcaga tactcttt                                                 18

<210> SEQ ID NO 248
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 248
tgcataggaa tgctaatt                                                 18

<210> SEQ ID NO 249
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 249
tgaattaaaa tcctgctt                                                 18

<210> SEQ ID NO 250
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 250
tccattaaaa tactattt                                                 18

<210> SEQ ID NO 251
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 251
tgaattgaga gaagcatt                                                 18

<210> SEQ ID NO 252
<211> LENGTH: 18
<212> TYPE: DNA
<213> ORGANISM: Artificial Sequence
<220> FEATURE:
<223> OTHER INFORMATION: Synthetic Polynucleotide
```

```
<400> SEQUENCE: 252
tgaagtggga tactgtta                                                  18

<210> SEQ ID NO 253
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 253
tgaattatga agctactt                                                  18

<210> SEQ ID NO 254
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 254
tgaataagga tgctatta                                                  18

<210> SEQ ID NO 255
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 255
tgaatgggga cacagcca                                                  18

<210> SEQ ID NO 256
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 256
taaatggaaa tgctgttc                                                  18

<210> SEQ ID NO 257
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 257
ggaaatggga tactgagt                                                  18

<210> SEQ ID NO 258
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 258
tggatcgaag tgattatt                                                  18

<210> SEQ ID NO 259
<211> LENGTH: 18
```

```
<212> TYPE: DNA
<213> ORGANISM: Artificial Sequence
<220> FEATURE:
<223> OTHER INFORMATION: Synthetic Polynucleotide

<400> SEQUENCE: 259
tgaattgaga ttcacagc                                            18

<210> SEQ ID NO 260
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 260
tgaattagga atctgatt                                            18

<210> SEQ ID NO 261
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 261
taaattaaaa tactccag                                            18

<210> SEQ ID NO 262
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 262
tgaataggaa tattcttt                                            18

<210> SEQ ID NO 263
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 263
tagattgaaa tgctgttt                                            18

<210> SEQ ID NO 264
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 264
tgactagaaa tgatgatt                                            18

<210> SEQ ID NO 265
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 265
```
tgaatttaaa aaatgtcc                                           18

<210> SEQ ID NO 266
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 266
tgaatttaaa aaatgtcc                                           18

<210> SEQ ID NO 267
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 267
tggatccaga tactcttt                                           18

<210> SEQ ID NO 268
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 268
tggagtgaga tcctgttt                                           18

<210> SEQ ID NO 269
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 269
tgaacttgga tgatatat                                           18

<210> SEQ ID NO 270
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 270
tgtattggga taccattt                                           18

<210> SEQ ID NO 271
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 271
tcaattggga tgatcata                                           18

<210> SEQ ID NO 272
<211> LENGTH: 18
<212> TYPE: DNA
<213> ORGANISM: Artificial Sequence

```
<220> FEATURE:
<223> OTHER INFORMATION: Synthetic Polynucleotide

<400> SEQUENCE: 272
tgaaagggaa agttggat                                                   18

<210> SEQ ID NO 273
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 273
tggtttggga tcctgtgt                                                   18

<210> SEQ ID NO 274
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 274
tgaaatggga tgagcttg                                                   18

<210> SEQ ID NO 275
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 275
tgaattggga tactgtag                                                   18

<210> SEQ ID NO 276
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 276
tgaattgtgg tattgcct                                                   18

<210> SEQ ID NO 277
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 277
tttattttac tgttttta                                                   18

<210> SEQ ID NO 278
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 278 tttattttt tattttta                                                    18
```

```
<210> SEQ ID NO 279
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 279 tttattttt tattttta                                                  18

<210> SEQ ID NO 280
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 280 tttattttt tattttta                                                  18

<210> SEQ ID NO 281
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 281 tttattttt tattttta                                                  18

<210> SEQ ID NO 282
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 282 tttattttt tattttta                                                  18

<210> SEQ ID NO 283
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 283 tttattttt tattttta                                                  18

<210> SEQ ID NO 284
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 284 tttatttac tatttata                                                  18

<210> SEQ ID NO 285
<211> LENGTH: 18
<212> TYPE: DNA
<213> ORGANISM: Artificial Sequence
<220> FEATURE:
<223> OTHER INFORMATION: Synthetic Polynucleotide
```

<400> SEQUENCE: 285
gttatatgac tatttta                                                        18

<210> SEQ ID NO 286
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 286
tttattttat tatttta                                                        18

<210> SEQ ID NO 287
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 287
tttattttat tatttta                                                        18

<210> SEQ ID NO 288
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 288
ggtatattat aattttta                                                       18

<210> SEQ ID NO 289
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 289
tttattgtaa tatttta                                                        18

<210> SEQ ID NO 290
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 290
tttatttatt tatttta                                                        18

<210> SEQ ID NO 291
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 291
tttattttat tatttta                                                        18

<210> SEQ ID NO 292

<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 292
attattttat tgtttttt                                                 18

<210> SEQ ID NO 293
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 293
tttatgttac tatttcta                                                 18

<210> SEQ ID NO 294
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 294
tttattttat tattttta                                                 18

<210> SEQ ID NO 295
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 295 tttattttt tattttta                                                  18

<210> SEQ ID NO 296
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 296
tttattttat tattatta                                                 18

<210> SEQ ID NO 297
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 297
attattttaa tgttttta                                                 18

<210> SEQ ID NO 298
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 298
tttatttatt tattttta                                           18

<210> SEQ ID NO 299
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 299
tttttattat tattttta                                           18

<210> SEQ ID NO 300
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 300
tttattttct tattttta                                           18

<210> SEQ ID NO 301
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 301
attattttat tattttta                                           18

<210> SEQ ID NO 302
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 302
attattttat tattttta                                           18

<210> SEQ ID NO 303
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 303 tttattttt tattttta                                            18

<210> SEQ ID NO 304
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 304
tttattttat tgttatta                                           18

<210> SEQ ID NO 305
<211> LENGTH: 18
<212> TYPE: DNA

```
<213> ORGANISM: Artificial Sequence
<220> FEATURE:
<223> OTHER INFORMATION: Synthetic Polynucleotide

<400> SEQUENCE: 305
tttatttgat tatcttta                                                    18

<210> SEQ ID NO 306
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 306
tctattttat tatttttt                                                    18

<210> SEQ ID NO 307
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 307
tttattctat tttttta                                                     18

<210> SEQ ID NO 308
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 308
tttattttac tattttta                                                    18

<210> SEQ ID NO 309
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 309
tttatgtttt tattttta                                                    18

<210> SEQ ID NO 310
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 310
tttattttat tattttaa                                                    18

<210> SEQ ID NO 311
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 311
cttaaataaa tattttta                                                    18
```

<210> SEQ ID NO 312
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 312
tttatggttt tgtcttta                                            18

<210> SEQ ID NO 313
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 313
cagcagctgc ccggt                                               15

<210> SEQ ID NO 314
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 314
cagatcgcga agagaggggg agtaacagcg gtag                          34

<210> SEQ ID NO 315
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 315
cagatcgcgc agagaggggg agtaacagcg gtag                          34

<210> SEQ ID NO 316
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 316
cagatcgcgc agcaggggggg agtaacagcg gtag                         34

<210> SEQ ID NO 317
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 317
atcgtagccc aattgtcca                                           19

<210> SEQ ID NO 318
<211> LENGTH: 22
<212> TYPE: DNA
<213> ORGANISM: Artificial Sequence
<220> FEATURE:

<223> OTHER INFORMATION: Synthetic Polynucleotide

<400> SEQUENCE: 318
gttggttctt tggatcaatg cg        22

<210> SEQ ID NO 319
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 319
aagttctctc gggaatccgt tggttggttc tttggatca        39

<210> SEQ ID NO 320
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 320
gaagttctct cgggaatttg ttggttggtt tgttggatca atgcgggagc atgaggcaga        60
ccttgttgga ctgcatc        77

<210> SEQ ID NO 321
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 321
cttttgacta gttgggatcc cgcgacttga tgggaagttc tctcgggaat        50

<210> SEQ ID NO 322
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(36)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 322
caccactntt cattacacct gcagctnnnn nnnnnnagta tcaattctgg aagancgtca        60
cgct        64

<210> SEQ ID NO 323
<211> LENGTH: 66
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature

```
<222> LOCATION: (8)..(8)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 323
caccactntt cattacacct gcagctnnnn nnnnnnnnag tatcaattct ggaagancgt    60
cacgct                                                              66

<210> SEQ ID NO 324
<211> LENGTH: 68
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(40)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 324
caccactntt cattacacct gcagctnnnn nnnnnnnnnn agtatcaatt ctggaaganc    60
gtcacgct                                                            68

<210> SEQ ID NO 325
<211> LENGTH: 70
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(42)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 325
caccactntt cattacacct gcagctnnnn nnnnnnnnnn nnagtatcaa ttctggaaga    60 ncgtcacgct                                                          70

<210> SEQ ID NO 326
<211> LENGTH: 72
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
```

<223> OTHER INFORMATION: n is a, c, g, or t
<220> FEATURE:
<221> NAME/KEY: misc_feature
<222> LOCATION: (27)..(44)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 326
caccactntt cattacacct gcagctnnnn nnnnnnnnnn nnnnagtatc aattctggaa    60
gancgtcacg ct                                                       72

<210> SEQ ID NO 327
<211> LENGTH: 74
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(46)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 327
caccactntt cattacacct gcagctnnnn nnnnnnnnnn nnnnnnagta tcaattctgg    60
aagancgtca cgct                                                     74

<210> SEQ ID NO 328
<211> LENGTH: 76
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (27)..(48)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 328
caccactntt cattacacct gcagctnnnn nnnnnnnnnn nnnnnnnnag tatcaattct    60
ggaagancgt cacgct                                                   76

<210> SEQ ID NO 329
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

```
<220> FEATURE:
<221> NAME/KEY: misc_feature
<222> LOCATION: (27)..(50)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 329
caccactntt cattacacct gcagctnnnn nnnnnnnnnn nnnnnnnnnn agtatcaatt    60
ctggaaganc gtcacgct                                                  78

<210> SEQ ID NO 330
<211> LENGTH: 61
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(34)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 330
ccacgctntc ttcattacac ctgcnnnnnn nnnncataca gtcagtatca ncctcgggac    60
t                                                                    61

<210> SEQ ID NO 331
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 331
ccacgctntc ttcattacac ctgcnnnnnn nnnnnncata cagtcagtat cancctcggg    60
act                                                                  63

<210> SEQ ID NO 332
<211> LENGTH: 65
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
```

```
<221> NAME/KEY: misc_feature
<222> LOCATION: (25)..(38)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 332
ccacgctntc ttcattacac ctgcnnnnnn nnnnnnnnca tacagtcagt atcancctcg    60
ggact                                                               65

<210> SEQ ID NO 333
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(40)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 333
ccacgctntc ttcattacac ctgcnnnnnn nnnnnnnnnn catacagtca gtatcancct    60
cgggact                                                             67

<210> SEQ ID NO 334
<211> LENGTH: 69
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(42)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 334
ccacgctntc ttcattacac ctgcnnnnnn nnnnnnnnnn nncatacagt cagtatcanc    60
ctcgggact                                                           69

<210> SEQ ID NO 335
<211> LENGTH: 71
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
```

<222> LOCATION: (25)..(44)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 335
ccacgctntc ttcattacac ctgcnnnnnn nnnnnnnnnn nnnncataca gtcagtatca    60
ncctcgggac t                                                        71

<210> SEQ ID NO 336
<211> LENGTH: 73
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(46)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 336
ccacgctntc ttcattacac ctgcnnnnnn nnnnnnnnnn nnnnnncata cagtcagtat    60
cancctcggg act                                                      73

<210> SEQ ID NO 337
<211> LENGTH: 75
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (25)..(48)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 337
ccacgctntc ttcattacac ctgcnnnnnn nnnnnnnnnn nnnnnnnnca tacagtcagt    60
atcancctcg ggact                                                    75

<210> SEQ ID NO 338
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(37)

<223> OTHER INFORMATION: n is a, c, g, or t

<400> SEQUENCE: 338
ctccgcgtnt gaattgggat gctgtttnnn nnnnnntttt attttactgt ctttaggtac    60
ccca    64

<210> SEQ ID NO 339
<211> LENGTH: 66
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(39)
<223> OTHER INFORMATION: n is a, c, g, or t

<400> SEQUENCE: 339
ctccgcgtnt gaattgggat gctgtttnnn nnnnnnnnnt tattttact gtctttaggt    60 acccca    66

<210> SEQ ID NO 340
<211> LENGTH: 68
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(41)
<223> OTHER INFORMATION: n is a, c, g, or t

<400> SEQUENCE: 340
ctccgcgtnt gaattgggat gctgtttnnn nnnnnnnnnn ntttattta ctgtctttag    60 gtacccca    68

<210> SEQ ID NO 341
<211> LENGTH: 70
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(43)
<223> OTHER INFORMATION: n is a, c, g, or t

<400> SEQUENCE: 341
ctccgcgtnt gaattgggat gctgtttnnn nnnnnnnnn nnntttattt tactgtcttt    60
aggtacccca    70

<210> SEQ ID NO 342
<211> LENGTH: 72
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(45)
<223> OTHER INFORMATION: n is a, c, g, or t

<400> SEQUENCE: 342
ctccgcgtnt gaattgggat gctgtttnnn nnnnnnnnnn nnnnntttat tttactgtct    60
ttaggtaccc ca                                                       72

<210> SEQ ID NO 343
<211> LENGTH: 74
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(47)
<223> OTHER INFORMATION: n is a, c, g, or t

<400> SEQUENCE: 343
ctccgcgtnt gaattgggat gctgtttnnn nnnnnnnnnn nnnnnnnttt attttactgt    60
ctttaggtac ccca                                                     74

<210> SEQ ID NO 344
<211> LENGTH: 76
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(49)
<223> OTHER INFORMATION: n is a, c, g, or t

<400> SEQUENCE: 344
ctccgcgtnt gaattgggat gctgtttnnn nnnnnnnnnn nnnnnnnnnt ttattttact    60
gtctttaggt acccca                                                   76

<210> SEQ ID NO 345
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (28)..(51)
<223> OTHER INFORMATION: n is a, c, g, or t

<400> SEQUENCE: 345
```

```
ctccgcgtnt gaattgggat gctgtttnnn nnnnnnnnnn nnnnnnnnnn ntttatttta      60
ctgtctttag gtacccca                                                   78

<210> SEQ ID NO 346
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 346
aatgatacgg cgaccaccga gatctacact ctttccctac acgacgctct tccgatctac      60
tgt                                                                   63

<210> SEQ ID NO 347
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 347
acagtagatc ggaagagcgt cgtgtaggga aagagtgtag atctcggtgg                 50

<210> SEQ ID NO 348
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 348
aatgatacgg cgaccaccga gatctacact ctttccctac acgacgctct tccgatctct      60
gaa                                                                   63

<210> SEQ ID NO 349
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 349
ttcagagatc ggaagagcgt cgtgtaggga aagagtgtag atctcggtgg                 50

<210> SEQ ID NO 350
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 350
aatgatacgg cgaccaccga gatctacact ctttccctac acgacgctct tccgatcttg      60
caa                                                                   63

<210> SEQ ID NO 351
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 351
```

```
ttgcaagatc ggaagagcgt cgtgtaggga aagagtgtag atctcggtgg            50
```

<210> SEQ ID NO 352
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 352

```
aatgatacgg cgaccaccga gatctacact ctttccctac acgacgctct tccgatcttg   60
act                                                                 63
```

<210> SEQ ID NO 353
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 353

```
agtcaagatc ggaagagcgt cgtgtaggga aagagtgtag atctcggtgg            50
```

<210> SEQ ID NO 354
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 354

```
aatgatacgg cgaccaccga gatctacact ctttccctac acgacgctct tccgatctgc   60
att                                                                 63
```

<210> SEQ ID NO 355
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 355

```
aatgcagatc ggaagagcgt cgtgtaggga aagagtgtag atctcggtgg            50
```

<210> SEQ ID NO 356
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 356

```
aatgatacgg cgaccaccga gatctacact ctttccctac acgacgctct tccgatctca   60
tga                                                                 63
```

<210> SEQ ID NO 357
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 357
tcatgagatc ggaagagcgt cgtgtaggga aagagtgtag atctcggtgg    50

<210> SEQ ID NO 358
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 358
aatgatacgg cgaccaccga gatctacact ctttccctac acgacgctct tccgatctat    60
gct    63

<210> SEQ ID NO 359
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 359
agcatagatc ggaagagcgt cgtgtaggga aagagtgtag atctcggtgg    50

<210> SEQ ID NO 360
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 360
aatgatacgg cgaccaccga gatctacact ctttccctac acgacgctct tccgatctct    60
agt    63

<210> SEQ ID NO 361
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 361
actagagatc ggaagagcgt cgtgtaggga aagagtgtag atctcggtgg    50

<210> SEQ ID NO 362
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 362
aatgatacgg cgaccaccga gatctacact ctttccctac acgacgctct tccgatctgc    60
taa    63

<210> SEQ ID NO 363
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 363
ttagcagatc ggaagagcgt cgtgtaggga aagagtgtag atctcggtgg    50

<210> SEQ ID NO 364
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 364
aatgatacgg cgaccaccga gatctacact ctttccctac acgacgctct tccgatctca   60
gta                                                                 63

<210> SEQ ID NO 365
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 365
tactgagatc ggaagagcgt cgtgtaggga agagtgtag atctcggtgg               50

<210> SEQ ID NO 366
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 366
aatgatacgg cgaccaccga gatctacact ctttccctac acgacgctct tccgatctgt   60
act                                                                 63

<210> SEQ ID NO 367
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 367
agtacagatc ggaagagcgt cgtgtaggga agagtgtag atctcggtgg               50

<210> SEQ ID NO 368
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 368
aatgatacgg cgaccaccga gatctacact ctttccctac acgacgctct tccgatctac   60
tgt                                                                 63

<210> SEQ ID NO 369
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 369
acagtagatc ggaagagcgt cgtgtaggga agagtgtag atctcggtgg               50

<210> SEQ ID NO 370
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 370
aatgatacgg cgaccaccga gatctacact ctttccctac acgacgctct tccgatctgc    60
taa                                                                  63

<210> SEQ ID NO 371
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 371
ttagcagatc ggaagagcgt cgtgtaggga aagagtgtag atctcggtgg               50

<210> SEQ ID NO 372
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 372
aatgatacgg cgaccaccga gatctacact ctttccctac acgacgctct tccgatctca    60
gta                                                                  63

<210> SEQ ID NO 373
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 373
tactgagatc ggaagagcgt cgtgtaggga aagagtgtag atctcggtgg               50

<210> SEQ ID NO 374
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 374
aatgatacgg cgaccaccga gatctacact ctttccctac acgacgctct tccgatctgt    60
act                                                                  63

<210> SEQ ID NO 375
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 375
agtacagatc ggaagagcgt cgtgtaggga aagagtgtag atctcggtgg               50

-continued

```
<210> SEQ ID NO 376
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 376
aatgatacgg cgaccaccga gatctacact ctttccctac acgacgctct tccgatctac      60
tgt                                                                    63

<210> SEQ ID NO 377
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 377
acagtagatc ggaagagcgt cgtgtaggga aagagtgtag atctcggtgg                 50

<210> SEQ ID NO 378
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 378
aatgatacgg cgaccac                                                     17

<210> SEQ ID NO 379
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(29)
<223> OTHER INFORMATION: n is a, c, g, or t

<400> SEQUENCE: 379
gttcagacgt gtgctcttcc gatctnnnna gtggtgagcg tgacg                      45

<210> SEQ ID NO 380
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(29)
<223> OTHER INFORMATION: n is a, c, g, or t

<400> SEQUENCE: 380
gttcagacgt gtgctcttcc gatctnnnna cgcggagtgg ggtacc                     46

<210> SEQ ID NO 381
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (22)..(25)
```

<223> OTHER INFORMATION: n is a, c, g, or t

<400> SEQUENCE: 381
cagacgtgtg ctcttccgat cnnnnagcgt ggagtcccga gg          42

<210> SEQ ID NO 382
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 382
aatgatacgg cgaccac          17

<210> SEQ ID NO 383
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 383
caagcagaag acggcatacg agattgttga ctgtgactgg agttcagacg tgtgctcttc          60

<210> SEQ ID NO 384
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 384
caagcagaag acggcatacg agatacggaa ctgtgactgg agttcagacg tgtgctcttc          60

<210> SEQ ID NO 385
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 385
caagcagaag acggcatacg agattctaac atgtgactgg agttcagacg tgtgctcttc          60

<210> SEQ ID NO 386
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 386
caagcagaag acggcatacg agatcgggac gggtgactgg agttcagacg tgtgctcttc          60

<210> SEQ ID NO 387
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 387
caagcagaag acggcatacg agatcgtgat gtgactggag ttcagacgtg tgctcttccg          60

```
<210> SEQ ID NO 388
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 388
gtacccagat cggaagagca cacgtctgaa ctccagtcac acagtgatct cgtatgccgt    60
cttctgcttg                                                          70

<210> SEQ ID NO 389
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 389
gtgactggag ttcagacgtg tgctcttccg atctg                              35

<210> SEQ ID NO 390
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 390
gtacgatgcg atcggaagag cacacgtctg aactccagtc acttaggcat ctcgtatgcc    60
gtcttctgct tg                                                       72

<210> SEQ ID NO 391
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 391
gtgactggag ttcagacgtg tgctcttccg atcgcatc                           38

<210> SEQ ID NO 392
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 392 tcggaacgt gatcggaaga gcacacgtct gaactccagt caccgtctaa tctcgtatgc     60
cgtcttctgc ttg                                                      73

<210> SEQ ID NO 393
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 393
gtgactggag ttcagacgtg tgctcttccg atcacgtt                           38

<210> SEQ ID NO 394
```

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 394
caagcagaag acggcatacg a                                              21

<210> SEQ ID NO 395
<211> LENGTH: 77
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(62)
<223> OTHER INFORMATION: n is a, c, g, or t

<400> SEQUENCE: 395
aatgatacgg cgaccaccga gatctacact ctttccctac acgacgctct tccgatctnn    60
nncgtcacgc tcaccac                                                   77

<210> SEQ ID NO 396
<211> LENGTH: 79
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(62)
<223> OTHER INFORMATION: n is a, c, g, or t

<400> SEQUENCE: 396
aatgatacgg cgaccaccga gatctacact ctttccctac acgacgctct tccgatctnn    60
nnggtacccc actccgcgt                                                 79

<210> SEQ ID NO 397
<211> LENGTH: 79
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (59)..(62)
<223> OTHER INFORMATION: n is a, c, g, or t

<400> SEQUENCE: 397
aatgatacgg cgaccaccga gatctacact ctttccctac acgacgctct tccgatctnn    60
nncctcggga ctccacgct                                                 79

<210> SEQ ID NO 398
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 398
caagcagaag acggcatacg a                                              21

<210> SEQ ID NO 399
<211> LENGTH: 17
```

<212> TYPE: DNA
<213> ORGANISM: Artificial Sequence
<220> FEATURE:
<223> OTHER INFORMATION: Synthetic Polynucleotide

<400> SEQUENCE: 399
aatgatacgg cgaccac                                                      17

<210> SEQ ID NO 400
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 400
acactctttc cctacacgac gctcttccga tct                                    33

<210> SEQ ID NO 401
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 401
gatcggaaga gcacacgtct gaactcca                                          28

<210> SEQ ID NO 402
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 402
aatgatacgg cgaccaccga gatctacact ctttccctac acgac                       45

<210> SEQ ID NO 403
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 403
caagcagaag acggcatacg agatgtgcgg acgtgactgg agttcagacg tgtgct           56

<210> SEQ ID NO 404
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 404
caagcagaag acggcatacg agatcgtttc acgtgactgg agttcagacg tgtgct           56

<210> SEQ ID NO 405
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 405
caagcagaag acggcatacg agataaggcc acgtgactgg agttcagacg tgtgct        56

<210> SEQ ID NO 406
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 406
caagcagaag acggcatacg agattccgaa acgtgactgg agttcagacg tgtgct        56

<210> SEQ ID NO 407
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 407
caagcagaag acggcatacg agattacgta cggtgactgg agttcagacg tgtgct        56

<210> SEQ ID NO 408
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 408
caagcagaag acggcatacg agatatccac tcgtgactgg agttcagacg tgtgct        56

<210> SEQ ID NO 409
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 409
caagcagaag acggcatacg agataaagga atgtgactgg agttcagacg tgtgct        56

<210> SEQ ID NO 410
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 410
caagcagaag acggcatacg agatatatca gtgtgactgg agttcagacg tgtgct        56

<210> SEQ ID NO 411
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 411
cgacggtcta gagtcttcat tacacctgca gctctcattt tccatacagt              50

<210> SEQ ID NO 412
<211> LENGTH: 50
<212> TYPE: DNA
<213> ORGANISM: Artificial Sequence

```
<220> FEATURE:
<223> OTHER INFORMATION: Synthetic Polynucleotide

<400> SEQUENCE: 412
cgacggtcta gagtcttcat tacatctgca cctctcattt tccatacagt         50

<210> SEQ ID NO 413
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 413
cgacggtcta gagtcttcaa tacacctgta gctctcattt tccatacagt         50

<210> SEQ ID NO 414
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 414
cgacggtcta gagtcttcgt tacacctgca tctctcattt tccatacagt         50

<210> SEQ ID NO 415
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 415
cgacggtcta gagtcttaat tgcacctgca gctctcattt tccatacagt         50

<210> SEQ ID NO 416
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 416
ccgacgaagc ttttcttcca gaattgatac tgactgtatg gaaaatga         48

<210> SEQ ID NO 417
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 417
ccgacgaagc ttttcttaca gaattcatac tgactgtatg gaaaatga         48

<210> SEQ ID NO 418
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 418
ccgacgaagc ttttcctcca gagttgatac tgactgtatg gaaaatga         48
```

<210> SEQ ID NO 419
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 419
ccgacgaagc ttttcttcct gaattgataa tgactgtatg gaaaatga                    48

<210> SEQ ID NO 420
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 420
ccgacgaagc ttttcttcca gcattgttac tgactgtatg gaaaatga                    48

<210> SEQ ID NO 421
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 421
cgacggtcta gatttgaatt gggatgctgt ttttaggtat tctattcaaa tt               52

<210> SEQ ID NO 422
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 422
cgacggtcta gatttgaatt gggttgctgt ttttaggtat tctattcaaa tt               52

<210> SEQ ID NO 423
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 423
cgacggtcta gatttgaatt gcgatgctgt ttttaggtat tctattcaaa tt               52

<210> SEQ ID NO 424
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 424
cgacggtcta gatttgagtt gggatgctgt ttttaggtat tctattcaaa tt               52

<210> SEQ ID NO 425
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 425
cgacggtcta gatttgaatt gggatgctga ttttaggtat tctattcaaa tt        52

<210> SEQ ID NO 426
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 426
ccgacgaagc ttaataaaga cagtaaaata aatttgaata gaatacctaa aa        52

<210> SEQ ID NO 427
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 427
ccgacgaagc ttaataaaga cagtgaaata aatttgaata gaatacctaa aa        52

<210> SEQ ID NO 428
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 428
ccgacgaagc ttaataaaga tagtaaaata aatttgaata gaatacctaa aa        52

<210> SEQ ID NO 429
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 429
ccgacgaagc ttaataaaga cagtaagata aatttgaata gaatacctaa aa        52

<210> SEQ ID NO 430
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 430
ccgacgaagc ttaataacga cagtaaaata aatttgaata gaatacctaa aa        52

<210> SEQ ID NO 431
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 431
cgacggtcta gaaaggtctt cattacacct gcagctctca ttttccatac agtca      55

<210> SEQ ID NO 432

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 432
cgacggtcta gagtcttcat tacacctgta gctctcattt tc                42

<210> SEQ ID NO 433
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 433
cgacggtcta gagtcttcat aacacctgca gctctcattt tc                42

<210> SEQ ID NO 434
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 434
cgacggtcta gagtcttcat tacacccgca gctctcattt tc                42

<210> SEQ ID NO 435
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 435
cgacggtcta gagtcttcat aacacctgta gctctcattt tc                42

<210> SEQ ID NO 436
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 436
cgacggtcta gagtcttcat tatacctaca gctctcattt tc                42

<210> SEQ ID NO 437
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 437
cgacggtcta gagtcttcat tgcacccgca gctctcattt tc                42

<210> SEQ ID NO 438
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 438
ccgacgaagc tttcttccag aattgatact gactgtatgg aaaatgagag ct         52

<210> SEQ ID NO 439
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 439
ccgacgaagc tttcttccag aattgatact aactgtatgg aaaatgagag ct         52

<210> SEQ ID NO 440
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 440
ccgacgaagc tttcttccag aattgatact gactgtatcg aaaatgagag ct         52

<210> SEQ ID NO 441
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 441
ccgacgaagc tttcttccag aattgatact gactgaatgg aaaatgagag ct         52

<210> SEQ ID NO 442
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 442
ccgacgaagc tttcttccag aattgatacc gactgtatgg aaaatgagag ct         52

<210> SEQ ID NO 443
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 443
ccgacgaagc tttcttccag aattgatact aactgtatcg aaaatgagag ct         52

<210> SEQ ID NO 444
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 444
ccgacgaagc tttcttccag aattgatact gaatgtgtgg aaaatgagag ct         52

<210> SEQ ID NO 445
<211> LENGTH: 52
<212> TYPE: DNA

```
<213> ORGANISM: Artificial Sequence
<220> FEATURE:
<223> OTHER INFORMATION: Synthetic Polynucleotide

<400> SEQUENCE: 445
ccgacgaagc tttcttccag aattgatact gatagtatgg aaaatgagag ct        52

<210> SEQ ID NO 446
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 446
gcgacacgga aatgttgaat actcat                                      26

<210> SEQ ID NO 447
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 447
cagcgagtca gtgagcga                                               18

<210> SEQ ID NO 448
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(44)
<223> OTHER INFORMATION: n is a, c, g, or t

<400> SEQUENCE: 448
caccactnnn nnnnnnnnnn nnnnnnnnnn nnnnnnnnnn nnnncgtcac gct        53

<210> SEQ ID NO 449
<211> LENGTH: 55
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(46)
<223> OTHER INFORMATION: n is a, c, g, or t

<400> SEQUENCE: 449
caccactnnn nnnnnnnnnn nnnnnnnnnn nnnnnnnnnn nnnnnncgtc acgct      55

<210> SEQ ID NO 450
<211> LENGTH: 57
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(48)
<223> OTHER INFORMATION: n is a, c, g, or t

<400> SEQUENCE: 450
caccactnnn nnnnnnnnnn nnnnnnnnnn nnnnnnnnnn nnnnnnnncg tcacgct    57
```

<210> SEQ ID NO 451
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(50)
<223> OTHER INFORMATION: n is a, c, g, or t

<400> SEQUENCE: 451
caccactnnn nnnnnnnnnn nnnnnnnnnn nnnnnnnnnn nnnnnnnnn cgtcacgct     59

<210> SEQ ID NO 452
<211> LENGTH: 61
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(52)
<223> OTHER INFORMATION: n is a, c, g, or t

<400> SEQUENCE: 452
caccactnnn nnnnnnnnnn nnnnnnnnnn nnnnnnnnnn nnnnnnnnnn nncgtcacgc     60
t     61

<210> SEQ ID NO 453
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(54)
<223> OTHER INFORMATION: n is a, c, g, or t

<400> SEQUENCE: 453
caccactnnn nnnnnnnnnn nnnnnnnnnn nnnnnnnnnn nnnnnnnnnn nnnncgtcac     60
gct     63

<210> SEQ ID NO 454
<211> LENGTH: 65
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(56)
<223> OTHER INFORMATION: n is a, c, g, or t

<400> SEQUENCE: 454
caccactnnn nnnnnnnnnn nnnnnnnnnn nnnnnnnnnn nnnnnnnnnn nnnnnncgtc     60
acgct     65

<210> SEQ ID NO 455
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:

<221> NAME/KEY: misc_feature
<222> LOCATION: (8)..(58)
<223> OTHER INFORMATION: n is a, c, g, or t

<400> SEQUENCE: 455
caccactnnn nnnnnnnnnn nnnnnnnnnn nnnnnnnnnn nnnnnnnnnn nnnnnnncg    60 tcacgct    67

<210> SEQ ID NO 456
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(52)
<223> OTHER INFORMATION: n is a, c, g, or t

<400> SEQUENCE: 456
ccacgctntn nnnnnnnnnn nnnnnnnnnn nnnnnnnnnn nnnnnnnnnn nncctcggga    60
ct    62

<210> SEQ ID NO 457
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(54)
<223> OTHER INFORMATION: n is a, c, g, or t

<400> SEQUENCE: 457
ccacgctntn nnnnnnnnnn nnnnnnnnnn nnnnnnnnnn nnnnnnnnnn nnnncctcgg    60
gact    64

<210> SEQ ID NO 458
<211> LENGTH: 66
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(56)
<223> OTHER INFORMATION: n is a, c, g, or t

<400> SEQUENCE: 458
ccacgctntn nnnnnnnnnn nnnnnnnnnn nnnnnnnnnn nnnnnnnnnn nnnnnncctc    60
gggact    66

<210> SEQ ID NO 459
<211> LENGTH: 68

<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(58)
<223> OTHER INFORMATION: n is a, c, g, or t

<400> SEQUENCE: 459
ccacgctntn nnnnnnnnnn nnnnnnnnnn nnnnnnnnnn nnnnnnnnnn nnnnnnnncc    60
tcgggact                                                              68

<210> SEQ ID NO 460
<211> LENGTH: 70
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(60)
<223> OTHER INFORMATION: n is a, c, g, or t

<400> SEQUENCE: 460
ccacgctntn nnnnnnnnnn nnnnnnnnnn nnnnnnnnnn nnnnnnnnnn nnnnnnnnnn    60
cctcgggact                                                            70

<210> SEQ ID NO 461
<211> LENGTH: 72
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(62)
<223> OTHER INFORMATION: n is a, c, g, or t

<400> SEQUENCE: 461
ccacgctntn nnnnnnnnnn nnnnnnnnnn nnnnnnnnnn nnnnnnnnnn nnnnnnnnnn    60
nncctcggga ct                                                         72

<210> SEQ ID NO 462
<211> LENGTH: 74
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(64)
<223> OTHER INFORMATION: n is a, c, g, or t

```
<400> SEQUENCE: 462
ccacgctntn nnnnnnnnnn nnnnnnnnnn nnnnnnnnnn nnnnnnnnnn        60
nnnncctcgg gact                                                74

<210> SEQ ID NO 463
<211> LENGTH: 76
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(66)
<223> OTHER INFORMATION: n is a, c, g, or t

<400> SEQUENCE: 463
ccacgctntn nnnnnnnnnn nnnnnnnnnn nnnnnnnnnn nnnnnnnnnn        60
nnnnnncctc gggact                                              76

<210> SEQ ID NO 464
<211> LENGTH: 64
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(55)
<223> OTHER INFORMATION: n is a, c, g, or t

<400> SEQUENCE: 464
ctccgcgtnn nnnnnnnnnn nnnnnnnnnn nnnnnnnnnn nnnnggtac         60 ccca                                                           64

<210> SEQ ID NO 465
<211> LENGTH: 66
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(57)
<223> OTHER INFORMATION: n is a, c, g, or t

<400> SEQUENCE: 465
ctccgcgtnn nnnnnnnnnn nnnnnnnnnn nnnnnnnnnn nnnnnnggt         60 accca                                                          66

<210> SEQ ID NO 466
<211> LENGTH: 68
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(59)
<223> OTHER INFORMATION: n is a, c, g, or t

<400> SEQUENCE: 466
ctccgcgtnn nnnnnnnnnn nnnnnnnnnn nnnnnnnnnn nnnnnnnng         60
``` gtacccca                                                              68

<210> SEQ ID NO 467
<211> LENGTH: 70
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(61)
<223> OTHER INFORMATION: n is a, c, g, or t

<400> SEQUENCE: 467
ctccgcgtnn nnnnnnnnn nnnnnnnnn nnnnnnnnn nnnnnnnnn nnnnnnnnn      60 nggtacccca                                                              70

<210> SEQ ID NO 468
<211> LENGTH: 72
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(63)
<223> OTHER INFORMATION: n is a, c, g, or t

<400> SEQUENCE: 468
ctccgcgtnn nnnnnnnnn nnnnnnnnn nnnnnnnnn nnnnnnnnn nnnnnnnnn      60 nnnggtaccc ca                                                           72

<210> SEQ ID NO 469
<211> LENGTH: 74
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(65)
<223> OTHER INFORMATION: n is a, c, g, or t

<400> SEQUENCE: 469
ctccgcgtnn nnnnnnnnn nnnnnnnnn nnnnnnnnn nnnnnnnnn nnnnnnnnn      60 nnnnnggtac ccca                                                         74

<210> SEQ ID NO 470
<211> LENGTH: 76
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(67)
<223> OTHER INFORMATION: n is a, c, g, or t

<400> SEQUENCE: 470
ctccgcgtnn nnnnnnnnn nnnnnnnnn nnnnnnnnn nnnnnnnnn nnnnnnnnn      60 nnnnnnnggt acccca                                                       76

<210> SEQ ID NO 471
<211> LENGTH: 78
<212> TYPE: DNA

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(69)
<223> OTHER INFORMATION: n is a, c, g, or t

<400> SEQUENCE: 471
ctccgcgtnn nnnnnnnnn nnnnnnnnnn nnnnnnnnnn nnnnnnnnnn nnnnnnnnnn    60 nnnnnnnng gtacccca    78

<210> SEQ ID NO 472
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 472
tcacttgggt ggtggctgtg    20

<210> SEQ ID NO 473
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 473
agtccaagac cagcctgggg    20

<210> SEQ ID NO 474
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 474
gaacctgttg tctaatccag cgtc    24

<210> SEQ ID NO 475
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 475
agtccaagac cagcctgggg    20

<210> SEQ ID NO 476
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 476
tgacctgttt gttcaggtct tcc    23

<210> SEQ ID NO 477
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 477
tccagttgct gtcccttcag a         21

<210> SEQ ID NO 478
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 478
gcccggcctg tcctgtattt         20

<210> SEQ ID NO 479
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 479
tggctattct agttcttttg cat         23

<210> SEQ ID NO 480
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 480
cgctgaaggc tgtcacccta a         21

<210> SEQ ID NO 481
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 481
ccaccaccac acaacttcac a         21

<210> SEQ ID NO 482
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 482
ttccaggtcc tttgcacaaa ta         22

<210> SEQ ID NO 483
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 483
caccgaaagc aacccattcc         20

<210> SEQ ID NO 484
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 484
ttcattctca ccatctggaa ttgg                                    24

<210> SEQ ID NO 485
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 485
tggcatgtgg atcagtaccc a                                       21

<210> SEQ ID NO 486
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 486
ctgacgtcca tgtcaacggg                                         20

<210> SEQ ID NO 487
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 487
gctcctttct gagaagcacc cat                                     23

<210> SEQ ID NO 488
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 488
atgagggctt ggattggctg                                         20

<210> SEQ ID NO 489
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 489
ggaggccttc attgtgtcac g                                       21

<210> SEQ ID NO 490
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 490
cgtggtcccc cagaaatcac                                              20

<210> SEQ ID NO 491
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 491
gattgcatag gttagcattg cc                                           22

<210> SEQ ID NO 492
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 492
ttccagcgaa tggaaagtgc t                                            21

<210> SEQ ID NO 493
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 493
aagcatgctc acactgtggt gta                                          23

<210> SEQ ID NO 494
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 494
tgaccctcca gcaaaggtga                                              20

<210> SEQ ID NO 495
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 495
gctttgcttg cactgtgcct t                                            21

<210> SEQ ID NO 496
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 496
tcaaaaggat gtgatctgcc aca                                          23

<210> SEQ ID NO 497
```

```
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 497
ccagggctca attcttagac cg                                          22

<210> SEQ ID NO 498
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 498
tgttcatgcc tgcacagtgg                                             20

<210> SEQ ID NO 499
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 499
tttggcaagg aattcacagt tc                                          22

<210> SEQ ID NO 500
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 500
ggaggatgtc tttgtggtag ggg                                         23

<210> SEQ ID NO 501
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 501
tcccccaact tcactgtttt t                                           21

<210> SEQ ID NO 502
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 502
ttctctgttt ccagtgattt caga                                        24

<210> SEQ ID NO 503
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 503
```
tggcttggtt aatggacaat gg                                          22

<210> SEQ ID NO 504
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 504
tgggcttcgt tgacttaaag ag                                          22

<210> SEQ ID NO 505
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 505
tcttaaacat gtggaaccca gtcat                                       25

<210> SEQ ID NO 506
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 506
gcagattcat tagcgtttgt ggc                                         23

<210> SEQ ID NO 507
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 507
ccaaggatca ataccttttgg agga                                       24

<210> SEQ ID NO 508
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 508
ttcccctaac cagggggcagt                                            20

<210> SEQ ID NO 509
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 509
agcgcctgat tcgagatcct                                             20

<210> SEQ ID NO 510
<211> LENGTH: 21
<212> TYPE: DNA

<213> ORGANISM: Artificial Sequence
<220> FEATURE:
<223> OTHER INFORMATION: Synthetic Polynucleotide

<400> SEQUENCE: 510
cctgccattg aattccagcc t                                    21

<210> SEQ ID NO 511
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 511
gactgccact gcactcccac                                      20

<210> SEQ ID NO 512
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 512
cctcccattt tccttcctcc a                                    21

<210> SEQ ID NO 513
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 513
tcctccaatt ttccttcctc ca                                   22

<210> SEQ ID NO 514
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 514
ctgggagaca caggtggcag                                      20

<210> SEQ ID NO 515
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 515
ctgggagaca caggtggcag                                      20

<210> SEQ ID NO 516
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 516
ctgggagaca caggtggcag                                      20

<210> SEQ ID NO 517
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 517
gcatgccaaa gaaattgtag gc                                              22

<210> SEQ ID NO 518
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 518
gcatctctgc attcctcaga agtgg                                           25

<210> SEQ ID NO 519
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 519
gggataccaa agagcttttg ttttgtt                                         27

<210> SEQ ID NO 520
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 520
tgcagctacg gatgaaaacc at                                              22

<210> SEQ ID NO 521
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 521
gcataaagca caggatggga ga                                              22

<210> SEQ ID NO 522
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 522
tgggttaagt aatttcgaaa ggagaa                                          26

<210> SEQ ID NO 523
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 523
gagtgagcca ctgcacccag								20

<210> SEQ ID NO 524
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 524
cctccctctg gctccctccc								20

<210> SEQ ID NO 525
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 525
tgctccctga ccttcctgag a								21

<210> SEQ ID NO 526
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 526
ggtggaacaa tccacctgta ttagc								25

<210> SEQ ID NO 527
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 527
ggctttgcaa acataaacac tca								23

<210> SEQ ID NO 528
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 528
cactggaacc caggaggtgg								20

<210> SEQ ID NO 529
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 529
cagcctgcct gggtgacag								19

```
<210> SEQ ID NO 530
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 530
gccactgcat tgcattttcc                                                  20

<210> SEQ ID NO 531
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 531
gggaggatct ctcgagtcca gg                                               22

<210> SEQ ID NO 532
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 532
tgtttagtaa ttaagaccct ggctttc                                          27

<210> SEQ ID NO 533
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 533
gcccttTgat ttcatctgtt tccc                                             24

<210> SEQ ID NO 534
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 534
aaactggcac atgtactcct                                                  20

<210> SEQ ID NO 535
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 535
gggtggaagg tgagaggaga tt                                               22

<210> SEQ ID NO 536
<211> LENGTH: 21
<212> TYPE: DNA
<213> ORGANISM: Artificial Sequence
<220> FEATURE:
<223> OTHER INFORMATION: Synthetic Polynucleotide
```

```
<400> SEQUENCE: 536
cctcccattt tccttcctcc a                                          21

<210> SEQ ID NO 537
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 537
agccaagatt gcaccattgc                                            20

<210> SEQ ID NO 538
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 538
tggttggatt ttggctctgt cac                                        23

<210> SEQ ID NO 539
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 539
tggttacttt taaagggtca tgatgga                                    27

<210> SEQ ID NO 540
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 540
gggacacaga gccaaaccgt                                            20

<210> SEQ ID NO 541
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 541
cagtcattgt ttctaggtag ggga                                       24

<210> SEQ ID NO 542
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 542
tggataacct gcagatttgt ttctg                                      25

<210> SEQ ID NO 543
<211> LENGTH: 22
```

```
<212> TYPE: DNA
<213> ORGANISM: Artificial Sequence
<220> FEATURE:
<223> OTHER INFORMATION: Synthetic Polynucleotide

<400> SEQUENCE: 543
tcgtgtgtgt gtgtttgctt ca                                              22

<210> SEQ ID NO 544
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 544
tgggaatgta aatctgactg gctg                                            24

<210> SEQ ID NO 545
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 545
gctgcaattg cttttggca                                                  20

<210> SEQ ID NO 546
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 546
gaccatgaca agcagcggca                                                 20

<210> SEQ ID NO 547
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 547
aagaacctgt tgtctaatcc agca                                            24

<210> SEQ ID NO 548
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 548
ctgcaaagaa ggccaggca                                                  19

<210> SEQ ID NO 549
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 549
```
aagaacctgt tgtctaatcc agca							24

<210> SEQ ID NO 550
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 550
ccatatggtc cctgtcgcaa							20

<210> SEQ ID NO 551
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 551
acagggagag ccaccaatgc							20

<210> SEQ ID NO 552
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 552
cacccacaca tgcacttccc							20

<210> SEQ ID NO 553
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 553
ccatgcccta gggatttgtg ga						22

<210> SEQ ID NO 554
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 554
tggacctaag agtcctgccc at						22

<210> SEQ ID NO 555
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 555
cagctggcga gaactgcaaa							20

<210> SEQ ID NO 556
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 556
gcaaggtcgt tggatagaag ttga                                          24

<210> SEQ ID NO 557
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 557
tgatctgccc accccagact                                               20

<210> SEQ ID NO 558
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 558
tctggctgga ctgctctggt t                                             21

<210> SEQ ID NO 559
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 559
tagaacatgc ccgcgaacag                                               20

<210> SEQ ID NO 560
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 560
tttgaattcc ccctccccat                                               20

<210> SEQ ID NO 561
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 561
ggcagatggt ggcaggtctt                                               20

<210> SEQ ID NO 562
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 562
ccacctcccc cactgcaata                                               20

```
<210> SEQ ID NO 563
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 563
aactccacct gggtgcccta                                                     20

<210> SEQ ID NO 564
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 564
ggagcaggag ttggtggcat                                                     20

<210> SEQ ID NO 565
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 565 gccctgttg gttgactccc                                                      20

<210> SEQ ID NO 566
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 566
aagcccagga ataagggcca                                                     20

<210> SEQ ID NO 567
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 567
ttgcttgagg cggaagttgc                                                     20

<210> SEQ ID NO 568
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 568
ccccagggac tgagcatgag                                                     20

<210> SEQ ID NO 569
<211> LENGTH: 20
<212> TYPE: DNA
<213> ORGANISM: Artificial Sequence
<220> FEATURE:
<223> OTHER INFORMATION: Synthetic Polynucleotide
```

-continued

```
<400> SEQUENCE: 569
ggggacagac tgtgagggct                                          20

<210> SEQ ID NO 570
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 570
ggcctctttg agggccagtt                                          20

<210> SEQ ID NO 571
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 571
aaaagagcag ggctgccatc                                          20

<210> SEQ ID NO 572
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 572
tggatgtgcc ctctaccaca                                          20

<210> SEQ ID NO 573
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 573
tcatgcctgc acagtggttg                                          20

<210> SEQ ID NO 574
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 574
cgctgccaag caaactcaaa                                          20

<210> SEQ ID NO 575
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 575
gcaatgagca tgtggacacc a                                        21

<210> SEQ ID NO 576
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 576
gtcgcaaaac agccagttgc                                               20

<210> SEQ ID NO 577
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 577
cctgcaagga gcaaggcttc                                               20

<210> SEQ ID NO 578
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 578
ggacaagagg gccagggttt                                               20

<210> SEQ ID NO 579
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 579
tgaaaaccca cagagtggga ga                                            22

<210> SEQ ID NO 580
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 580
tgcatgggtg taaatgtagc agaaa                                         25

<210> SEQ ID NO 581
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 581 gccctcccttt gaatcaggct                                              20

<210> SEQ ID NO 582
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 582
```
gtggtgagtg ggtgtggcag                                              20

<210> SEQ ID NO 583
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 583
agcgcctgat tcgagatcct                                              20

<210> SEQ ID NO 584
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 584
tgtctgcctt tcctgtcccc                                              20

<210> SEQ ID NO 585
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 585
ggataccctt gcctccccac                                              20

<210> SEQ ID NO 586
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 586
ctgggagaca caggtggcag                                              20

<210> SEQ ID NO 587
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 587
ctgggagaca caggtggcag                                              20

<210> SEQ ID NO 588
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 588
aggaccaatg gggccaatct                                              20

<210> SEQ ID NO 589
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 589
aggaccaatg gggccaatct                                              20

<210> SEQ ID NO 590
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 590
aggaccaatg gggccaatct                                              20

<210> SEQ ID NO 591
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 591
ttccccctgt catggtcttc a                                            21

<210> SEQ ID NO 592
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 592
agaaactgag caagcctcag tcaa                                         24

<210> SEQ ID NO 593
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 593
cagaggctgc atgatgccta ata                                          23

<210> SEQ ID NO 594
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 594
tcagaatacc tccccgccag                                              20

<210> SEQ ID NO 595
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 595 tccctctttta acggttatgt tggc                                        24
```

<210> SEQ ID NO 596
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 596
atgtgcccca cacattgcc                                                19

<210> SEQ ID NO 597
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 597
cgtgtggtgg tggcacaag                                                19

<210> SEQ ID NO 598
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 598
accagggcct gttgggggtt                                               20

<210> SEQ ID NO 599
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 599
ccattggaat gagaaccttc tgg                                           23

<210> SEQ ID NO 600
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 600
gaatgtgaca ccaccaccgc                                               20

<210> SEQ ID NO 601
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 601
ccttctgagc agctgggaca a                                             21

<210> SEQ ID NO 602
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 602
cctcccattg gagccttggt                                               20

<210> SEQ ID NO 603
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 603
catctgagct caaaactgct gc                                            22

<210> SEQ ID NO 604
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 604
tgagggcagg tctgtttcct g                                             21

<210> SEQ ID NO 605
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 605
ccttgcctga cttgccctgt                                               20

<210> SEQ ID NO 606
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 606
gcgacaggta caaagcagtc cat                                           23

<210> SEQ ID NO 607
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 607
cattgctgcc attgcactcc                                               20

<210> SEQ ID NO 608
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 608
acatgatttg atttttcatg tgttt                                         25

```
<210> SEQ ID NO 609
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 609
cgcagatggg catgttattg                                                 20

<210> SEQ ID NO 610
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 610
gactgccact gcactcccac                                                 20

<210> SEQ ID NO 611
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 611
gtccctgacg gaggctgaga                                                 20

<210> SEQ ID NO 612
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 612
tgtcaatatc aataccctgc tttcctc                                         27

<210> SEQ ID NO 613
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 613
aaaaatggat gcaaagccaa a                                               21

<210> SEQ ID NO 614
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 614
tgtgcacatg taccctaaaa ct                                              22

<210> SEQ ID NO 615
<211> LENGTH: 20
<212> TYPE: DNA
<213> ORGANISM: Artificial Sequence
<220> FEATURE:
<223> OTHER INFORMATION: Synthetic Polynucleotide
```

-continued

```
<400> SEQUENCE: 615
ttggcaattt gggtgcaaca                                                     20

<210> SEQ ID NO 616
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 616
tgagcccagg agtttcaggc                                                     20

<210> SEQ ID NO 617
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 617
cagtggttcg ggaaacagca                                                     20

<210> SEQ ID NO 618
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 618
ctggaactct gggcatggct                                                     20

<210> SEQ ID NO 619
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 619
tggacccctc ccttacacc                                                      19
```